United States Patent
LaRosa et al.

(10) Patent No.: US 12,350,356 B2
(45) Date of Patent: *Jul. 8, 2025

(54) TOPICAL SUNSCREEN

(71) Applicant: Concept Matrix Solutions, Woodland Hills, CA (US)

(72) Inventors: Tony LaRosa, Woodland Hills, CA (US); Robert Davidson, Woodland Hills, CA (US); David Reid, Woodland Hills, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/947,002

(22) Filed: Jul. 14, 2020

(65) Prior Publication Data

US 2021/0093529 A1 Apr. 1, 2021

Related U.S. Application Data

(60) Provisional application No. 62/978,347, filed on Feb. 19, 2020, provisional application No. 62/907,835, filed on Sep. 30, 2019.

(51) Int. Cl.

| | |
|---|---|
| *A61K 8/362* | (2006.01) |
| *A61K 8/29* | (2006.01) |
| *A61K 8/34* | (2006.01) |
| *A61K 8/368* | (2006.01) |
| *A61K 8/44* | (2006.01) |
| *A61K 8/81* | (2006.01) |
| *A61K 8/92* | (2006.01) |
| *A61Q 17/04* | (2006.01) |

(52) U.S. Cl.
CPC .............. *A61K 8/362* (2013.01); *A61K 8/29* (2013.01); *A61K 8/345* (2013.01); *A61K 8/368* (2013.01); *A61K 8/445* (2013.01); *A61K 8/8194* (2013.01); *A61K 8/922* (2013.01); *A61K 8/927* (2013.01); *A61Q 17/04* (2013.01); *A61K 2800/30* (2013.01); *A61K 2800/43* (2013.01); *A61K 2800/48* (2013.01); *A61K 2800/522* (2013.01); *A61K 2800/524* (2013.01)

(58) Field of Classification Search
CPC ............ A61K 2800/43; A61K 2800/48; A61K 2800/522; A61K 2800/524; A61Q 17/04
See application file for complete search history.

(56) References Cited

U.S. PATENT DOCUMENTS

| | | | | |
|---|---|---|---|---|
| 5,525,336 | A * | 6/1996 | Green .................. | A61K 8/64 |
| | | | | 435/68.1 |
| 6,224,888 | B1 * | 5/2001 | Vatter .................. | A61K 8/28 |
| | | | | 424/78.03 |
| 2004/0101499 | A1 * | 5/2004 | Jacobson-Alti .......... | A61K 8/37 |
| | | | | 424/64 |
| 2005/0266064 | A1 * | 12/2005 | McCarthy .............. | A61K 8/676 |
| | | | | 514/474 |
| 2011/0206628 | A1 * | 8/2011 | Takakura ................ | A61Q 17/04 |
| | | | | 424/60 |
| 2011/0206790 | A1 * | 8/2011 | Weiss .................... | A61K 8/604 |
| | | | | 424/745 |
| 2018/0185426 | A1 * | 7/2018 | McMahon ........... | A61K 9/0014 |
| 2018/0207213 | A1 * | 7/2018 | Mcelvany ............ | A61Q 19/001 |
| 2018/0264042 | A1 * | 9/2018 | Lait ..................... | A61K 9/0014 |
| 2018/0344663 | A1 * | 12/2018 | Vu ......................... | A61K 9/007 |

OTHER PUBLICATIONS

Lubrizol, Carbopol polymer excipients—Homopolymer, Copolymers & Interpolymers, accessed Jan. 25, 2022, pp. 1-6 (Year: 2022).*

* cited by examiner

*Primary Examiner* — Andrew S Rosenthal
*Assistant Examiner* — Lyndsey M Beckhardt
(74) *Attorney, Agent, or Firm* — Carlson, Caspers, Vandenburgh & Lindquist, P.A.

(57) ABSTRACT

Provided herein is a topical sunscreen composition that includes an external sunscreen agent, one or more pharmaceutically acceptable excipients, and at least one of a cannabinoid, terpene, and flavonoid. Also provided is a method that includes topically administering to a skin surface of a subject (e.g., human) the topical sunscreen composition.

15 Claims, No Drawings

TOPICAL SUNSCREEN

RELATED U.S. APPLICATION DATA

This application claims priority to provisional patent application No. 62/907,835 filed on Sep. 30, 2019, and provisional patent application No. 62/978,347 filed Feb. 19, 2020, the contents of which are incorporated by reference herein in their entirety.

SUMMARY OF THE INVENTION

The present invention provides for a topical sunscreen composition that includes an external sunscreen agent solvent emulsifier; thickening agent emollient and at least one of a cannabinoid, terpene, and flavonoid.

The present invention also provides for a method that includes topically administering to a skin surface of a subject (e.g., human adolescent or adult) the topical composition described herein.

The present invention also provides for a method that includes topically administering to a skin surface of a subject (e.g., human adolescent or adult) the topical composition described herein to prevent sunburn. In doing so, topically administering to the skin surface of the subject the topical composition described herein will also prevent, treat, or ameliorate (i) wrinkles, (ii) fine lines, (iii) blemishes, (iv) skin discoloration, (v) dry skin, (vi) skin irritation, (vii) saggy skin, (viii) inelastic skin, (ix) enlarged pores, (x) acne scars, (xi) inflammation, (xii) crow's feet, (xiii) laugh lines, (xiv) drooping eyelids, (xv) crepey skin, (xvi) frown lines, (xvii) dull skin tone, (xiii) dark circles under the eyes, (xix) lackluster skin, (xx) itchy skin, (xxi) hyperpigmentation, (xxii) uneven skin tone, (xxiii) signs of aging, and (xxiv) collagen loss.

The present invention also provides for a method that includes topically administering to a skin surface of a subject (e.g., human adolescent or adult) the topical composition described herein to help prevent sunburn and at least one of: to reduce signs of aging, cleanse the skin, remove excess oil, reduce the size and redness of acne scars, renew skin, normalize skin, exfoliate the skin, provide smooth & soft skin texture, invigorate skin by lifting away dead skin cells, clear skin, reduce appearance of pores, help balance skin's pH level, provide clearer complexion, and/or provide softer & smoother skin.

DETAILED DESCRIPTION

Compositions of the present invention are beneficial in preventing sunburn. Additionally, such compositions are beneficial in preventing, treating, managing, and/or ameliorating a variety of dermal conditions, such as (i) wrinkles, (ii) fine lines, (iii) blemishes, (iv) skin discoloration, (v) dry skin, (vi) skin irritation, (vii) saggy skin, (viii) inelastic skin, (ix) enlarged pores, (x) acne scars, (xi) inflammation, (xii) crow's feet, (xiii) laugh lines, (xiv) drooping eyelids, (xv) crepey skin, (xvi) frown lines, (xvii) dull skin tone, (xviii) dark circles under the eyes, (xix) lackluster skin, (xx) itchy skin, (xxi) hyperpigmentation, (xxii) uneven skin tone, and (xxiii) collagen loss. M ore specifically, the compositions are beneficial to help prevent sunburn, as well as to reduce signs of aging, cleanse the skin, remove excess oil, reduce the size and redness of acne scars, renew skin, normalize skin, exfoliate the skin, provide smooth & soft skin texture, invigorate skin by lifting away dead skin cells, clear skin, reduce appearance of pores, help balance skin's pH level, provide clearer complexion, and/or provide softer & smoother skin.

In another aspect, the invention relates to a method of preventing sunburn in combination with a method of treating or ameliorating and signs of aging. The method includes administering to a person at risk of sunburn, an effective amount of one or more compositions as described herein.

The compositions of the present invention include at least one of a cannabinoid, terpene, and flavonoid. Without wishing to be limited to any particular theory, it is currently believed that the cannabinoid, terpene, and/or flavonoid provides stability to the composition, which serves to prevent phase separation of an aqueous and a lipid phase in the composition at elevated temperatures (e.g. temperatures of more than about 25° C.), which might promote improved or prolonged contact to the skin, resulting in the observed increased retention times of the active(s) in the dermis and epidermis.

Across multiple topical dosage forms (e.g., creams, gels, lotions, ointments, foams, etc.) the cannabinoid, terpene, and/or flavonoid can be present in an amount, such that it exhibits activity as an active ingredient for the intended purpose (e.g., sunscreen). In doing so, the cannabinoid, terpene, and/or flavonoid may further have a synergistic effect with the active ingredient(s) present therein. In other aspects, the cannabinoid, terpene, and/or flavonoid can be present in sub-therapeutic amounts.

It is currently believed that the topical use of the cannabinoid, terpene, and/or flavonoid provides additional benefits, which include: smoothing skin, strengthening underlying epidermal tissue, removing dead skin cells, balancing oil production, and helping the skin retain moisture levels. It is further believed that the cannabinoid, terpene, and/or flavonoid helps cleanse and moisturize the skin. Healthy skin is just like any other organ In your body: It continuously needs oxygen and nutrients to be brought to the cells, and toxins need to be washed away. It is further believed that the cannabinoid, terpene, and/or flavonoid contrinbutes to the optimal skin health while leaving skin feeling and looking youthful.

It is also currently believed that some consumers have a preference to use a topical skin product that is environmentally friendly to produce and includes fewer toxic chemicals that are otherwise put into the environment when creating topical skin products. Inclusion of substances, such as cannabinoid, terpene, and flavonoid (which are natural products), are viable options for such consumers.

Definitions

The term "topical sunscreen composition" refers to a topical composition containing an external sunscreen agent, various inactive ingredients or excipients, and at least one of a terpene and cannabinoid. The composition is suitable for the prophylactic treatment of sunburn.

The term"sunscreen" refers to a product with a topical formulation that can be configured and formulated to exist in various dosage forms, such as, e.g., gel, pump gel, gel packet, cream, lotion, roll-on liquid, roll-on gel, spray, pump spray, aerosol spray, stick, patch, ointment, liniment, or balmlotion that contains an external sunscreen agent that reflects ultraviolet radiation from the skin to prevent sunburn.

The term "sunburn" refers to a radiation burn of the skin due to overexposure of ultraviolet radiation (ie. UV radiation from the sun). Common symptoms include redness of the skin that can be hot and painful to the touch, general fatigue or mild dizziness.

The term "external sunscreen agent" or "sunscreen agent" refers to any chemical and/or biological agent (i.e. an antimicrobial peptide) that when topically administered onto the skin, effectively prevents and leads to a visible reduction of symptoms associated with sunburn of the skin. Representative sunscreen agents include, for example 2-ethylhexyl-4-phenylbenzophenone-2-carboxylic acid; allantoin (with aminobenzoic acid); amiloxate (isoamyl p-methoxycinnamate); aminobenzoic acid (PABA); avobenzone; bemotrizinol; bisoctrizole; bomelone (5-(3,3-dimethyl-2-norbornyliden)3-pentene-2-one); camphor; cinoxate; diethylhexyl butamido triazone; digalloyl trioleate; diolamine methoxycinnamate (diethanolamine methoxycinnamate); dioxybenzone; dipropylene glycol salicylate; drometrizole trisiloxane; ecamsule; ensulizole (phenylbenzimidazole sulfonic acid); enzacamene (4-methylbenzylidene camphor); ethyl 4-(bis(hydroxypropyl)] aminobenzoate (roxadimate); glyceryl aminobenzoate (lisadimate, glyceryl PABA); homosalate; lawsone (w/ dihydroxyacetone); meradimate (menthyl anthranilate); octinoxate (octyl methoxycinnamate; ethylhexyl methoxycinnamate); octisalate (octyl salicylate; ethylhexyl salicylate); octocrylene; octyl triazone (ethylhexyl triazone); oxybenzone (benzophenone-3); padimate a; padimate o; red petrolatum; sodium 3,4-dimethylphenyl-glyoxylate; sulisobenzone; titanium dioxide; trolamine salicylate; zinc oxide; and zinc phenol sulfonate.

The term "solvent" refers to a substance, typically a liquid at ambient conditions, capable of dissolving another substance (a solute), resulting in a solution. When one substance is dissolved into another, a solution is formed. This is opposed to the situation when the compounds are insoluble like sand in water. In solution, all of the ingredients are uniformly distributed at a molecular level and no residue remains. The mixing is referred to as miscibility, whereas the ability to dissolve one compound into another is known as solubility. However, in addition to mixing, both substances in the solution interact with each other. When something is dissolved, molecules of the solvent arrange themselves around molecules of the solute. H eat is involved and entropy is increased making the solution more thermodynamically stable than the solute alone. This arrangement is mediated by the respective chemical properties of the solvent and solute, such as hydrogen bonding, dipole moment and polarizability.

The term "emulsifier" refers to a substance capable of forming or promoting an emulsion. An emulsion is a mixture of two or more liquids that are normally immiscible (non-mixable or unblendable). Emulsions are part of a more general class of two-phase used systems of matter called colloids. Although the terms colloid and emulsion are sometimes interchangeable, emulsion should be used when both the dispersed and the continuous phase are liquids. In an emulsion, one liquid (the dispersed phase) is dispersed in the other (the continuous phase). Examples of emulsions include vinaigrettes, milk, mayonnaise, and some cutting fluids for metal working. The photo-sensitive side of photographic film is an example of a colloid.

The term "thickening agent" or "viscosity-increasing agent" refers to a substance which can increase the thickness or viscosity of a liquid without substantially changing its other properties. Some thickening agents are gelling agents (gellants), forming a gel, dissolving in the liquid phase as a colloid mixture that forms a weakly cohesive internal structure. Others act as mechanical thixotropic additives with discrete particles adhering or interlocking to resist strain. Typical gelling agents include natural gums, starches, pectins, agar-agar and gelatin. Often they are based on polysaccharides or proteins. Examples include: Alginic acid, sodium alginate, potassium alginate, ammonium alginate, calcium alginate—polysaccharides from brown algae; Agar (polysaccharide obtained from red algae); Carrageenan (polysaccharide obtained from red seaweeds); Locust bean gum (natural gum polysaccharide from the seeds of the carob tree); Pectin (polysaccharide obtained from apple or citrus-fruit); and Gelatin (made by partial hydrolysis of animal collagen). The thickening agent or viscosity-increasing agent also includes cellulose thickeners, such as e.g., hydroxypropyl cellulose, hydroxyethyl cellulose, hydroxypropyl cellulose, hydroxypropyl methyl cellulose, methyl cellulose, carbopols, polyacrylic acid, and polyvinyl alcohol.

The term "emollient" refers to lubricating ingredients (i.e., fats, phospholipids and sterols) that soften and smooth skin while helping it to retain moisture. Emollients are typically nonpolar and can come from natural or synthetic sources in the form of plant oils, mineral oils, shea butter, cocoa butter, petrolatum, cholesterol, silicones or animal oils (including emu, mink and lanolin).

The term "cannabinoid" refers to a class of diverse chemical compounds that act on cannabinoid receptors on cells that repress neurotransmitter release in the brain. These receptor proteins include the endocannabinoids (produced naturally in the body by humans and animals), the phytocannabinoids (found in *Cannabis* and some other plants), and synthetic cannabinoids (manufactured chemically). The most notable cannabinoid is the phytocannabinoid Δ9-tetrahydrocannabinol (THC), the primary psychoactive compound of *Cannabis*. Cannabidiol (CBD) is another major constituent of the plant, representing up to 40% in extracts of the plant resin. There are at least 85 different cannabinoids isolated from *Cannabis*, exhibiting varied effects. The cannabinoid can be synthetically prepared, or alternatively, can be obtained naturally (e.g., from plant matter). Either way, the cannabinoid can have the requisite purity (e.g., at least 95 wt. % pure, at least 98 wt. % pure, at least 99 wt. % pure, or at least 99.5 wt % pure).

| Cannabinoids isolated from *Cannabis* |
|---|
| 1. Cannabigerol ((E)-CBG-C5) |
| 2. Cannabigerol monomethyl ether ((E)-CBGM-C5 A) |
| 3. Cannabinerolic acid A ((Z)-CBGA-C5 A) |
| 4. Cannabigerovarin ((E)-CBGV-C3) |
| 5. Cannabigerolic acid A ((E)-CBGA-C5 A) |
| 6. Cannabigerolic acid A monomethyl ether ((E)-CBGAM-C5 A) |
| 7. Cannabigerovarinic acid A ((E)-CBGVA-C3 A) |
| 8. (±)-Cannabichromene (CBC-C5) |
| 9. (+)-Cannabichromenic acid ACBCA-C5 A |
| 10. (+)-Cannabivarichromene or (+)-Cannabichromevarin (CBCV-C3) |
| 11. (+)-Cannabichromevarinic acid A (CBCVA-C3 A) |
| 12. (−)-Cannabidiol (CBD-C5) |
| 13. Cannabidiol momomethyl ether (CBDM-C5) |
| 14. Cannabidiol-C4 (CBD-C4) |
| 15. (−)-Cannabidivarin CBDV-C3 |
| 16. Cannabidiorcol (CBD-C1) |
| 17. Cannabidiolic acid (CBDA-C5) |
| 18. Cannabidivarinic acid (CBDVA-C3) |
| 19. Cannabinodiol (CBND-C5) |
| 20. Cannabinodivarin (CBND-C3) |
| 21 Δ9-Tetrahydrocannabinol (Δ9-THC-C5) |
| 22. Δ9-Tetrahydrocannabinol-C4 (Δ9-THC-C4) |
| 23. Δ9-Tetrahydrocannabivarin (Δ9-THCV-C3) |
| 24. Δ9-Tetrahydrocannabiorcol (Δ9-THCO-C1) |

| Cannabinoids isolated from *Cannabis* |
|---|
| 25. Δ9-Tetrahydro- cannabinolic acid A (Δ9-THCA-C5 A) |
| 26. Δ9-Tetrahydro- cannabinolic acid B (Δ9-THCA-C5 B) |
| 27. Δ9-Tetrahydro- cannabinolic acid-C4A and/or B (Δ9-THCA-C4A and/or B) |
| 28. Δ9-Tetrahydro- cannabivarinic acid A (Δ9-THCVA-C3A) |
| 29. Δ9-Tetrahydro- cannabiorcolic acid A and/or B (Δ9-THCOA-C1A and/or B) |
| 30. (−)-Δ8-trans-(6aR,10aR)-Δ8-Tetrahydrocannabinol (Δ8-THC-C5) |
| 31. (−)-Δ8-trans-(6aR,10aR)- Tetrahydrocannabinolic acid A (Δ8-THCA-C5 A) |
| 32. (−)-(6aS,10aR)-Δ9-Tetrahydrocannabinol ((−)-cis-Δ9-THC-C5) |
| 33. Cannabinol (CBN-C5) |
| 34. Cannabinol-C4 (CBN-C4) |
| 35. Cannabivarin (CBN-C3) |
| 36. Cannabinol-C2 (CBN-C2) |
| 37. Cannabiorcol (CBN-C1) |
| 38. Cannabinolic acid A (CBNA-C5 A) |
| 39. Cannabinol methyl ether (CBNM-C5) |
| 40. (−)-(9R,10R)-trans- Cannabitriol ((−)-trans-CBT-C5) |
| 41. (+)-(9S,10S)-Cannabitriol ((+)-trans-CBT-C5) |
| 42. (±)-(9R,10S/9S,10R)- Cannabitriol ((±)-cis-CBT-C5) |
| 43. (−)-(9R,10R)-trans- 10-O-Ethyl-cannabitriol ((−)-trans-CBT-OEt-C5) |
| 44. (±)-(9R,10R/9S,10S)- Cannabitriol-C3 ((±)-trans-CBT-C3) |
| 45. 8,9-Dihydroxy-Δ6a(10a)- tetrahydrocannabinol (8,9-Di-OH-CBT-C5) |
| 46. Cannabidiolic acid A cannabitriol ester (CBDA-C5 9-OH-CBT-C5 ester) |
| 47. (−)-(6aR,9S,10S,10aR)- 9,10-Dihydroxy- hexahydrocannabinol, Cannabiripsol (Cannabiripsol-C5) |
| 48. (−)-6a,7,10a-Trihydroxy-Δ9-tetrahydrocannabinol ((−)-Cannabitetrol) |
| 49. 10-Oxo-Δ6a(10a)- tetrahydrocannabinol (OTHC) |
| 50. (5aS,6S,9R,9aR)- Cannabielsoin (CBE-C5) |
| 51. (5aS,6S,9R,9aR)- C3-Cannabielsoin (CBE-C3) |
| 52. (5aS,6S,9R,9aR)- Cannabielsoic acid A (CBEA-C5 A) |
| 53. (5aS,6S,9R,9aR)- Cannabielsoic acid B (CBEA-C5 B) |
| 54. (5aS,6S,9R,9aR)- C3-Cannabielsoic acid B (CBEA-C3 B) |
| 55. Cannabiglendol-C3 (OH-iso-HHCV-C3) |
| 56. Dehydrocannabifuran (DCBF-C5) |
| 57. Cannabifuran (CBF-C5) |
| 58. (−)-Δ7-trans-(1R,3R,6R)-Isotetrahydrocannabinol |
| 59. (±)-Δ7-1,2-cis- (1R,3R,6S/1S,3S,6R)- Isotetrahydro- cannabivarin |
| 60. (−)-Δ7-trans-(1R,3R,6R)- Isotetrahydrocannabivarin |
| 61. (±)-(1aS,3aR,8bR,8cR)- Cannabicyclol (CBL-C5) |
| 62. (±)-(1aS,3aR,8bR,8cR)- Cannabicyclolic acid A (CBLA-C5 A) |
| 63. (±)-(1aS,3aR,8bR,8cR)- Cannabicyclovarin (CBLV-C3) |
| 64. Cannabicitran (CBT-C5) |
| 65. Cannabichromanone (CBCN-C5) |
| 66. Cannabichromanone-C3 (CBCN-C3) |
| 67. Cannabicoumaronone (CBCON-C5) |
| 68. Cannabielsoin acid A (CBEA-A) |
| 69. 10-Ethoxy-9-hydroxy-delta-6a-tetrahydrocannabinol |
| 70. Cannabitriolvarin (CBTV) |
| 71. Delta-9-tetrahydrocannabiorcolic acid (THCA-C1) |
| 72. Delta-7-cis-iso-tetrahydrocanna |
| 73. Cannabichromanon (CBCF) |

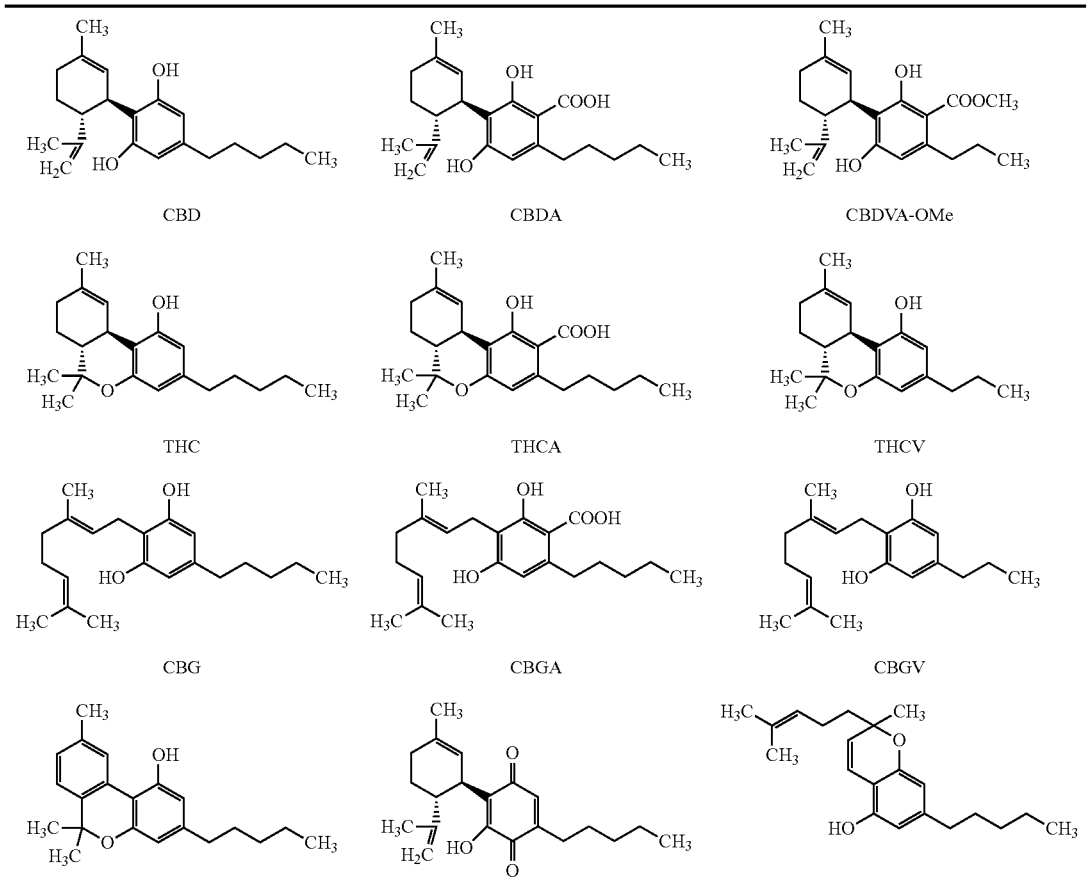

Structure of common cannabinoids: CBD, CBDA, CBDVA-OMe, THC, THCA, THCV, CBG, CBGA, CBGV

Structure of common cannaboinoids

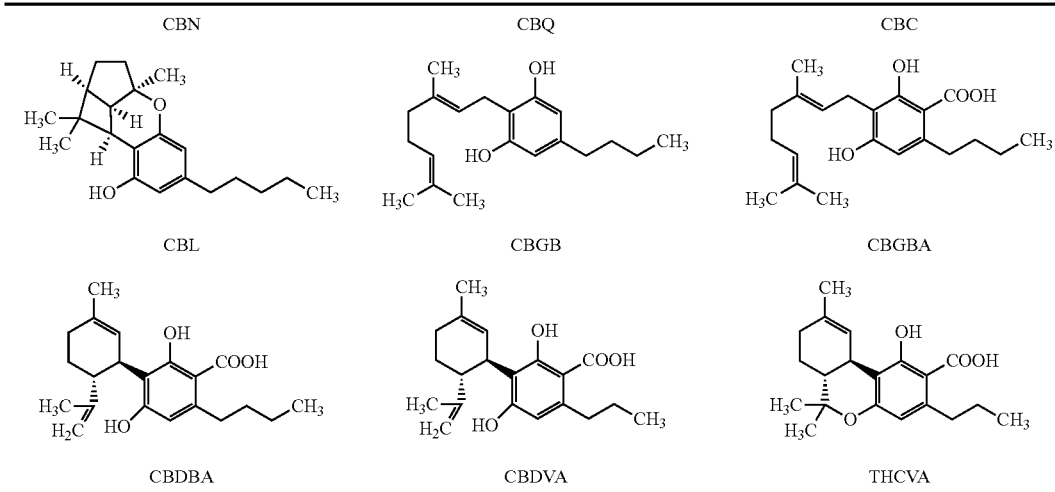

Synthetically prepared cannabinoids, that are commercially available (e.g., Purisys™ of Athens, GA), are provided below.

| Common Name | Other Names | Alkyl Tail Length | CAS # |
|---|---|---|---|
| TETRAHYDROCANNABIVARIN FAMILY | | | |
| Δ9-Tetrahydrocannabivarin | Δ9-THCV | C3 | 31262-37-0 |
| Δ8-Tetrahydrocannabivarin | Δ8-THCV | C3 | 31262-38-1 |
| Δ9-Tetrahydrocannabivarin Naphtoylester | Δ9-THCV-NE | C3 | N/A |
| Δ8-Tetrahydrocannabivarin Naphtoylester | Δ8-THCV-NE | C3 | N/A |
| Δ9-Tetrahydrocannabivarinic Acid | Δ9-THCVA-A, Δ9-THC-VA-B | C3 | 39986-26-0 |

| Common Name | Other Names | Alkyl Tail Length | CAS # |
|---|---|---|---|
| CANNABIDIOLVARIN FAMILY | | | |
| (−)-Cannabidivarin | (−)-CBDV | C3 | 24274-48-4 |
| (+)-Cannabidivarin | (+)-CBDV | C3 | 1637328-94-9 |
| Cannabidivarinic Acid | CBDVA | C3 | 31932-13-S |
| Cannabidivarin Quinone | CBQV | C3 | N/A |

| Common Name | Other Names | Alkyl Tail Length | CAS # |
|---|---|---|---|
| TETRAHYDROCANNABIBUTOL FAMILY | | | |
| Δ9-Tetrahydrocannabibutol | Δ9-THCB | C4 | 60008-00-6 |
| Δ8-Tetrahydrocannabibutol | Δ8-THCB | C4 | 51768-59-3 |
| Δ9-Tetrahydrocannabibutol Naphtoylester | Δ9-THCB-NE | C4 | 60007-98-9 |
| Δ8-Tetrahydrocannabibutol Naphtoylester | Δ8-THCB-NE | C4 | N/A |
| Δ9-Tetrahydrocannabibutolic Acid | Δ9-THCBA-A, Δ9-THC-BA-B | C4 | 60007-98-9 |

| Common Name | Other Names | Alkyl Tail Length | CAS # |
|---|---|---|---|
| CANNABIDIBUTOL FAMILY | | | |
| (−)-Cannabidibutol | (−)-CBDB | C4 | 60113-11-3 |
| (+)-Cannabidibutol | (+)-CBDB | C4 | N/A |
| Cannabidibutolic Acid | CBDBA | C4 | N/A |

| Common Name | Other Names | Alkyl Tail Length | CAS # |
|---|---|---|---|
| RARE CANNABINOIDS | | | |
| Cannabinol | CBN, USP Impurity | C5 | 521-35-7 |
| Cannabinolic Acid | CBNA | C5 | 2808-39-1 |
| Cannabigerol | CBG | C5 | 25654-31-3 |
| Cannabigerolic Acid | CBGA | C5 | 25555-57-1 |
| Cannabichromene | CBC | C5 | 20675-51-8 |
| Cannabichromenic Acid | CBCA | C5 | 185505-15-1 |
| Cannbicyclol | CBL | C5 | 21366-63-2 |
| Cannabicyclolic Acid | CBLA | C5 | 2283314-84-9 |
| Cannabivarin | CBNV | C3 | 33745-21-0 |
| Cannabivarinic Acid | CBNVA | C3 | 64846-02-2 |
| Cannbigerivarin | CBGV | C3 | 55824-11-8 |
| Cannabigerivarinic Acid | CBGVA | C3 | 64924-07-8 |
| Cannbichromevarin | CBCV | C3 | 57130-04-8 |
| Cannabichromevarinic Acid | CBCVA | C3 | 64898-02-8 |
| Cannabicyclolvarin | CBLV | C3 | 55870-47-8 |
| Cannabicyclolvarinic Acid | CBLVA | C3 | 2281847-63-8 |
| 3-Butylcannabinol | CBNB | C4 | 60007-99-0 |
| 3-Butylcannabinolic Acid | CBNBA | C4 | N/A |
| Cannabigerol Butyl | CBGB | C4 | N/A |
| Cannabigerol Butyric Acid | CBGBA | C4 | N/A |
| Cannabichromene Butyl | CBCB | C4 | N/A |
| Cannabichromene Buytric Acid | CBCBA | C4 | N/A |
| Cannabicyclol Butyl | CBLB | C4 | N/A |
| Cannabicyclol Butyric Acid | CBLBA | C4 | N/A |

The term "terpene" refers to a hydrocarbon or derivative thereof, found as a natural product and biosynthesized by oligomerization of isoprene units. A terpene can be acyclic, monocycliC, bicyclic, or multicyclic. Examples include, e.g., sesquiterpenes (e.g., (−)-β-caryophyllene, humulene, vetivazulene, guaiazulene, longifolene, copaene, and patchoulol), monoterpenes (e.g., limonene and pulegone), monoterpenoids (e.g., carvone), diterpenes (e.g., taxadiene), and triterpenes (e.g., squalene, betulin, betulinic acid, lupane, lupeol, betulin-3-caffeate, allobetulin, and cholesterol). The terpene can be synthetically prepared, or alternatively, can be obtained naturally (e.g., from plant matter). Either way, the terpene can have the requisite purity (e.g., at least 95 wt. % pure, at least 98 wt. % pure, at least 99 wt. % pure, or at least 99.5 wt. % pure).

| Terpene | Plant | Genus | Species |
|---|---|---|---|
| Myrcene | Myrtles | *Myrtus* | *communis; nivellei; phyllireaefolia* |
|  | Cannabis | *Cannabis* | *sativa; ruderalis; indica* |
| Linalool | Mint | *Mentha* | *spicata; arvensis; canadensis* |
|  | Lavender | *Lavandula* (subgenus: *Fabricia; Sabaudia*) | *spica, angustifolia; latifolia; lanata; dentata; stoechas; pedunculata; viridis* |
| Terpineol | Orange peel | *Citrus* | *reticulata* |
|  | Junipers | *Juniperus* | *communis; chinensis; conferta; rigida* |
| Camphene | Chrysanthemum | *Chrysanthemum* | *indicum* |
|  | Ginger | *Zingiber* | *officinale* |
| Bisabolol | Chamomile | *Matricaria* (or *Chamaemelum*) | *chamomilla* (or *nobile*) |
|  | Figwort | *Myoporum* | *crassifolium* |
| Nerolidol | Cannabis | *Cannabis* | *sativa; ruderalis; indica* |
| Limonene | Citrus Lemon | *Citrus* | *limon* |
| Humulene | Hops | *Humulus* | *lupulus; japonicus; yunnanensis* |
| Terpinolene | Cannabis | *Cannabis* | *sativa, ruderalis; indica* |
| Carene | Rosemary | *Salvia* | *rosmarinus; jordanii* |
|  | Cedar | *Cedrus* | *atlantica; brevifolia; deodara; libani* |
| Eucalyptol | Eucalyptus | *Eucalyptus* | *obliqua* |
|  | Cannabis | *Cannabis* | *sativa; ruderalis; indica* |
|  | Camphor laurel | *Cinnamomum* | *camphora* |
|  | Bay leaves | *Laurus* | *nobilis* |
|  | Wormwood | *Artemisia* | *vulgaris* |
| Ocimene | Hops | *Humulus* | *lupulus; japonicus; yunnanensis* |
|  | Kumquats | *Citrus* | *japonica* |
|  | Mango | *Mangifera* | *indica* |
|  | Basil | *Ocimum* | *basilicum* |
|  | bergamot orange | *Citrus* | *× aurantium* |
| Carophyllene | Peppercorn | *Piper* | *nigrum* |
|  | Cloves | *Syzgium* | *aromaticum* |
|  | Cannabis | *Cannabis* | *sativa; ruderalis; indica* |
|  | Rosemary | *Salvia* | *rosmarinus; jordanii* |
|  | Hops | *Humulus* | *lupulus; japonicus; yunnanensis* |
| Valencene | Nootka cypress | *Callitropsis* | *nootkatensis* |
| Geraniol | Roses | *Rosa* (subgenus: Banksianae, Bracteatae, Caninae, Carolinae, Chinensis, Gallicanae, Gymnocarpae, Laevigatae, Pimpinellifoliae, Synstylae) | *persica; minutifolia; stellata* |
|  | Wine grapes | *Vitis* | *vinifera* |
| Borneol | Borneo camphor | *Dryobalanops* | *aromatica* |
|  | Ngai camphor; sambong | *Blumea* | *balsamifera* |
| Pulegone | Catnip | *Nepeta* | *cataria* |
|  | Peppermint | *Mentha* | *piperita* |
|  | Pennyroyal | *Hedeoma* | *pulegioides* |
| Guaiazulene | Chamomile | *Matricaria* (or *Chamaemelum*) | *chamomilla* (or *nobile*) |
|  | Guaiacum tree | *Guaiacum* | *sanctum, angustifolium, coulteri, officinale* |
| Lupeol | Lupine seed | *Lupinus* | *luteus* |
| Lupane | Lupine seed | *Lupinus* | *luteus* |
| Betulin Betulinic acid Lupeol | Brich tree | *Betula* (Subgenus: Betulenta, Betulaster, Neurobetula, Chamaebetula) | *alleghaniensis, cordifolia, glandulosa, lenta, michauxii, minor, nana, neoalaskana, nigra, occidentalis, papyrifera, populifolia, pumila, uber* |

| Terpene | Plant | Genus | Species |
|---|---|---|---|
| Squalene | Amaranth seed | *Amaranthus* (subgenus: *Acnida*; *Albersia*) | *acanthochiton, acutilobus, albus, anderssonii, californicus* |
| | Wheat germ | *Triticum* | *aestivum* |
| | Olive | *Olea* | *europaea* |
| Carvone | Caraway seed | *Carum* | *carvi* |
| | Spearmint | *Mentha* | *spicata* |
| | Dill | *Anethum* | *graveolens* |
| Patchoulol | Patchouli | *Pogostemon* | *cablin* |
| Copaene | Copaiba tree | *Copaifera* | *langsdorfii* |
| Longifolene | Pine | *Pinus* | *longifolia* |
| Pinene | Pine | *Pinus* (subgenus: *Strobus*; *Pinus*) | *densata, densiflora, pinea, sylvestris* |
| Vetivazulene | Vetiver | *Chrysopogon* | *zizanioides* |
| Nerol | Lemon Grass | *Cymbopogon* | *nardus; citratus; flexuosus, martinii, schoenanthus* |

Synthetically prepared terpenes, which are commercially available (e.g., Purisys™ of Athens, GA), are provided below.

| Terpene | CAS # |
|---|---|
| Alpha-Pinene | 51634232009 |
| Beta-Pinene | 51634232109 |
| Beta-Myrcene | 51634232209 |
| Alpha-Terpinene | 51634232309 |
| Limonene | 51634232409 |
| Beta-Ocimene | 51634232509 |
| Terpinolene | 51634232609 |
| Linalool | 51634232709 |
| Fenchyl Alcohol | 51634232809 |
| Borneol Isomers | 51634232909 |
| Alpha-Terpineol | 51634233009 |
| Trans-caryophyllene | 51634233109 |
| Alpha-humulene | 51634233209 |
| Trans-nerolidol | 51634233309 |

-continued

| Terpene | CAS # |
|---|---|
| Guaiol | 51634233409 |
| Alpha-Bisabolol | 51634233509 |

The term "flavonoid" refers to ubiquitous plant natural products with various polyphenolic structures. Flavonoids can be extracted from fruits, vegetables, grains, bark, roots, stems, flowers, and teas or can be biosynthetically produced. The role of flavonoids in plants includes UV protection, aid in plant growth, defense against plaques, and provide the color and aroma of flowers.

Flavonoids can be divided into classes (e.g., anthocyanin, chalcone, flavone, flavonol, isoflavone, and flavonone) and subclasses depending on the carbon of the C ring on which the B ring is attached and the degree of unsaturation and oxidation of the C ring.

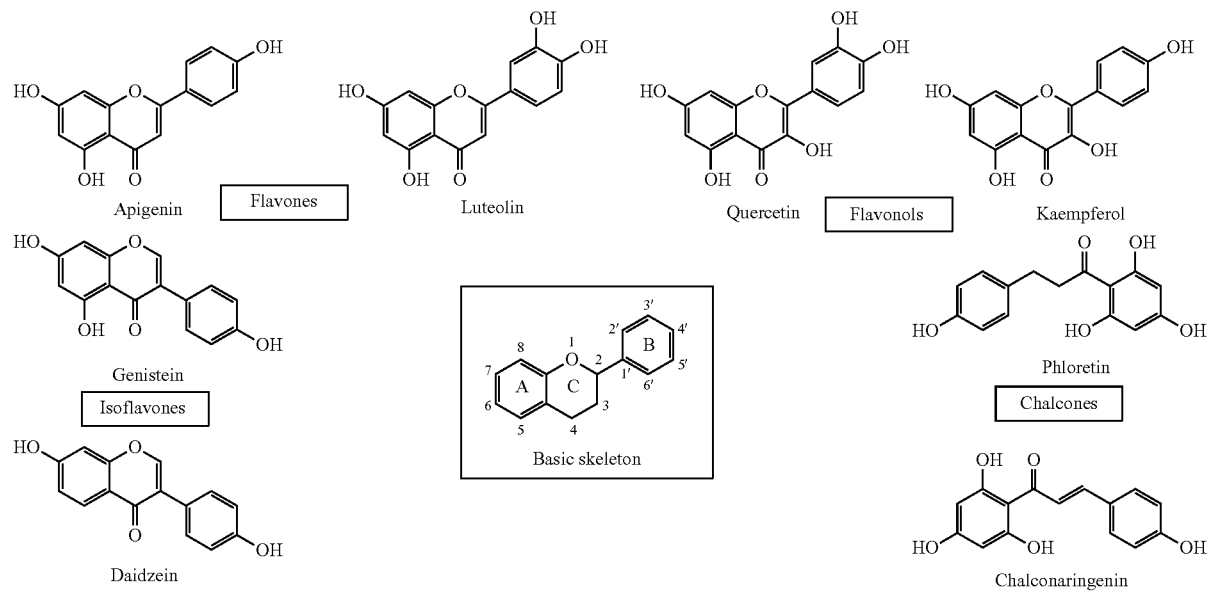

-continued

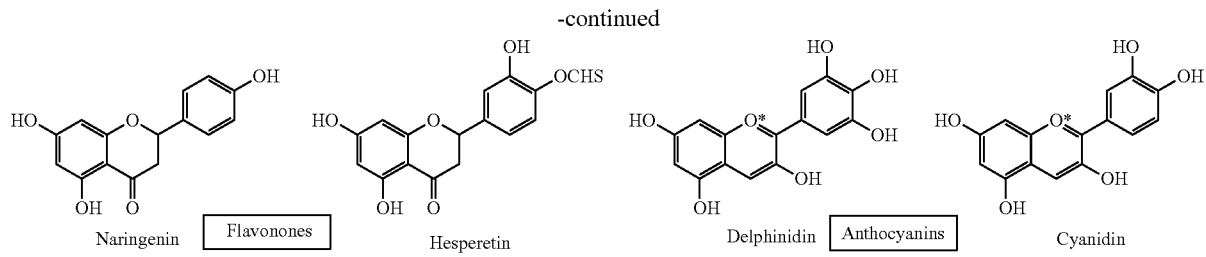

| Flavonoid classes | Subclasses | Natural sources | Examples of natural sources |
|---|---|---|---|
| Anthocyanins | Cyanidin, Malvidin, Delphinidin, Peonidin | Fruits, vegetables, nuts, dried fruits, medicinal plants | Cranberries, plums, cherries, sweet potatoes, black currants, red grapes, merlot grapes, raspberries, strawberries, blueberries, bilberries and blackberries |
| Chalcones | Phloretin, Arbutin, Phloridzin | Fruits, vegetables, medicinal plants | Tomatoes, pears, strawberries, bearberries and certain wheat products |
| Flavonones | Hesperitin, Naringin, Naringenin, Eriodictyol, Hesperidin | Fruits (citrus), medicinal plants | Oranges, lemons, grapes, rosehips |
| Flavones | Apigenin, Tangeretin, Baicalein, Rpoifolin | Fruits, medicinal plants | Celery, parsley, red peppers, chamomile, mint, ginkgo biloba, broccoli, green pepper, thyme, dandelion, perilla, tea, carrot, rosemary, oregano, Cannabis sativa |
| Flavonols | Quercetin, Myricetin, Rutin, Morin, Kaempferol | Fruits, vegetables, medicine plants | Onion, kale, lettuce, tomatoes, apples, grapes, berries, tea, red wine, broccoli, potatoes, brussel sprouts, squash, cucumbers, lettuce, green beans, spinach, peaches, blackberries |
| Isoflavonoids | Genistin, Genistein, Daidzein, Glycetein, Daidzin | Legumes, medicinal plants | Soybeans, lupin, fava beans, kudzu, psoralea, red clover, alfalfa sprouts, peanuts, chickpeas |

| Flavonoid classes | Structure of flavonoid classes |
|---|---|
| Anthocyanins | Double bonds between positions 1 and 2, 3 and 4 of the C ring; Hydroxyl groups at positions 5 and 7 in the A ring and 3', 4' and/or 5' of the B ring; Methylation or acylation at the hydroxyl groups on the A and B rings vary |
| Chalcones | Absence of 'C ring' of the basic flavonoid skeleton structure |
| Flavonones | C ring is saturated (contains no double bonds) |
| Flavones | Double bond between positions 2 and 3 and a ketone in position 4 of the C ring; Most have a hydroxyl group in |

| Flavonoid classes | Structure of flavonoid classes |
| --- | --- |
| | position 5 or 7 of the A ring of the A ring or 3' and 4' of the B ring (varies according to the taxonomic classification of the particular plant) |
| Flavonols | Double bond between positions 2 and 3, a ketone in position 4 and hydroxyl group in position 3 of the C ring, the ketone group the C ring may also be glycosylated; very diverse in methylation and hydroxylation patterns |
| Isoflavonoids | B ring is attached to the 3 position of the C ring and contains a hydroxyl group at the 4' position; hydroxylation of the A ring varies |

Studies on flavonoids have revealed an increasing number of health benefits showing anti-oxidant, anti-inflammatory, anti-mutagenic, and anti-carcinogenic properties by inhibiting numerous pro-inflammatory and pro-oxidative enzymes (e.g., xanthine oxidase (XO), cyclo-oxygenase (COS), lipoxygenase, phosphoinositide 3-kinase, and acetyicholinesterase). This may have benefits towards numerous diseases and medical conditions (e.g., pain, cancer, artherscle-rosis, Alzheimer's disease). There is a growing interest in the medicinal properties of Cannabis (Cannabis sativa, Cannabis indica, Cannabis ruderalis). Studies have shown that Cannaflavin A and Cannflavin B, prenylated flavones, have anti-inflammatory properties greater than aspirin. Cannflavin A and B can be isolated from Cannabis sativa and biosynthesized.

Synthetically prepared flavonoids, which are commercially available (e.g., Cannflavin B from Toronto Research Chemicals), are provided below.

| Flavonoid | CAS # |
| --- | --- |
| Cannflavin A | 76735-57-4 |
| Cannflavin B | 76735-58-5 |
| Myricetin | 529-44-2 |
| (−)-Epigallocathechin gallate | 989-51-5 |
| Polyphenon 60 from green tea | 138988-88-2 |
| (−)-Gallocathechin | 3371-27-5 |
| Kaempferol | 520-18-3 |
| (±)-Catechin hydrate | 7295-85-4 (anhydrous) |
| Galangin | 548-83-4 |
| Hesperidin | 520-26-3 |
| Baicalein | 491-67-8 |
| Icariin | 489-32-7 |
| Orientin | 28608-75-5 |
| Liquiritigenin | 578-86-9 |
| Acacetin | 480-44-4 |
| Diosmetin | 520-34-3 |
| Scutellarein | 529-53-3 |
| Luteolin | 491-70-3 |

The term "transdermal delivery agent" refers to a substance that aids or facilitates the passage of desired compounds, such as pharmaceutically active ingredients (e.g., external sunscreen agent), cannabinoids, and/or terpenes, at least partially through one or more layers of the skin, including the dermis and epidermis.

The term "antioxidant" refers to an oxidation preventive agent that reduces excessive production of reactive oxygen species. Antioxidants can come from natural products or sources such as vitamin E (tocopherol), vitamin C (ascorbic acid), vitamin A, β-carotene, superoxide dismutase, coenzyme Q. Synthetically derived antioxidants include 3,5-tert-butyl-4-hydroxytoluene (BHT) and 2,3-tert-butyl-hydroxy-anisole (BHA) which have been developed to inhibit oxidation of a lipid or the like.

The term "fragrance" refers to a combination of chemicals that gives each product its distinct scent. Chemical ingredients may be derived from synthetic or natural raw materials that can add or mask a scent. The ingredients are capable of imparting or modifying the odor of skin or hair or other substrate.

The term "coloring agent" refers to a natural or synthetic compound that provides a pigment used to enhance the product's appearance and aesthetic value.

The term "exfoliant" refers to an additive used in an attempt to remove dead skin cells exposing the living layer. This provides the skin a smoother softer more youthful appearance, as well as allowing the living layers to grow and stay healthy. Exfoliating topical compositions conventionally use an abrasive compound in a scrubbing motion to remove dead skin cells from the face. Common exfoliants include powders from ground apricot seeds, crushed walnut shells, coconut shells, almond seeds and shells, and sawdust, various solid polymer powders, and various inorganic particles such as sand, salt, alumina, silica, alumino-silicates, lava stone, various phosphates, borates, sulfates, and carbonates.

The term "skin surface" refers to interface of an organism with the environment, which prevents moisture loss from the body, and is a barrier functioning to prevent the invasion of biotoxic substances, such as microorganisms and allergens, from the environment. The skin contains two layers consisting of an outer epidermis and an inner dermis.

The term "human" refers to a person who can benefit from the pharmaceutical formulations and methods of the present invention. The person that could benefit from the presently described pharmaceutical formulations and methods may be an adolescent or adult. A human may be referred to as an individual, patient, subject, or recipient.

The term "topical formulation" is used herein to generally include a formulation that can be applied to skin or a mucosa. Topical formulations may, for example, be used to confer therapeutic benefit to a patient or cosmetic benefits to a consumer. Topical formulations can be used for both topical and transdermal administration of substances. The topical formulations can be configured and formulated to exist in various dosage forms, such as, e.g., gel, pump gel, gel packet, cream, lotion, roll-on liquid, roll-on gel, spray, pump spray, aerosol spray, stick, patch, ointment, liniment, or balm.

The term "topical administration" is used herein to generally include the delivery of a substance, such as a therapeutically active agent (e.g., external sunscreen agent), to the skin or a localized region of the body.

The term "transdermal administration" is used herein to generally include administration through at least a portion of the skin. Transdermal administration is often applied for delivering desired substances to tissues underlying the skin with minimal to no systemic absorption. As such, the transdermal administration delivers desired substances at least partially through one or more layers of the skin, including the dermis and epidermis.

The term "subject" is used herein to generally include humans, particularly human adolescents (e.g., 12-17 years old) and human adults (e.g., at least 18 years old).

The term "effective amount" is used herein to generally include an amount of topical formulation (or external sunscreen agent) effective for treating or preventing sunburn in a subject as described herein.

The term "treating" with regard to a subject, refers to improving at least one symptom of the subject's disorder. Treating includes curing, improving, or at least partially ameliorating the disorder or the symptoms thereof.

Method of Manufacturing

As described herein, the compositions of the present invention are suitable for topical (e.g., dermal or intradermal) administration and include, e.g., liquid or semi-solid preparations (e.g., liniments, lotions, gels, sprays, foams, film forming systems, microneedles, micro- or nano-emulsions), and oil-in-water or water-in-oil emulsions (e.g., creams, ointments or pastes). These topical dosage forms can be prepared employing well-known and routine procedures, equipment, techniques, and substances. See, eg, A. Williams, Transdermal and Topical Delivery Systems, Pharmaceutical Press, London and Chicago, 2003; L. Lachman, The Theory and Practice of Industrial Pharmacy, 4th Ed., Stipes Publishing, 2015; Remington, Pharmaceutical Sciences, $22^{nd}$ Rev., Pharmaceutical Press, 2012; H. Benson, Topical and Transdermal Drug Delivery: Principles and Practice 1st Edition, Wiley, 2012; D. Osborne, Topical Drug Delivery Formulations (Drugs and the Pharmaceutical Sciences) 1st Edition, CRC Press, 1989; and M. Brown, The A rt and Science of Dermal Formulation Development (Drugs and the Pharmaceutical Sciences) 1st Edition, CRC Press, 2019.

EXAMPLES

Production Examples 1-283 below illustrate active ingredients (external sunscreen agents) formulated with suitable inactive ingredients to provide various dosage forms (e.g., creams and lotions), having specific SPFs. As described herein, the formulations illustrated in Production Examples 1-283 can be formulated to further include a cannabinoid, terpene, flavonoid, or combination thereof.

Production Example 1. SPF 30 Cream (Octinoxate, Oxybenzone, and Zinc Oxide)

Active Ingredient
 Octinoxate 7.5% (Sunscreen)
 Zinc Oxide 4.0% (Sunscreen)
 Oxybenzone 2.5% (Sunscreen)
Inactive Ingredients
 Water, dimethicone, butylene glycol, Butyrospermum parkii (shea butter), octyldodecyl neopentanoate, biosaccharide gum-1, ascorbyl glucoside, sucrose, polyglyceryl-10 pentastearate, behenyl alcohol, tocopheryl acetate, sodium hyaluronate, squalane, Gentiana lutea (gentian) root extract, Hordeum vulgare (barley) extract, Triticum vulgare (wheat) germ extract, hydrolyzed rice bran extract, algae extract, Palmaria palmata extract, Porphyra yezoensis (algae) extract, silk powder, caffeine, acetyl glucosamine, polyglyceryl-6 polyricinoleate, dipotassium glycyrrhizate, tourmaline, cholesterol, alumina, silica, polyethylene, sodium stearoyl lactylate, xanthan gum, tromethamine, caprylyl glycol, pentylene glycol, hexylene glycol, isopropyl titanium triisostearate, glyceryl stearate, peg-100 stearate, citric acid, stearic acid, fragrance (parfum), disodium edta, phenoxyethanol, sodium benzoate, chlorphenesin, mica, titanium dioxide Production Example 2. SPF 30 Cream (Octinoxate, Octisalate, Oxybenzone, and Titanium Dioxide)

Active Ingredient
 Octinoxate 7.5% (Sunscreen)
 Octisalate 4.0% (Sunscreen)
 Oxybenzone 2.5% (Sunscreen)
 Titanium Dioide 1.1% (Sunscreen)
Inactive Ingredients
 Water, dimethicone, butylene glycol, propanediol, glyceryl stearate, phenyl trimethicone, behenyl alcohol, trioctyldodecyl citrate, polymethylsilsesquioxane, ascorbyl glucoside, peg-40 stearate, polyglyceryl-10 pentastearate, octyldodecyl stearoyl stearate, tocopheryl acetate, tocopheryl linoleate/oleate, sodium hyaluronate, lecithin, squalane, Cucumis sativus (cucumber) fruit extract, Gentiana lutea (gentian) root extract, Glycyrrhiza glabra (licorice) root extract, Hordeum vulgare (barley) extract\extrait d'orge, hydrolyzed rice bran extract, Laminaria saccharina extract, Pyrus malus (apple) fruit extract, Salicornia herbacea extract, Scutellaria baicalensis root extract, Triticum vulgare (wheat) germ extract, caffeine, glycerin, ergothioneine, octyldodecyl neopentanoate, polyglyceryl-6 polyricinoleate, cholesterol, sodium pca, oryzanol, trehalose, acetyl hexapeptide-8, bisabolol, dimethoxytolyl propylresorcinol, aluminum hydroxide, silica, urea, polyquaternium-51, sucrose, xanthan gum, ammonium acryloyldimethyltaurate/vp copolymer, sodium ethyltaurate/vp copolymer, sodium stearoyl lactylate, glycyrrhetinic acid, linoleic acid, stearic acid, isopropyl titanium triisostearate, disodium edta, pentaerythrityl tetra-di-t butyl hydroxyhydrocinnamate, tetrahexyldecyl ascorbate, sodium dehydroacetate, phenoxyethanol, chlorphenesin, mica, titanium dioxide, iron oxides, zinc oxide Production Example 3. SPF 15 Liquid Active Ingredient
 Octinoxate 7.50% (Sunscreen)
Inactive Ingredients
 Water, dimethicone, silica, cetyl dimethicone, phenyl trimethicone, butylene glycol, polydecene, glyceryl dilaurate, isostearic acid, tromethamine, tocopheryl acetate, sodium hyaluronate, sucrose, hydrogenated lecithin, caffeine, linoleic acid, xanthan gum, cellulose gum, cholesterol, polyethylene, magnesium aluminum silicate, PEG-9 dimethicone, ethylhexylglycerin, caprylyl glycol, hexylene glycol, tetradibutyl pentaerithrityl hydroxyhydrocinnamate, steareth-21, steareth-2, stearic acid, polyperfluoromethylisopropyl ether, tetrasodium edta, benzoic acid, dehydroacetic acid, phenoxyethanol, mica, titanium dioxide, iron oxides, chromium oxide greens

Production Example 4. SPF 30 Cream (Ocisalate, Homosalate, Oxybenzone, Avobenzonee and Oxtocrylene)

Active Ingredient
  Octisalate 5.0% (Sunscreen)
  Homosalate 5.0% (Sunscreen)
  Oxybenzone 4.0% (Sunscreen)
  Avobenzone 3.0% (Sunscreen)
  Octocrylene 2.7% (Sunscreen)
Inactive Ingredients
  Water, methyl trimethicone, butyleneglycol, butyloctyl salicylate, neopentyl glycol diheptanoate, *Butyrospermum parkii* (Shea butter), PEG-100 stearate, silica, dipentaerythrityl tri-polyhydroxystearate, lauryl PEG-9, polydimethylsiloxyethyl dimethicone, dimethicone, glyceryl stearate, laurdimonium hydroxypropyl hydrolyzed soy protein, *Rosmarinus officinalis* (rosemary) extract, *Perilla ocymoides* leaf extract, plankton extract, caffeine, potassium cetyl phosphate, sucrose, styrene/acrylates copolymer, C30-38 olefin/isopropyl maleate/ma copolymer, cetyl alcohol, vp/eicosene copolymer, ethylhexylglycerin, ammonium acryloyldimethyltaurate/vp copolymer, PEG-8 laurate, sodium ma, phospholipids, lecithin, C1-8 alkyl tetrahydroxycyclohexanoate, hydroxyethylcellulose, tocopheryl acetate, caprylyl glycol, ascorbyl tocopheryl maleate, stearic acid, xanthan gum, maltodextrin, ferulic acid, hexylene glycol, nordihydroguaiaretic acid, disodium edta, phenxyethanol, mica, sodium dehydroacetate

Production Example 5. SPF 50 Cream (Oxybenzone, Octisalate, Homosalate, Avobenzone, and Octocrylene)

Active Ingredient
  Oxybenzone 5.0% (Sunscreen)
  Octisalate 5.0% (Sunscreen)
  Homosalate 5.0% (Sunscreen)
  Avobenzone 3.0% (Sunscreen)
  Octocrylene 2.7% (Sunscreen)
Inactive Ingredients
  Water, methyl trimethicone, butylene glycol, butyloctyl salicylate, neopentyl glycol diheptanoate, *Butyrospermum parkii* (Shea butter), PEG-100 stearate, silica, dipentaertivityl tri-polyhydroxystearate, lauryl PEG-9, polydimethylsiloxyethyl dimethicone, dimethicone, glyceryl stearate, laurdimonium hydroxypropyl hydrolyzed soy protein, *Rosmarinus officinalis* (rosemary) extract, *Perilla ocymoides* leaf extract, caffeine, potassium cetyl phosphate, sucrose, styrene/acrylates copolymer, C30-38 olefin/isopropyl maleate/ma copolymer, cetyl alcohol, vp/eicosene copolymer, ethylhexylglycerin, ammonium acryloyldimethyltaurate/vp copolymer, PEG-8 laurate, sodium ma, lecithin, arginine ferulate, tocopheryl acetate, caprylyl glycol, propyl gallate, ascorbyl tocopheryl maleate, stearic acid, xanthan gum, hexylene glycol, nordihydroguaiaretic acid, disodium edta, phenxyethanol, mica, sodium dehydroacetate

Production Example 6. SPF 30 Liquid (Titanium Dioxide and Zinc Oxide)

Active Ingredient
  Titanium dioxide 3.2% (Sunscreen)
  Zinc oxide 2.0% (Sunscreen)
Inactive Ingredient
  Water, dimethicone, butyloctyl salicylate, methyl trimethicone, isononyl isononanoate, neopentyl glycol diheptanoate, diethylhexyl succinate, c12-15 alkyl benzoate, butylene glycol, dipentaerythrityl tri-polyhydroxystearate, lauryl peg-9 polydimethylsiloxyethyl dimethicone, trimethylsiloxysilicate, hydroxyapatite, cetyl peg/ppg-10/1 dimethicone, hydrolyzed wheat protein/pvp crosspolymer, caprylyl glycol, dimethicone silylate, triethoxycaprylylsilane, dimethicone crosspolymer-3, dipropylene glycol, dimethicone/peg-10/15 crosspolymer, isostearic acid, silica, polyhydroxystearic acid, sodium citrate, phenoxyethanol, iron oxides

Production Example 7. SPF 30 Cream (Oxtinoxate, Octisalate, Titanium Dioxide, and Zinc Oxide)

Active Ingredient
  Oxtinoxate 7.5% (Sunscreen)
  Octisalate 4.50% (Sunscreen)
  Titanium dioxide 4.6% (Sunscreen)
  Zinc oxide 5.0% (Sunscreen)
Inactive Ingredient
  Water, C12-15 alkyl benzoate, caprylyl dimethicone, neopentyl glycol diheptanoate, sucrose, polyglyceryl-10 pentastearate, pentylene glycol, ethylhexyl methoxycrylene, dimethicone, behenyl alcohol, peg-100 stearate, hydrogenated lecithin, butylene glycol, dipentaerythrityl tri-polyhydroxystearate, *Cucumis sativus* (cucumber) fruit extract, *Hordeum vulgare* (barley) extract\extrait d'orge, *Sigesbeckia orientalis* (st. paul's wort) extract, glycerin, caffeine, sodium rna, sodium hyaluronate, tocopheryl acetate, propylene glycol dicaprate, isohexadecane, *Helianthus annuus* (sunflower) seedcake, pvp/hexadecene copolymer, isostearic acid, sodium stearoyl lactylate, polyhydroxystearic acid, silica, acrylamide/sodium acryloyldimethyltaurate copolymer, xanthan gum, polysorbate 80, dimethicone silylate, polyethylene, trisodium edta, bht, phenoxyethanol

Production Example 8. SPF 30 Liquid (Avobenzone, Homosalate, and Octisalate)

Active Ingredient
  Avobenzone 3.0% (Sunscreen)
  Homosalate 10.0% (Sunscreen)
  Octisalate 4.5% (Sunscreen)
Inactive Ingredient
  Alcohol denat, octyldodecyl neopentanoate, butyloctyl salicylate, polyester-8, acrylates/octylacrylamide copolymer, ethylhexyl methoxycrylene, dimethicone, trimethylsiloxysilicate, tocopheryl acetate, ethyl cellulose

Production Example 9. SPF 30 Cream (Avobenzone, Homosalate, Octisalate, Octocrylene, and Oxybenzone)

Active Ingredient
  Avobenzone 3.0% (Sunscreen)
  Homosalate 5.0% (Sunscreen)
  Octisalate 5.0% (Sunscreen)
  Octocrylene 2.7% (Sunscreen)
  Oxybenzone 4.0% (Sunscreen)
Inactive Ingredient
  Water, methyl trimethicone, butylene glycol, butyloctyl salicylate, neopentyl glycol diheptanoate, *Butyrospermum parkii* (shea butter), peg-100 stearate, silica, dipentaerythrityl tri-polyhydroxystearate, lauryl peg-9 polydimethylsiloxyethyl dimethicone, dimethicone, glyceryl stearate, laurdimonium hydroxypropyl hydrolyzed soy protein, *Rosmarinus officinalis* (rosemary) extract, *Perilla ocymoides* leaf extract, caffeine, potassium cetyl phosphate, sucrose, styrene/acrylates copolymer, c30-38 olefin/isopropyl maleate/ma copolymer, cetyl alcohol, vp/eicosene copolymer, ethylhexylglycerin, ammonium acryloyldimethyltaurate/vp copolymer, peg-8 laurate, sodium rna, lecithin, arginineferulate, tocopheryl acetate, caprylyl glycol, ascorbyl tocopheryl maleate, propyl gallate, stearic acid, xanthan gum, hexylene glycol, nordihydroguaiaretic acid, disodium edta, phenoxyethanol, sodium dehydroacetate, mica Production Example 10. SPF 30 Cream
(Avobenzone, Homosalate, Octisalate, Octocrylene, and Oxybenzone)

Active Ingredient
  Avobenzone 3.0% (Sunscreen)
  Homosalate 5.0% (Sunscreen)
  Octisalate 5.0% (Sunscreen)
  Octocrylene 2.7% (Sunscreen)
  Oxybenzone 4.0% (Sunscreen)
Inactive Ingredient
  Water, methyl trimethicone, butylene glycol, butyloctyl salicylate, neopentyl glycol diheptanoate, *Butyrospermum parkii* (shea butter), peg-100 stearate, silica, dipentaerythrityl tri-polyhydroxystearate, lauryl peg-9 polydimethylsiloxyethyl dimethicone, dimethicone, glyceryl stearate, laurdimonium hydroxypropyl hydrolyzed soy protein, *Rosmarinus officinalis* (rosemary) extract, *Perilla ocymoides* leaf extract, plankton extract, caffeine, potassium cetyl phosphate, sucrose, styrene/acrylates copolymer, c30-38 olefin/isopropyl maleate/ma copolymer, cetyl alcohol, vp/eicosene copolymer, ethylhexylglycerin, ammonium acryloyldimethyltaurate/vp copolymer, peg-8 laurate, sodium ma, lecithin, propyl gallate, arginine ferulate, tocopheryl acetate, caprylyl glycol, ascorbyl tocopheryl maleate, stearic acid, xanthan gum, hexylene glycol, nordihydroguaiaretic acid, disodium edta, phenoxyethanol, mica, sodium dehydroacetate Production Example 11. SPF 50 Cream
(Avobenzone, Homosalate, Octisalate, Octocrylene, and Oxybenzone)

Avobenzone 3.0% (Sunscreen)
  Homosalate 5.0% (Sunscreen)
  Octisalate 5.0% (Sunscreen)
  Octocrylene 2.7% (Sunscreen)
  Oxybenzone 5.0% (Sunscreen)
Inactive Ingredient
  Water, methyl trimethicone, butylene glycol, butyloctyl salicylate, neopentyl glycol diheptanoate, *Butyrospermum parkii* (shea butter), peg-100 stearate, silica, dipentaerythrityl tri-polyhydroxystearate, lauryl peg-9 polydimethylsiloxyethyl dimethicone, dimethicone, glyceryl stearate, laurdimonium hydroxypropyl hydrolyzed soy protein, *Rosmarinus officinalis* (rosemary) extract, *Perilla ocymoides* leaf extract, caffeine, potassium cetyl phosphate, sucrose, styrene/acrylates copolymer, c30-38 olefin/isopropyl maleate/ma copolymer, cetyl alcohol, vp/eicosene copolymer, ethylhexylglycerin, ammonium acryloyldimethyltaurate/vp copolymer, peg-8 laurate, sodium rna, lecithin, arginine ferulate, tocopheryl acetate, caprylyl glycol, propyl gallate, ascorbyl tocopheryl maleate, stearic acid, xanthan gum, hexylene glycol, nordihydroguaiaretic acid, disodium edta, phenoxyethanol, mica, sodium dehydroacetate Production Example 12. SPF 50 Cream
(Avobenzone, Homosalate, Octisalate, Octocrylene, and Oxybenzone)

Active Ingredient
  Avobenzone 3.0% (Sunscreen)
  Homosalate 5.0% (Sunscreen)
  Octisalate 5.0% (Sunscreen)
  Octocrylene 2.7% (Sunscreen)
  Oxybenzone 5.0% (Sunscreen)
Inactive Ingredient
  Water, methyl trimethicone, butylene glycol, butyloctyl salicylate, neopentyl glycol diheptanoate, *Butyrospermum parkii* (shea butter), peg-100 stearate, silica, dipentaerythrityl tri-polyhydroxystearate, lauryl peg-9 polydimethylsiloxyethyl dimethicone, dimethicone, glyceryl stearate, laurdimonium hydroxypropyl hydrolyzed soy protein, *Rosmarinus officinalis* (rosemary) extract, *Perilla ocymoides* leaf extract, plankton extract, caffeine, potassium cetyl phosphate, sucrose, styrene/acrylates copolymer, c30-38 olefin/isopropyl maleate/ma copolymer, cetyl alcohol, vp/eicosene copolymer, ethylhexylglycerin, ammonium acryloyldimethyltaurate/vp copolymer, peg-8 laurate, sodium ma, lecithin, propyl gallate, arginineferulate, tocopheryl acetate, caprylyl glycol, ascorbyl tocopheryl maleate, stearic acid, xanthan gum, hexylene glycol, nordihydroguaiaretic acid, disodium edta, phenoxyethanol, mica, sodium dehydroacetate Production Example 13. SPF 40 Cream
(Octinoxate, Octisalate, Zinc Oxide, Titanium Dioxide)

Active Ingredient
  Octinoxate 7.5% (Sunscreen)
  Octisalate 5.0% (Sunscreen)
  Zinc oxide 4.6% (Sunscreen)
  Titanium dioxide 1.7% (Sunscreen)
Inactive Ingredient
  Water (aqua purificata) purified, butylene glycol, c12-15 alkyl benzoate, dimethicone, jojoba esters, caprylic/capric triglyceride, cetearyl alcohol, silica, *micrococcus* lysate, *Gentiana lutea* (gentian) root extract, *Coffea robusta* seed extract, *Helianthus annuus* (sunflower) seedcake, *Cucumis sativus* (cucumber) fruit extract, sea whip extract, cholesterol, *Astrocaryum murumuru* butter, *Hordeum vulgare* (barley) extract, linoleic acid, *Butyrospermum parkii* (shea butter), caffeine, *Salvia sclarea* (clary) extract, sodium rna, sodium hyaluronate, phytosphingosine, tocopheryl acetate, sodium dna, cetearyl glucoside, zeolite, stearic acid, *Chamomilla recutita* (*matricaria*), sucrose, peg-100 stearate, lecithin, trehalose, hydrogenated lecithin, hexylene glycol, propylene glycol dicaprate, tricaprylin, polyhydroxystearic acid, polyethylene, methyl gluceth-20, ethylhexyl stearate, carbomer, behenyl alcohol, alumina, ethylhexyl palmitate, caprylyl glycol, cetyl alcohol, triethoxycaprylylsilane, xanthan gum, aluminum stearate, disodium edta, bht, phenoxyethanol, mica, titanium dioxide, iron oxides Production Example 14. SPF 20 Lotion (Octisalate, Avobenzone, and Octocrylene)

Active Ingredient
  Octisalate 5.0% (Sunscreen)
  Avobenzone 3.0% (Sunscreen)
  Octocrylene 2.7% (Sunscreen)

Inactive Ingredient

Water, dimethicone, yeast extract, butyloctyl salicylate, peg-100 stearate, trisiloxane, butylene glycol, hdi/trimethylol hexyllactone crosspolymer, ascorbyl glucoside, cococaprylate/caprate, polyethylene, glyceryl stearate, peg-6, glycerin, *Olea europaea* (olive) fruit extract, *Citrus grandis* (grapefruit) peel extract, *Triticum vulgare* (wheat bran) extract, *Laminaria saccharina* extract, *Trametes versicolor* extract, *Cucumis sativus* (cucumber) fruit extract, *Pyrus malus* (apple) fruit extract, *Scutellaria baicalensis* root extract punica granatum (pomegranate) fruit juice, *Oryza sativa* (rice) bran extract, salicylic acid, caffeine, linoleic acid, cholesterol, acetyl glucosamine, sodium rna, dipotassium glycyrrhizate, steareth-21, sucrose, tromethamine, di-c12-18 alkyl dimonium chloride, sodium hyaluronate, cetyl alcohol, ammonium acryloyldimethyltaurate/vp copolymer, lauryl peg-9 polydimethylsiloxyethyl dimethicone, caprylyl glycol, dimethiconol, trehalose, tocopheryl acetate, hexylene glycol, silica, sodium hydroxide, xanthan gum, disodium edta, phenoxyethanol

Production Example 15. SPF 21 Lotion (Avobenzone, Octinoxate, Octisalate, and Oxybenzone)

Active Ingredient
  Avobenzone 3.0% (Sunscreen)
  Octinoxate 7.4% (Sunscreen)
  Octisalate 5.0% (Sunscreen)
  Oxybenzone 2.0% (Sunscreen)
Inactive Ingredient Water, butylene glycol, dimethicone, neopentyl glycol diheptanoate, cetearyl alcohol, silica, peg-100 stearate, *Lactobacillus* ferment, *Hordeum vulgare* (barley) extract\extrait d'orge, algae extract, *Cucumis sativus* (cucumber) fruit extract, *Helianthus annuus* (sunflower) seedcake, cholesterol, cetearyl glucoside, propylene glycol dicaprate, *Chamomilla recutita* (*matricaria*), tridecyl trimellitate, hydrogenated lecithin, stearyl alcohol, zeolite, tridecyl stearate, isododecane, dipentaerythrityl hexacaprylate/hexacaprate, pvp, oleth-10, laureth-4, laureth-23, caprylyl glycol, hexylene glycol, polyethylene, tromethamine, carbomer, sodium citrate, disodium edta, sodium benzoate, potassium sorbate, chlorphenesin, phenoxyethanol, yellow 5, yellow 6, red 33

Production Example 16. SPF 25 Cream (Avobenzone and Octisalate)

Active Ingredient
  Avobenzone 3.0% (Sunscreen)
  Octisalate 5.0% (Sunscreen)
Inactive Ingredient Water, glycerin, neopentyl glycol diheptanoate, polyester-8, dimethicone, sorbitan stearate, butyloctyl salicylate, polysorbate 60, butylene glycol, sodium acrylates copolymer, niacinamide, sodium hyaluronate, acetyl carnitine hcl, creatine, *Brassica oleracea* gemmifera (brussels sprouts) extract, *Vaccinium angustifolium* (blueberry) fruit extract, *Brassica oleracea italica* (broccoli) extract, *Daucus carota sativa* (carrot) root extract, *Brassica oleracea acephala* (kale) leaf extract, *Spinacia oleracea* (spinach) leaf extract, albiziajulibrissin bark extract, *Cucumis sativus* (cucumber) fruit extract, *Vaccinium macrocarpon* (cranberry) fruit extract, plankton extract, *Laminaria saccharina* extract, caffeine, adenosine phosphate, sea whip extract, yeast extract\faex\extrait de levure, sodium rna, phytic acid, *lactobacillus* ferment, algae extract, *Hordeum vulgare* (barley) extract\extrait d'orge, silica, resveratrol, cetyl alcohol, tocopheryl acetate, *sigesbeckia orientalis* (st paul's wort) extract, pentylene glycol, trehalose, styrene/acrylates copolymer, lecithin, *Helianthus annuus* (sunflower) seedcake, *micrococcus* lysate, *Arabidopsis thaliana* extract, biosaccharide gum-4, ergothioneine, *Oryza sativa* (rice) bran extract, capryloyl glycine, salicylic acid, isohexadecane, peg-8 laurate, polysorbate 80, etylhexylglycerin, propylene glycol dicaprate, 7-dehydrocholesterol, peg-100 stearate, acrylamide/sodium acryloyldimethyltaurate copolymer, tetrahexyldecyl ascorbate, propylene glycol caprylate, polyethylene, disodium edta, bht, phenoxyethanol, chlorphenesin, mica, titanium dioxide

Production Example 17. SPF 50 Lotion (Titanium Dioxide and Zinc Oxide)

Active Ingredient
  Titanium dioxide 6.2% (Sunscreen)
  Zinc oxide 4.0% (Sunscreen)
Inactive Ingredient Water, dimethicone, butyloctyl salicylate, polydiethyl siloxane, C12-15 alkyl benzoate, isononyl isononanoate, diethylhexyl succinate, neopentyl glycol diheptanoate•methyl trimethicone, butylene glycol, ethylhexyl methoxycrylene, lauryl peg-9 polydimethylsiloxyethyl dimethicone, silica, laureth-4, cetyl peg/ppg-10/1 dimethicone, dipentaerythrityl tri-polyhydroxystearate, dimethicone silylate, hydrolyzed wheat protein/pvp crosspolymer, isostearic acid, caprylyl glycol, dimethicone crosspolymer-3, polyhydroxystearic acid, triethoxycaprylylsilane, dimethicone/peg-10/15 crosspolymer, dipropylene glycol, phenoxyethanol, iron oxides, iron oxides

Production Example 18. SPF 15 Cream (Titanium Dioxide and Zinc Oxide)

Active Ingredient
  Titanium dioxide 6.4% (Sunscreen)
  Zinc oxide 2.0% (Sunscreen)
Inactive Ingredient Water, trioctyldodecyl citrate, cyclopentasiloxane, butylene glycol, C12-15 alkyl benzoate, steareth-2, stearyl dimethicone, tricaprylyl citrate, silica, barium sulfate, sorbitan tristearate, aluminum stearate, ascophyllum nodosum extract, *Asparagopsis armata* extract, lecithin, sea whip extract, glyceryl stearate, tocopheryl acetate, PEG-100 stearate, sucrose, pantethine, caffeine, octyldodecyl neopentanoate, ceteth-2, PEG-40 stearate, dimethicone, cetearyl alcohol, PEG/PPG-18/18 dimethicone, steareth-20, bisabolol, magnesium ascorbyl phosphate, polyglyceryl-6 polyricinoleate, sorbitol, phytosphingosine, sodium stearate, magnesium aluminum silicate, caprylyl glycol, isopropyl titaniu triisostearate, stearic acid, hexyleneglycol, xanthan gum, disodium edta, phenoxyethanol, iron oxides, chromium hydroxide green

Production Example 19. SPF 15 Cream (Octinoxate, Octisalate, and Titanium Dioxide)

Active Ingredient
  Oxtinoxate 7.5% (Sunscreen)
  Octisalate 3.5% (Sunscreen)
  Titanium dioxide 1.7% (Sunscreen)

Inactive Ingredient

Water, neopentyl glycol diheptanoate, *Simmondsia chinensis* (jojoba) butter, glycerin, petrolatum, octyldodecyl neopentanoate, di-C12-15 alkyl fumarate, dimethicone, hydrogenated lecithin, butylene glycol, hydrogenated polyisobutene, hexyldecyl stearate, *sigesbeckia orientalis* (st. paul's wort) extract, whey protein\*lactis* protein\protéine du petit-lait, *salvia sclarea* (clary) extract, *Chlorella vulgaris* extract, *Commiphora mukul* resin extract, *Litchi chinensis* seed extract, *Laminaria digitata* extract, cladosiphon okamuranus extract, plankton extract, *Astrocaryum murumuru* seed butter, acetyl hexapeptide-8, lecithin, polyethylene, pentylene glycol, potato starch modified, ergothioneine, glyceryl stearate, caffeine, sorbitol, behenyl alcohol, sodium hyaluronate, methicone, tocopheryl acetate, peg-100 stearate, pentaerythrityl tetraethylhexanoate, caprylyl glycol, C12-16 alcohols, cholesterol, caprylic/capric triglyceride, polysilicone-11, dextrin, palmitic acid, tetrahexyldecyl ascorbate, hexylene glycol, citric acid, xanthan gum, alumina, ammonium acryloyldimethyltauratelvp copolymer, sodium hydroxide, disodium edta, potassium sorbate, phenoxyethanol, red 4, yellow 5, titanium dioxide, mica Production Example 20. SPF 21 Lotion
(Octinoxate, Octisalate, Avobenzone, and Oxybenzone)

Active Ingredient
  Oxtinoxate 7.4% (Sunscreen)
  Octisalate 5.0% (Sunscreen)
  Avobenzone 3.0% (Sunscreen)
  Oxybenzone 2.0% (Sunscreen)
Inactive Ingredient Water, butylene glycol, dimethicone, neopentyl glycol diheptanoate, cetearyl alcohol, silica, PEG-100 stearate, *lactobacillus* ferment, *Hordeum vulgare* (barley) extract, algae extract, *Cucumis sativus* (cucumber) fruit extract, *Helianthus annuus* (sunflower) seedcake, cholesterol, cetearyl glucoside, propylene glycol dicaprate, *Chamomilla recutita* (*matricaria*), tridecyl trimellitate, hydrogenated lecithin, stearyl alcohol, zeolite, tridecyl stearate, isododecane, dipentaerythrityl, hexacaprylate/hexacaprate, pvp, oleth-10, laureth-4, laureth-23, caprylyl glycol, hexylene glycol, polyethylene, tromethamine, carbomer, sodium citrate, disodium edta, sodium enzoate, potassium sorbate, chlorphenesin, phenoxyethanol, yellow 5, yellow 6, red 33

Production Example 21. SPF 15 Liquid
(Avobenzone, Octinoxate, and Octisalate)

Active Ingredient
  Avobenzone 2.0% (Sunscreen)
  Octinoxate 7.5% (Sunscreen)
  Octisalate 5.0% (Sunscreen)
Inactive Ingredient Water, octyldodecyl neopentanoate, hdi/trimethylol hexyllactone crosspolymer, neopentyl glycol diheptanoate, dimethicone, silica, steareth-21, butylene glycol, pentylene glycol, *Sigesbeckia orientalis* (st paul's wort) extract, *Rosmarinus officinalis* (rosemary) extract, polyethylene, coffee robusta seed extract, *Polygonum cuspidatum* root extract, laurdimonium hydroxypropyl hydrolyzed soy protein, *saccharomyces* lysate extract, steareth-2, *Astrocaryum murumuru* seed butter, glycerin, hydrogenated lecithin, ethylhexyl stearate, polysilicone-11, sucrose, pvp/hexadecene copolymer, acetyl glucosamine, isohexadecane, ethyl hexyl glycerin, caffeine, trimethylsiloxysilicate, glyceryl polymethacrylate, acrylates/c10-30 alkyl acrylate crosspolymer, linoleic acid, tromethamine, tetrahexyldecyl ascorbate, adenosine phosphate, peg-8, lecithin, sodium dna, arginine ferulate, acetyl hexapeptide-8, sodium hyaluronate, phytantriol, caprylyl glycol, xanthan gum, ascorbyl tocopheryl maleate, phytosphingosine, propylene glycol dicaprate, acrylamide/sodium acryloyldimethyltaurate copolymer, hexylene glycol, nordihydroguaiaretic acid, potassium sulfate, sodium carbomer, disodium edta, sorbic acid, chlorphenesin, potassium sorbate, phenoxyethanol Production Example 22. SPF 15 Lotion
(Octinoxate, Octisalate, Avobenzone)

Active Ingredient
  Oxtinoxate 7.5% (Sunscreen)
  Octisalate 5.0% (Sunscreen)
  Avobenzone 2.0% (Sunscreen)
Inactive Ingredient Water, octyldodecyl neopentanoate, hdi/trimethylol hexyllactone crosspolymer, neopentyl glycol diheptanoate, dimethicone, silica, steareth-21, butylene glycol, pentylene glycol, *Sigesbeckia orientalis* (st paul's wort) extract, *Rosmarinus officinalis* (rosemary) extract, polyethylene, *Coffea robusta* seed extract, *Polygonum cuspidatum* root extract, laurdimonium hydroxypropyl hydrolyzed soy protein, *saccharomyces* lysate extract, steareth-2, *Astrocaryum murumuru* seed butter, glycerin, hydrogenated lecithin, ethylhexyl stearate, polysilicone-11, sucrose, pvp/hexadecene copolymer, acetyl glucosamine, isohexadecane, ethylhexyiglycerin, caffeine, trimethylsiloxysilicate, glyceryl polymethacrylate, acrylates/c10-30 alkyl acrylate crosspolymer, linoleic acid, cholesterol, polysorbate 80, palmitoyl oligopeptide, ethylhexyl palmitate, tromethamine, tetrahexyldecyl ascorbate, adenosine phosphate, peg-8, lecithin, sodium dna, arginineferulate, acetyl hexapeptide-8, sodium hyaluronate, phytantriol, caprylyl glycol, xanthan gum, ascorbyl tocopheryl maleate, phytosphingosine, propylene glycol dicaprate, acrylamide/sodium acryloyldimethyltaurate copolymer, hexylene glycol, nordihydroguaiaretic acid, potassium sulfate, sodium carbomer, disodium edta, sorbic acid, chlorphenesin, potassium sorbate, phenoxyethanol Production Example 23. SPF 15 Cream
(Avobenzone and Octisalate)

Active Ingredient
  Avobenzone 3.0% (Sunscreen)
  Octisalate 5.0% (Sunscreen)
Inactive Ingredient Water, glycerin, butyloctyl salicylate, polyester-8, octyldodecyl neopentanoate, behenyl alcohol, butylene glycol, myristyl myristate, cetyl esters, ammonium acryloyldimethyltaurate/vp copolymer, *Tamarindus indica* seed extract, plankton extract, *Centaurium erythraea* (centaury) extract, *sigesbeckia orientalis* (st. Paul's wort) extract, glyceryl stearate, algae extract, caffeine, *Camellia sinensis* leaf extract, *saccharomyces* ferment filtrate, whey protein\*lactis* protein\protéine du petit-lait, nylon-12, acetyl hexapeptide-8, sucrose, biotin, ergothioneine, myristyl laurate, lauryl peg-9 polydimethylsiloxyethyl dimethicone, polyethylene, aminopropyl ascorbyl phosphate, *Glycine soja* (soybean) protein, peg-100 stearate, steareth-2, dimethicone, acetyl glucosamine, *Astrocaryum murumuru* seed butter, trisiloxane, caprylyl glycol, tocopheryl acetate, myristyl alcohol, sodium hyaluronate, hexylene glycol, hydroxyethylcellulose, sodium benzoate, sodium citrate, lecithin, disodium edta, phenoxyethanol, yellow 5, red 4

Production Example 24. SPF 15 Cream
(Avobenzone and Octisalate)

Active Ingredient
  Avobenzone 3.0% (Sunscreen)
  Octisalate 5.0% (Sunscreen)
Inactive Ingredient
  Water, butyloctyl salicylate, glycerin, polyester-8, polysorbate 60, cetyl alcohol, butylene glycol, sorbitan stearate, dimethicone, tridecyl stearate, peg-100 stearate, *saccharomyces* ferment filtrate, sodium hyaluronate, *Camellia sinensis* leaf extract, *Astrocaryum murumuru* seed butter, tridecyl trimellitate, dipentaerythrityl hexacaprylataf hexacaprate, algae extract, plankton extract, *Laminaria saccharina* extract, *Tamarindus indica* seed extract, *Sigesbeckia orientalis* (st. paul's wort) extract, acetyl glucosamine, whey protein\*lactis* protein\protéine du petit-lait, *Glycine soja* (soybean) protein, *Centaurium erythraea* (centaury) extract, cetyl palmitate, polyethylene, acrylates/c10-30 alkyl acrylate crosspolymer, acetyl hexapeptide-8, biotin, aminopropyl ascorbyl phosphate, sorbitan palmitate, sorbitan olivate, ethylhexylglycerin, caffeine, tocopheryl acetate, ethylene\va copolymer, sodium polyacrylate, trehalose, ergothioneine, lecithin, hydroxyethylcellulose, sodium benzoate, sodium hydroxide, pentylene glycol, disodium edta, phenoxyethanol, chlorphenesin, yellow 5, red 4

Production Example 25. SPF 15 Cream
(Avobenzone and Octisalate)

Active Ingredient
  Avobenzone 3.0% (Sunscreen)
  Octisalate 5.0% (Sunscreen)
Inactive Ingredient
  Water, glycerin, butyloctyl salicylate, *Butyrospermum parkii* (shea butter), polyester-8, cetearyl alcohol, butylene glycol, glyceryl stearate, peg-100 stearate, sucrose polystearate, cetyl alcohol, dimethicone, *Theobroma grandiflorum* seed butter, polyethylene, nylon-12, *Astrocaryum murumuru* seed butter, *Camellia sinensis* leaf extract, biotin, *Sigesbeckia orientalis* (st paul's wort) extract, *Centaurium erythraea* (centaury) extract, algae extract, *Tamarindus indica* seed extract, whey protein\*lactis* protein\protéine du petit-lait, *Glycine soja* (soybean) protein, ergothioneine, acetyl hexapeptide-8, *Saccharomyces* ferment filtrate, plankton extract, hydrogenated polyisobutene, acetyl glucosamine, caffeine, aminopropyl ascorbyl phosphate, caprylyl glycol, tocopheryl acetate, lecithin, sodium hyaluronate, ammonium acryloyldimethyltaurate/vp copolymer, pentaerythrityl tetra-di-t-butyl hydroxyhydrocinnamate, polysilicone-11, potassium sorbate, sodium benzoate, hydroxyethylcellulose, citric acid, xanthan gum, sodium citrate, phenoxyethanol, yellow 5, red 4

Production Example 26. SPF 15 Cream
(Homosalate, Octisalate, Avobenzone, and Octocrylene)

Active Ingredient
  Homosalate 10.0% (Sunscreen)
  Octisalate 5.0% (Sunscreen)
  Avobenzone 3.0% (Sunscreen)
  Octocrylene 2.7% (Sunscreen)

Inactive Ingredient
  Water, butylene glycol, isononyl isononandate, butyloctyl salicylate, triacontanyl pvp, polyester-8, silica, *Rosmarinus officinalis* (rosemary) extract, *Perilla ocymoides* leaf extract, stearyl dimethicone, caffeine, plankton extract, sucrose, hydrogenated lecithin, potassium cetyl phosphate, laurdimonium hydroxypropyl hydrolyzed soy protein, PEG-100 stearate, cetyl alcohol, polyethylene, acrylic acid/vp crosspolymer, vp/eicosene copolymer, tocopheryl acetate, tromethamine, sodium ma, aloe barbadensis powder, phospholipids, lecithin, magnesium ascorbyl phosphate, sodium hyaluronate, hydroxypropyl methylcellulose, C1-8 alkyl tetrahydroxycyclohexanoate, hydroxyethylcellulose, ascorbyl tocopheryl maleate, maltodextrin, caprylyl glycol, hexylene glycol, nordihydroguaiaretic acid, ferulic acid, disodium edta, phenoxyethanol, chiorphenesin, mica Production Example 27. SPF 30 Cream (Octisalate, Homosalate, Oxybenzone, Avobenzone, Octocrylene)

Octisalate 5.0% (Sunscreen)
Homosalate 5.0% (Sunscreen)
Oxybenzone 4.0% (Sunscreen)
Avobenzone 3.0% (Sunscreen)
Octocrylene 2.7% (Sunscreen)
Inactive Ingredient
  Water, methyl trimethicone, butyleneglycol, butyloctyl salicylate, neopentyl glycol diheptanoate, *Butyrospermum parkii* (shea butter), peg-100 stearate, silica, dipentaerythrityl tri-polyhydroxystearate, lauryl peg-9 polydimethylsiloxyethyl dimethicone, dimethicone, glyceryl stearate, laurdimonium hydroxypropyl hydrolyzed soy protein, *Rosmarinus officinalis* (rosemary) extract, *Perilla ocymoides* leaf extract, caffeine, potassium cetyl phosphate, sucrose, styrene/acrylates copolymer, c30-38 olefin/isopropyl maleate/ma copolymer, cetyl alcohol, vp/eicosene copolymer, ethylhexylglycerin, ammonium acryloyldimethyltaurate/vp copolymer, peg-8 laurate, sodium rna, lecithin, arginine ferulate, tocopheryl acetate, caprylyl glycol, ascorbyl tocopheryl maleate, propyl gallate, stearic acid, xanthan gum, hexylene glycol, nordihydroguaiaretic acid, disodium edta, phenoxyethanol, sodium dehydroacetate, mica Production Example 28. SPF 50 Lotion (Titanium Dioxide and Zinc Oxide)

Active Ingredient
  Titanium dioxide 6.3% (Sunscreen)
  Zinc oxide 4.0% (Sunscreen)
Inactive Ingredient
  Water, dimethicone, butyloctyl salicylate, polydiethylsiIoxane, c12-15 alkyl benzoate, isononyl isononanoate, diethylhexyl succinate, neopentyl glycol diheptanoate, methyl trimethicone, butylene glycol, ethylhexyl methoxycrylene, lauryl peg-9 polydimethylsiloxyethyl dimethicone, silica, dipentaerythrityl tripolyhydroxystearate, laureth-4, cetyl peg/ppg-10/1 dimethicone, dimethicone/peg-10/15 crosspolymer, dimethicone silylate, hydrolyzed wheat protein/pvp crosspolymer, triethoxycaprylylsilane, dimethicone crosspolymer-3, isostearic acid, caprylyl glycol, polyhydroxystearic acid, dipropylene glycol, phenoxyethanol, iron oxides, iron oxides Production Example 29. SPF 25 Cream
(Avobenzone, Octisalate, Octocrylene, and Oxybenzone)

Active Ingredient
  Avobenzone 3.0% (Sunscreen)
  Octisalate 5.0% (Sunscreen)
  Octocrylene 1.3% (Sunscreen)
  Oxybenzone 5.0% (Sunscreen)
Inactive Ingredient
  Water, dimethicone, butylene glycol, butyloctyl salicylate, isononyl isononanoate, polyester-8, silica, glycerin, polysilicone-11, *Triticum vulgare* (wheat bran) extract, algae extract, *laminaria* saccharin extract, *Olea europaea* (olive) fruit extract, *coffea robusta* seed extract, *Echinacea pallida* (coneflower) extract, *Rosmarinus officinalis* (rosemary) extract, sea whip extract, *Astrocaryum murumuru* seed butter, adenosine phosphate, trehalose, disodium nadh, padina pavonica (thallus) extract, creatine, sodium ma, caffeine, *micrococcus* lysate, nordihydroguaiaretic acid, sodium dna, phytosphingosine, linoleic acid, cholesterol, ascorbyl tocopheryl maleate, sodium hyaluronate, aminopropyl ascorbyl phosphate, tocopheryl acetate, trisiloxane, sucrose, laurdimonium hydroxypropyl hydrolyzed soy protein, lecithin, hexylene glycol, ethylhexyl stearate, ethylhexyl palmitate, decarboxy carnosine hcl, propylene glycol dicaprate, *Chamomilla recutita* (*matricaria*), zeolite, caprylyl glycol, polyethylene, xanthan gum, laureth-4, laureth-23, polysorbate 20, ammonium acryloyldimethyltauratelvp copolymer, acrylic acid/vp crosspolymer, arginine ferulate, tromethamine, disodium edta, phenoxyethanol Production Example 30. SPF 35 Liquid
(Octinoxlate, Octisalate, Oxybenzone, Titanium Dioxide)

Active Ingredient
  Octinoxate 7.5% (Sunscreen)
  Oxtisalate 4.0% (Sunscreen)
  Oxybenzone 2.5% (Sunscreen)
  Titanium dioxide 1.1% (Sunscreen)
Inactive Ingredient
  Water, dimethicone, butylene glycol, phenyl trimethicone, pentylene glycol, glyceryl stearate, behenyl alcohol, trioctyldodecyl citrate, polymethylsilsesquioxane, octyldodecyl stearoyl stearate, PEG-40 stearate, polyglyceryl-10 pentastearate, ammonium acryloyldimethyltaurate/vp copolymer, *Triticum vulgare* (wheat) germ extract, *Hordeum vulgare* (barley) extract, *Cucumis sativus* (cucumber) fruit extract, *laminaria* saccharin extract, *Pyrus malus* (apple) fruit extract, *Scutellaria baicalensis* root extract, polyquaternium-51, acetyl hexapeptide-8, trehalose, oryzanol, octyldodecyl neopentanoate, urea, polyglyceryl-6 polyricinoleate, propylene glycol laurate, glycyrrhetinic acid, tocopheryl acetate, sucros, glycerin, sodium stearoyl lactylate, caffeine, linoleic acid, cholesterol, lecithin, squalane, sodium pca, isopropyl titanium triisostearate, propylene glycol stearate, stearic acid, polysorbate 20, sorbitan laurate, xanthan gum, aluminum hydroxide, sodium hyaluronate, silica, disodium edta, pentaerythrityl tetra-di-t butyl hydroxyhydrocinnamate, sodium dehydroacetate, chlorphenesin, phenoxyethanol, titanium dioxide, zinc oxide, iron oxides Production Example 31. SPF 30 Cream
(Homosalate, Octisalate, Avobenzone, and Octocrylene)

Active Ingredient
  Avobenzone 3.0% (Sunscreen)
  Homosalate 5.0% (Sunscreen)
  Octisalate 5.0% (Sunscreen)
  Octocrylene 2.7% (Sunscreen)
Inactive Ingredient
  Water, butyloctyl salicylate, behenyl alcohol, nylon-12, octyldodecyl neopentanoate, butylene glycol, dimethicone, myristyl myristate, cetyl esters, ascorbyl glucoside, polyethylene, ammonium acryloyldimethyltaurate/vp copolymer, *Citrus aurantium dulcis* (orange) peel oil1, *Pelargonium graveolens* flower oil1, *Cananga odorata* flower oil1, *Eugenia caryophyllus* (clove) bud oil1, *Rosa damascena* flower oil1, *Jasminum officinale* (jasmine) oil1, *Viola odorata* flower/leaf extract, *Polianthes tuberosa* extract, farnesol, eugenol, benzyl salicylate, citronellol, citral, benzyl benzoate, geraniol, *Rosa roxburghii* fruit extract, *Paeonia albiflora* (peony) root extract, molasses extract\*Saccharum officinarum*\extrait de mélasse, *Citrus grandis* (grapefruit) peel extract, *Triticum vulgare* (wheat) germ extract, *Hordeum vulgare* (barley) extract\extrait d'orge, *Palmaria palmata* extract, mores nigra (mulberry) root extract, punica granatum (pomegranate) fruit juice, *Scutellaria baicalensis* root extract, hydrolyzed rice bran extract, *Gentiana lutea* (gentian) root extract, *Curcuma longa* (tumeric) root extract, *Vitis vinifera* (grape) fruit extract, sucrose2, glyceryl stearate, peg-100 stearate, peg-6, glycerin, cholesterol, linoleic acid, salicylic acid, di-ppg-2 myreth-10 adipate, sodium hyaluronate, betaine, dipotassium glycyrrhizate, steareth-21, trehalose, tocopheryl acetate, myristyl laurate, trisiloxane, di-c12-18 alkyl dimonium chloride, caprylyl glycol, squalane, myristyl alcohol, tromethamine, sodium dehydroacetate, hexylene glycol, sodium hydroxide, phenoxyethanol, mica Production Example 32. SPF 15 Liquid
(Octinoxate, Octisalate, and Avobenzone)

Active Ingredient
  Oxtinoxate 7.5% (Sunscreen)
  Octisalate 5.0% (Sunscreen)
  Avobenzone 2.0% (Sunscreen)
Inactive Ingredient
  Water, dimethicone, caprylic/capric/myristic/stearic triglyceride, butylene glycol, cyclopentasiloxane, steareth-2, cetyl ricinoleate, di-c12-15 alkyl fumarate, polysilicone-11, pentylene glycol, steareth-21, *Coffea arabica* (coffee) seed extract, *Triticum vulgare* (wheat) germ extract, *Laminaria ochroleuca* extract, *Hordeum vulgare* (barley) extract\extrait d'orge, *Camellia sinensis* (white tea) leaf extract, polyethylene, hydrogenated lecithin, stearyl alcohol, polyaminopropyl biguanide, linoleic acid, cholesterol, dimethicone copolyol, squalane, caffeine, sodium pca, urea, caprylic/capric triglyceride, hexylene glycol, sodium hyaluronate, pantethine, polyquaternium-51, sodium hydroxide, trehalose, oryzanol, ascorbyl tocopheryl maleate, tromethamine, glycerin, peg-9 dimethicone, behenyl alcohol, pvp/hexadecene copolymer, carbomer, caprylyl glycol, fragrance, disodium edta, linalool, limonene, citral, sorbic acid, phenoxyethanol, potassium sorbate, chlorphenesin, titanium dioxide, iron oxides, bismuth oxychioride, ferric ammonium ferrocyanide, mica, red 7 lake

Production Example 33. SPF 50 Cream
(Homosalate, Octisalate, Avobenzone, Oxybenzone)

Active Ingredient

Homosalate 5.0% (Sunscreen)

Octisalate 5.0% (Sunscreen)

Avobenzone 3.0% (Sunscreen)

Oxygenzone 3.0% (Sunscreen)

Inactive Ingredient

Water, butyloctyl salicylate, methyl trimethicone, neopentyl glycol diheptanoate, polyester-8, *Aleurites moluccana* (kukui) seed oil, lauryl peg-9 polydimethylsiloxyethyl dimethicone, peg-100 stearate, butylene glycol, glyceryl stearate, dipentaerythrityl tri-polyhydroxystearate, yeast extract\faex\extrait de levure, *Curcuma longa* (tumeric) root extract, *Laminaria ochroleuca* extract, morns nigra (mulberry) root extract, acetyl glucosamine, *Scutellaria baicalensis* root extract, why protein\lactis protein\ proteine du petit lait, caffeine, ammonium acryloyldimethyltaurate/vp copolymer, *Vitis vinifera* (grape) fruit extract, potassium cetyl phosphate, cetyl alcohol, vp/eicosene copolymer, C30-38 olefin/isopropyl maleate/ma copolymer, stearic acid, ethylhexyglycerin, caprylyl glycol, dehydroxanthan gum, caprylic/capnc triglyceride, disodium edta, sodium dehydroacetate, phenoxyethanol, mica

Production Example 34. SPF 25 Cream
(Octinoxate, Octisalate, Oxybenzone, Titanium Dioxide, and Zinc Oxide)

Active Ingredient

Octinoxate 7.50% (Sunscreen)

Octisalate 4.00% (Sunscreen)

Oxybenzone 2.50% (Sunscreen)

Titanium Dioxide 1.10% (Sunscreen)

Zinc Oxide 3.30% (Sunscreen)

Inactive Ingredient water\aqua\eau•dimethicone•butylene glycol•phenyl trimethicone•pentylene glycol•glyceryl stearate •behenyl alcohol •trioctyldodecyl citrate •polymethylsilsesquioxane •octyldodecyl stearoyl stearate •peg-40 stearate •polyglyceryl-10 pentastearate •*Pyrus malus* (apple) fruit extract •*Laminaria saccharina* extract •*Cucumis sativus* (cucumber) fruit extract •*Triticum vulgare* (wheat) germ extract •acetyl hexapeptide-8•*Scutellaria baicalensis* root extract •*Hordeum vulgare* (barley) extract\extrait d'orge •polyquaternium-51 •oryzanol •glycyrrhetinic acid •octyldodecyl neopentanoate •trehalose •propylene glycol laurate •sucrose •glycerin •cholesterol •caffeine •sodium hyaluronate •linoleic acid •lecithin •squalane •propylene glycol stearate •urea •ammonium acryloyldimethyltaurate/vp copolymer •polyglyceryl-6 polyricinoleate •polysorbate 20 •tocopheryl acetate•sodium stearoyl lactylate•stearic acid•sorbitan laurate •xanthan gum •alumina •sodium pca •isopropyl titanium triisostearate •sodium dehydroacetate •triethoxycaprylylsilane •disodium edta •silica •chlorphenesin •phenoxyethanol •[+/− mica •ferric ferrocyanide (ci 77510) •ferric ammonium ferrocyanide (ci 77510) •chromium hydroxide green (ci 77289) •chromium oxide greens (ci 77288) •carmine (ci 75470) •titanium dioxide (ci 77891) •iron oxides (ci 77491) •iron oxides (ci 77492) •iron oxides (ci 77499) •yellow 5 lake (ci 19140) •blue 1 lake

Production Example 35. SPF 25 Cream
(Homosalate, Octinoxate, Oxybenzone, Avobenzone)

Active Ingredient

Homosalate 10.00% (Sunscreen)

Octinoxate 7.50% (Sunscreen)

Oxybenzone 5.00% (Sunscreen)

Avobenzone 2.00% (Sunscreen)

Inactive Ingredient

Water\Aqua\Eau, C12-15 Alkyl Ethylhexanoate, Butyloctyl Salicylate, *Butyrospermum parkii* (Shea Butter), Propanediol, Cetyl Alcohol, Cetearyl Alcohol, Glyceryl Stearate, Bis-Diglyceryl Polyacyladipate-2, Polyacrylamide, Tocopheryl Acetate, Neopentyl Glycol Diheptanoate, Sucrose, Polyethylene, *Olea Europaea* (Olive) Fruit Extract, *Salvia Sclarea* (Clary) Extract, *Epilobium Angustifolium* Extract, *Triticum Vulgare* (Wheat Bran) Extract, *Pisum Sativum* (Pea) Extract, *Bambusa Vulgaris* (Bamboo) Extract, *Rosmarinus Officinalis* (Rosemary), *Oenothera biennis* (Evening Primrose) Oil, *Pelargonium graveolens* (Geranium) Flower Oil, *Citrus grandis* (Grapefruit) Peel Oil, *Citrus aurantium amara* (Bitter Orange) Oil, *Anthemis nobilis* (Chamomile), Whey Protein\*Lactis* Protein\Proteine Du Petit-Lait, Cholesterol, Linoleic Acid, Caffeine, Acetyl Hexapeptide-8, Sorbitan Stearate, Peg-40 Stearate, C13-14 Isoparaffin, Caprylyl Glycol, Dicetyl Phosphate, Ceteth-10 Phosphate, Laureth-7, Glucosamine HCl, Tetrahexyldecyl Ascorbate, Sodium Hyaluronate, Sodium Hydroxide, HexyleneGlycol, Xanthan Gum, Citric Acid, Tetrasodium Edta, Geraniol, Linalool, Limonene, Citral, Citronellol, Phenoxyethanol

Production Example 36. SPF 25 Cream
(Octinoxate, Homosalate, Oxybenzone, and Avobenzone)

Active Ingredient

Avobenzone 2.00% (Sunscreen)

Homosalate 5.00% (Sunscreen)

Octinoxate 7.50% (Sunscreen)

Oxybenzone 5.00% (Sunscreen)

Inactive Ingredient water\aqua\eau, glycerin, peg-4 di heptanoate, bis-diglyceryl polyacyladipate, *Butyrospermum parkii* (shea butter), cetearyl alcohol, cetyl alcohol, glyceryl stearate, hydroxyethyl acrylate/sodium acryloyldimethyl taurate copolymer, *Epilobium angustifolium* extract, sodium hyaluronate, tocopheryl acetate, squalane, ethylhexylglycerin, *Oenothera biennis* (evening primrose) oil, *Rosmarinus officinalis* (rosemary), *Anthemis nobilis* (chamomile), *Pelargonium graveolens* (geranium) flower oil, *Angelica archangelica* seed oil, *Citrus aurantium amara* (bitter orange) oil, phenyl trimethicone, dimethicone, lecithin, butylene glycol, peg-12 dimethicone, dicetyl phosphate, ceteth-10 phosphate, *Astrocaryum murumuru* seed butter, sorbitan stearate, polysorbate 60, peg-40 stearate, *Citrus grandis* (grapefruit) peel oil, alumina, propylene glycol stearate, polysorbate 20, acetyl hexapeptide-8, sorbitan laurate, propylene glycol laurate, pentaerythrityl tetra-di-t-butyl hydroxyhydrocinnamate, xanthan gum, citric acid, tetrasodium edta, potassium sorbate, chlorphenesin, phenoxyethanol, limonene, citronellol, geraniol, linalool, citral, [+/− titanium dioxide (ci 77891), iron oxides (ci 77491, ci 77492, ci 77499), mica]

Production Example 37. SPF 25 Cream
(Octinoxate, Homosalate, Oxybenzone,
Avobenzone)

Active Ingredient
Avobenzone 2.00% (Sunscreen)
Homosalate 5.00% (Sunscreen)
Octinoxate 7.50% (Sunscreen)
Oxybenzone 5.00% (Sunscreen)
Inactive Ingredient
Water, glycerin, PEG-4 diheptanoate, bis-diglyceryl polyacyladipate-2, *Butyrospermum parkii* (shea butter), cetearyl alcohol, cetyl alcohol, glyceryl stearate, hydroxyethyl acrylate/sodium acryloyldimethyl tauratecopolymer, *Epilobium angustifolium* extract, sodium hyaluronate, tocopheryl acetate, squalane, ethylhexylglycerin, *Oenothera biennis* (evening primrose) oil, *Rosmarinus officinalis* (rosemary) *Anthemis nobilis* (chamomile), *Pelargonium graveolens* (geranium) glower oil, *Angelica archangelica* seed oil, *Citrus aurantium amara* (bitter orange) oil, phenyl trimethicone, dimethicone, lecithin, butylene glycol, PEG-12 dimethicone, dicetyl phosphate, ceteth-10 phosphate, *Astrocaryum murumuru* seed butter, sorbitan stearate, polysobate 60, peg-40 stearate, *Citrus grandis* (grapefruit) peel oil, alumina, propylene glycol stearate, polysorbate 20, acetyl hexapeptide-8, sorbitan laurate, propylene glycol laurate, pentaerythrityl tetra-di-t-butyl hydroxyhydrocinnamate, xanthan gum, citric acid, tetrasodium edta, potassium sorbate, chlorphenesin, phenoxyethanol, limonene, citronellol, geraniol, linalool, citral, titanium dioxide, iron oxides, mica Production Example 38. SPF 15 Lotion (Octinoxate
and Titanium Dioxide)

Active Ingredient
Octinoxate 7.50% (Sunscreen)
Titanium Dioxide 3.00% (Sunscreen)
Inactive Ingredient
Water, phenyl trimethicone, butylene glycol, pentaerythrityl tetraoctanoate, *Simmondsia chinensis* (jojoba) seed oil, petrolatum, biosaccharide gum-1, steareth-21, glyceryl stearate, sodium hyaluronate, tocopheryl acetate, polymethyl methacrylate, magnesium aluminum silicate, ethyl hexyl glycerin, caprylyl glycol, cetyl alcohol, acrylamide/sodium acryloyldimethyltaurate copolymer, peg-12 dimethicone, isohexadecane, lecithin, xanthan gum, steareth-2, potassium stearate, citric acid, fragrance (parfum), limonene, Linalool, benzyl salicylate, polysorbate 80, disodium edta, phenoxyethanol, sorbic acid, titanium dioxide, iron oxides Production Example 39. SPF 110 Lotion
(Avobenzone, Homosalate, Octisalate, Octocrylene,
and Oxybenzone)

Active Ingredient
Avobenzone 3% (Sunscreen)
Homosalate 15% (Sunscreen)
Octisalate 5% (Sunscreen)
Octocrylene 10% (Sunscreen)
Oxybenzone 6% (Sunscreen)
Inactive Ingredient
Water, Styrene/Acrylates Copolymer, Silica, Beeswax, Cyclopentasiloxane, Ethylhexylglycerin, Glyceryl Stearate, PEG-100 Stearate, Acrylates/Dimethicone Copolymer, Acrylates/C10-30 Alkyl Acrylate Crosspolymer, Chlorphenesin, Disodium EDTA, Triethanolamine, Dipotassium Glycyrrhizate, BHT, Methylisothiazolinone, Diethylhexyl 2,6-Naphthalate, Fragrance Production Example 40. SPF 70 Lotion
(Avobenzone, Homosalate, Octisalate, Octocrylene,
and Oxybenzone)

Active Ingredient
Avobenzone 3% (Sunscreen)
Homosalate 15% (Sunscreen)
Octisalate 5% (Sunscreen)
Octocrylene 2.8% (Sunscreen)
Oxybenzone 6% (Sunscreen)
Inactive Ingredient
water, styrene/acrylates copolymer, silica, diethylhexyl 2,6-naphthalate, beeswax, caprylyl methicone, cetyl dimethicone, ethylhexylglycerin, glyceryl stearate, PEG-100 stearate, sodium polyacrylate, caprylyl glycol, acrylates/C12-22 alkyl methacrylatecopolymer, ethylhexyl stearate, dimethicone, xanthan gum, trimethylsiloxysilicate, disodium EDTA, *Tanacetum parthenium* (feverfew) leaf/flower/stem juice, dipotassium glycyrrhizate, BHT, trideceth-6, tocopherol, *Glycine soja* (soybean) seed extract, polyaminopropyl biguanide, methylisothiazolinone, fragrance Production Example 41. SPF 25 Lotion
(Avobenzone, Homosalate, Octisalate, Octocrylene,
and Oxybenzone)

Active Ingredient
Avobenzone 3% (Sunscreen)
Homosalate 2% (Sunscreen)
Octisalate 4% (Sunscreen)
Octocrylene 1.8% (Sunscreen)
Oxybenzone 3% (Sunscreen)
Inactive Ingredient
Water, C12-15 Alkyl Benzoate, Glycerin, Diethylhexyl 2,6-Naphthalate, Cetearyl Alcohol, Dimethicone, PEG-12 Glyceryl Dimyristate, Glyceryl Stearate, PEG-100 Stearate, BHT, Beta-Glucan, *Tanacetum Parthenium* (Feverfew) Leaf/Flower/Stem juice*, Cyclohexasiloxane, Cyclopentasiloxane, Acrylates/C10-30 Alkyl Acrylate Crosspolymer, Steareth-21, Cetearyl Glucoside, Behenyl Alcohol, Trisiloxane, Sodium Hydroxide, Tetrasodium EDTA, Methylisothiazolinone, Pentylene Glycol, Methylparaben, Propylparaben, Fragrance, May Also Contain: Caprylyl Glycol, Ethylhexylglycerin Production Example 42. SPF 25 Lotion
(Avobenzone, Homosalate, Octisalate, Octocrylene,
and Oxybenzone)

Active Ingredient
Avobenzone 2% (Sunscreen)
Homosalate 7% (Sunscreen)
Octisalate 4% (Sunscreen)
Octocrylene 1.5% (Sunscreen)
Oxybenzone 2% (Sunscreen)
Inactive Ingredient
Water, glycerin, C12-15 alkyl benzoate, cetearyl alcohol, silica, diethylhexyl 2,6 naphthalate, glyceryl stearate, PEG-100 stearate, caprylyl glycol, erythorbic acid, retinol, polysorbate 20, sodium hyaluronate, dimethicone, arachidyl alcohol, cetearyl glucoside, behenyl alcohol, arachidyl glucoside, acrylates/C10-30 alkyl acrylate crosspolymer, dipotassium glycyrrhizate, triethanolamine, 1,2-hexanediol, methylparaben, methylisothiazolinone, propylparaben Production Example 43. SPF 30 Lotion
(Avobenzone, Homosalate, Octisalate, Octocrylene, and Oxybenzone)

Active Ingredient
  Avobenzone 3% (Sunscreen)
  Homosalate 4% (Sunscreen)
  Octisalate 5% (Sunscreen)
  Octocrylene 5% (Sunscreen)
  Oxybenzone 5% (Sunscreen)
Inactive Ingredient
  water, PPG-15 stearyl ether, cyclopentasiloxane, glycerin, silica, isohexadecane, polyamide-5, ascorbyl glucoside, niacinamide, pentyleneglycol, cetyl alcohol, glyceryl stearate, styrene/acrylates copolymer, dimethicone, tocopheryl acetate, BHT, retinol, polysorbate 20, cyclohexasiloxane, butylene glycol, ascorbic acid, PEG-8, dimethicone-crosspolymer, ammonium acryloyldimethyltaurate/VP copolymer, potassium cetyl phosphate, PEG-75 stearate, trisiloxane, sodium polyacrylate, ceteth-20, steareth-20, bisabolol, hydroxyphenyl propamidobenzoic acid, laureth-23, laureth-4, dipotassium glycyrrhizate, sodium hydroxide, citric acid, disodium EDTA, caprylyl glycol, hinokitiol, titanium dioxide, mica, fragrance Production Example 44. SPF 20 Lotion
(Avobenzone, Homosalate, Octisalate, Octocrylene, and Oxybenzone)

Active Ingredient
  Avobenzone 1.8% (Sunscreen)
  Homosalate 7% (Sunscreen)
  Octisalate 4% (Sunscreen)
  Octocrylene 1.5% (Sunscreen)
  Oxybenzone 2% (Sunscreen)
Inactive Ingredient
  Water, Glycerin, Soybean (GlycineSoja) Seed Extract, C12-15 Alkyl Benzoate, Dimethicone, Diethylhexyl 2,6-Napthalate, Phenyl Trimethicone, Cetearyl Alcohol, Cetearyl Glucoside, Benzyl Alcohol, Feverfew (Chrysanthemum Parthenium) Extract, Silica, Tocopherol, Dipotassium Glycyrrhizate, Ethylene Acrylic Acid Copolymer, Steareth-2, Steareth-21, Titanium Dioxide, Mica, Polymethyl Methacrylate, 1,2 Hexanediol, Caprylyl Glycol, Methylisothiazolinone, Polysorbate 20, Acrylamide/Ammonium Acrylate Copolymer, Polyisobutene, Acrylates/C10-30 Alkyl Acrylate Crosspolymer, Aluminum Starch Octenylsuccinate, Arachidyl Alcohol, Behenyl Alcohol, Arachidyl Glucoside, Methylparaben, Propylparaben, Triethanolamine, Fragrance Production Example 45. SPF 30 Lotion
(Avobenzone, Homosalate, Octisalate, Octocrylene, and Oxybenzone)

Active Ingredient
  Avobenzone 2.7% (Sunscreen)
  Homosalate 8% (Sunscreen)
  Octisalate 4% (Sunscreen)
  Octocrylene 3.5% (Sunscreen)
  Oxybenzone 4% (Sunscreen)
Inactive Ingredient
  Dimethicone, Potassium Cetyl Phosphate, Benzyl Alcohol, Diethylhexyl 2,6-Naphthalate, Caprylyl Glycol, Silica, Cetyl Dimethicone, Beeswax, PPG-12/SM DI Copolymer, Ethylhexylglycerin, Dimethicone/PEG-10/15 Crosspolymer, Trisiloxane, Ethylhexyl Stearate, Behenyl Alcohol, Sodium Polyacrylate, Trideceth-6, Disodium EDTA, Glyceryl Stearate, PEG-100 Stearate, Xanthan Gum, Chlorphenesin, Fragrance Production Example 46. SPF 30 Lotion
(Avobenzone, Homosalate, Octisalate, Octocrylene, and Oxybenzone)

Active Ingredient
  Avobenzone 2.7% (Sunscreen)
  Homosalate 8% (Sunscreen)
  Octisalate 5% (Sunscreen)
  Octocrylene 3.5% (Sunscreen)
  Oxybenzone 4% (Sunscreen)
Inactive Ingredient
  Water, Dimethicone, Potassium Cetyl Phosphate, Benzyl Alcohol, Diethylhexyl 2,6-Naphthalate, Caprylyl Glycol, Silica, Cetyl Dimethicone, Beeswax, PPG-12/SM DI Copolymer, Ethylhexylglycerin, Dimethicone/PEG-10/15 Crosspolymer, Trisiloxane, Ethylhexyl Stearate, Behenyl Alcohol, Sodium Polyacrylate, Trideceth-6, Disodium EDTA, Glyceryl Stearate, PEG-100 Stearate, Xanthan Gum, Chlorphenesin, Fragrance Production Example 47. SPF 70 Lotion
(Avobenzone, Homosalate, Octisalate, Octocrylene, and Oxybenzone)

Active Ingredient
  Avobenzone 3% (Sunscreen)
  Homosalate 10% (Sunscreen)
  Octisalate 5% (Sunscreen)
  Octocrylene 4.5% (Sunscreen)
  Oxybenzone 4% (Sunscreen)
Inactive Ingredient
  Water, Styrene/Acrylates Copolymer, Dimethicone, Potassium Cetyl Phosphate, Benzyl Alcohol, Silica, Diethylhexyl 2,6-Naphthalate, Dimethicone/PEG-10/15 Crosspolymer, Trisiloxane, Cetyl Dimethicone, Beeswax, Etylhexylglycerin, Sodium Polyacrylate, Xanthan Gum, Ethylhexyl Stearate, Acrylates/C12-22 Alkyl Methacrylate Copolymer, Behenyl Alcohol, Trideceth-6, Disodium EDTA, Glyceryl Stearate, PEG-100 Stearate, Caprylyl Glycol, Chlorphenesin, Fragrance Production Example 48. SPF 70 Lotion
(Avobenzone, Homosalate, Octisalate, Octocrylene, Oxybenzone)

Active Ingredient
  Avobenzone 3% (Sunscreen)
  Homosalate 10% (Sunscreen)
  Octisalate 5% (Sunscreen)
  Octocrylene 4.5% (Sunscreen)
  Oxybenzone 4% (Sunscreen)
Inactive Ingredient
  water, styrene/acrylates copolymer, dimethicone, potassium cetyl phosphate, benzyl alcohol, silica, diethylhexyl 2,6-naphthalate, dimethicone/PEG-10/15 crosspolymer, trisiloxane, cetyl dimethicone, beeswax, ethylhexylglycerin, sodium polyacrylate, xanthan gum, ethylhexyl stearate, acrylates/C12-22 alkyl methacrylate copolymer, behenyl alcohol, trideceth-6, disodium EDTA, glyceryl stearate, PEG-100 stearate, caprylyl glycol, chlorphenesin, fragrance

Production Example 49. SPF 30 Emulsion
(Avobenzone, Homosalate, Octisalate, and Octocrylene)

Active Ingredient
  Avobenzone 1.5% (Sunscreen)
  Homosalate 5% (Sunscreen)
  Octisalate 4% (Sunscreen)
  Octocrylene 6% (Sunscreen)
Inactive Ingredient
  Water, Glycerin, Caprylyl Methicone, Diisopropyl Adipate, Acetyl Glucosamine, Silica, Dimethicone, Dicaprylyl Carbonate, Sodium Acryloyldimethyltaurate VP Crosspolymer, Polyurethane-62, Caprylyl Glycol, Phenoxyethanol, Dimethicone Crosspolymer, Fragrance, Glyceryl Stearate, Chlorphenesin, Tocopheryl Acetate, Sodium Ascorbyl Phosphate, Citric Acid, Disodium EDTA, Trideceth-6, *Moringa Oleifera* Seed Extract, Mica, Titanium Dioxide

Production Example 50. SPF 30 Lotion
(Avobenzone, Homosalate, Octisalate, Octocrylene, and Oxybenzone)

Active Ingredient
  Avobenzone 2.5% (Sunscreen)
  Homosalate 5% (Sunscreen)
  Octisalate 4% (Sunscreen)
  Octocrylene 3% (Sunscreen)
  Oxybenzone 4% (Sunscreen)
Inactive Ingredient
  water, silica, cetyl dimethicone, styrene/acrylates copolymer, C12-15 alkyl benzoate, steareth-100, ethylhexylglycerin, phenoxyethanol, caprylyl glycol, sodium polyacrylate, dimethicone, steareth-2, polyester-7, chlorphenesin, propylene glycol, ethylhexyl stearate, neopentyl glycol diheptanoate, bisabolol, disodium EDTA, butylene glycol, acrylates/dimethicone copolymer, diethylhexyl 2,6-naphthalate, mannan, xanthan gum, BHT, capryloyl glycine, trideceth-6, sarcosine, *Cedrus atlantica* bark extract, *Cinnamomum zeylanicum* bark extract *Portulaca oleracea* extract

Production Example 51. SPF 55 Lotion
(Avobenzone, Homosalate, Octisalate, Octocrylene, and Oxybenzone)

Active Ingredient
  Avobenzone 2.7% (Sunscreen)
  Homosalate 4% (Sunscreen)
  Octisalate 4.5% (Sunscreen)
  Octocrylene 6% (Sunscreen)
  Oxybenzone 4.5% (Sunscreen)
Inactive Ingredient
  water, silica, cetyl dimethicone, styrene/acrylates copolymer, C12-15 alkyl benzoate, steareth-100, ethylhexylglycerin, phenoxyethanol, caprylyl glycol, sodium polyacrylate, dimethicone, steareth-2, polyester-7, chlorphenesin, propylene glycol, ethylhexyl stearate, neopentyl glycol diheptanoate, bisabolol, disodium EDTA, butylene glycol, acrylates/dimethicone copolymer, diethylhexyl 2,6-naphthalate, mannan, xanthan gum, BHT, capryloyl glycine, trideceth-6, sarcosine, *Cedrus atlantica* bark extract, *Cinnamomum zeylanicum* bark extract, *Portulaca oleracea* extract

Production Example 52. SPF 70 Lotion
(Avobenzone, Homosalate, Octisalate, Octocrylene, and Oxybenzone)

Active Ingredient
  Avobenzone 3% (Sunscreen)
  Homosalate 15% (Sunscreen)
  Octisalate 5% (Sunscreen)
  Octocrylene 4% (Sunscreen)
  Oxybenzone 6% (Sunscreen)
Inactive Ingredient
  water, dimethicone, cetyl PEG/PPG-10/1 dimethicone, PEG-30 dipolyhydroxystearate, glyceryl behenate, sodium polyacrylate, silica, ethylhexylglycerin, decylene gycol, tocopheryl acetate, acrylates/dimethicone copolymer, chlorphenesin, phenoxyethanol

Production Example 53. SPF 30 Lotion
(Avobenzone, Homosalate, Octisalate, Octocrylene, and Oxybenzone)

Active Ingredient
  Avobenzone 3% (Sunscreen)
  Homosalate 8% (Sunscreen)
  Octisalate 5% (Sunscreen)
  Octocrylene 4% (Sunscreen)
  Oxybenzone 4% (Sunscreen)
Inactive Ingredient
  Water, Dimethicone, Cetyl PEG/PPG-10/1 Dimethicone, Trisiloxane, PEG-30 Dipolyhydroxystearate, Sodium Polyacrylate, Silica, Tocopheryl Acetate, Ethylhexylglycerin, Decylene Glycol, Acrylates/Dimethicone Copolymer, Glyceryl Behenate, Glyceryl Dibehenate, Tribehenin, Phenoxyethanol, Chlorphenesin, Fragrance

Production Example 54. SPF 50 Lotion
(Avobenzone, Homosalate, Octisalate, Octocrylene, and Oxybenzone)

Active Ingredient
  Avobenzone 2.7% (Sunscreen)
  Homosalate 9% (Sunscreen)
  Octisalate 4.5% (Sunscreen)
  Octocrylene 8% (Sunscreen)
  Oxybenzone 4.5% (Sunscreen)
Inactive Ingredient
  Water, Dimethicone, Cetyl PEG/PPG-10/1 Dimethicone, PEG-30 Dipolyhydroxystearate, Glyceryl Behenate, Sodium Polyacrylate, Silica, Tocopheryl Acetate, Ethylhexylglycerin, Decylene Glycol, Acrylates/Dimethicone Copolymer, Phenoxyethanol, Chlorphenesin, Fragrance

Production Example 55. SPF 50 Lotion
(Avobenzone, Homosalate, Octisalate, Octocrylene, and Oxybenzone)

Active Ingredient
  Avobenzone 2.7% (Sunscreen)
  Homosalate 9% (Sunscreen)
  Octisalate 4.5% (Sunscreen)
  Octocrylene 8% (Sunscreen)
  Oxybenzone 4.5% (Sunscreen)
Inactive Ingredient
  water, dimethicone, PEG-30 dipolyhydroxystearate, glyceryl behenate, cetyl PEG/PPG-10/1 dimethicone, sodium polyacrylate, silica, phenoxyethanol, ethylhexylglycerin, chlorphenesin, decylene glycol, tocopheryl acetate, acrylates/dimethicone copolymer, fragrance

Production Example 56. SPF 70 Lotion
(Avobenzone, Homosalate, Octisalate, Octocrylene, and Oxybenzone)

Active Ingredient
Avobenzone 3% (Sunscreen)
Homosalate 15% (Sunscreen)
Octisalate 5% (Sunscreen)
Octocrylene 4% (Sunscreen)
Oxybenzone 6% (Sunscreen)
Inactive Ingredient
Water, Dimethicone, Cetyl PEG/PPG-10/1 Dimethicone, PEG-30 Dipolyhydroxystearate, Sodium Polyacrylate, Silica, Tocopheryl Acetate, Ethylhexylglycerin, Decylene Glycol, Acrylates/Dimethicone Copolymer, Glyceryl Behenate, Glyceryl Dibehenate, Tribehenin, Phenoxyethanol, Chlorphenesin, Fragrance

Production Example 57. SPF 30 Lotion
(Avobenzone, Homosalate, Octisalate, Octocrylene, and Oxybenzone)

Active Ingredient
Avobenzone 3% (Sunscreen)
Homosalate 12% (Sunscreen)
Octisalate 5% (Sunscreen)
Octocrylene 5% (Sunscreen)
Oxybenzone 3% (Sunscreen)
Inactive Ingredient
Water, Butylene Glycol, C12-15 Alkyl Benzoate, Tetrahydroxypropyl Etylenediamine, Silica, Cetearyl Alcohol, Cyclopentasiloxane, Dimethicone, Steareth-2, Glyceryl Stearate, Steareth-21, Aluminum Starch Octenylsuccinate, Cetearyl Glucoside, C13-14 Isoparaffin, Dimethicone/Vinyl Dimethicone Crosspolymer, Arachidyl Alcohol, PEG-100 Stearate, Disodium EDTA, Polyacrylamide, Behenyl Alcohol, Acrylates/C10-30 Alkyl Acrylate Crosspolymer, Propylparaben, Pentaerythrityl Tetra-di-t-butyl Hydroxyhydrocinnamate, Arachidyl Glucoside, Laureth-7, Citric Acid, Benzyl Alcohol, Phenoxyethanol, Methylparaben, Ethylparaben, Fragrance

Production Example 58. SPF 20 Cream
(Avobenzone, Homosalate, Octisalate, and Octocrylene)

Active Ingredient
Avobenzone 2% (Sunscreen)
Homosalate 4% (Sunscreen)
Octisalate 4% (Sunscreen)
Octocrylene 2% (Sunscreen)
Inactive Ingredient
water, glycerin, dimethicone, isononyl isononanoate, ethylhexyl palmitate, steareth-2, *Butyrospermum parkii* (shea) butter, styrene/acrylates copolymer, silica, steareth-21, methyl methacrylate crosspolymer, BHT, ascorbyl glucoside, tocopheryl acetate, behenyl alcohol, dimethicone crosspolymer, xylitylglucoside, mica, titanium dioxide, ammonium acryloyldimethyltauratelV P copolymer, *sclerotium* gum, calcium chloride, cholecalciferol, caprylic/capric triglyceride, disodium EDTA, caprylyl glycol, phenoxyethanol, propylparaben, ehylparaben, methylparaben, citric acid, sodium hydroxide, fragrance

Production Example 59. SPF 50 Lotion
(Avobenzone, Homosalate, Octisalate, Octocrylene, and Oxybenzone)

Active Ingredient
Avobenzone 3% (Sunscreen)
Homosalate 12% (Sunscreen)
Octisalate 5% (Sunscreen)
Octocrylene 2.35% (Sunscreen)
Oxybenzone 6% (Sunscreen)
Inactive Ingredient
Water, Dimethicone, Trisiloxane, Diethylhexyl 2,6-Naphthalate, Glycerin, Glyceryl Stearate, PEG-100 Stearate, Cetearyl Alcohol, Potassium Cetyl Phosphate, Behenyl Alcohol, Caprylyl Methicone, Ethylhexylglycerin, Pantothenic Acid, Retinyl Palmitate, Ascorbic Acid, Tocopheryl Acetate, Tocopherol, BHT, Polymethyl Methacrylate, Hydrogenated Palm Glycerides, Styrene/Acrylates Copolymer, Cetearyl Glucoside, Xanthan Gum, Disodium EDTA, Methylparaben, Propylparaben, Methylisothiazolinone, Benzyl Alcohol

Production Example 60. SPF 50 Lotion (Titanium Dioxide and Zinc Oxide)

Active Ingredient
Titanium Dioxide 5% (Sunscreen)
Zinc Oxide 3% (Sunscreen)
Inactive Ingredient
Water, C12-15 Alkyl Benzoate, Ethylhexyl Isononanoate, Styrene/Acrylates Copolymer, Glyceryl Stearate, Glycerin, Silica, Ethylhexyl Hydroxystearate, Dimethicone, Aluminum Stearate, Cetyl Alcohol, PEG-100 Stearate, Ethylhexylglycerin, Polyhydroxystearic Acid, Phenoxyethanol, Hydroxyethyl Acrylate/Sodium Acryloyldimethyl Taurate Copolymer, PEG-75 Stearate, Pentylene Glycol, Caprylyl Glycol, Bisabolol, Isohexadecane, Chlorphenesin, Ceteth-20, Steareth-20, PPG-12/SM DI Copolymer, Disodium EDTA, Polysorbate 60, Triethoxycaprylylsilane, Dipropylene Glycol Dibenzoate, PPG-15 Stearyl Ether Benzoate, BHT, Alumina

Production Example 61. SPF 50 Lotion (Titanium Dioxide and Zinc Oxide)

Active Ingredient
Titanium Dioxide 5% (Sunscreen)
Zinc Oxide 3% (Sunscreen)
Inactive Ingredient
Water, C12-15 alkyl benzoate, ethylhexyl isononanoate, styrene/acrylates copolymer, dimethicone, silica, ethylhexyl hydroxystearate, glycerin, glyceryl stearate, cetyl alcohol, PEG-100 stearate, ethylhexylglycerin, polyhydroxystearic acid, phenoxyethanol, alumina, hydroxyethyl acrylate/sodium acryloyldimethyl taurate copolymer, PEG-75 stearate, pentylene glycol, bisabolol, caprylyl glycol, isohexadecane, chlorphenesin, aluminum stearate, disodium EDTA, PPG-12/SM DI copolymer, ceteth-20, steareth-20, dipropyleneglycol dibenzoate, triethoxycaprylylsilane, polysorbate 60, PPG-15 stearyl ether benzoate, BHT

Production Example 62. SPF 15 Cream
(Avobenzone, Octisalate, Octocrylene, and Oxybenzone)

Active Ingredient
Avobenzone 1.5% (Sunscreen)
Octisalate 5% (Sunscreen)

Octocrylene 3% (Sunscreen)
Oxybenzone 4% (Sunscreen)
Inactive Ingredient
    water, glycerin, C12-15 alkylbenzoate, cetearyl alcohol, glyceryl stearate, cetyl alcohol, dimethicone, PEG-75 stearate, tocopheryl acetate, phenoxyethanol, panthenol, caprylyl glycol, carbomer, cetearyl glucoside, butylene glycol, methylparaben, ceteth-20, steareth-20, *Camellia oleifera* leaf extract, propylparaben, chlorphenesin, BHT, disodium EDTA, sodium hydroxide, tocopherol, retinal, polysorbate 20

Production Example 63. SPF 20 Lotion (Octinoxate and Octisalate)

Octinoxate 7% (Sunscreen)
Octisalate 3% (Sunscreen)
Inactive Ingredient
    Water, Titanium Dioxide, Isopropyl Isostearate, Cyclopentasiloxane, Dimethicone, Butylene Glycol, Glyceryl Stearate, Cetyl Alcohol, Cetearyl Alcohol, PEG-75 Stearate, Lauroyl Lysine, Tocopheryl Acetate, *Olea Europaea* (Olive) Fruit Extract, BHT, Erythorbic Acid, Bisabolol, Retinyl Palmitate, Retinol, Arginine, Slica, Polysorbate 20, PEG-100 Stearate, Isostearyl Palmitate, *Sclerotium* Gum, Polysilicone-11, Ammonium Polyacryloyldimethyl Taurate, Ceteth-20, Steareth-20, Tetrasodium EDTA, Iron Oxides, Methylparaben, Propylparaben, Ethylparaben, Phenoxyethanol, Fragrance Production Example 64. SPF 20 Lotion (Octinoxate, Octisalate, and Titanium Dioxide)

Active Ingredient
    Octinoxate 7% (Sunscreen)
    Octisalate 3% (Sunscreen)
    Titanium dioxide 5.1% (Sunscreen)
Inactive Ingredient
    water, isopropyl isostearate, cylcopentasiloxane, dimethicone, butyleneglycol, glyceryl stearate, cetyl alcohol, cetearyl alcohol, tocopheryl acetate, retinyl palmitate, retinol, arginine, olive (*Olea europaea*) fruit extract, *Camellia oleifera* leaf extract, BHT, silica, polysorbate 20, *sclerotium* gum, tetrasodium EDTA, erythorbic acid, isostearyl palmitate, polysilicone-11, PEG-100 stearate, ammonium polyacryloyldimethyl taurate, PEG-75 stearate, ceteth-20, steareth-20, iron oxides, lauroyl lysine, ethylparaben, methylparaben, propylparaben, phenoxyethanol, fragrance Production Example 65. SPF 20 Lotion (Octinoxate and Octisalate)

Active Ingredient
    Octinoxate 7% (Sunscreen)
    Octisalate 3% (Sunscreen)
Inactive Ingredient
    Water, Isopropyl Isostearate, Cylcopentasiloxane, Dimethicone, Butylene Glycol, Glyceryl Stearate, Cetyl Alcohol, Cetearyl Alcohol, Phenoxyethanol, PEG-75 Stearate, Tocopheryl Acetate, Isostearyl Palmitate, *Olea Europaea* (Olive) Leaf Extract, *Sclerotium* Gum, Polysilicone-11, Ceteth-20, Steareth-20, Methylparaben, Silica, Polysorbate 20, Lauroyl Lysine, Ethylparaben, BHT, PEG-100 Stearate, Erythorbic Acid, Retinyl Palmitate, Arginine, Tetrasodium EDTA, Ammonium Polyacryloyldimethyl Taurate, Retinol, Fragrance, Titanium Dioxide, Iron Oxides Production Example 66. SPF 15 Lotion (Avobenzone, Octisalate, Octocrylene, and Oxybenzone)

Active Ingredient
    Avobenzone 1.5% (Sunscreen)
    Octisalate 5% (Sunscreen)
    Octocrylene 3% (Sunscreen)
    Oxybenzone 4% (Sunscreen)
Inactive Ingredient
    water, glycolic acid, dicaprylyl maleate, C12-15 alkyl benzoate, stearic acid, glycerin, cetyl alcohol, PEG-100 stearate, glyceryl stearate, sodium hydroxide, phenoxyethanol, *sclerotium* gum, tocopheryl acetate, caprylyl glycol, fragrance, xanthan gum, methylparaben, panthenol, bisabolol, propylparaben, tetrasodium EDTA, ascorbic acid Production Example 67. SPF 15 Lotion (Octinoxate and Oxybenzone)

Active Ingredient
    Octinoxate 7.5% (Sunscreen)
    Oxybenzone 5% (Sunscreen)
Inactive Ingredient
    Water, Glycolic Acid, C12-15 Alkyl Benzoate, Dicaprylyl Maleate, Sodium Glycolate, Cetyl Alcohol, Glycerin, Stearic Acid, Glyceryl Stearate, PEG-100 Stearate, Tocopheryl Acetate, Retinyl Palmitate, Ascorbic Acid Polypeptide, Panthenol, Bisabolol, Tetrasodium EDTA, Xanthan Gum, Methyl paraben, Propylparaben, Diazolidinyl Urea, Fragrance Production Example 68. SPF 15 Lotion (Avobenzone, Homosalate, Octisalate, Octocrylene, and Oxybenzone)

Active Ingredient
    Avobenzone 3% (Sunscreen)
    Homosalate 12% (Sunscreen)
    Octisalate 5% (Sunscreen)
    Octocrylene 5% (Sunscreen)
    Oxybenzone 3% (Sunscreen)
Inactive Ingredient
    water, butylene glycol, silica, tetrahydroxypropyl ethylenediamine, C12-15 alkyl benzoate, cetearyl alcohol, dimethicone, benzyl alcohol, cyclopentasiloxane, steareth-2, glyceryl stearate, steareth-21, phenoxyethanol, citric acid, dimethicone/vinyl dimethicone crosspolymer, cetearyl glucoside, aluminum starch octenylsuccinate, polyacrylamide, fragrance, arachidyl alcohol, PEG-100 stearate, C13-14 isoparaffin, methylparaben, ethylparaben disodium EDTA, behenyl alcohol, acrylates/C10-30 alkyl acrylate crosspolymer, pentaerythrityl tetra-di-t-butyl hydroxyhydrocinnamate, propylparaben, arachidyl glucoside, laureth-7, polymethyl methacrylate, tocopheryl acetate, pantothenic acid, ascorbic acid, retinyl palmitate Production Example 69. SPF 30 Liquid (Homosalate, Octinoxate, Octisalate, Oxybenzone, and Titanium Dioxide)

Active Ingredient
    Homosalate 5% (Sunscreen)
    Octinoxate 7.5% (Sunscreen)
    Octisalate 5% (Sunscreen)
    Oxybenzone 4% (Sunscreen)
    Titanium Dioxide 2.9% (Sunscreen)

Inactive Ingredient

Water, phenyl trimethicone, cetyl dimethicone, butylene glycol, silica, cetearyl alcohol, glyceryl stearate, PEG 100 stearate, barium sulfate, pantothenic acid, ascorbic acid, tocopheryl acetate, retinyl palmiatte, squalane, bisabolol, dipotassium glycyrrhizate, polysorbate 60, PEG-12 dimethicone, polymethyl methacrylate, polysorbate 20, magnesium aluminum silicate, cetyl hydroxyethylcellulose, tetrasodium EDTA, xanthan gum, hydroxyethyl acrylate/sodium acryloyldimethyl taurate, caprylyl glycol, sorbic acid, phenoxyethanol M ay contain: iron oxides, mica, titanium dioxide

Production Example 70. SPF 15 Lotion (Avobenzone, Octinoxate, and Octisalate)

Active Ingredient
 Avobenzone 3% (Sunscreen)
 Octinoxate 7.5% (Sunscreen)
 Octisalate 2% (Sunscreen)
Inactive Ingredient
 Water, C12-15 Alkyl Benzoate, Cetearyl Alcohol, *Glycine Soja* (Soybean) Seed Extract, Dimethicone, Glycerin, Bis-Phenylpropyl Dimethicone, Phenoxyethanol, Arachidyl Alcohol, Cetearyl Glucoside, Panthenol, Benzyl Alcohol, Ethylene/Acrylic Acid, Copolymer, Behenyl Alcohol, Steareth-2, Fragrance, Steareth-21, Titanium Dioxide, Mica, Polyacrylamide, Polymethyl Methacrylate, Arachidyl Glucoside, Disodium EDTA, Methylparaben, C13-14 Isoparaffin, Propylparaben, Ethylparaben, Laureth-7, Silica, Benzalkonium Chloride, Iodopropynyl Butylcarbamate, BHT

Production Example 71. SPF 25 Gel (Avobenzone, Homosalate, Octisalate, and Octocrylene)

Active Ingredient
 Avobenzone 2% (Sunscreen)
 Homosalate 4% (Sunscreen)
 Octisalate 4% (Sunscreen)
 Octocrylene 2% (Sunscreen)
Inactive Ingredient
 Water, Glycerin, Caprylyl Methicone, Methyl Methacrylate Crosspolymer, Pentylene Glycol, Sodium Acryloyldimethyltaurate/VP Crosspolymer, Phenoxyethanol, Glyceryl Stearate, Chlorphenesin, Tocopheryl Acetate, Sodium Hyaluronate, Disodium EDTA, Ethylhexylglycerin, Fragrance, Sodium Hydroxide, Blue 1, Red 40

Production Example 72. SPF 15 Gel (Avobenzone, Homosalate, Octisalate, and Octocrylene)

Active Ingredient
 Avobenzone 2% (Sunscreen)
 Homosalate 4% (Sunscreen)
 Octisalate 4% (Sunscreen)
 Octocrylene 2% (Sunscreen)
Inactive Ingredient
 Water, Glycerin, Caprylyl Methicone, Methyl Methacrylate Crosspolymer, Pentylene Glycol, Sodium Acryloyldimethyltaurate/VP Crosspolymer, Benzyl Alcohol, Glyceryl Stearate, Chlorphenesin, Sodium Hyaluronate, Disodium EDTA, Fragrance, Sodium Hydroxide, Blue 1, Red 40

Production Example 73. SPF 30 Lotion (Avobenzone, Homosalate, Octisalate, and Octocrylene)

Active Ingredient
 Avobenzone 1.5% (Sunscreen)
 Homosalate 5% (Sunscreen)
 Octisalate 4% (Sunscreen)
 Octocrylene 6% (Sunscreen)
Inactive Ingredient
 Water, Glycerin, Alcohol Denat., Caprylyl Methicone, Diisopropyl Adipate, Silica, Dicaprylyl Carbonate, Dimethicone, Polyurethane-62, Phenoxyethanol, Hydroxyacetophenone, Pentylene Glycol, Sodium Acryloyldimethyltaurate/VP Crosspolymer, Dimethicone Crosspolymer, Acrylates/Dimethicone Copolymer, Glyceryl Stearate, Fragrance, Chlorphenesin, Tocopheryl Acetate, Disodium EDTA, Trideceth-6, Hydrolyzed Hyaluronic Acid, Sodium Hydroxide, Blue 1

Production Example 74. SPF 50 Lotion (Avobenzone, Homosalate, Octisalate, Octocrylene, and Oxybenzone)

Active Ingredient
 Avobenzone 2.7% (Sunscreen)
 Homosalate 9% (Sunscreen)
 Octisalate 5% (Sunscreen)
 Octocrylene 9% (Sunscreen)
 Oxybenzone 4.5% (Sunscreen)
Inactive Ingredient
 Water, Glycerin, Alcohol Denat, Caprylyl Methicone, Diisopropyl Adipate, Silica, Dicaprylyl Carbonate, Dimethicone, Polyurethane-62, Phenoxyethanol, Hydroxyacetophenone, Pentylene Glycol, Aluminum Starch Octenylsuccinate, Sodium Acryloyldimethyltaurate/VP Crosspolymer, Acrylates/Dimethicone Copolymer, Glyceryl Stearate, Fragrance, Chlorphenesin, Menthyl Lactate, Tocopheryl Acetate, Disodium EDTA, Trideceth-6, Hydrolyzed Hyaluronic Acid, Sodium Hydroxide, Violet 2, Blue 1

Production Example 75. SPF 15 Cream (Avobenzone, Octisalate, Octocrylene, and Oxybenzone)

Active Ingredient
 Avobenzone 1.5% (Sunscreen)
 Octisalate 5% (Sunscreen)
 Octocrylene 3% (Sunscreen)
 Oxybenzone 4% (Sunscreen)
Inactive Ingredient
 Water, Glycerin, C12-15 Alkyl Benzoate, Cetearyl Alcohol, Glyceryl Stearate, Cetyl Alcohol, Dimethicone, PEG-75 Stearate, Panthenol, Tocopheryl Acetate, Phenoxyethanol, Caprylyl Glycol, Carbomer, Cetearyl Glucoside, Butylene Glycol, Methylparaben, Ceteth-20, Steareth-20, *Camellia oleifera* Leaf Extract, Propylparaben, Chlorphenesin, BHT, Disodium EDTA, Sodium Hydroxide, Tocopherol, Polysorbate 20, Retinol

Production Example 76. SPF 15 Cream (Ensulizole and Octinoxate)

Active Ingredient
 Ensulizole 1% (Sunscreen)
 Octinoxate 6% (Sunscreen)
Inactive Ingredient
 Water, C12-15 Alkyl Benzoate, Cetyl Alcohol, Glycerin, Cetearyl Alcohol, Triethanolamine, Dimethicone, Phenoxyethanol, Panthenol, Retinol, Tocopheryl Acetate, *Camellia oleifera* Leaf Extract, BHT, Tocopherol, Cetearyl Glucoside, Butylene Glycol, Polysorbate 20, Carbomer, Disodium EDTA, Titanium Dioxide, Polyhydroxystearic Acid, Silica, Alumina, Methylparaben, Isopropylparaben, Isobutylparaben, Butylparaben

Production Example 77. SPF 30 Lotion (Avobenzone, Homosalate, Octisalate, Octocrylene, and Oxybenzone)

Active Ingredient
  Avobenzone 3% (Sunscreen)
  Homosalate 12% (Sunscreen)
  Octisalate 5% (Sunscreen)
  Octocrylene 1.7% (Sunscreen)
  Oxybenzone 3% (Sunscreen)
Inactive Ingredient
  Water, C12-15 Alkyl Benzoate, Dimethicone, *Glycine Soja* (Soybean) Seed Extract, Cetearyl Alcohol, Diethylhexyl 2,6-Naphthalate, Ethylene/Acrylic Acid Copolymer, Glycerin, Panthenol, Phenyl Trimethicone, Silica, Aluminum Starch Octenylsuccinate, Arachidyl Alcohol, Cetearyl Glucoside, Methylparaben, Steareth-2, Polyacrylate-13, Behenyl Alcohol, Titanium Dioxide, Steareth-21, Mica, Polymethyl Methacrylate, Disodium EDTA, Polyisobutene, Arachidyl Glucoside, Pentaerythrityl Tetra-di-t-butyl Hydroxyhydrocinnamate, Boron Nitride, Polysorbate 20, Propylparaben, Ethylparaben, Benzalkonium Chloride, Phenoxyethanol, Fragrance

Production Example 78. SPF 20 Lotion (Avobenzone, Homosalate, Octisalate, Octocrylene, and Oxybenzone)

Active Ingredient
  Avobenzone 3% (Sunscreen)
  Homosalate 12% (Sunscreen)
  Octisalate 5% (Sunscreen)
  Octocrylene 1.7% (Sunscreen)
  Oxybenzone 3% (Sunscreen)
Inactive Ingredient
  water, octyldodecyl neopentanoate, glycerin, *Glycine soja* (soybean) seed extract, emulsifying wax NF, glyceryl stearate, PEG-100 stearate, dimethicone, silica, phenoxyethanol, panthenol, tocopheryl acetate ethylhexylglycerin, caprylyl glycol, acrylates/C10-30 alkyl acrylate crosspolymer, bisabolol, fragrance, *Camellia oleifera* leaf extract, methylparaben, allantoin, disodium EDTA, sodium hydroxide, butylene glycol

Production Example 79. SPF 20 Lotion

Active Ingredient
  Avobenzone 3% (Sunscreen)
  Homosalate 12% (Sunscreen)
  Octisalate 5% (Sunscreen)
  Octocrylene 1.7% (Sunscreen)
  Oxybenzone 3% (Sunscreen)
Inactive Ingredient
  Water, Octyldodecyl Neopentanoate, Glycerin, *Glycine Soja* (Soybean) Seed Extract, Emulsifying Wax, Glyceryl Stearate, PEG-100 Stearate, Dimethicone, Silica, Phenoxyethanol, Panthenol, Tocopheryl Acetate, Ethylhexylglycerin, Acrylates/C10-30 Alkyl Acrylate Crosspolymer, Caprylyl Glycol, Fragrance, Bisabolol, *Camellia Sinensis* Leaf Extract, Methylparaben, Disodium EDTA, Allantoin, Butylene Glycol, Sodium Hydroxide

Production Example 80. SPF 25 Lotion (Titanium Dioxide and Zinc Oxide)

Active Ingredient
  Titanium Dioxide 4.1% (Sunscreen)
  Zinc Oxide 3% (Sunscreen)
Inactive Ingredient
  Water, Caprylic/Capric Triglyceride, Cocoglycerides, Glycerin, Cetearyl Olivate, Caprylyl Methicone, Polyglyceryl-3 Diisostearate, Sorbitan Olivate, Cetearyl Alcohol, *Butyrospermum parkii* (Shea) Butter, Heptyl Undecylenate, Aluminum Starch Octenylsuccinate, Gluconolactone, Xanthan Gum, Caprylyl Glycol, Glyceryl Behenate, Aluminum Hydroxide, Stearic Acid, Phenylethyl Resorcinol, Benzyl Alcohol, Ethylhexyiglycerin, Cetearyl Glucoside, Sodium Benzoate, Chlorphenesin, 1,2-Hexanediol, Triethoxycaprylylsilane, Fragrance, *Citrus limon* (Lemon) Peel Extract, Tropolone, Mica, Titanium Dioxide, Iron Oxides

Production Example 81. SPF 15 Lotion (Avobenzone, Octisalate, Octocrylene, and Oxybenzone)

Active Ingredient
  Avobenzone 1.5% (Sunscreen)
  Octisalate 5% (Sunscreen)
  Octocrylene 3% (Sunscreen)
  Oxybenzone 4% (Sunscreen)
Inactive Ingredient
  Water, Octyldodecyl Neopentanoate, Glycerin, Emulsifying Wax NF, Glyceryl Stearate, PEG-100 Stearate, Dimethicone, Phenoxyethanol, Ethylhexylglycerin, Caprylyl Glycol, Carbomer, Triethanolamine, Methylparaben, Disodium EDTA, Ethylene Brassylate, Dipropylene Glycol, Dimethyl Heptenal

Production Example 82. SPF 35 Lotion (Avobenzone, Homosalate, Octisalate, Octocrylene, and Oxybenzone)

Active Ingredient
  Avobenzone 3% (Sunscreen)
  Homosalate 12% (Sunscreen)
  Octisalate 5% (Sunscreen)
  Octocrylene 2.35% (Sunscreen)
  Oxybenzone 6% (Sunscreen)
Inactive Ingredient
  Water, Dimethicone, Diethylhexyl 2,6-Naphthalate, Glycerin, Trisiloxane, PEG-100 Stearate, Glyceryl Stearate, Cetearyl Alcohol, Behenyl Alcohol, Caprylyl Methicone, Potassium Cetyl Phosphate, Styrene/Acrylates Copolymer, Hydrogenated Palm Glycerides, Benzyl Alcohol, Ethylhexylglycerin, Methylparaben, Cetearyl Glucoside, Xanthan Gum, Propylparaben, Disodium EDTA, BHT, Methylisothiazolinone

Production Example 83. SPF 45 Lotion (Titanium Dioxide and Zinc Oxide)

Active Ingredient
  Titanium Dioxide 5.1% (Sunscreen)
  Zinc Oxide 2.9% (Sunscreen)
Inactive Ingredient
  Aluminum Hydroxide, C12-15 Alkyl Benzoate, Carbomer, Cetyl Alcohol, Cetyl Dimethicone, Cetyl Hydroxyethylcellulose, Cetyl PEG/PPG-10/1 Dimethicone, Dimethicone, Dimethicone Crosspolymer, Dimethicone/Vinyl Dimethicone Crosspolymer, Disodium Phosphate, Ethylhexylglycerin, Glycerin, Hexyl Laurate, Hydrated Silica, Isopropyl Myristate, Magnesium Sulfate, Phenoxyethanol, Polyglyceryl-4 Isostearate, Silica, Sodium Hydroxide, Sodium Phosphate, Stearic Acid, Styrene/Acrylates Copolymer, triethoxycaprylylsilane, Trisiloxane, Water

Production Example 84. SPF 50 Lotion (Zinc Oxide)

Active Ingredient
    Zinc Oxide 21.6% (Sunscreen)
Inactive Ingredient
    Water, C12-15 Alkyl Benzoate, Styrene/Acrylates Copolymer, Octyldodecyl Citrate Crosspolymer, Phenyl Trimethicone, Cetyl PEG/PPG-10/1 Dimethicone, Dimethicone, Polyhydroxystearic Acid, Glycerin, Ethyl Methicone, Cetyl Dimethicone, Silica, *Chrysanthemum parthenium* (Feverfew) Flower/Leaf/Stem Juice, Glyceryl Behenate, Phenethyl Alcohol, Caprylyl Glycol, Cetyl Dimethicone/Bis-Vinyldimethicone Crosspolymer, Acryiates/Dimethicone Copolymer, Sodium Chloride, Phenoxyethanol, Chlorphenesin

Production Example 85. SPF 50 Liquid (Titanium Dioxide and Zinc Oxide)

Active Ingredient
    Titanium Dioxide 5% (Sunscreen)
    Zinc Oxide 3% (Sunscreen)
Inactive Ingredient
    BHT, Bisabolol, C12-15 Alkyl Benzoate, Caprylyl Glycol, Cetyl PEG/PPG-10/1 Dimethicone, Dimethicone, DMDM Hydantoin, Magnesium Sulfate, Polyglyceryl-4 Diisostearate/Poiyhydroxystearate/Sebacate, PPG-12/SM DI Copolymer, Silica, Styrene/Acrylates Copolymer, Triethoxycaprylylsilane, Trisiloxane, Water

Production Example 86. SPF 30 Lotion (Avobenzone, Homosalate, Octisalate, and Octocrylene)

Active Ingredient
    Avobenzone 2% (Sunscreen)
    Homosalate 4% (Sunscreen)
    Octisalate 4% (Sunscreen)
    Octocrylene 2% (Sunscreen)
    Oxybenzone 6% (Sunscreen)
Inactive Ingredient
    water, dimethicone, isononyl isononanoate, glycerin, trisiloxane, cetyl alcohol, styrene/acrylates copolymer, steareth-21, nylon-12, dimethicone/vinyl dimethicone crosspolymer, retinol, hydrolyzed *Myrtus communis* leaf extract, ascorbic acid, BHT, silica, sodium hyaluronate, caprylyl glycol, stearyl alcohol, glyceryl stearate, PEG-100 stearate, acrylates/C10-30 alkyl acrylate crosspolymer, xanthan gum, polysorbate 20, disodium EDTA, sodium hydroxide, phenoxyethanol, chlorphenesin, fragrance

Production Example 87. SPF 50 Lotion (Titanium Dioxide and Zinc Oxide)

Active Ingredient
    Titanium Dioxide 4.9% (Sunscreen)
    Zinc Oxide 2.9% (Sunscreen)
Inactive Ingredient
    BHT, Bisabolol, C12-15 Alkyl Benzoate, Caprylyl Glycol, Cetyl PEG/PPG-10/1 Dimethicone, Dimethicone, DMDM Hydantoin, Magnesium Sulfate, Polyglyceryl-4 Diisostearate/Polyhydroxystearate/Sebacate, PPG-12/SM DI Copolymer, Silica, Styrene/Acrylates Copolymer, Triethoxycaprylylsilane, Trisiloxane, Water

Production Example 88. SPF 60 Lotion (Titanium Dioxide and Zinc Oxide)

Active Ingredient
    Titanium Dioxide 4.9% (Sunscreen)
    Zinc Oxide 4.7% (Sunscreen)
Inactive Ingredient
    water, butyloctyl salicylate, beeswax, styrene/acrylates copolymer, silica, butylene glycol, PEG-8, glyceryl stearate, PEG-100 stearate, cetyl dimethicone, benzyl alcohol, dimethicone, methicone, arachidyl alcohol, polyhydroxystearic acid, hydroxyethyl acrylate/sodium acryloyldimethyl taurate copolymer, PEG-8 laurate, xanthan gum, isohexadecane, behenyl alcohol, trisiloxane, ethylhexylglycerin, disodium EDTA, trimethylsiloxysilicate, arachidyl glucoside, bisabolol, dipotassiurn glycyrrhizate, triethoxycaprylylsilane, BHT, polysorbate 60, stearic acid, methylisothiazolinone, polyaminopropyl biguanide, polymethyl methacrylate, tocopheryl acetate, ascorbic acid, pantothenic acid, retinyl palmitate, alumina

Production Example 89. SPF 30 Lotion (Zinc Oxide)

Active Ingredient
    Zinc Oxide 18.24% (Sunscreen)
Inactive Ingredient
    Water, C12-15 Alkyl Benzoate, Styrene/Acrylates Copolymer, Dimethicone, Phenyl Trimethicone, Cetyl PEG/PPG-10/1 Dimethicone, Polyhydroxystearic Acid, Glycerin, Dipropylene Glycol Dibenzoate, Cetyl Dimethicone, Silica, *Chrysanthemum parthenium* (Feverfew) Flower/Leaf/Stem Juice, Glyceryl Behenate, Phenethyl Alcohol, Caprylyl Glycol, Acrylates/Dimethicone Copolymer, PPG-15 Stearyl Ether Benzoate, Sodium Chloride, Phenoxyethanol, Chlorphenesin

Production Example 90. SPF 50 Lotion (Zinc Oxide)

Active Ingredient
    Zinc Oxide 21.6% (Sunscreen)
Inactive Ingredient
    Water, C12-15 Alkyl Benzoate, Octyldodecyl Citrate Crosspolymer, Styrene/Acrylates Copolymer, Phenyl Trimethicone, Cetyl PEG/PPG-10/1 Dimethicone, Dimethicone, Polyhydroxystearic Acid, Glycerin, Ethyl Methicone, Cetyl Dimethicone, Silica, Colloidal Oatmeal, Tocopheryl Acetate, *Chrysanthemum parthenium* (Feverfew) Flower/Leaf/Stem Juice, Glyceryl Behenate, Phenethyl Alcohol, Caprylyl Glycol, Cetyl Dimethicone/Bis-Vinyldimethicone Crosspolymer, Acrylates/Dimethicone Copolymer, Sodium Chloride, Phenoxyethanol, Chlorphenesin

Production Example 91. SPF 100 Lotion (Avobenzone, Homosalate, Octisalate, Octocrylene, and Oxybenzone)

Active Ingredient
    Avobenzone 3% (Sunscreen)
    Homosalate 15% (Sunscreen)
    Octisalate 5% (Sunscreen)

Octocrylene 10% (Sunscreen)
Oxybenzone 6% (Sunscreen)

Inactive Ingredient

Water, Styrene/Acrylates Copolymer, Silica, Beeswax, *Glycine soja* (Soybean) Seed Extract, Cyclopentasiloxane, Glyceryl Stearate, PEG-100 Stearate, Ethylhexylglycerin, Acrylates/Dimethicone Copolymer, Tocopherol, Caprylyl Glycol, Acrylates/C10-30 Alkyl Acrylate Crosspolymer, Chlorphenesin, Triethanolamine, Disodium EDTA, Dipotassium Glycyrrhizate, BHT, *Chrysanthemum parthenium* (Feverfew) Leaf/Flower/Stem Juice, Methylisothiazolinone, Diethylhexyl 2,6-Naphthalate, Fragrance Production Example 92. SPF 100 Lotion
(Avobenzone, Homosalate, Octisalate, Octocrylene, and Oxybenzone)

Active Ingredient
Avobenzone 3% (Sunscreen)
Homosalate 15% (Sunscreen)
Octisalate 5% (Sunscreen)
Octocrylene 10% (Sunscreen)
Oxybenzone 6% (Sunscreen)

Inactive Ingredient

Water, Styrene/Acrylates Copolymer, Silica, Beeswax, *Glycine soja* (Soybean) Seed Extract, Cyclopentasiloxane, Glyceryl Stearate, PEG-100 Stearate, Ethylhexylglycerin, Acrylates/Dimethicone Copolymer, Tocopherol, Caprylyl Glycol, Acrylates/C10-30 Alkyl Acrylate Crosspolymer, Chlorphenesin, Triethanolamine, Disodium EDTA, Dipotassium Glycyrrhizate, BHT, *Chrysanthemum parthenium* (Feverfew) Leaf/Flower/Stem Juice, Methylisothiazolinone, Diethylhexyl 2,6-Naphthalate Production Example 93. SPF 70 Lotion
(Avobenzone, Homosalate, Octisalate, Octocrylene, and Oxybenzone)

Active Ingredient
Avobenzone 3% (Sunscreen)
Homosalate 15% (Sunscreen)
Octisalate 5% (Sunscreen)
Octocrylene 4% (Sunscreen)
Oxybenzone 5% (Sunscreen)

Inactive Ingredient

Acrylates/C10-30 Alkyl Acrylate Crosspolymer, Acrylates/Dimethicone Copolymer, dipic Acid/Dietylene Glycol/Glycerin Crosspolymer, Artemia Extract, Beeswax, Benzyl Alcohol, BHT, Bisabolol, Cyclopentasiloxane, Diethylhexyl 2,6-Naphthalate, Dipotassium Glycyrrhizate, Disodium EDTA, Ethylhexylglycerin, Ethylparaben, Glycerin, Glyceryl Stearate, Methylisothiazolinone, Methylparaben, Octadecene/MA Copolymer, PEG-100 Stearate, Propylparaben, *Saccharomyces*/Calcium Ferment, *Saccharomyces*/Magnesium Ferment, *Saccharomyces*/Potassium Ferment, *Saccharomyces*/Sodium Ferment, *Saccharomyces*/Zinc Ferment, Silica, Triethanolamine, Water Production Example 94. SPF 25 Cream
(Avobenzone, Homosalate, Octisalate, and Octocrylene)

Active Ingredient
Avobenzone 2% (Sunscreen)
Homosalate 4% (Sunscreen)
Octisalate 4% (Sunscreen)
Octocrylene 2% (Sunscreen)

Inactive Ingredient

Water, Propylene Glycol, Glycerin, Dimethicone, Steareth-2, Ethylhexyl Palmitate, Isononyl Isononanoate, *Butyrospermum parkii* (Shea) Butter, Styrene/Acrylates Copolymer, Methyl Methacrylate Crosspolymer, Steareth-21, Hexylresorcinol, Behenyl Alcohol, Bisabolol, Ascorbyl Glucoside, Anhydroxylitol, Xylitol, Xylitylglucoside, Dimethicone Crosspolymer, Caprylyl Glycol, Ammonium Acryloyldimethyltaurate VP Copolymer, *Sclerotium* Gum, Disodium EDTA, Sodium Hydroxide, Mica, Titanium Dioxide, Methylparaben, Propylparaben, Ethylparaben, Phenoxyethanol, Fragrance Production Example 95. SPF 15 Lotion
(Avobenzone, Octinoxate, and Octisalate)

Active Ingredient
Avobenzone 3% (Sunscreen)
Octisalate 7.5% (Sunscreen)
Octocrylene 2% (Sunscreen)

Inactive Ingredient

Water, C12-15 Alkyl Benzoate, Cetearyl Alcohol, Dimethicone, Trisiloxane, Glycerin, Arachidyl Alcohol, Phenyl Trimethicone, Cetearyl Glucoside, Phenoxyethanol, Ethylene/Acrylic Acid Copolymer, Benzyl Alcohol, Propylene Glycol, Behenyl Alcohol, Steareth-2, Sodium Cocoyl Amino Acids, Butylene Glycol, Fragrance, Steareth-21, Polyacrylamide, Arachidyl Glucoside, Disodium EDTA, *Chrysanthemum parthenium* (Feverfew) Flower/Leaf/Stem juice, Chlorphenesin, Acrylates/C10-30 Alkyl Acrylate Crosspolymer, Propyl paraben, C13-14 Isoparaffin, Ethylparaben, Pentaerythrityl Tetra-di-t-butyl Hydroxyhydrocinnamate, Sarcosine, Laureth-7, *Artemisia abrotanum* Flower/Leaf/Stem Extract, Sodium Hydroxide, *Chamomilla recutita* (*Matricaria*) Flower Extract, Potassium Aspartate, Magnesium Aspartate, *Codium Tomentosum* Extract Production Example 96. SPF 30 Lotion
(Avobenzone, Homosalate, Octisalate, Octocrylene, and Oxybenzone)

Active Ingredient
Avobenzone 3% (Sunscreen)
Homosalate 8% (Sunscreen)
Octisalate 5% (Sunscreen)
Octocrylene 4% (Sunscreen)
Oxybenzone 4% (Sunscreen)

Inactive Ingredient water, silica, dimethicone, potassium cetyl phosphate, benzyl alcohol, beeswax, glyceryl stearate, PEG-100 stearate, caprylyl methicone, cetyl dimethicone, caprylyl glycol, etylhexylglycerin, dimethicone/PEG-10/15 crosspolymer, sodium polyacrylate, behenyl alcohol, xanthan gum, acrylates/C12-22 alkyl methacrylatecopolymer, ethylhexyl stearate, chlorphenesin, disodium EDTA, fragrance, diethylhexyl 2,6-naphthalate, BHT, trideceth-6

Production Example 97. SPF 55 Lotion
(Avobenzone, Homosalate, Octisalate, Octocrylene, and Oxybenzone)

Active Ingredient
Avobenzone 3% (Sunscreen)
Homosalate 10% (Sunscreen)
Octisalate 5% (Sunscreen)
Octocrylene 2.8% (Sunscreen)
Oxybenzone 6% (Sunscreen)

Inactive Ingredient
Butyloctyl salicylate, caprylyl Methicone, Behenyl Alcohol, VP/hexadecene copolymer, BHT, Methylparaben, trimethylsiloxysilicate, Propylparaben, Diethylhexyl 2,6-Naphthalate, Dimethicone, sodium polyacrylate, Disodium EDTA, Ethylhexyl Stearate, Ethylhexylglycerin, Fragrance, Glyceryl Stearate, PEG-100 Stearate, Phenoxyethanol, Silica, Ethylparaben, Iodopropynyl butylcarbamate, Trideceth-6, Water, Xanthan Gum

Production Example 98. SPF 100 Lotion
(Avobenzone, Homosalate, Octisalate, Octocrylene, and Oxybenzone)

Active Ingredient
- Avobenzone 3% (Sunscreen)
- Homosalate 15% (Sunscreen)
- Octisalate 5% (Sunscreen)
- Octocrylene 10% (Sunscreen)
- Oxybenzone 6% (Sunscreen)

Inactive Ingredient
Water, Styrene/Acrylates Copolymer, Silica, Beeswax, Cyclopentasiloxane, Ethyl hexyl glycerin, Glyceryl Stearate, PEG-100 Stearate, Acrylates/Dimethicone Copolymer, Acrylates/C10-30 Alkyl Acrylate Crosspolymer, Fragrance, Chlorphenesin, Triethanolamine, Diethylhexyl 2,6-Naphthalate, Dipotassium Glycyrrhizate, Disodium EDTA, BHT, Methylisothiazolinone

Production Example 99. SPF 45 Lotion
(Avobenzone, Homosalate, Octisalate, Octocrylene, and Oxybenzone)

Active Ingredient
- Avobenzone 3% (Sunscreen)
- Homosalate 10% (Sunscreen)
- Octisalate 5% (Sunscreen)
- Octocrylene 2.8% (Sunscreen)
- Oxybenzone 6% (Sunscreen)

Inactive Ingredient
water, butyloctyl salicylate, styrene/acrylates copolymer, silica, diethylhexyl 2,6-naphthalate, VP/hexadecene copolymer, dimethicone, caprylyl methicone, phenoxyethanol, ethylhexylglycerin, glyceryl stearate, PEG-100 stearate, trimethylsiloxysilicate, sodium polyacrylate, methylparaben, behenyl alcohol, xanthan gum, propylparaben, ethylparaben, fragrance, disodium EDTA, BHT, iodopropynyl butylcarbamate

Production Example 100. SPF 55 Lotion
(Avobenzone, Homosalate, Octisalate, Octocrylene, and Oxybenzone)

Active Ingredient
- Avobenzone 3% (Sunscreen)
- Homosalate 10% (Sunscreen)
- Octisalate 5% (Sunscreen)
- Octocrylene 2.8% (Sunscreen)
- Oxybenzone 6% (Sunscreen)

Inactive Ingredient
water, butyloctyl salicylate, styrene/acrylates copolymer, silica, diethylhexyl 2,6-naphthalate, VP/hexadecene copolymer, dimethicone, caprylyl methicone, phenoxyethanol, ethyl glyceryl stearate, PEG-100 stearate, trimethylsiloxysilicate, sodium polyacrylate, methylparaben, behenyl alcohol, xanthan gum, propylparaben, ethylparaben, fragrance, disodium EDTA, BHT, iodopropynyl butylcarbamate

Production Example 101. SPF 70 Lotion

Active Ingredient
- Avobenzone 3% (Sunscreen)
- Homosalate 15% (Sunscreen)
- Octisalate 5% (Sunscreen)
- Octocrylene 2.8% (Sunscreen)
- Oxybenzone 6% (Sunscreen)

Inactive Ingredient
water, styrene/acrylates copolymer, silica, diethylhexyl 2,6-naphthalate, beeswax, caprylyl methicone, cetyl dimethicone, ethylhexylglycerin, glyceryl stearate, PEG-100 stearate, sodium polyacrylate, acrylates/C12-22 alkyl methacrylate copolymer, dimethicone, xanthan gum, trimethylsiloxysilicate, disodium EDTA, fragrance, dipotassium glycyrrhizate, BHT, methylisothiazolinone, polyaminopropyl biguanide

Production Example 102. SPF 85 Lotion
(Avobenzone, Homosalate, Octisalate, Octocrylene, and Oxybenzone)

Active Ingredient
- Avobenzone 3% (Sunscreen)
- Homosalate 15% (Sunscreen)
- Octisalate 5% (Sunscreen)
- Octocrylene 4.5% (Sunscreen)
- Oxybenzone 6% (Sunscreen)

Inactive Ingredient
water, butyloctyl salicylate, silica, beeswax, styrene/acrylates copolymer, ethylhexylglycerin, glyceryl stearate, PEG-100 stearate, acrylates/C10-30 alkyl acrylate crosspolymer, triethanolamine, cyclopentasiloxane, acrylates/C12-22 alkyl methacrylate copolymer, acrylates/dimethicone copolymer, chlorphenesin, fragrance, diethylhexyl 2,6-naphthalate, dipotassium glycyrrhizate, disodium EDTA, BHT, methylisothiazolinone

Production Example 103. SPF 70 Liquid
(Avobenzone, Homosalate, Octisalate, Octocrylene, and Oxybenzone)

Active Ingredient
- Avobenzone 3% (Sunscreen)
- Homosalate 10% (Sunscreen)
- Octisalate 5% (Sunscreen)
- Octocrylene 7.5% (Sunscreen)
- Oxybenzone 5% (Sunscreen)

Inactive Ingredient
Acrylates/Dimethicone Copolymer, Ascorbic Acid, BHT, Bisabolol, Butylene Glycol, C12-15 Alkyl Benzoate, *Camellia oleifera* Leaf Extract, Caprylyl Glycol, Cetyl Dimethicone, Chlorphenesin, Cyclopentasiloxane, Diethylhexyl 2,6-Naphthalate, Disodium EDTA, Ethylhexylglycerin, Fragrance, Mannan, Pantothenic Acid, Pentylene Glycol, Phenoxyethanol, Polyester-7, Polymethyl Methacrylate, *Portulaca oleracea* Extract, Retinyl Palmitate, Silica, Steareth-100, Steareth-2, Styrene/Acrylates Copolymer, Tocopheryl Acetate, Water, Xanthan Gum Production Example 104. SPF 45 Lotion
(Avobenzone, Homosalate, Octisalate, Octocrylene, and Oxybenzone)

Active Ingredient
 Avobenzone 3% (Sunscreen)
 Homosalate 4% (Sunscreen)
 Octisalate 5% (Sunscreen)
 Octocrylene 4% (Sunscreen)
 Oxybenzone 5% (Sunscreen)
Inactive Ingredient
 Acrylates/C10-30 Alkyl Acrylate Crosspolymer, Acrylates/Dimethicone Copolymer, Beeswax, Benzyl Alcohol, Caprylyl Glycol, Cetyl Dimethicone/Bis-Vinyldimethicone Crosspolymer, Chlorphenesin, Diethylhexyl 2,6-Naphthalate, Dimethicone, Dipotassium Glycyrrhizate, Disodium EDTA, Ethyl Methicone, Ethylhexylglycerin, Fragrance, Glyceryl Behenate, Glyceryl Dibehenate, Glyceryl Stearate, *Nelumbo nucifera* Flower Wax, Octyldodecyl Citrate Crosspolymer, *Oryza sativa* (Rice) Starch, PEG-100 Stearate, Phenoxyethanol, Silica, Tribehenin, Triethanolamine, Water Production Example 105. SPF 30 Lotion
(Homosalate, Octinoxate, Octisalate and Titanium Dioxide)

Active Ingredient
 Homosalate 5% (Sunscreen)
 Octinoxate 7.5% (Sunscreen)
 Octisalate 5% (Sunscreen)
 Titanium dioxide 2.3% (Sunscreen)
Inactive Ingredient
 Alumina, Aluminum Stearate, Bisabolol, Butylene Glycol, Caprylyl Glycol, Cetearyl Alcohol, Cetearyl Glucoside, *Tanacetum parthenium* (Feverfew) Leaf/Flower/Stem Juice, Glyceryl Stearate, Hexylene Glycol, Hydrogenated Palm Glycerides, Hydrogenated Palm Kernel Glycerides, Hydroxyethyl Acrylate/Sodium Acryloyldimethyl Taurate Copolymer, Hydroxyethylcellulose, Isohexadecane, Magnesium Aluminum Silicate, Methylisothiazolinone, PEG-100 Stearate, Phenyl Trimethicone, Polyhydroxystearic Acid, Polysorbate 20, Polysorbate 60, PPG-3 Myristyl Ether Neoheptanoate, Silica, Tetrasodium EDTA, Triethylhexanoin, Water, Xanthan Gum Production Example 106. SPF 30 Lotion
(Avobenzone, Homosalate, Octisalate, and Octocrylene)

Active Ingredient
 Avobenzone 2% (Sunscreen)
 Homosalate 4% (Sunscreen)
 Octisalate 4% (Sunscreen)
 Octocrylene 2% (Sunscreen)
Inactive Ingredient
 Water, Propylene Glycol, Glycerin, Isononyl Isononanoate, Dimethicone, Steareth-2, Ethylhexyl Palmitate, Styrene/Acrylates Copolymer, *Butyrospermum parkii* (Shea) Butter, Vinyl Dimethicone/Methicone Silsesquioxane Crosspolymer, Hexylresorcinol, Steareth-21, Behenyl Alcohol, Phenoxyethanol, Dimethicone Crosspolymer, Ammonium Acryloyldimethyltaurate VP Copolymer, Ascorbyl Glucoside, Fragrance, *Sclerotium* Gum, Chlorphenesin, Disodium EDTA, Tocopheryl Acetate, Maltodextrin, Ethylhexylglycerin, Sodium Hydroxide, Butylene Glycol, *Peucedanum graveolens* (Dill) Extract, *Rubus fruticosus* (Blackberry) Leaf Extract, Xanthan Gum Production Example 107. SPF 30 Lotion
(Avobenzone, Homosalate, Octisalate, and Octocrylene)

Active Ingredient
 Avobenzone 1.5% (Sunscreen)
 Homosalate 5% (Sunscreen)
 Octisalate 4% (Sunscreen)
 Octocrylene 6% (Sunscreen)
Inactive Ingredient
 Water, Caprylyl Methicone, Glycerin, Methyl Methacrylate Crosspolymer, Sodium Acryloyldimethyltaurate/VP Crosspolymer, Chlorphenesin, Phenoxyethanol, Hexylresorcinol, Pentylene Glycol, Glyceryl Stearate, Polyacrylate-13, Steareth-21, Fragrance, Tocopheryl Acetate, Ascorbyl Glucoside, Polyisobutene, Maltodextrin, Disodium EDTA, *Ilex paraguariensis* Leaf Extract, Sodium Hydroxide, Polysorbate 20, Butylene Glycol, *Moringa oleifera* Seed Extract, *Rubus fruticosus* (Blackberry) Leaf Extract, *Peucedanum graveolens* (Dill) Extract, Xanthan Gum Production Example 108. SPF 15 Lotion
(Avobenzone, Octisalate, Octocrylene, and Oxybenzone)

Active Ingredient
 Avobenzone 3% (Sunscreen)
 Homosalate 5% (Sunscreen)
 Octisalate 1.7% (Sunscreen)
 Octocrylene 3% (Sunscreen)
Inactive Ingredient
 Water, Glycerin, Distearyldimonium Chloride, C12-15 Alkyl Benzoate, Cetyl Alcohol, Diethylhexyl 2,6-Naphthalate, Dimethicone, *Avena sativa* (Oat) Kernel Flour, Methylparaben, Steareth-21, Disodium EDTA, Benzalkonium Chloride Production Example 109. SPF 30 Cream (Titanium Dioxide and Zinc Oxide)

Active Ingredient
 Titanium Dioxide 4.3% (Sunscreen)
 Zinc Oxide 3% (Sunscreen)
Inactive Ingredient
 Water, C12-15 Alkyl Benzoate, Cetyl Dimethicone, Styrene/Acrylates Copolymer, Trisiloxane, Dimethicone, PEG-8, Beeswax, Dimethylimidazolidinone Rice Starch, Polyamide-5, Butylene Glycol, Ethylhexylglycerin, Glyceryl Stearate, PEG-100 Stearate, Benzyl Alcohol, Arachidyl Alcohol, Polyhydroxystearic Acid, Caprylyl Glycol, Glycerin, Pentylene Glycol, Behenyl Alcohol, Dipropylene Glycol Dibenzoate, Xanthan Gum, Triethoxycaprylylsilane, Citric Acid, Bisabolol, Acrylates/Dimethicone Copolymer, Arachidyl Glucoside, Chlorphenesin, Hydroxyethyl Acrylate/Sodium Acryloyldimethyl Taurate Copolymer, PPG-15 Stearyl Ether Benzoate, Squalane, Dipotassium Glycyrrhizate, Polyaminopropyl Biguanide, Sodium Citrate, Hydroxyphenyl Propamidobenzoic Acid, Polysorbate 60, *Avena sativa* (Oat) Kernel Extract

Production Example 110. SPF 30 Lotion
(Avobenzone, Homosalate, Octisalate, Octocrylene, and Oxybenzone)

Active Ingredient
 Avobenzone 3% (Sunscreen)
 Homosalate 12% (Sunscreen)
 Octisalate 5% (Sunscreen)
 Octocrylene 1.7% (Sunscreen)
 Oxybenzone 3% (Sunscreen)
Inactive Ingredient
 Water, C12-15 Alkyl Benzoate, Glycerin, Silica, Dimethicone, Tetrahydroxypropyl Ethylenediamine, Diethylhexyl 2,6-Naphthalate, Cetearyl Alcohol, Cetearyl Glucoside, Aluminum Starch Octenylsuccinate, Cyclopentasiloxane, Phenoxyethanol, Steareth-2, Steareth-21, Citric Acid, Dimethicone/Vinyl Dimethicone Crosspolymer, Polyacrylamide, Methylparaben, Fragrance, Arachidyl Alcohol, C13-14 Isoparaffin, Disodium EDTA, Behenyl Alcohol, Acrylates/C10-30 Alkyl Acrylate Crosspolymer, Pentaerythrityl Tetra-di-t-butyl Hydroxyhydrocinnamate, Arachidyl Glucoside, Ethylparaben, Laureth-7, Propylparaben, Benzalkonium Chloride, Boron Nitride, Algae Extract, Hydrolyzed Wheat Protein, *Ganoderma lucidum* (Mushroom) Stem Extract, *Lentinus edodes* Extract, Sodium Hydroxide

Production Example 111. SPF 15 Lotion
(Avobenzone, Octinoxate, and Octisalate)

Active Ingredient
 Avobenzone 3% (Sunscreen)
 Octinoxate 7.5% (Sunscreen)
 Octisalate 2% (Sunscreen)
Inactive Ingredient
 Water, C12-15 Alkyl Benzoate, Cetearyl Alcohol, Dimethicone, *Glycine Soja* (Soybean) Seed Extract, Phenyl Trimethicone, Glycerin, Arachidyl Alcohol, Cetearyl Glucoside, Phenoxyethanol, Benzyl Alcohol, Panthenol, Ethylene/Acrylic Acid Copolymer, Behenyl Alcohol, Steareth-2, Fragrance, Steareth-21, Polymethyl Methacrylate, Polyacrylamide, Arachidyl Glucoside, Disodium EDTA, C13-14 Isoparaffin, Laureth-7, Silica, Benzalkonium Chloride, Iodopropynyl Butylcarbamate, BHT, Sodium Hydroxide, Citric Acid, Titanium Dioxide, Mica

Production Example 112. SPF 30 Lotion
(Avobenzone, Homosalate, Octisalate, Octocrylene, and Oxybenzone)

Active Ingredient
 Avobenzone 3% (Sunscreen)
 Homosalate 12% (Sunscreen)
 Octisalate 5% (Sunscreen)
 Octocrylene 1.7% (Sunscreen)
 Oxybenzone 3% (Sunscreen)
Inactive Ingredient
 Water, C12-15 Alkyl Benzoate, Dimethicone, Cetearyl Alcohol, *Glycine Soja* (Soybean) Seed Extract, Diethylhexyl 2,6-Naphthalate, Glycerin, Ethylene/Acrylic Acid Copolymer, Phenoxyethanol Phenyl Trimethicone, Silica, Panthenol, Arachidyl Alcohol, Aluminum Starch Octenylsuccinate, Cetearyl Glucoside, Methylparaben, Steareth-2, Fragrance, Polyacrylate-13, Behenyl Alcohol, Steareth-21, Polymethyl Methacrylate, Disodium EDTA, Polyisobutene, Arachidyl Glucoside, Pentaerythrityl Tetra-di-t-butyl Hydroxyhydrocinnamate, Propylparaben, Ethylparaben, Benzalkonium Chloride, Polysorbate 20, Boron Nitride, Titanium Dioxide, Mica

Production Example 113. SPF 30 Lotion
(Avobenzone, Homosalate, Octisalate, and Octocrylene)

Active Ingredient
 Avobenzone 1.5% (Sunscreen)
 Homosalate 5% (Sunscreen)
 Octisalate 4% (Sunscreen)
 Octocrylene 6% (Sunscreen)
Inactive Ingredient
 Water, Caprylyl Methicone, Glycerin, Methyl Methacrylate Crosspolymer, *Glycine soja* (Soybean) Seed Extract, Sodium Acryloyldimethyltaurate/VP Crosspolymer, Pentylene Glycol, Hydroxyacetophenone, Fragrance, Phenoxyethanol, Glyceryl Stearate, Polyacrylate-13, Chlorphenesin, Tocopheryl Acetate, Steareth-21, Polyisobutene, Disodium EDTA, Silica, Polysorbate 20, Sodium Hydroxide, Titanium Dioxide, Mica

Production Example 114. SPF 70 Cream
(Avobenzone, Homosalate, Octisalate, Octocrylene, and Oxybenzone)

Active Ingredient
 Avobenzone 3% (Sunscreen)
 Homosalate 15% (Sunscreen)
 Octisalate 5% (Sunscreen)
 Octocrylene 10% (Sunscreen)
 Oxybenzone 6% (Sunscreen)
Inactive Ingredient
 Water, Styrene/Acrylates Copolymer, Silica, Dimethicone, Benzyl Alcohol, Glycerin, Ethylhexylglycerin, Glyceryl Stearate, PEG-100 Stearate, Beeswax, Acrylates/Dimethicone Copolymer, Behenyl Alcohol, Phenoxyethanol, Caprylyl Glycol, Acrylates/C10-30 Alkyl Acrylate Crosspolymer, Chlorphenesin, Propylene Glycol, Sodium Hydroxide, Diethylhexyl 2,6-Naphthalate, Disodium EDTA, Fragrance, *Avena sativa* (Oat) Kernel Flour, *Avena sativa* (Oat) Kernel Extract, *Codium tomentosum* Extract, Hydrolyzed Oat Protein, Potassium Palmitoyl Hydrolyzed Oat Protein

Production Example 115. SPF 30 Lotion
(Avobenzone, Homosalate, Octisalate, Octocrylene, and Oxybenzone)

Active Ingredient
 Avobenzone 3% (Sunscreen)
 Homosalate 8% (Sunscreen)
 Octisalate 4% (Sunscreen)
 Octocrylene 4% (Sunscreen)
 Oxybenzone 5% (Sunscreen)
Inactive Ingredient
 Water, Glycerin, Silica, Cetyl Dimethicone, Dimethicone, Beeswax, Benzyl Alcohol, Ethylhexylglycerin, Glyceryl Stearate, PEG-100 Stearate, Behenyl Alcohol, Phenoxyethanol, Caprylyl Methicone, Caprylyl Glycol, Acrylates/Dimethicone Copolymer, Acrylates/C10-30 Alkyl Acrylate Crosspolymer, Propylene Glycol, Chlorphenesin, Diethylhexyl 2,6-Naphthalate, Disodium EDTA, Sodium Hydroxide, Fragrance, *Avena sativa* (Oat) Kernel Flour, *Avena* sativa (Oat) Kernel Extract, *Codium tomentosum* Extract, Hydrolyzed Oat Protein, Potassium Palmitoyl Hydrolyzed Oat Protein

Production Example 116. SPF 50 Cream
(Avobenzone, Homosalate, Octisalate, Octocrylene, and Oxybenzone)

Active Ingredient
  Avobenzone 3% (Sunscreen)
  Homosalate 10% (Sunscreen)
  Octisalate 5% (Sunscreen)
  Octocrylene 6% (Sunscreen)
  Oxybenzone 5% (Sunscreen)
Inactive Ingredient
  Water, Glycerin, Silica, Cetyl Dimethicone, Dimethicone, Beeswax, Benzyl Alcohol, Ethylhexylglycerin, Glyceryl Stearate, PEG-100 Stearate, Behenyl Alcohol, Phenoxyethanol, Caprylyl Methicone, Caprylyl Glycol, Acrylates/Dimethicone Copolymer, Acrylates/C10-30 Alkyl Acrylate Crosspolymer, Propylene Glycol, Chlorphensin, Diethylhexyl 2,6-Naphthalate, Disodium EDTA, Sodium Hydroxide, Fragrance, *Avena sativa* (Oat) Kernel Flour, *Avena sativa* (Oat) Kernel Extract, *Codium tomentosum* Extract, Hydrolyzed Oat Protein, Potassium Palmitoyl Hydrolyzed Oat Protein

Production Example 117. SPF 30 Lotion
(Avobenzone, Homosalate, Octisalate, Octocrylene, and Oxybenzone)

Active Ingredient
  Avobenzone 3% (Sunscreen)
  Homosalate 12% (Sunscreen)
  Octisalate 5% (Sunscreen)
  Octocrylene 1.7% (Sunscreen)
  Oxybenzone 3% (Sunscreen)
Inactive Ingredient
  Water, Octyldodecyl Neopentanoate, Glycerin, Butylene Glycol, Cetyl Alcohol, Potassium Cetyl Phosphate, Phenoxyethanol, Silica, Candelilla/Jojoba/Rice Bran Polyglyceryl-3 Esters, Glyceryl Stearate, Microcrystalline Cellulose, Fragrance, Hydrolyzed *Caesalpinia spinosa* Gum, Cetearyl Alcohol, Sodium Stearoyl Lactylate, Magnesium Aluminum Silicate, Chlorphenesin, Sodium PCA, Urea, Cetyl Hydroxyetylcellulose, *Artemisia abrotanum* Extract, Panthenol, Tocopheryl Acetate, Sodium Ascorbyl Phosphate, Retinyl Palmitate, Disodium EDTA, Etylhexylglycerin, *Caesalpinia spinosa* Gum, Trehalose, Cellulose Gum, Polyquaternium-51, Triacetin, Sodium Hyaluronate, Sodium Hydroxide, Citric Acid

Production Example 118. SPF 15 Lotion
(Avobenzone, Octinoxate, and Octisalate)

Active Ingredient
  Avobenzone 3% (Sunscreen)
  Octinoxate 7.5% (Sunscreen)
  Octisalate 2% (Sunscreen)
Inactive Ingredient
  Water, C12-15 Alkyl Benzoate, Cetearyl Alcohol, Dimethicone, Cyclopentasiloxane, Glycerin, Arachidyl Alcohol, Phenyl Trimethicone, Phenoxyethanol, Cyclohexasiloxane, Cetearyl Glucoside, Benzyl Alcohol, Panthenol, Et ylene/Acrylic Acid Copolymer, Sodium Cocoyl Amino Acids, Behenyl Alcohol, Steareth-2, Steam-21, Fragrance, Polyacrylamide, Arachidyl Glocoside, Disodium EDTA, Methylparaben, C13-14 Isoparaffin, *Chrysanthemum parthenium* (Feverfew) Flower/Leaf/Stem Juice, Pentaerythrityl Tetra-di-t-butyl Hydroxyhydrocinnamate, C12-16 Alkyl PEG-2 Hydroxypropyl Hydroxyethyl Ethylcellulose, Propylparaben, Sarcosine, Ethylparaben, Laureth-7, Iodopropynyl Butylcarbamate, Potassium Aspartate, Magnesium Aspartate

Production Example 119. SPF 50 Lotion (Zinc Oxide)

Active Ingredient
  Zinc oxide 21.6% (Sunscreen)
Inactive Ingredient
  Water, C12-15 Alkyl Benzoate, Styrene/Acrylates Copolymer, Octyldodecyl Citrate Crosspolymer, Phenyl Trimethicone, Cetyl PEG/PPG-10/1 Dimethicone, Dimethicone, Polyhydroxystearic Acid, Glycerin, Ethyl Methicone, Silica, Cetyl Dimethicone, Triethoxycaprylylsilane, Phenoxyethanol, Glyceryl Behenate, Sodium Chloride, Acrylates/Dimethicone Copolymer, Chlorphenesin, Phenethyl Alcohol, *Avena sativa* (Oat) Kernel Flour, Caprylyl Glycol, Cetyl Dimethicone/Bis-Vinyldimethicone Crosspolymer, *Chrysanthemum parthenium* (Feverfew) Flower/Leaf/Stem Juice

Production Example 120. SPF 50 Lotion (Zinc Oxide)

Active Ingredient
  Zinc oxide 21.6% (Sunscreen)
Inactive Ingredient
  Water, C12-15 Alkyl Benzoate, Styrene/Acrylates Copolymer, Octyldodecyl Citrate Crosspolymer, Phenyl Trimethicone, Cetyl PEG/PPG-10/1 Dimethicone, Dimethicone, Polyhydroxystearic Acid, Glycerin, Ethyl Methicone, Cetyl Dimethicone, Silica, Phenethyl Alcohol, Colloidal Oatmeal, *Chrysanthemum parthenium* Flower/Leaf/Stem Juice, Caprylyl Glycol, Glyceryl Behenate, Sodium Chloride, Acrylates/Dimethicone Copolymer, Cetyl Dimethicone/Bis-Vinyldimethicone Crosspolymer, Chlorphenesin, Phenoxyethanol.

Production Example 121. SPF 55 Cream
(Avobenzone, Homosalate, Octisalate, Octocrylene, and Oxybenzone)

Active Ingredient
  Avobenzone 3% (Sunscreen)
  Homosalate 10% (Sunscreen)
  Octisalate 5% (Sunscreen)
  Octocrylene 2.8% (Sunscreen)
  Oxybenzone 6% (Sunscreen)
Inactive Ingredient
  Water, Butyloctyl Salicylate, Styrene/Acrylates Copolymer, Silica, Diethylhexyl 2,6-Naphthalate, VP/Hexadecene Copolymer, Dimethicone, Phenoxyethanol, *Avena sativa* (Oat) Kernel Flour, Ethylhexylglycerin, Caprylyl Methicone, Glyceryl Stearate, PEG-100 Stearate, Trimethylsiloxysilicate, Sodium Polyacrylate, Ethylhexyl Stearate, Methylparaben, Behenyl Alcohol, Xanthan Gum, Propylparaben, Ethylparaben, Disodium EDTA, BHT, Trideceth-6

Production Example 122. SPF 30 Lotion (Avobenzone, Homosalate, Octisalate, and Octocrylene)

Active Ingredient
Avobenzone 1.5% (Sunscreen)
Homosalate 5% (Sunscreen)
Octisalate 4% (Sunscreen)
Octocrylene 6% (Sunscreen)
Inactive Ingredient
Water, Caprylyl Methicone, Glycerin, *Glycine soja* (Soybean) Seed Extract, Methyl Methacrylate Crosspolymer, Sodium Acryloyldimethyltaurate/VP Crosspolymer, Hydroxyacetophenone, Pentylene Glycol, Polyacrylate-13, Glyceryl Stearate, Phenoxyethanol, Fragrance, Chlorphenesin, Tocopheryl Acetate, Steareth-21, Polyisobutene, Disodium EDTA, Silica, Polysorbate 20, Sodium Hydroxide, Titanium Dioxide, Mica

Production Example 123. SPF 15 Lotion (Avobenzone, Octisalate, Octocrylene, and Oxybenzone)

Active Ingredient
Avobenzone 3% (Sunscreen)
Homosalate 5% (Sunscreen)
Octisalate 1.7% (Sunscreen)
Octocrylene 3% (Sunscreen)
Inactive Ingredient
Water, Glycerin, Distearyldimonium Chloride, C12-15 Alkyl Benzoate, Cetyl Alcohol, Diethylhexyl 2,6-Naphthalate, Dimethicone, *Avena sativa* (Oat) Kernel Flour, Methylparaben, Steareth-21, Disodium EDTA, Benzalkonium Chloride

Production Example 124. SPF 50 Lotion (Zinc Oxide)

Active Ingredient
Zinc oxide 21.6% (Sunscreen)
Inactive Ingredient
Water, C12-15 Alkyl Benzoate, Styrene/Acrylates Copolymer, Octyl dodecyl Citrate Crosspolymer, Phenyl Trimethicone, Cetyl PEG/PPG-10/1 Dimethicone, Dimethicone, Polyhydroxystearic Acid, Glycerin, Ethyl Methicone, Silica, Cetyl Dimethicone, Triethoxycaprylylsilane, Phenoxyethanol, Glyceryl Behenate, Sodium Chloride, Acrylates/Dimethicone Copolymer, Chlorphenesin, Phenethyl Alcohol, *Avena sativa* (Oat) Kernel Flour, Caprylyl Glycol, Cetyl Dimethicone/Bis-Vinyldimethicone Crosspolymer, *Chrysanthemum parthenium* (Feverfew) Flower/Leaf/Stem Juice

Production Example 125. SPF 50 Cream (Titanium Dioxide and Zinc Oxide)

Active Ingredient
Titanium Dioxide 6% (Sunscreen)
Zinc oxide 3% (Sunscreen)
Inactive Ingredient
Water, C12-15 Alkyl Benzoate, Cetyl Dimethicone, Styrene/Acrylates Copolymer, PEG-8, Beeswax, Dimethylimidazolidinone Rice Starch, Polyamide-5, Butylene Glycol, Ethylhexylglycerin, Glyceryl Stearate, PEG-100 Stearate, Benzyl Alcohol, Dimethicone, Polyhydroxystearic Acid, Arachidyl Alcohol, Caprylyl Glycol, Trisiloxane, Dipropylene Glycol Dibenzoate, Glycerin, Pentylene Glycol, Behenyl Alcohol, Triethoxycaprylylsilane, Xanthan Gum, Citric Acid, Bisabolol, Acrylates/Dimethicone Copolymer, Arachidyl Glucoside, PPG-15 Stearyl Ether Benzoate, Chlorphenesin, Hydroxyethyl Acrylate/Sodium Acryloyldimethyl Taurate Copolymer, Squalane, Dipotassium Glycyrrhizate, Polyaminopropyl Biguanide, Sodium Citrate, Hydroxyphenyl Propamidobenzoic Acid, Polysorbate 60, A vena Saliva (Oat) Kernel Extract

Production Example 126. SPF 90 Lotion (Avobenzone, Homosalate, Octisalate, Octocrylene, and Oxybenzone)

Active Ingredient
Avobenzone 3% (Sunscreen)
Homosalate 15% (Sunscreen)
Octisalate 5% (Sunscreen)
Octocrylene 10% (Sunscreen)
Oxybenzone 6% (Sunscreen)
Inactive Ingredient
Water, Styrene/Acrylates Copolymer, Silica, Beeswax, *Glycine soja* (Soybean) Seed Extract, Cyclopentasiloxane, Glyceryl Stearate, PEG-100 Stearate, Ethylhexylglycerin, Acrylates/Dimethicone Copolymer, Tocopherol, Caprylyl Glycol, Fragrance, Acrylates/C10-30 Alkyl Acrylate Crosspolymer, Triethanolamine, Algae Extract, Chlorphenesin, Disodium EDTA, Dipotassium Glycyrrhizate, BHT, *Ganoderma lucidum* (Mushroom) Stem Extract, *Lentinus edodes* Extract, *Chrysanthemum parthenium* (Feverfew) Flower/Leaf/Stem juice, Methylisothiazolinane, Diethylhexyl 2,6-Naphthalate

Production Example 127. SPF 55 Lotion (Avobenzone, Homosalate, Octisalate, Octocrylene, and Oxybenzone)

Active Ingredient
Avobenzone 3% (Sunscreen)
Homosalate 15% (Sunscreen)
Octisalate 5% (Sunscreen)
Octocrylene 2.8% (Sunscreen)
Oxybenzone 6% (Sunscreen)
Inactive Ingredient
Water, Styrene/Acrylates Copolymer, Silica, Diethylhexyl 2,6-Naphthalate, Beeswax, Caprylyl Methicone, Cetyl Dimethicone, Ethylhexylglycerin, Glyceryl Stearate, PEG-100 Stearate, Sodium Polyacrylate, Fragrance, Caprylyl Glycol, Acrylates/C12-22 Alkyl Methacrylate Copolymer, Ethylhexyl Stearate, Dimethicone, Xanthan Gum, Algae Extract, Trimethylsiloxysilicate, Disodium EDTA, *Tanacetum parthenium* (Feverfew) Leaf/Flower/Stem Juice, Dipotassium Glycyrrhizate, BHT, Trideceth-6, *Ganoderma lucidum* (Mushroom) Stem Extract, *Lentinus edodes* Extract, Polyaminopropyl Biguanide, Methylisothiazolinone, Tocopherol, *Glycine soja* (Soybean) Seed Extract

Production Example 128. SPF 50 Lotion (Zinc Oxide)

Active Ingredient
Zinc oxide 21.6% (Sunscreen)
Inactive Ingredient
Water, C12-15 Alkyl Benzoate, Dimethicone, Glycerin, Phenoxyethanol, Phenyl Trimethicone, Styrene/Acrylates copolymer, Octyl dodecyl Citrate Crosspolymer, Cetyl PEG/ PPG-10/1 Dimethicone, Polyhydroxystearic acid, Silica, Ethyl methicone, Cetyl Dimethicone, Triethoxycaprylylsilane, Glyceryl Behenate, Sodium Chloride, Acrylates/Dimethicone copolymer, Chlorphenesin, Phenethyl alcohol, *Avena sativa* (Oat) Kernel flour, Caprylyl Glycol, Cetyl Dimethicone/Bis-Vinyldimethicone Crosspolymer, *Chrysanthemum parthenium* (Feverfew) Flower/Leaf/Stem juice Production Example 129. SPF 15 Lotion
(Avobenzone, Octinoxate, and Octisalate)

Active Ingredient
  Avobenzone 3% (Sunscreen)
  Octinoxate 7.5% (Sunscreen)
  Octisalate 2% (Sunscreen)
Inactive Ingredient
  Water, C12-15 Alkyl Benzoate, Cetearyl Alcohol, Dimethicone, *Glycine soja* (Soyabean) Seed Extract, Phenyl Trimethicone, Glycerin, Arachidyl Alcohol, Cetearyl Glycoside, Phenoxyethanol, Benzyl Alcohol, Panthenol, Ethylene/Acrylic Acid Copolymer, Behenyl Alcohol, Steareth-2, Fragrance, Steareth-21, Polymethyl Methacrylate, Polyacrylamide, Arachidyl Glucoside, Disodium EDTA, C13-14 Isoparaffin, Laureth-7, Silica, Benzalkonium Chloride, Iodopropynyl Butylcarbamate, BHT, Sodium Hydroxide, Citric Acid, Titanium Dioxide, Mica Production Example 130. SPF 30 Cream
(Avobenzone, Homosalate, Octisalate, Octocrylene, and Oxybenzone)

Active Ingredient
  Avobenzone 3% (Sunscreen)
  Homosalate 12% (Sunscreen)
  Octisalate 5% (Sunscreen)
  Octocrylene 1.7% (Sunscreen)
  Oxybenzone 3% (Sunscreen)
Inactive Ingredient
  Water, C12-15 Alkyl Benzoate, *Glycine soja* (Soyabean) Seed Extract, Dimethicone, Cetearyl Alcohol, Diethylhexyl 2,6-Naphthalate, Glycerin, Ethylene/Acrylic Acid Copolymer, Phenoxyethanol, Phenyl Trimethicone, Silica, Panthenol, Arachidyl Alcohol, Cetearyl Glucoside, Methylparaben, Aluminum Starch Octenylsuccinate, Steareth-2, Fragrance, Polyacrylate-13, Behenyl Alcohol, Steareth-21, Polymethyl Methacrylate, Disodium EDTA, Arachidyl Glucoside, Polyisobutene, Pentaerythrityl Tetra-di-t-butyl Hydroxyhydrocinnamate, Ethylparaben, Propylparaben, Benzalkonium Chloride, Boron Nitride, Polysorbate 20, Titanium Dioxide, Mica Production Example 131. SPF 30 Lotion
(Avobenzone, Homosalate, Octisalate, Octocrylene, and Oxybenzone)

Active Ingredient
  Avobenzone 3% (Sunscreen)
  Homosalate 12% (Sunscreen)
  Octisalate 5% (Sunscreen)
  Octocrylene 1.7% (Sunscreen)
  Oxybenzone 3% (Sunscreen)
Inactive Ingredient
  Water, C12-15 Alkyl Benzoate, *Glycine soja* (Soyabean) Seed Extract, Dimethicone, Cetearyl Alcohol, Diethylhexyl 2,6-Naphthalate, Glycerin, Ethylene/Acrylic Acid Copolymer, Phenoxyethanol, Phenyl Trimethicone, Silica, Panthenol, Arachidyl Alcohol, Cetearyl Glucoside, Methylparaben, Aluminum Starch Octenylsuccinate, Steareth-2, Fragrance, Polyacrylate-13, Behenyl Alcohol, Steareth-21, Polymethyl Methacrylate, Disodium EDTA, Arachidyl Glucoside, Polyisobutene, Pentaerythrityl Tetra-di-t-butyl Hydroxyhydrocinnamate, Ethylparaben, Propylparaben, Benzalkonium Chloride, Boron Nitride, Polysorbate 20, Titanium Dioxide, Mica Production Example 132. SPF 30 Lotion
(Avobenzone, Homosalate, Octisalate, and Octocrylene)

Active Ingredient
  Avobenzone 1.5% (Sunscreen)
  Homosalate 5% (Sunscreen)
  Octisalate 4% (Sunscreen)
  Octocrylene 6% (Sunscreen)
Inactive Ingredient
  Water, Caprylyl Methicone, Glycerin, Methyl Methacrylate Crosspolymer, *Glycine soja* (Soybean) Seed Extract, Sodium Acryloyldimethyltaurate VP Crosspolymer, Pentylene Glycol, Hydroxyacetophenone, Fragrance, Phenoxyethanol, Glyceryl Stearate, Polyacrylate-13, Chlorphenesin, Tocopheryl Acetate, Steareth-21, Polyisobutene, Disodium EDTA, Silica, Polysorbate 20, Sodium Hydroxide, Titanium Dioxide, Mica Production Example 133. SPF 15 Lotion
(Avobenzone, Octinoxate, and Octisalate)

Active Ingredient
  Avobenzone 3% (Sunscreen)
  Octinoxate 7.5% (Sunscreen)
  Octisalate 2% (Sunscreen)
Inactive Ingredient
  Water, C12-15 Alkyl Benzoate, Cetearyl Alcohol, Dimethicone, *Glycine soja* (Soybean) Seed Extract, Phenyl Trimethicone, Glycerin, Arachidyl Alcohol, Cetearyl Glucoside, Phenoxyethanol, Benzyl Alcohol, Panthenol, Ethylene/Acrylic Acid Copolymer, Behenyl Alcohol, Steareth-2, Fragrance, Steareth-21, Polymethyl Methacrylate, Polyacrylamide, Arachidyl Glucoside, Disodium EDTA, C13-14 Isoparaffin, Laureth-7, Silica, Benzalkonium Chloride, Iodopropynyl Butylcarbamate, BHT, Sodium Hydroxide, Citric Acid, Titanium Dioxide, Mica Production Example 134. SPF 15 Cream
(Avobenzone, Octinoxate, and Octisalate)

Active Ingredient
  Avobenzone 3% (Sunscreen)
  Octinoxate 7.5% (Sunscreen)
  Octisalate 2% (Sunscreen)
Inactive Ingredient
  Water, C12-15 Alkyl Benzoate, Cetearyl Alcohol, Dimethicone, *Glycine soja* (Soybean) Seed Extract, Phenyl Trimethicone, Glycerin, Arachidyl Alcohol, Cetearyl Glucoside, Phenoxyethanol, Benzyl Alcohol, Panthenol, Ethylene/Acrylic Acid Copolymer, Behenyl Alcohol, Steareth-2, Fragrance, Steareth-21, Polymethyl Methacrylate, Polyacrylamide, Arachidyl Glucoside, Disodium EDTA, C13-14 Isoparaffin, Laureth-7, Silica, Benzalkonium Chloride, Iodopropynyl Butylcarbamate, BHT, Sodium Hydroxide, Citric Acid, Titanium Dioxide, Mica Production Example 135. SPF 30 Lotion
(Avobenzone, Homosalate, Octisalate, Octocrylene,
and Oxybenzone)

Active Ingredient
  Avobenzone 3% (Sunscreen)
  Homosalate 8% (Sunscreen)
  Octisalate 4% (Sunscreen)
  Octocrylene 4% (Sunscreen)
  Oxybenzone 5% (Sunscreen)
Inactive Ingredient
  Water, Glycerin, Silica, Cetyl Dimethicone, Dimethicone, Beeswax, Benzyl Alcohol, Ethylhexylglycerin, Glyceryl Stearate, PEG-100 Stearate, Behenyl Alcohol, Phenoxyethanol, Caprylyl Methicone, Caprylyl Glycol, Acrylates/Dimethicone Copolymer, Acrylates/C10-30 Alkyl Acrylate Crosspolymer, Propylene Glycol, Chlorphenesin, Diethylhexyl 2,6-Naphthalate, Disodium EDTA, Sodium Hydroxide, Fragrance, *Avena sativa* (Oat) Kernel Flour, *Avena sativa* (Oat) Kernel Extract, *Codium tomentosum* Extract, Hydrolyzed Oat Protein, Potassium Palmitoyl Hydrolyzed Oat Protein Production Example 136. SPF 50 Cream
(Avobenzone, Homosalate, Octisalate, Octocrylene,
and Oxybenzone)

Active Ingredient
  Avobenzone 3% (Sunscreen)
  Homosalate 10% (Sunscreen)
  Octisalate 5% (Sunscreen)
  Octocrylene 6% (Sunscreen)
  Oxybenzone 5% (Sunscreen)
Inactive Ingredient
  Water, Glycerin, Silica, Cetyl Dimethicone, Dimethicone, Beeswax, Benzyl Alcohol, Ethylhexylglycerin, Glyceryl Stearate, PEG-100 Stearate, Behenyl Alcohol, Phenoxyethanol, Caprylyl Methicone, Caprylyl Glycol, Acrylates/Dimethicone Copolymer, Acrylates/C10-30 Alkyl Acrylate Crosspolymer, Propylene Glycol, Chlorphensin, Diethylhexyl 2,6-Naphthalate, Disodium EDTA, Sodium Hydroxide, Fragrance, *Avena sativa* (Oat) Kernel Flour, *Avena sativa* (Oat) Kernel Extract, *Codium tomentosum* Extract, Hydrolyzed Oat Protein, Potassium Palmitoyl Hydrolyzed Oat Protein Production Example 137. SPF 70 Lotion
(Avobenzone, Homosalate, Octisalate, Octocrylene,
and Oxybenzone)

Active Ingredient
  Avobenzone 3% (Sunscreen)
  Homosalate 15% (Sunscreen)
  Octisalate 5% (Sunscreen)
  Octocrylene 6% (Sunscreen)
  Oxybenzone 6% (Sunscreen)
Inactive Ingredient
  Water, Styrene/Acrylates Copolymer, Silica, Dimethicone, Benzyl Alcohol, Glycerin, Ethylhexylglycerin, Glyceryl Stearate, PEG-100 Stearate, Beeswax, Acrylates/Dimethicone Copolymer, Behenyl Alcohol, Phenoxyethanol, Caprylyl Glycol, Acrylates/C10-30 Alkyl Acrylate Crosspolymer, Chlorphenesin, Propylene Glycol, Sodium Hydroxide, Diethylhexyl 2,6-Naphthalate, Disodium EDTA, Fragrance, *Avena sativa* (Oat) Kernel Flour, *Avena sativa* (Oat) Kernel Extract, *Codium tomentosum* Extract, Hydrolyzed Oat Protein, Potassium Palmitoyl Hydrolyzed Oat Protein Production Example 138. SPF 15 Lotion
(Avobenzone, Octinoxate, and Octisalate)

Active Ingredient
  Avobenzone 3% (Sunscreen)
  Octinoxate 7.5% (Sunscreen)
  Octisalate 2% (Sunscreen)
Inactive Ingredient
  Water, C12-15 Alkyl Benzoate, Cetearyl Alcohol, Dimethicone, Cyclopentasiloxane, Glycerin, Arachidyl Alcohol, Phenyl Trimethicone, Phenoxyethanol, Cyclohexasiloxane, Cetearyl Glucoside, Benzyl Alcohol, Panthenol, Ethylene/Acrylic Acid Copolymer, Behenyl Alcohol, Steareth-2, Sodium Cocoyl Amino Acids, Polyacrylamide, Fragrance, Steareth-21, Arachidyl Glucoside, Disodium EDTA, Methylparaben, C13-14 Isoparaffin, *Chrysanthemum parthenium* (Feverfew) Flower/Leaf/Stem Juice, Pentaerythrityl Tetra-di-t-butyl Hydroxyhydrocinnamate, Sarcosine, Laureth-7, Potassium Aspartate, Magnesium Aspartate Production Example 139. SPA 30 Lotion (Titanium
Dioxide and Zinc Oxide)

Active Ingredient
  Titanium Dioxide 4.3% (Sunscreen)
  Zinc Oxide 3% (Sunscreen)
Inactive Ingredient
  Water, C12-15 Alkyl Benzoate, Cyclopentasiloxane, Glycerin, Styrene/Acrylates Copolymer, Isopropyl Myristate, Cetyl Dimethicone, Octyldodecyl Neopentanoate, Glyceryl Behenate, PEG-100 Stearate, Glyceryl Stearate, Benzyl Alcohol, Aluminum Stearate, Arachidyl Alcohol, Ethylhexylglycerin, Polyhydroxystearic Acid, Caprylyl Glycol, Behenyl Alcohol, Alumina, Hydroxyethyl Acrylate/Sodium Acryloyldimethyl Taurate Copolymer, Xanthan Gum, Citric Acid, Methyldihydrojasmonate, Squalane, Arachidyl Glucoside, Dimethicone, Chlorphenesin, Triethoxycaprylylsilane, Dipropylene Glycol Dibenzoate, *Chrysanthemum parthenium* (Feverfew) Flower/Leaf/Stem Juice, PPG-15 Stearyl Ether Benzoate, Acrylates/Dimethicone Copolymer, Sodium Citrate, Polysorbate 60, Alpha-Isomethyl Ionone (and) Methyl Ionones, Ceramide NP, *Avena sativa* (Oat) Kernel Extract Production Example 140. SPF 15 Lotion
(Octinoxate and Zinc Oxide)

Active Ingredient
  Octinoxate 6.0% (Sunscreen)
  Zinc Oxide 3% (Sunscreen)
Inactive Ingredient
  Water, glycerin, isohexadecane, sodium hyaluronate, aloe barbadensis leaf extract, tocopheryl acetate, steareth-21, cyclopentasiloxane, polyacrylamide, stearyl alcohol, C13-14 isoparaffin, behenyl alcohol, fragrance, ethylhexyl salicylate, cetyl alcohol, DMDM hydantoin, PEG/PPG-20/20 dimethicone, laureth-7, steareth-2, disodium EDTA, triethoxycaprylylsilane, oleth-3 phosphate, iodopropynyl butylcarbamate.

Production Example 141. SPF 15 Lotion
(Avobenzone, Homosalate, Octisalate, and Octocrylene)

Active Ingredient
  Avobenzone 3.0% (Sunscreen)
  Homosalate 4.0% (Sunscreen)
  Octisalate 4.5% (Sunscreen)
  Octocrylene 2.6% (Sunscreen)
Inactive Ingredient
  water, glycerin, polyethylene, niacinamide, dimethicone, isopropyl isostearate, propylene glycol, panthenol, aloe barbadensis leaf extract, tocopheryl acetate, dimethiconol, hydroxyethyl acrylate/sodium acryloyldimethyl taurate copolymer, isohexadecane, titanium dioxide, stearyl alcohol, caprylyl glycol, behenyl alcohol, 1,2-hexanediol, phenoxyethanol, cetyl alcohol, PEG-100 stearate, polysorbate 60, sodium benzoate, cetearyl glucoside, cetearyl alcohol, fragrance, stearic acid, disodium EDTA, citric acid.

Production Example 142. SPF 15 Lotion
(Octinoxate and Zinc Oxide)

Active Ingredient
  Octinoxate 6.0% (Sunscreen)
  Zinc Oxide 3% (Sunscreen)
Inactive Ingredient
  Water, glycerin, isohexadecane, tocopheryl acetate*, ethylhexyl salicylate**, steareth-21, cyclopentasiloxane, polyacrylamide, stearyl alcohol, C13-14 isoparaffin, behenyl alcohol, fragrance, cetyl alcohol, DMDM hydantoin, PEG/PPG-20/20 dimethicone, laureth-7, steareth-2, disodium EDTA, triethoxycaprylylsilane, oleth-3 phosphate, iodopropynyl butylcarbamate, MDM hydantoin. *Vitamin E, **Beta-hydroxy

Production Example 143. SPF 15 Cream
(Octinoxate and Zinc Oxide)

Active Ingredient
  Octinoxate 6.0% (Sunscreen)
  Zinc Oxide 3% (Sunscreen)
Inactive Ingredient
  water, glycerin, isopropyl palmitate, isohexadecane, tocopheryl acetate, aloe barbadensis leaf extract, steareth-21, stearyl alcohol, cetyl alcohol, behenyl alcohol, dimethicone, polyacrylamide, C13-14 isoparaffin, DMDM hydantoin, steareth-2, disodium EDTA, dimethiconol, laureth-7, triethoxycaprylylsilane, oleth-3 phosphate, iodopropynyl butylcarbamate.

Production Example 144. SPF 15 Lotion
(Octinoxate and Zinc Oxide)

Active Ingredient
  Octinoxate 6.0% (Sunscreen)
  Zinc Oxide 3% (Sunscreen)
Inactive Ingredient
  water, glycerin, isohexadecane, tocopheryl acetate, aloe barbadensis leaf extract, steareth-21, cyclopentasiloxane, polyacrylamide, stearyl alcohol, behenyl alcohol, C13-14 isoparaffin, DMDM hydantoin, cetyl alcohol, PEG/PPG-20/20 dimethicone, steareth-2, disodium EDTA, laureth-7, triethoxycaprylylsilane, oleth-3 phosphate, iodopropynyl butylcarbamate.

Production Example 145. SPF 15 Cream
(Avobenzone, Homosalate, Octisalate, and Octocrylene)

Active Ingredient
  Avobenzone 3.0% (Sunscreen)
  Homosalate 4.0% (Sunscreen)
  Octisalate 4.5% (Sunscreen)
  Octocrylene 2.6% (Sunscreen)
Inactive Ingredient
  Water, glycerin, dimethicone, isopropyl isostearate, hydroxyethyl acrylate/sodium acryloyldimethyl taurate copolymer, stearyl alcohol, propylene glycol, niacinamide, cetyl alcohol, behenyl alcohol, panthenol, tocopheryl acetate, caprylyl glycol, 1,2-hexanediol, phenoxyethanol, dimethiconol, PEG-100 stearate, fragrance, sodium benzoate, cetearyl glucoside, cetearyl alcohol, disodium EDTA, stearic acid, palmitic acid, ascorbic acid.

Production Example 146. SPF 15 Lotion
(Avobenzone, Homosalate, Octisalate, and Octocrylene)

Active Ingredient
  Avobenzone 3.0% (Sunscreen)
  Homosalate 4.0% (Sunscreen)
  Octisalate 4.5% (Sunscreen)
  Octocrylene 2.6% (Sunscreen)
Inactive Ingredient
  Water, polyethylene, glycerin, dimethicone, isopropyl isostearate, hydroxyethyl acrylate/sodium acryloyldimethyl taurate copolymer, propylene glycol, niacinamide, panthenol, tocopheryl acetate, stearyl alcohol, caprylyl glycol, behenyl alcohol, 1,2-hexanediol, phenoxyethanol, cetyl alcohol, dimethiconol, PEG-100 stearate, fragrance, sodium benzoate, cetearyl glucoside, cetearyl alcohol, disodium EDTA, stearic acid, palmitic acid, ascorbic acid.

Production Example 147. SPF 15 Lotion
(Avobenzone, Homosalate, Octisalate, and Octocrylene)

Active Ingredient
  Avobenzone 3.0% (Sunscreen)
  Homosalate 4.0% (Sunscreen)
  Octisalate 4.5% (Sunscreen)
  Octocrylene 2.6% (Sunscreen)
Inactive Ingredient
  Water, glycerin, polyethylene, dimethicone, isopropyl isostearate, hydroxyethyl acrylate/sodium acryloyldimethyl taurate copolymer, propylene glycol, niacinamide*, panthenol**, tocopheryl acetate, stearyl alcohol, caprylyl glycol, behenyl alcohol, 1,2-hexanediol, phenoxyethanol, cetyl alcohol, dimethiconol, PEG-100 stearate, fragrance, sodium benzoate, cetearyl glucoside, cetearyl alcohol, disodium EDTA, stearic acid, palmitic acid, ascorbic acid.

Production Example 148. SPF 15 Lotion
(Octinoxate and Zinc Oxide)

Active Ingredient
  Octinoxate 6% (Sunscreen)
  Zinc oxide 3% (Sunscreen)
Inactive ingredient
  water, glycerin, isohexadecane, aloe barbadensis leaf extract, tocopheryl acetate, steareth-21, cyclopentasiloxane, polyacrylamide, stearyl alcohol, C13-14 isoparaffin, behenyl alcohol, DMDM hydantoin, cetyl alcohol, PEG/PPG-20/20 dimethicone, laureth-7, steareth-2, disodium EDTA, triethoxycaprylylsilane, oleth-3 phosphate, BHT, iodopropynyl butylcarbamate.

Production Example 149. SPA 15 Lotion
(Octinoxate and Zinc Oxide)

Active Ingredient
Octinoxate 6% (Sunscreen)
Zinc oxide 3% (Sunscreen)
Inactive Ingredient
Water, glycerin, isohexadecane, aloe barbadensis leaf extract, tocopheryl acetate*, BHT, cyclopentasiloxane, C13-14 isoparaffin, steareth-21, PEG/PPG-20/20 dimethicone, laureth-7, steareth-2, stearyl alcohol, behenyl alcohol, cetyl alcohol, disodium EDTA, polyacrylamide, oleth-3 phosphate, triethoxycaprylylsilane, DMDM hydantoin, iodopropynyl butylcarbamate.

Production Example 150. SPF 30 Lotion
(Octinoxate, Octisalate, Octocrylene, and Zinc Oxide)

Active Ingredient
Octinoxate 7.5% (Sunscreen)
Octisalate 2.5% (Sunscreen)
Octocrylene 2.5% (Sunscreen)
Zinc oxide 7% (Sunscreen)
Inactive Ingredient
Water, isohexadecane, glycerin, niacinamide, panthenol, *Camellia sinensis* leaf extract, tocopheryl acetate, aloe barbadensis leaf extract, steareth-21, cyclopentasiloxane, polyacrylamide, stearyl alcohol, polymethylsilsesquioxane, polyethylene, C13-14 isoparaffin, behenyl alcohol, DMDM hydantoin, cetyl alcohol, triethoxycaprylylsilane, PEG/PPG-20/20 dimethicone, laureth-7, steareth-2, oleth-3 phosphate, disodium EDTA, iodopropynyl butyl carbamate.

Production Example 151. SPF 30 Lotion
(Avobenzone, Homosalate, Octisalate, Octocrylene, and Oxybenzone)

Active Ingredient
Avobenzone 3% (Sunscreen)
Homosalate 15% (Sunscreen)
Octisalate 5% (Sunscreen)
Octocrylene 2.6% (Sunscreen)
Oxybenzone 6% (Sunscreen)
Inactive Ingredient
water, glycerin, polymethylsilsesquioxane, niacinamide*, polyethylene, pentylene glycol, palmitoyl pentapeptide-4, panthenol*, tocopheryl acetate^, *Camellia sinensis* leaf extract^^, allantoin, carnosine, dimethicone, hydroxyethyl acrylate/sodium acryloyldimethyl taurate copolymer, benzyl alcohol, titanium dioxide, stearyl alcohol, behenyl alcohol, polyacrylamide, PEG-100 stearate, cetyl alcohol, methylparaben, propylparaben, fragrance, ethylparaben, C13-14 isoparaffin, cetearyl glucoside, cetearyl alcohol, dimethiconol, sodium ascorbyl phosphate, citric acid, BHT, laureth-7, disodium EDTA, stearic acid, palmitic acid, iodopropynyl butylcarbamate.

Production Example 152. SPF 25 Cream
(Avobenzone, Homosalate, Octisalate, Octocrylene, and Oxybenzone)

Active Ingredient
Avobenzone 3% (Sunscreen)
Homosalate 8% (Sunscreen)
Octisalate 4% (Sunscreen)
Octocrylene 5% (Sunscreen)
Inactive Ingredient
Water, tapioca starch, glycerin, niacinamide*, dimethicone, panthenol**, *Camellia sinensis* leaf extract***, sodium polyacrylate starch, stearyl alcohol, caprylyl glycol, behenyl alcohol, 1,2-hexanediol, phenoxyethanol, inositol, cetyl alcohol, dimethiconol, PEG-100 stearate, polymethylsilsesquioxane, fragrance, cetearyl glucoside, cetearyl alcohol, BHT, disodium EDTA, stearic acid, palmitic acid, zinc gluconate, magnesium aspartate, copper gluconate.
*Vitamin 83, Pro-Vitamin B5, *Green Tea

Production Example 153. SPF 30 Lotion
(Avobenzone, Homosalate, Octisalate, Octocrylene, and Oxybenzone)

Active Ingredient
Avobenzone 3% (Sunscreen)
Homosalate 15% (Sunscreen)
Octisalate 5% (Sunscreen)
Octocrylene 2.6% (Sunscreen)
Oxybenzone 6.0% (Sunscreen)
Inactive Ingredient
Water, glycerin, niacinamide, polymethylsilsesquioxane, polyethylene, pentylene glycol, palmitoyl pentapeptide-4, palmitoyl dipeptide-7, carnosine, panthenol, tocopheryl acetate, allantoin, *Camellia sinensis* leaf extract, dimethicone, hydroxyethyl acrylate/sodium acryloyldimethyl taurate copolymer, benzyl alcohol, titanium dioxide, stearyl alcohol, behenyl alcohol, PEG-100 stearate, cetyl alcohol, methylparaben, polyacrylamide, propylparaben, ethylparaben, cetearyl glucoside, cetearyl alcohol, C13-14 isoparaffin, dimethiconol, sodium ascorbyl phosphate, citric acid, BHT, disodium EDTA, laureth-7, stearic acid, palmitic acid, iodopropynyl butylcarbamate.

Production Example 154. SPF 30 Cream
(Avobenzone and Octinoxate)

Active Ingredient
Avobenzone 3% (Sunscreen)
Octinoxate 7.5% (Sunscreen)
Inactive Ingredient
water, glycerin, niacinamide*, tapioca starch, dimethicone, ethylhexyl methoxycrylene, panthenol, tocopheryl acetate*, palmitoyl pentapeptide-4^, sodium PEG-7 olive oil carboxylate, *Peucedanum graveolens* (dill) extract, stearyl alcohol, polyacrylamide, behenyl alcohol, cetyl alcohol, C13-14 isoparaffin, caprylyl glycol, 1,2-hexanediol, phenoxyethanol, PEG-100 stearate, titanium dioxide, fragrance, dimethiconol, laureth-7, sodium benzoate, cetearyl glucoside, cetearyl alcohol, polymethylsilsesquioxane, disodium EDTA, stearic acid, palmitic acid

Production Example 155. SPF 30 Cream (Avobenzone, Homosalate, Octisalate, and Octocrylene)

Active Ingredient
  Avobenzone 3% (Sunscreen)
  Homosalate 9% (Sunscreen)
  Octisalate 4.5% (Sunscreen)
  Octocrylene 6.0% (Sunscreen)
Inactive Ingredient
  Water, glycerin, tapioca starch, niacinamide*, panthenol, tocopheryl acetate*, palmitoyl pentapeptide-4^, *Ceratonia siliqua* (carob) fruit extract, *Camellia sinensis* leaf extract, dimethicone, caprylyl glycol, dimethiconol, cetearyl glucoside, cetearyl alcohol, sodium PEG-7 olive oil carboxylate, stearic acid, palmitic acid, stearyl alcohol, cetyl alcohol, behenyl alcohol, disodium EDTA, hydroxyethyl acrylate/sodium acryloyldimethyl taurate copolymer, PEG-100 stearate, titanium dioxide, polymethylsilsesquioxane, 1,2-hexanediol, phenoxyethanol, iodopropynyl butylcarbamate, fragrance.

Production Example 156. SPF 50 Lotion (Avobenzone, Homosalate, Octisalate, Octocrylene, and Oxybenzone)

Active Ingredient
  Avobenzone 3% (Sunscreen)
  Homosalate 15% (Sunscreen)
  Octisalate 5% (Sunscreen)
  Octocrylene 2.7% (Sunscreen)
  Oxybenzone 6% (Sunscreen)
Inactive Ingredient
  water, glycerin, polymethylsilsesquioxane, niacinamide*, polyethylene, pentylene glycol, palmitoyl pentapeptide-4, panthenol*, ascorbic acid^, tocopheryl acetate^^, *Camellia sinensis* leaf extract^^^, allantoin, carnosine, dimethicone, hydroxyethyl acrylate/sodium acryloyldimethyl taurate copolymer, benzyl alcohol, stearyl alcohol, behenyl alcohol, PEG-100 stearate, cetyl alcohol, methylparaben, fragrance, propylparaben, ethylparaben, cetearyl glucoside, cetearyl alcohol, dimethiconol, disodium EDTA, stearic acid, palmitic acid, iodopropynyl butylcarbamate.

Production Example 157. SPF 15 (Avobenzone, Homosalate, Octisalate, and Octocrylene)

Active Ingredient
  Avobenzone 3% (Sunscreen)
  Homosalate 4% (Sunscreen)
  Octisalate 4.5% (Sunscreen)
  Octocrylene 2.6% (Sunscreen)
Inactive Ingredient
  water, glycerin, niacinamide*, polymethylsilsesquioxane, dimethicone, isopropyl isostearate, hydroxyethyl acrylate/sodium acryloyldimethyl taurate copolymer, panthenol, palmitoyl pentapeptide-4*, tocopheryl acetate^, *Camellia sinensis* leaf extract^^, ascorbic acid^^^, allantoin, PTFE, titanium dioxide, stearyl alcohol, caprylyl glycol, behenyl alcohol, 1,2-hexanediol, phenoxyethanol, cetyl alcohol, dimethiconol, PEG-100 stearate, fragrance, sodium benzoate, cetearyl glucoside, cetearyl alcohol, sodium PEG-7 olive oil carboxylate, BHT, disodium EDTA, stearic acid, palmitic acid

Production Example 158. SPF 25 Cream (Avobenzone, Homosalate, Octisalate, Octocrylene, and Oxybenzone)

Active Ingredient
  Avobenzone 3% (Sunscreen)
  Homosalate 8% (Sunscreen)
  Octisalate 4% (Sunscreen)
  Octocrylene 5% (Sunscreen)
Inactive Ingredient
  Water, tapioca starch, glycerin, niacinamide, dimethicone, palmitoyl pentapeptide-4, sodium hyaluronate, panthenol, sodium polyacrylate starch, stearyl alcohol, caprylyl glycol, behenyl alcohol, 1,2-hexanediol, phenoxyethanol, cetyl alcohol, dimethiconol, PEG-100 stearate, fragrance, polymethylsilsesquioxane, *Ceratonia siliqua* (carob) fruit extract, cetearyl glucoside, cetearyl alcohol, disodium EDTA, stearic acid, palmitic acid.

Production Example 159. SPF 35 Lotion (Avobenzone, Homosalate, Octisalate, and Octocrylene)

Active Ingredient
  Avobenzone 3% (Sunscreen)
  Homosalate 9% (Sunscreen)
  Octisalate 4.5% (Sunscreen)
  Octocrylene 6% (Sunscreen)
Inactive Ingredient
  Water, tapioca starch, dimethicone, niacinamide*, *Camellia sinensis* leaf extract, BHT, caprylyl glycol, dimethiconol, cetearyl glucoside, cetearyl alcohol, tocopheryl acetate*, stearic acid, palmitic acid, disodium EDTA, PEG-100 stearate, polymethylsilsesquioxane, sodium polyacrylate starch, 1,2-hexanediol, phenoxyethanol, iodopropynyl butylcarbamate, fragrance.
  *Vitamin B3, Green Tea, *Vitamin E

Production Example 160. SPF 15 Lotion (Avobenzone, Homosalate, Octisalate, and Octocrylene)

Active Ingredient
  Avobenzone 3% (Sunscreen)
  Homosalate 4% (Sunscreen)
  Octisalate 4.5% (Sunscreen)
  Octocrylene 2.6% (Sunscreen)
Inactive Ingredient
  water, glycerin, niacinamide 1, dimethicone, isopropyl isostearate, panthenol 2, tocopheryl acetate 3, *Camellia sinensis* leaf extract, hydroxyethyl acrylate/sodium acryloyldimethyl taurate copolymer, benzyl alcohol, PTFE, titanium dioxide, stearyl alcohol, behenyl alcohol, cetyl alcohol, methylparaben, dimethiconol, PEG-100 stearate, ethylparaben, carbomer, propylparaben, sodium ascorbyl phosphate, cetearyl glucoside, cetearyl alcohol, sodium hydroxide, BHT, disodium EDTA, stearic acid, palmitic acid, zinc oxide, iodopropynyl butylcarbamate, triethoxycaprylylsilane.

Production Example 161. SPF 30 Lotion
(Avobenzone, Homosalate, Octisalate, Octocrylene, and Oxybenzone)

Active Ingredient
  Avobenzone 3% (Sunscreen)
  Homosalate 15% (Sunscreen)
  Octisalate 5.0% (Sunscreen)
  Octocrylene 2.6% (Sunscreen)
  Oxybenzone 6.0% (Sunscreen)
Inactive Ingredient
  Water, glycerin, polymethylsilsesquioxane, niacinamide, polyethylene, pentylene glycol, tocopheryl acetate, panthenol, dimethicone, hydroxyethyl acrylate/sodium acryloyldimethyl taurate copolymer, benzyl alcohol, titanium dioxide, stearyl alcohol, behenyl alcohol, polyacrylamide, PEG-100 stearate, cetyl alcohol, methylparaben, fragrance, ethylparaben, C13 14 isoparaffin, propylparaben, cetearyl glucoside, cetearyl alcohol, dimethiconol, laureth-7, disodium EDTA, stearic acid, palmitic acid, iodopropynyl butylcarbamate.

Production Example 162. SPF 15 Lotion
(Avobenzone, Homosalate, Octisalate, and Octocrylene)

Active Ingredient
  Avobenzone 3% (Sunscreen)
  Homosalate 15% (Sunscreen)
  Octisalate 5.0% (Sunscreen)
  Octocrylene 2.6% (Sunscreen)
  Oxybenzone 6.0% (Sunscreen)
Inactive Ingredient
  water, glycerin, niacinamide 1, dimethicone, isopropyl isostearate, polymethylsilsesquioxane, panthenol 2, hydroxyethyl acrylate/sodium acryloyldimethyl taurate copolymer, tocopheryl acetate 3, benzyl alcohol, isohexadecane, stearyl alcohol, behenyl alcohol, cetyl alcohol, methylparaben, dimethiconol, PEG-100 stearate, ethylparaben, propylparaben, polysorbate 60, cetearyl glucoside, cetearyl alcohol, stearic acid, disodium EDTA, iodopropynyl butylcarbamate.
1. Vitamin B3, 2. Pro-vitamin B5, 3. Vitamin E

Production Example 163. SPF 15 Lotion
(Avobenzone, Homosalate, Octisalate, and Octocrylene)

Active Ingredients
  Avobenzone 3% (Sunscreen)
  Homosalate 4% (Sunscreen)
  Octisalate 4.5% (Sunscreen)
  Octocrylene 2.6% (Sunscreen)
Inactive Ingredient
  water, glycerin, niacinamide, tapioca starch, aluminum starch octenylsuccinate, acetyl glucosamine, dimethicone, panthenol, stearyl alcohol, behenyl alcohol, cetyl alcohol, tocopheryl acetate, hydroxyethyl acrylate/sodium acryloyldimethyl taurate copolymer, polyethylene, benzyl alcohol, titanium dioxide, isohexadecane, nylon-12, methylparaben, dimethiconol, ethylparaben, allantoin, PEG-100 stearate, propylparaben, cetearyl glucoside, cetearyl alcohol, sodium ascorbyl phosphate, polysorbate 60, sodium PEG-7 olive oil carboxylate, disodium EDTA, stearic acid, *Camellia sinensis* leaf extract, iodopropynyl butylcarbamate, iron oxides.

Production Example 164. SPF 15 Lotion
(Avobenzone, Homosalate, Octisalate, and Octocrylene)

Active Ingredient
  Avobenzone 3% (Sunscreen)
  Homosalate 4% (Sunscreen)
  Octisalate 4.5% (Sunscreen)
  Octocrylene 2.6% (Sunscreen)
Inactive Ingredient
  Water, glycerin, niacinamide*, dimethicone, isopropyl isostearate, panthenol, tocopheryl acetate*, sodium ascorbyl phosphate^, retinyl propionate^^, *Camellia sinensis* leaf extract*, BHT^**, tapioca starch, dimethiconol, cetearyl glucoside, cetearyl alcohol, stearic acid, palmitic acid, stearyl alcohol, cetyl alcohol, behenyl alcohol, disodium EDTA, hydroxyethyl acrylate/sodium acryloyldimethyl taurate copolymer, carbomer, sodium hydroxide, PEG-100 stearate, titanium dioxide, polymethylsilsesquioxane, benzyl alcohol, methylparaben, ethylparaben, propylparaben, iodopropynyl butylcarbamate
  *Vitamin B3, Pro-Vitamin B5, *Vitamin E, ^Vitamin C, ^^Vitamin A, ^*Green Tea Antioxidant, ^**Antioxidant

Production Example 165. SPF 25 Cream
(Avobenzone, Homosalate, Octisalate, Octocrylene, and Oxybenzone)

Active Ingredient
  Avobenzone 3% (Sunscreen)
  Homosalate 8% (Sunscreen)
  Octisalate 4.5% (Sunscreen)
  Octocrylene 5% (Sunscreen)
Inactive Ingredient
  Water, tapioca starch, glycerin, niacinamide*, dimethicone, panthenol, tocopheryl acetate*, sodium ascorbyl phosphate^, *Camellia sinensis* leaf extract^^, sodium polyacrylate starch, stearyl alcohol, caprylyl glycol, behenyl alcohol, 1,2-hexanediol, phenoxyethanol, cetyl alcohol, dimethiconol, PEG-100 stearate, fragrance, polymethylsilsesquioxane, cetearyl glucoside, cetearyl alcohol, BHT, disodium EDTA, stearic acid, palmitic acid.
  *Vitamin B3, Pro-Vitamin B5, *Vitamin E, ^Vitamin C, ^^Green Tea

Production Example 166. SPF 25 Cream
(Avobenzone, Homosalate, Octisalate, Octocrylene, and Oxybenzone)

Active Ingredient
  Avobenzone 3% (Sunscreen)
  Homosalate 8% (Sunscreen)
  Octisalate 4.5% (Sunscreen)
  Octocrylene 5% (Sunscreen)
Inactive Ingredient
  Water, tapioca starch, glycerin, niacinamide*, dimethicone, panthenol, tocopheryl acetate*, sodium ascorbyl phosphate^, *Camellia sinensis* leaf extract^^, BHT, caprylyl glycol, dimethiconol, cetearyl glucoside, cetearyl alcohol, stearic acid, palmitic acid, stearyl alcohol, cetyl alcohol, behenyl alcohol, disodium EDTA, PEG-100 stearate, polymethylsilsesquioxane, sodium polyacrylate starch, 1,2-hexanediol, phenoxyethanol.
  *Vitamin B3, Pro-Vitamin B5, *Vitamin E, ^Vitamin C, ^^Green Tea

Production Example 167. SPF 30 Lotion
(Avobenzone, Homosalate, Octisalate, Octocrylene and Oxybenzone)

Active Ingredient
  Avobenzone 3% (Sunscreen)
  Homosalate 5% (Sunscreen)
  Octisalate 5% (Sunscreen)
  Octocrylene 7% (Sunscreen)
  Oxybenzone 6% (Sunscreen)
Inactive Ingredient
  Water, glycerin, propanediol, alcohol denat, dimethicone, isodecyl neopentanoate, cyclopentasiloxane, PEG-100 stearate, glyceryl stearate, arachidyl alcohol, potassium cetyl phosphate, VP/eicosene copolymer, silica, C13-14 isoparaffin, arachidyl glucoside, behenyl alcohol, isoeugenol, fragrance, *Vitis vinifera* (grape) fruit extract, trimethylsiloxysilicate, p-anisic acid, disodium EDTA, tocopherol, laureth-7, xanthan gum, polyacrylamide

Production Example 168. SPF 50 Lotion
(Avobenzone, Homosalate, Octisalate, Octocrylene and Oxybenzone)

Active Ingredient
  Avobenzone 3% (Sunscreen)
  Homosalate 15% (Sunscreen)
  Octisalate 5% (Sunscreen)
  Octocrylene 5% (Sunscreen)
  Oxybenzone 6% (Sunscreen)
Inactive Ingredient
  water, dimethicone, isododecane, styrene/acrylates copolymer, propanediol, glycerin, silica, isononyl isononanoate, inulin lauryl carbamate, nylon-12, caprylyl methicone, synthetic wax, poly C10-30 alkyl acrylate, PEG-8 laurate, stearyl alcohol, dimethiconol, triethanolamine, isoeugenol, fragrance, *Vitis vinifera* (grape) fruit extract, phenoxyethanol, p-anisic acid, ammonium acryloyldimethyltaurate/steareth-25 methacrylate crosspolymer, chlorphenesin, disodium EDTA, tocopherol, sucrose tristearate, xanthan gum, polymethyl methacrylate

Production Example 169. SPF 30 Lotion
(Avobenzone, Homosalate, Octisalate and Octocrylene)

Active Ingredient
  Avobenzone 2.96% (Sunscreen)
  Homosalate 8.78% (Sunscreen)
  Octisalate 4.86% (Sunscreen)
  Octocrylene 5.92% (Sunscreen)
Inactive Ingredient
  water, cyclopentasiloxane, dicaprylyl ether, alcohol denat., dimethicone, silica, styrene/acrylates copolymer, PEG-30 dipolyhydroxystearate, cyclohexasiloxane, polymethylsilsesquioxane, nylon-12, PEG-8 laurate, dicaprylyl carbonate, dodecene, sodium chloride, *Vitis vinifera* (grape) fruit extract, aluminum hydroxide, phenoxyethanol, iron oxides, p-anisic acid, tocopherol, disodium EDTA, poloxamer 407, disodium stearoyl glutamate, lauryl PEG/PPG-18/18 methicone, caprylyl glycol, isostearyl alcohol, disbeardimonium hectorite, poly C10-30 alkyl acrylate

Production Example 170. SPF 30 Lotion
(Avobenzone, Homosalate, Octisalate, Octocrylene and Oxybenzone)

Active Ingredient
  Avobenzone 3% (Sunscreen)
  Homosalate 10% (Sunscreen)
  Octisalate 5% (Sunscreen)
  Octocrylene 5% (Sunscreen)
  Oxybenzone 3% (Sunscreen)
Inactive Ingredient
  water, cyclopentasiloxane, dicaprylyl ether, alcohol denat., silica, dimethicone, styrene/acrylates copolymer, PEG-30 di polyhydroxystearate, cyclohexasiloxane, polymethylsilsesquioxane, nylon-12, PEG-8 laurate, dicaprylyl carbonate, dodecene, methylparaben, sodium chloride, *Vitis vinifera* (grape) fruit extract, phenoxyethanol, disodium EDTA, poloxamer 407, tocopherol, lauryl PEG/PPG-18/18 methicone, caprylyl glycol, isostearyl alcohol, disteardimonium hectorite, poly C10-30 alkyl acrylate

Production Example 171. SPF 50 Lotion
(Avobenzone, Homosalate, Octisalate, Octocrylene and Oxybenzone)

Active Ingredient
  Avobenzone 3% (Sunscreen)
  Homosalate 15% (Sunscreen)
  Octisalate 5% (Sunscreen)
  Octocrylene 5% (Sunscreen)
  Oxybenzone 5% (Sunscreen)
Inactive Ingredient
  water, cyclopentasiloxane, alcohol denat, silica, dicaprylyl ether, styrene/acrylates copolymer, PEG-30 di polyhydroxystearate, dimethicone, cyclohexasiloxane, polymethylsilsesquioxane, nylon-12, PEG-8 laurate, dicaprylyl carbonate, dodecene, methylparaben, sodium chloride, *Vitis vinifera* (grape) fruit extract, phenoxyethanol, disodium EDTA, poloxamer 407, tocopherol, lauryl PEG/PPG-18/8 methicone, caprylyl glycol, isostearyl alcohol, disteardimonium hectorite, poly C10-30 alkyl acrylate

Production Example 172. SPF 15 Cream
(Avobenzone, Homosalate, Octisalate and Octocrylene)

Active Ingredient
  Avobenzone 3% (Sunscreen)
  Homosalate 5% (Sunscreen)
  Octisalate 5% (Sunscreen)
  Octocrylene 5% (Sunscreen)
Inactive Ingredient
  water, glycerin, alcohol denat, hydrogenated polyisobutene, bis-PEG-18 methyl ether dimethyl silane, dimethicone, cetearyl alcohol, PEG-100 stearate, PEG-20, petrolatum, *Butyrospermum parkii* (shea) butter, C13-14 isoparaffin, glyceryl stearate, dimethiconol, dimethyl isosorbide, cetearyl glucoside, neohesperidin dihydrochalcone, sodium cocoyl glutamate, sodium hyaluronate, sodium hydroxide, cyclodextrin, adenosine, *Vigna aconitifolia* seed extract, mannitol, disodium EDTA, disodium succinate, hydrolyzed *cicer* seed extract, capryloyl salicylic acid, laureth-7, yeast extract, xanthan gum, polyacrylamide, acrylates/C10-30 alkyl acrylate crosspolymer, cetyl alcohol, octyldodecanol, tocopheryl acetate, sodium dehydroacetate, phenoxyethanol, red 4, yellow 5, linalool, geraniol, alphaisomethyl ionone, limonene, hydroxycitronellal, cironellol, hexyl cinnamal, benzyl alcohol, benzyl salicylate, fragrance Production Example 173. SPF 30 Lotion
(Avobenzone, Homosalate, Octisalate and Octocrylene)

Active Ingredient
 Avobenzone 3% (Sunscreen)
 Homosalate 5% (Sunscreen)
 Octisalate 5% (Sunscreen)
 Octocrylene 7% (Sunscreen)
Inactive Ingredient
 water, glycerin, dicaprylyl ether, nylon-66, stearyl alcohol, alcohol denat., caprylic/capric triglyceride, PEG-100 stearate, glyceryl stearate, ammonium polyacryloyldimethyl taurate, phenoxyethanol, caprylyl glycol, hydrolyzed soy protein, fragrance, xanthan gum, disodium EDTA, tocopherol, *Pelargonium graveolens* flower oil, capryloyl salicylic acid, pentaerythrityl tetra-di-t-butyl hydroxyhydrocinnamate, limonene, propylene glycol, sodium hyaluronate, *Citrus aurantium dulcis* (orange) peel oil, citronellol, *Jasminum officinale* (jasmine) flower extract, linalool, geraniol, *Lavandula angustifolia* (lavender) oil, *Anthemis noblis* flower oil, *Rosmarinus officinalis* (rosemary) leaf oil, hydroxypalmitoyl sphinganine, citral, royal jelly extract, benzyl alcohol, eugenol, sodium hydroxide, citric acid Production Example 174. SPF 30 Oil (Avobenzone, Homosalate, Octisalate and Octocrylene)

Active Ingredient
 Avobenzone 2.96% (Sunscreen)
 Homosalate 8.78% (Sunscreen)
 Octisalate 4.88% (Sunscreen)
 Octocrylene 5.92% (Sunscreen)
Inactive Ingredient
 isopropyl myristate, caprylic/capric triglyceride, dicaprylyl ether, C12-15 alkyl benzoate, *Olea europaea* (olive) fruit oil, sorbitan trioleate, ethylhexyl palmitate, dimethicone, camelina saliva seed oil, acrylates/dimethicone copolymer, *Rosa canina* fruit oil, fragrance, capryloyl salicylic acid, tocopherol, pentaerythrityl tetra-di-t-butyl hydroxyhydrocinnamate, limonene, sorbitan oleate, *Pelargonium graveolens* flower oil, *Citrus aurantium dulcis* (orange) peel oil, linalool, citronellol, sorbitan laurate, *Rosmarinus officinalis* (rosemary) leaf oil, geraniol, hydroxypalmitoyl sphinganine, *Mentha piperita* (peppermint) oil, *Lavandula angustifolia* (lavender) oil, *Lavandula hybrida* oil, *Origanum majorana* leaf oil, *Anthemis nobilis* flower oil, benzyl alcohol, citral, propylene glycol, eugenol, coumarin, alpha-isomethyl ionone, myristyl malate phosphonic acid, propyl gallate, citric acid Production Example 175. SPF 20 Lotion
(Avobenzone, Octisalate and Octocrylene)

Active Ingredient
 Avobenzone 3% (Sunscreen)
 Octisalate 5% (Sunscreen)
 Octocrylene 5% (Sunscreen)
Inactive Ingredient
 water, glycerin, silica, dimethicone, PEG-100 stearate, glyceryl stearate, hydroxyproyl tetrahydropyrantriol, octyldodecanol, ammonium polyacryloyldimethyl taurate, benzyl alcohol, bisabolol, capryloyl salicylic acid, caprylyl glycol, citronellol, dicaprylyl carbonate, dimethicone/vinyl dimethicone crosspolymer, disodium EDTA, farnesol, fragrance, isoeugenol, limonene, linalool, palmitic acid, phenoxyethanol, phenylethyl resorcinol, propylene glycol, sodium hyaluronate, sodium hydroxide, steareth-100, stearic acid, tocopherol, xanthan gum Production Example 176. SPF 15 Cream
(Ensulizole and Octinoxate)

Active Ingredient
 Ensulizole 1.7% (Sunscreen)
 Octinoxate 7.5% (Sunscreen)
Inactive Ingredient
 water, cyclohexasiloxane, glycerin, mineral oil, myristyl myristatem stearic acid, ammonium polyacryloyldimethyl taurate, palmitic acid, triethanolamine, titanium dioxide, PEG-100 stearate, glyceryl stearate, acrylates copolymer, alpha-isomethyl ionone, alumina, benzyl alcohol, benzyl benzoate, butylparaben, capryloyl salicylic acid, cetyl alcohol, citronellol, coumarin, cyclodextrin, diazolidinyl urea, disodium EDTA, disodium succinate, fragrance, geraniol, hydrolyzed soy protein, *Jasminum officinale* (jasmin) flower extract, limonene, linalool, mannitol, methylparaben, PEG-20 stearate, phenoxyethanol, propylene glycol, *Rosa canina* fruit oil, sodium hydroxide, soluble collagen, stearyl alcohol, yeast extract Production Example 177. SPF 15 Lotion
(Ensulizole and Octinoxate)

Active Ingredient
 Ensulizole 2% (Sunscreen)
 Octinoxate 7% (Sunscreen)
Inactive Ingredient
 water, glycerin, cyclopentasiloxane, polyglyceryl-3 methylglucose distearate, triethanolamine, *Butyrospermum parkii* (shea butter), *Prunus armeniaca* (apricot) kernel oil, pentylene glycol, stearic acid, carbomer, panthenol, cetyl alcohol, xanthan gum, PEG-100 stearate, glyceryl stearate, stearyl alcohol, myristyl alcohol, disodium EDTA, phenoxyethanol, methylparaben, chlorphenesin, butylparaben, yellow 5, fragrance, limonene, benzyl salicylate, linalool, butylphenyl methylpropional, hexyl cinnamal, benzyl benzoate, citronellol, eugenol, citral.

Production Example 178. SPF 25 Lotion
(Avobenzone, Homosalate, Octisalate and Octocrylene)

Active Ingredient
 Avobenzone 3% (Sunscreen)
 Homosalate 2% (Sunscreen)
 Octisalate 5% (Sunscreen)
 Octocrylene 7% (Sunscreen)
Inactive Ingredient
 water, glycerin, aluminum starch octenylsuccinate, glyceryl stearate, behenyl alcohol, dimethicone, polymethylsilsesquioxane, glyceryl stearate citrate, sodium hydroxide, ammonium polyacryloyldimethyl taurate, disodium EDTA, disodium ethylene dicocamide PEG-15 disulfate, caprylyl glycol, xanthan gum, tocopheryl acetate, phenoxyethanol, chlorhexidine digluconate, fragrance

Production Example 179. SPF 25 Lotion
(Avobenzone, Homosalate, Octisalate and Octocrylene)

Active Ingredient
  Avobenzone 3% (Sunscreen)
  Homosalate 5% (Sunscreen)
  Octisalate 5% (Sunscreen)
  Octocrylene 5% (Sunscreen)
Inactive Ingredient
  water, glycerin, dimethicone, polyglyceryl-3 methylglucose distearate, aluminum starch octenylsuccinate, PEG-100 stearate, stearic acid, glyceryl stearate, sodium hydroxide, palmitic acid, ammonium polyacryloyldimethyl taurate, disodium EDTA, caprylyl glycol, xanthan gum, cetyl alcohol, tocopheryl acetate, phenoxyethanol, chlorhexidine digluconate, red 4, titanium dioxide, yellow 10, iron oxides, linalool, geraniol, eugenol, limonene, citronellol, benzyl alcohol, benzyl salicylate, fragrance

Production Example 180. SPF 25 Lotion
(Avobenzone, Homosalate, Octisalate and Octocrylene)

Active Ingredient
  Avobenzone 3% (Sunscreen)
  Homosalate 5% (Sunscreen)
  Octisalate 5% (Sunscreen)
  Octocrylene 5% (Sunscreen)
Inactive Ingredient
  water, glycerin, dimethicone, polyglyceryl-3 methylglucose distearate, aluminum starch octenylsuccinate, PEG-100 stearate, stearic acid, glyceryl stearate, sodium hydroxide, palmitic acid, ammonium polyacryloyldimethyl taurate, disodium EDTA, caprylyl glycol, xanthan gum, cetyl alcohol, tocopheryl acetate, phenoxyethanol, chlorhexidine digluconate, fragrance

Production Example 181. SPF 25 Lotion
(Avobenzone, Homosalate, Octisalate and Octocrylene)

Active Ingredient
  Avobenzone 3% (Sunscreen)
  Homosalate 2% (Sunscreen)
  Octisalate 5% (Sunscreen)
  Octocrylene 7% (Sunscreen)
Inactive Ingredient
  water, glycerin, aluminum starch octenylsuccinate, glyceryl stearate, behenyl alcohol, dimethicone, polymethylsilsesquioxane, glyceryl stearate citrate, sodium hydroxide, ammonium polyacryloyldimethyl taurate, disodium EDTA, disodium ethylene dicocamide PEG-15 disulfate, caprylyl glycol, xanthan gum, tocopheryl acetate, phenoxyethanol, chlorhexidine digluconate

Production Example 182. SPF 15 Lotion
(Avobenzone, Homosalate, Octisalate and Octocrylene)

Active Ingredient
  Avobenzone 3% (Sunscreen)
  Homosalate 2% (Sunscreen)
  Octisalate 5% (Sunscreen)
  Octocrylene 5.5% (Sunscreen)
Inactive Ingredient
  water, glycerin, dimethicone, myristyl myristate, *Shorea robusta* seed butter, stearic acid, palmitic acid, PEG-100 stearate, glyceryl stearate, beeswax, *Mentha piperita* (peppermint) leaf extract, PEG-20 stearate, stearyl alcohol, triethanolamine, silica silylate, cyclodextrin, adenosine, ammonium polyacryloyldimethyl taurate, disodium EDTA, capryloyl salicylic acid, caprylyl glycol, *Pisum sativum* (pea) extract, acrylaes copylymer, cetyl alcohol, retinyl palmitate, phenoxyethanol, linalool, limonene, fragrance

Production Example 183. SPF 30 Lotion
(Avobenzone, Octocrylene, Terephthalylidene Dicamphor Sulfonic Acid and Titanium Dioxide)

Active Ingredient
  Avobenzone 3% (Sunscreen)
  Octocrylene 10% (Sunscreen)
  Terephthalylidene dicamphor sulfonic acid 1% (Sunscreen)
  Titanium dioxide 2.2% (Sunscreen)
Inactive Ingredient
  water, propylene glycol, glycerin, cyclopentasiloxane, isopropyl palmitate, stearic acid, triethanolamine, VP/eicosene copolymer, dimethicone, panthenol, phenoxyethanol, PEG-100 stearate, glyceryl stearate, methylparaben, aluminum hydroxide, acrylates/C10-30 alkyl acrylate crosspolymer, chlorphenesin, tocopherol, disodium EDTA, propylparaben, xanthan gum

Production Example 184. SPF 18 Cream
(Ensulizole and Octinoxate)

Active Ingredient
  Ensulizole 2% (Sunscreen)
  Octinoxate 7.5% (Sunscreen)
Inactive Ingredient
  water, cyclohexasiloxane, glycerin, myristyl myristate, alcohol denat, triethanolamine, stearic acid, ammonium polyacryloyldimethyl taurate, palmitic acid, titanium dioxide, PEG-100 stearate, glyceryl stearate, beeswax, PEG-20 stearate, stearyl alcohol, *Glycine soja* (soybean) protein, alumina, phenethyl alcohol, hydrolyzed soy protein, yeast extract, acetyl trifluoromethyl phenyl valylglycine, acrylates, copolymer, cetyl alcohol, retinyl palmitate, potassium sorbate, methylparaben, sodium benzoate, phenoxyethanol, chlorphenesin, ethylparaben, linalool, geraniol, alpha-isomethyl ionone, amyl cinnamal, limonene, citral, citronellol, butylphenyl methylpropional, hexyl cinnamal, benzyl alcohol, benzyl benzoate, benzyl cinnamate, benzyl salicylate, fragrance

Production Example 185. SPF 20 Lotion
(Avobenzone Homosalate Octisalate Octocrylene)

Active Ingredient
  Avobenzone 3% (Sunscreen)
  Homosalate 10% (Sunscreen)
  Octisalate 5% (Sunscreen)
  Octocrylene 7% (Sunscreen)
Inactive Ingredient
  glycerin, cetyl alcohol, glyceryl stearate, PEG-40 stearate, sorbitan tristearate, *Glycine soja* (soybean) oil, sodium hydroxide, retinol, ammonium polyacryloyldimethyltaurate, hydrolyzed soy protein, caprylyl glycol, acetyl trifluoromethylphenyl valylglycine, phenoxyethanol, chlorhexidine digluconate, linalool, geraniol, alphaisomethyl ionone, coumarin, limonene, hydroxyisohexyl 3-cyclohexenecarboxaldehyde, citronellol, butylphenyl methylpropional, benzyl alcohol, benzyl salicylate, fragrance Production Example 186. SPF 30 Cream
(Avobenzone, Homosalate, Octisalate, Octocrylene and Oxybenzone)

Active Ingredient
 Avobenzone 3% (Sunscreen)
 Homosalate 10% (Sunscreen)
 Octisalate 5% (Sunscreen)
 Octocrylene 5% (Sunscreen)
 Oxybenzone 6% (Sunscreen)
Inactive Ingredient
dimethicone, c12-15 alkyl benzoate, talc, diisopropyl sebacate, silica, silica silylate, glycerin, trimethylsilsoxysilicate, dimethiconecrosspolymer, water Production Example 187. SPF 30 Lotion
(Avobenzone, Homosalate, Octisalate and Octocrylene)

Active Ingredient
 Avobenzone 3% (Sunscreen)
 Homosalate 5% (Sunscreen)
 Octisalate 5% (Sunscreen)
 Octocrylene 7% (Sunscreen)
Inactive Ingredient
 water, glycerin, silica, dimethicone, PEG-100 stearate, glyceryl stearate, adenosine, ammonium polyacryloyldimethyl taurate, benzyl alcohol, capryloyl salicylic acid, caprylyl glycol, cetyl alcohol, citric acid, citronellol, dicaprylyl carbonate, dimethicone/vinyl dimethicone crosspolymer, disodium EDTA, fragrance, hydroxypropyl tetrahydropyrantriol, isoeugenol, limonene, linalool, palmitic acid, phenoxyethanol, propylene glycol, sodium hyaluronate, sodium hydroxide, stearic acid, tocopherol, xanthan gum Production Example 188. SPF 30 Lotion
(Avobenzone, Homosalate, Octisalate and Octocrylene)

Active Ingredient
 Avobenzone 3% (Sunscreen)
 Homosalate 5% (Sunscreen)
 Octisalate 5% (Sunscreen)
 Octocrylene 7% (Sunscreen)
Inactive Ingredient
 water, glycerin, dimethicone, silica, PEG-100 stearate, glyceryl stearate, glycolic acid, ammonium polyacryloyldimethyl taurate, stearic acid, phenoxyethanol, palmitic acid, sodium hydroxide, dicaprylyl carbonate, titanium dioxide, mica, steareth-100, phenylethyl resorcinol, caprylyl glycol, fragrance, xanthan gum, dimethicone/vinyl dimethicone crosspolymer, disodium EDTA, tocopherol, sodium hylauronate, ascorbyl glucoside, pentaerythrityl tetra-di-t-butyl hydroxyhydrocinnamate, retinyl palmitate, limonene, myristic acid, t-butyl alcohol, hexyl cinnamal, linalool, benzyl salicylate, benzyl alcohol, tin oxide, citral Production Example 189. SPF 15 Cream
(Ensulizole, Octinoxate)

Active Ingredient
 Ensulizole 1.7% (Sunscreen)
 Octinoxate 7.5% (Sunscreen)

Inactive Ingredient
 water, glycerin, dimethicone, myristyl myristate, stearic acid, palmitic acid, stearyl alcohol, adenosine, cetyl alcohol, geraniol, eugenol, courmin, benzyl alcohol Production Example 190. SPF 15 Lotion Cream
(Ensulizole, Octocrylene)

Active Ingredient
 Ensulizole 2% (Sunscreen)
 Octocrylene 7% (Sunscreen)
Inactive Ingredient
 water, glycerin, cyclopentasiloxane, aluminum starch octenylsuccinate, octyldodecanol, ammonium polyacryloyldimethyl taurate, triethanolamine, hydrogenated lecithin, tocopheryl acetate, disodium phosphate, cholesterol, panthenol, capryloyl salicylic acid, sodium stearoyl glutamate, sodium phosphate, *Glycine soja* (soybean) oil, tocopherol, polycaprolactone, disodium EDTA, methylparaben, diazolidinyl urea, propylparaben, phenoxyethanol, fragrance, benzyl salicylate, butylphenyl methylpropional, hydroxyisohexyl 3-cyclohexene carboxaldehyde, alpha-isomethyl ionone, linalool, hexyl cinnamal, citronellol, geraniol Production Example 191. SPF 30 Lotion
(Avobenzone, Homosalate, Octisalate, Octocrylene)

Active Ingredient
 Avobenzone 3% (Sunscreen)
 Homosalate 4.7% (Sunscreen)
 Octisalate 5% (Sunscreen)
 Octocrylene 7% (Sunscreen)
Inactive Ingredient
 Water, isononyl isononanoate, glycerin, dimethicone, aluminum starch octenylsuccinate, sucrose tristearate, polymethylsilsesquioxane, polysorbate 61, peg-12 dimethicone, carbomer, *Glycine soja* (soybean) protein, triethanolamine, dimethiconol, sodium stearoyl glutamate, adenosine, disodium edta, hydrolyzed elastin, hydrolyzed soy protein, yeast extract, acetyl trifluoromethylphenyl valylglycine, xanthan gum, pentylene glycol, butylene glycol, retinyl palmitate, methylparaben, phenoxyethanol, caprylyl glycol, ethylparaben, linalool, geraniol, alpha-isomethyl ionone, amyl cinnamal, limonene, citronellol, butylphenyl methylpropional, hexyl cinnamal, benzyl alcohol, benzyl benzoate, benzyl salicylate, fragrance, potassium sorbate, sodium benzoate Production Example 192. SPF 50 Lotion
(Avobenzone, Homosalate, Octisalate, Octocrylene, Oxybenzone)

Active Ingredient
 Avobenzone 3% (Sunscreen)
 Homosalate 15% (Sunscreen)
 Octisalate 5% (Sunscreen)
 Octocrylene 5% (Sunscreen)
 Oxybenzone 6% (Sunscreen)
Inactive Ingredient
 water, silica, styrene/acrylates copolymer, butyloctyl salicylate, cyclopentasiloxane, glycerin, poly c10-30 alkyl acrylate, PEG-100 stearate, glyceryl stearate, caprylyl methicone, trisiloxane, PEG-8 laurate, dicaprylyl carbonate, potassium cetyl phosphate, dimethicone, triethanolamine, dimethicone crosspolymer, methylparaben, *Vitis vinifera* (grape) fruit extract, inulin lauryl carbamate, phenoxyethanol, chlorphenesin, disodium EDTA, tocopherol, caprylyl glycol, xanthan gum, acrylates/dimethicone copolymer, acrylates/c10-30 alkyl acrylate crosspolymer, ethyl paraben Production Example 193. SPF 50 Lotion
(Avobenzone, Homosalate, Octisalate, Octocrylene, Oxybenzone)

Active Ingredient
  Avobenzone 3% (Sunscreen)
  Homosalate 15% (Sunscreen)
  Octisalate 5% (Sunscreen)
  Octocrylene 7% (Sunscreen)
  Oxybenzone 6% (Sunscreen)
Inactive Ingredient
  dimethicone, water, isododecane, isononyl isononanoate, PEG-10 dimethicone, styrene/acrylates copolymer, PEG-30 dipolyhydroxystearate, dicaprylyl carbonate, trisiloxane, PEG-8 laurate, dimethicone/PEG-10/15 crosspolymer, sodium chloride, *Vitis vinifera* (grape) fruit extract, phenoxyethanol, p-anisic acid, disodium EDTA, tocopherol, propylene carbonate, disteardimonium hectorite Production Example 194. SPF 50 Lotion
(Avobenzone, Homosalate, Octisalate, Octocrylene, Oxybenzone)

Active Ingredient
  Avobenzone 3% (Sunscreen)
  Homosalate 15% (Sunscreen)
  Octisalate 5% (Sunscreen)
  Octocrylene 7% (Sunscreen)
  Oxybenzone 6% (Sunscreen)
Inactive Ingredient
  water, cyclopentasiloxane, alcohol denat., silica, dicaprylyl ether, styrene/acrylates copolymer, PEG-30 di polyhydroxystearate, dimethicone, cyclohexasiloxane, polymethylsilsesquioxane, nylon-12, PEG-8 laurate, dicaprylyl carbonate, dodecene, methylparaben, sodium chloride, *Vitis vinifera* (grape) fruit extract, phenoxyethanol, disodium EDTA, poloxamer 407, tocopherol, lauryl PEG/PPG-18/18 methicone, caprylyl glycol, isostearyl alcohol, disteardimonium hectorite, poly c10-30 alkyl acrylate Production Example 195. SPF 17 Liquid
(Octinoxate and Titanium Dioxide)

Active Ingredient
  Octinoxate 3% (Sunscreen)
  Titanium dioxide 15% (Sunscreen)
Inactive Ingredient
  water, isododecane, cyclopentasiloxane, glycerin, cyclohexasiloxane, PEG-10 dimethicone, methyl methacrylate crosspolymer, butylene glycol, dimethicone, isoeicosane, ascorbyl glucoside, disteardimonium hectorite, cetyl PEG/PPG-10/1 dimethicone, phenoxyethanol, sodium chloride, C9-15 fluoroalcohol phosphate, polyglyceryl-4 isostearate, hexyl laurate, caprylyl glycol, isostearyl neopentanoate, alumina, methylparaben, calcium pantetheine sulfonate, acetyl trifluoromethylphenyl valyglycine, hydroxypropyl tetrahydropyrantriol, *Pisum sativum* (pea) extract, retinyl palmitate, silica dimethyl silylate, polycaprolactone, soluble collagen, sodium hyaluronate; may contain: titanium dioxide, iron oxides, mica Production Example 196. SPF 30 Cream
(Avobenzone, Homosalate, Octisalate, and Octocrylene)

Active Ingredient
  Avobenzone 3% (Sunscreen)
  Homosalate 5% (Sunscreen)
  Octisalate 5% (Sunscreen)
  Octocrylene 7% (Sunscreen)
Inactive Ingredient
  water, glycerin, isohexadecane, dimethicone, propylene glycol, hydroxyethylpiperazine ethane sulfonic acid, polyacrylamide, dimethicone/vinyl dimethicone crosspolymer, bismuth oxychloride, inulin lauryl carbamate, c13-14 isoparaffin, ethylhexyl hydroxystearate, phenoxyethanol, fragrance, caprylyl glycol, stearyl alcohol, sorbic acid, laureth-7, xanthan gum, trisodium ethylenediamine disuccinate, *Castanea sativa* (chestnut) seed extract, glyceryl stearate, behenyl alcohol, limonene, glyceryl stearate citrate, disodium ethylene dicocamide PEG-15 disulfate, oxothiazolidinecarboxylic acid, citral Production Example 197. SPF 30 Lotion
(Ethyihexyl Triazone, Drometrizole Trisiloxane, Homosalate, Terephthalylidene Dicamphor Sulfonic Acid, Ethyihexyl Salicylate, Bis-Ethylhexyloxyphenol Methoxyphenyl Triazine and Diethylamino Hydroxybenzoyl Hexyl Benzoate)

Active Ingredient
  Ethylhexyl Triazone 3% (Sunscreen)
  Drometrizole Trisiloxane 5% (Sunscreen)
  Homosalate 10% (Sunscreen)
  Ecamsule 3% (Sunscreen)
  Octisalate 5% (Sunscreen)
  Bemotrizinol 4% (Sunscreen)
  Diethylamino hydroxybenzoyl hexyl benzoate 3% (Sunscreen)
Inactive Ingredient
  Aqua/Water, Glycerin, C12-15 Alkyl Benzoate, Alcohol Denat, *Zea mays* Starch/Corn Starch, Propylene Glycol, Synthetic Wax, Sulfonic Acid, Stearic Acid, Palmitic Acid, PEG-100 Stearate, Glyceryl Stearate, Parfum/Fragrance, Caprylyl Glycol, Acrylates/C10-30 Alkyl Acrylate Crosspolymer, Sodium Stearoyl Glutamate, *Glycine Soja* Oil/Soybean Oil, Tocopherol, Xanthan Gum, Benzyl Salicylate, Benzyl Alcohol, Myristic Acid Production Example 198. SPF 50 Lotion
(Ethyihexyl Triazone, Drometrizoletrisiloxane, Homosalate, Terephthalylidene Dicamphor Sulfonic Acid, Ethylhexyl Salicylate, Bis-Ethylhexyloxyphenol Methoxyphenyl Triazine and Diethylamino Hydroxybenzoyl Hexyl Benzoate)

Active Ingredient
  Ethylhexyl Triazone 3% (Sunscreen)
  Drometrizole Trisiloxane 5% (Sunscreen)
  Homosalate 10% (Sunscreen)
  Ecamsule 3%
  Octisalate 5% (Sunscreen)
  Bemotrizinol 4% (Sunscreen)
  Diethylamino hydroxybenzoyl hexyl benzoate 3% (Sunscreen)

Inactive Ingredient
Aqua/Water, Glycerin, C12-15 Alkyl Benzoate, Alcohol Denat, *Zea Mays* Starch/Corn Starch, Propylene Glycol, Synthetic Wax, Sulfonic Acid, Stearic Acid, Palmitic Acid, PEG-100 Stearate, Glyceryl Stearate, Parfum/Fragrance, Caprylyl Glycol, Acrylates/C10-30 Alkyl Acrylate Crosspolymer, Sodium Stearoyl Glutamate, *Glycine Soja* Oil/Soybean Oil, Tocopherol, Xanthan Gum, Benzyl Salicylate, Benzyl Alcohol, Myristic Acid Production Example 199. SPF 50 Lotion
(Drometrizole Trisiloxane, Titanium Dioxide, Ecamsule, Bemotrizinol, Diethylamino Hydroxybenzoyl Hexyl Benzoate and Octinoxate)

Active Ingredient
  Drometrizole Trisiloxane 5% (Sunscreen)
  Titanium dioxide 4% (Sunscreen)
  Ecamsule 12%
  Bemotrizinol 5% (Sunscreen)
  Diethylamino hydroxybenzoyl hexyl benzoate 5% (Sunscreen)
  Octinoxate 6.75% (Sunscreen)
Inactive Ingredient
Aqua/Water, Glycerin, Propylene Glycol, Alcohol Denat., Triethanolamine, Stearic Acid, Potassium Cetyl Phosphate, Nylon-12, Palmitic Acid, PEG-100 Stearate, Glyceryl Stearate, Phenoxyethanol, Cetyl Alcohol, Cellulose, Citric Acid, Aluminum Hydroxide, Caprylyl Glycol, Sodium Cocoyl Sarcosinate, Carbomer, Tocopherol, Tromethanime, *Scutellaria baicalensis* Extract/*Scutellaria baicalensis* Root Extract, Acrylamide/Sodium Acryloyldimethyltaurate Copolymer, Isohexadecane, Xanthan Gum, Myristic Acid, Disodium EDTA, Adenosine, Polysorbate 80, Arginine, Mannitol, Disodium Adenosine Triphosphate, RNA, Pyridoxane HCL, Sorbitan Oleate, Sorbitol, Pentylene Glycol, BHT, Histidine HCL, *Zea mays* Kernel Extract/Corn Kernel Extract, Sodium Chloride, Faex Extract/Yeast Extract, Phenylalanine, *Mentha piperita* Extract/Perppermint Extract, *Rosa gallica* Flower Extract, Tyrosine, Sorbic Acid Production Example 200. SPF 30 Lotion
(Avobenzone, Homosalate, Octisalate, Octocrylene and Oxybenzone)

Active Ingredient
  Avobenzone 2.24% (Sunscreen)
  Homosalate 8% (Sunscreen)
  Octisalate 2.4% (Sunscreen)
  Octocrylene 4.48% (Sunscreen)
Inactive Ingredient
  water, alcohol denat., dimethicone, cyclopentasiloxane, acrylates/di methicone copolymer, phenoxyethanol, caprylyl glycol, sodium polyacrylate, silica, acrylates/C10-30 alkyl acrylate crosspolymer, tocopherol, menthyl lactate, disodium EDTA Production Example 201. SPF 50 Lotion
(Avobenzone, Homosalate, Octisalate, Octocrylene and Oxybenzone)

Active Ingredient
  Avobenzone 3% (Sunscreen)
  Homosalate 10.72% (Sunscreen)
  Octisalate 3.21% (Sunscreen)
  Octocrylene 6% (Sunscreen)
Inactive Ingredient
  water, dimethicone, alcohol denat, styrene/acrylates copolymer, acrylates/dimethicone copolymer, phenoxyethanol, caprylyl glycol, sodium polyacrylate, silica, PEG-8 laurate, acrylates/C10-30 alkyl acrylate crosspolymer, tocopherol, menthyl lactate, disodium EDTA Production Example 202. SPF 50 Lotion
(Avobenzone, Homosalate, Octisalate, Octocrylene and Oxybenzone)

Active Ingredient
  Avobenzone 3% (Sunscreen)
  Homosalate 15% (Sunscreen)
  Octisalate 5% (Sunscreen)
  Octocrylene 5% (Sunscreen)
  Oxybenzone 6% (Sunscreen)
Inactive Ingredient
  water, dimethicone, isododecane, styrene/acrylates copolymer, propanediol, silica, isononyl isononanoate, inulin lauryl carbamate, nylon-12, caprylyl methicone, synthetic wax, poly C10-30 alkyl acrylate, p-anisic acid, sucrose tristearate, *Lycium barbarum* fruit extract, tocopherol, hydrolyzed *Triticum monococcum* seed extract, phenoxyethanol, stearyl alcohol, PEG-8 laurate, triethanolamine, polymethyl methacrylate, ammonium acryloyldimethyltaurate/steareth-25 methacrylate crosspolymer, dimethiconol, xanthan gum, disodium EDTA, glycerin Production Example 203. SPF 50 Lotion (Titanium Dioxide)

Active Ingredient
  Titanium dioxide 11% (Sunscreen)
Inactive Ingredient
  water, dimethicone, isododecane, c12-15 alkyl benzoate, talc, alcohol denat, undecane, propanediol, styrene/acrylates copolymer, butyloctyl salicylate, phenethyl benzoate, triethylhexanoin, isohexadecane, tridecane, dimethicone/PEG-10/15 crosspolymer, PEG-9 polydimethylsiloxyethyl dimethicone, aluminum hydroxide, aluminum stearate, phenoxyethanol, stearic acid, *Lycium barbarum* fruit extract, sodium chloride, caprylyl glycol, PEG-8 laurate, alumina, polyhydroxystearic acid, disteardimonium hectorite, propylene carbonate, tocopherol, benzoic acid, PEG-9

Production Example 204. SPF 50 Lotion
(Avobenzone, Homosalate, Octisalate, Octocrylene and Oxybenzone)

Active Ingredient
  Avobenzone 3% (Sunscreen)
  Homosalate 15% (Sunscreen)
  Octisalate 5% (Sunscreen)
  Octocrylene 5% (Sunscreen)
  Oxybenzone 6% (Sunscreen)
Inactive Ingredient
  water, dimethicone, isododecane, styrene/acrylates copolymer, propanediol, glycerin, silica, isononyl isononanoate, inulin lauryl carbamate, nylon-12, caprylyl methicone, synthetic wax, poly C10-30 alkyl acrylate, phenoxyethanol, *Lycium barbarum* fruit extract, sucrose tristearate, ammonium acryloyldimethyltaurate/steareth-25 methacrylate crosspolymer, PEG-8 laurate, stearyl alcohol, polymethyl methacrylate, p-anisic acid, chlorphenesin, dimethiconol, xanthan gum, disodium EDTA, tocopherol, triethanolamine, hydrolyzed *Triticum monococcum* seed extract

Production Example 205. SPF 30 Cream (Avobenzone, Homosalate, Octisalate and Octocrylene)

Active Ingredient
 Avobenzone 3% (Sunscreen)
 Homosalate 2.7% (Sunscreen)
 Octisalate 5% (Sunscreen)
 Octocrylene 7% (Sunscreen)
Inactive Ingredient
 water, glycerin, cetearyl alcohol, isohexadecane, glyceryl stearate, cyclohexasiloxane, isononyl isononanoate, *Butyrospermum parkii* (rhea) butter, PEG-100 stearate, ceteareth-20, phenoxyethanol, butylene glycol, ammonium polyacryloyldimethyl taurate, caprylyl glycol, tocopherol, chlorphenesin, xanthan gum, disodium EDTA, p-anisic acid, calcium PCA, adenosine, copper PCA, *alteromonas* ferment extract, *Corallina officinalis* extract, citric acid, sodium hydroxide

Production Example 206. SPF 50 Ointment (Avobenzone, Homosalate, Octisalate, Octocrylene and Oxybenzone)

Active Ingredient
 Avobenzone 3% (Sunscreen)
 Homosalate 10% (Sunscreen)
 Octisalate 5% (Sunscreen)
 Octocrylene 7.5% (Sunscreen)
 Oxybenzone 5% (Sunscreen)
Inactive Ingredient
 synthetic beeswax, isodecyl neopentanoate, C10-18 triglycerides, hydrogenated castor oil, *Euphorbia cerifera* (candelilla) wax, isopropyl palmitate, caprylic/capric triglyceride, squalane, isopropyl myristate, isodecyl salicylate, ozokerite, sorbitan isostearate, stearalkonium hectorite, PEG-5, pentaerythrityl ether, PPG-5 pentaerythrityl ether, polyisobutene, propylene carbonate, *Glycine soja* (soybean) sterols, tocopheryl acetate

Production Example 207. SPF 50 Ointment (Avobenzone Homosalate Octisalate Octocrylene Oxybenzone)

Active Ingredient
 Avobenzone 3% (Sunscreen)
 Homosalate 10% (Sunscreen)
 Octisalate 5% (Sunscreen)
 Octocrylene 7.5% (Sunscreen)
 Oxybenzone 5% (Sunscreen)
Inactive Ingredient
synthetic beeswax, isodecyl neopentanoate, C10-18 triglycerides, hydrogenated castor oil, *Euphorbia cerifera* (candelilla) wax, isopropyl palmitate, caprylic/capric triglyceride, squalane, isopropyl myristate, isodecyl salicylate, ozokerite, sorbitan isostearate, stearalkonium hectorite, PEG-5, pentaerythrityl ether, PPG-5 pentaerythrityl ether, polyisobutene, propylene carbonate, *Glycine soja* (soybean) sterols, tocopheryl acetate

Production Example 208. SPF 50 Lotion (Avobenzone Homosalate Octisalate Octocrylene Oxybenzone)

Active Ingredient
 Avobenzone 3% (Sunscreen)
 Homosalate 15% (Sunscreen)
 Octisalate 5% (Sunscreen)
 Octocrylene 7.5% (Sunscreen)
 Oxybenzone 6% (Sunscreen)
Inactive Ingredient
 Water, cyclopentasiloxane, alcohol denat., silica, dicaprytyl ether, styrene/acrylates copolymer, PEG-30 dipolyhydroxystearate, di methicone, cyclohexasiloxane, polymethylsiisequioxane, nylon-12, dicapryly caronate, phenoxyethanol, lauryl PEG/PPG-18/8 methicone, sodium chloride, caprylyl glycol, methylparaben, poly c10-30 alkyl acrylate, diistearmonium hectorite, disodium EDTA, dodecene, poloxamer 407

Production Example 209. SPF 50 Lotion (Avobenzone, Homosalate, Octisalate, Octocrylene and Oxybenzone)

Active Ingredient
 Avobenzone 3% (Sunscreen)
 Homosalate 10.72% (Sunscreen)
 Octisalate 3.21% (Sunscreen)
 Octocrylene 6% (Sunscreen)
 Oxybenzone 3.86% (Sunscreen)
Inactive Ingredient
 Water, cyclopentasiloxane, alcohol denat, silica, dicaprylyl ether, styrene/acrylates copolymer, PEG-30 di polyhydroxystearate, dimethicone, cyclohexasiloxane, polymethylsilsesquioxane, nylon-12, dicaprylyl carbonate, phenoxyethanol, lauryl PEG/PPG-18/18 methicone, sodium chloride, caprylyl glycol, PEG-8 laurate, poly C10-30 alkyl acrylate, disteardimonium hectorite, tocopherol, isostearyl alcohol, p-anisic acid, disodium EDTA, dodecene, poloxamer 407

Production Example 210. SPF 50 Lotion (Titanium Dioxide)

Active Ingredient
 Titanium dioxide 15% (Sunscreen)
Inactive Ingredient
 Water, isododecane, dimethicone, C12-15 alkyl benzoate, undecane, styrene/acrylates copolymer, caprylyl methicone, nylon-12, butyloctyl salicylate, phenethyl benzoate, dicaprylyl carbonate, silica, triethylhexanoin, isohexadecane, tridecane, dicaprylyl ether, talc, dimethicone/PEG-10/15 crosspolymer, aluminum hydroxide, stearic acid, pentylene glycol, PEG-9 polydimethylsiloxyethyl dimethicone, iron oxides, aluminum stearate, PEG-8 laurate, phenoxyethanol, magnesium sulfate, caprylyl glycol, alumina, polyhydroxystearic acid, disteardimonium hectorite, tocopherol, propylene carbonate, benzoic acid, disodium stearoyl glutamate, PEG-9

Production Example 211. SPF 20 Lotion (Avobenzone, Homosalate, Octisalate and Octocrylene)

Active Ingredient
 Avobenzone 3% (Sunscreen)
 Homosalate 8.8% (Sunscreen)
 Octisalate 4.9% (Sunscreen)
 Octocrylene 5.9% (Sunscreen)
Inactive Ingredient
 Water, glycerin, alcohol denat., tocopherol, aloe barbadensis leaf juice, phenoxyethanol, sodium hydroxide, caprylyl glycol, sodium polyacrylate, fragrance, acrylates/C10-30 alkyl acrylate crosspolymer, ascorbyl glucoside, caffeine, sodium hyaluronate, xanthan gum, menthyl lactate, disodium EDTA, limonene, ceramide N P, *Castanea sativa* (chestnut) seed extract, pentylene glycol, hydrolyzed soy protecin, linalool, citric acid, potassium sorbate, citral, sodium benzoate, ethyl hexyl glycerin

Production Example 212. SPF 15 Lotion
(Avobenzone, Octisalate and Octocrylene)

Active Ingredient
  Avobenzone 3% (Sunscreen)
  Octisalate 5% (Sunscreen)
  Octocrylene 5% (Sunscreen)
Inactive Ingredient
  Water, glycerin, alcohol denat, silica, cyclohexsiloxane, propylene glycol, synthetic fluorphlogopite, cetyl alcohol, dimethicone, stearic acid, palmitic acid, phenoxyethanol, PEG-100 stearate, glyceryl stearate, ammonium polyacryloyldimethyl taurate, fragrance, dimethiconol, *Zea mays* (corn) germ oil, caffeine, tocopherol, disodium EDTA, menthol, limonene, biosacchaide gum-1, sodium hydroxide, ascorbyl glucoside, *Castanea sativa* (chestnut) seed extract, *Citrus medica limonum* (lemon) juice, hydrolyzed soy protein, *Citrus aurantium dulcis* (orange) juice, linalool, citral, red 4, blue 1

Production Example 213. SPF 50 Lotion
(Avobenzone, Homosalate, Octisalate, Octocrylene and Oxybenzone)

Active Ingredient
  Avobenzone 3% (Sunscreen)
  Homosalate 15% (Sunscreen)
  Octisalate 5% (Sunscreen)
  Octocrylene 5% (Sunscreen)
  Oxybenzone 6% (Sunscreen)
Inactive Ingredient
  Water, cyclopentasiloxane, alcohol denat., silica, dicaprylyl ether, styrene/acrylates copolymer, PEG-30 di polyhydroxystearate, dimethicone, cyclohexasilloxane, polymethylsilsesquioxane, nylon-12, dicaprylyl carbonate, phenoxyethanol, lauryl PEG-PPG-18/18 methicone, sodium chloride, caprylyl glycol, PEG-8 laurate, methylparaben, tocopherol, poly c10-30 alkyl acrylate, disteardimonium hectorite, isostearyl alcohol, caffeine, ascorbyl glucoside, disodium EDTA, dodecene, poloxamer 407

Production Example 214. SPF 50 Lotion
(Avobenzone Homosalate Octisalate Octocrylene Oxybenzone)

Active Ingredient
  Avobenzone 3% (Sunscreen)
  Homosalate 15% (Sunscreen)
  Octisalate 5% (Sunscreen)
  Octocrylene 5% (Sunscreen)
  Oxybenzone 6% (Sunscreen)
Inactive Ingredient
  Water, cyclopentasiloxane, alcohol denat., silica, dicaprylyl ether, styrene/acrylates, copolymer, PEG-30 dipolyhydroxystearate, dimethicone, cyclohexasiloxane, polymethylsilsesquioxane, nylon-12, dicaprylyl carbonate, phenoxyethanol, lauryl PEG/PPG-18/18 methicone, sodium chloride, caprylyl glycol, PEG-8 laurate, methylparaben, tocopherol, poly c10-30 alkyl acrylate, disteardimonium hectorite, isostearyl alcohol, caffeine, ascorbyl glucoside, disodium EDTA, dodecene, poloxamer 407

Production Example 215. SPF 30 Cream
(Avobenzone, Homosalate, Octisalate and Octocrylene)

Active Ingredient
  Avobenzone 3% (Sunscreen)
  Homosalate 5% (Sunscreen)
  Octisalate 5% (Sunscreen)
  Octocrylene 7% (Sunscreen)
Inactive Ingredient
  Water, glycerin, dimethicone, glyceryl stearate, hydroxypropyl tetrahydropyrantriol, silica, PEG-100 stearate, propylene glycol, *Euphorbia cerifera* (candelilla) wax, phenoxyethanol, ammonium polyacryloyldimethyl taurate, stearic acid, dicaprylyl carbonate, cetyl alcohol, palmitic acid, capryloyl salicylic acid, caprylyl glycol, xanthan gum, dimethicone/vinyl dimethicone crosspolymer, fragrance, disodium EDTA, tocopherol, sodium hyaluronate, adenosine, linalool, sodium hydroxide, *Jasminum officinale* (jasmine) flower extract, citronellol, geraniol, citral, benzyl alcohol, citric acid

Production Example 216. SPF 30 Cream
(Avobenzone, Homosalate, Octisalate and Octocrylene)

Active Ingredient
  Avobenzone 3% (Sunscreen)
  Homosalate 5% (Sunscreen)
  Octisalate 5% (Sunscreen)
  Octocrylene 7% (Sunscreen)
Inactive Ingredient
  Water, glycerin, squalene, dimethicone, PEG-100 stearate, glyceryl stearate, silica, octyldodecanol, stearic acid, phenoxyethanol, palmitic acid, tocopherol, dicaprylyl carbonate, steareth-100, acrylates/c10-30 alkyl acrylate crosspolymer, *Ophiopogon japonicus* root extract, carbomer, chlorphenesin, capryloyl salicylic acid, caprylyl glycol, xanthan gum, dimethicone/vinyl dimethicone crosspolymer, disodium EDTA, sodium hydroxide, *Citrus aurantium dulcis* (orange) peel oil, limonene, ectoin, hydrolyzed hyaluronic acid, myristic acid, *Mentha piperita* (peppermint) oil, *pseudoalteromonas* ferment extract, ethylhexylglycerin, linalool, salicylic acid

Production Example 217. SPF 30 Cream
(Avobenzone, Homosalate, Octisalate and Octocrylene)

Active Ingredient
  Avobenzone 3% (Sunscreen)
  Homosalate 5% (Sunscreen)
  Octisalate 5% (Sunscreen)
  Octocrylene 7% (Sunscreen)
Inactive Ingredient
  Water, glycerin, dimethicone, glyceryl stearate, hydroxypropyl tetrahydropyrantriol, silica, PEG-100 stearate, propylene glycol, *Euphorbia cerifera* (candelilla) wax, phenoxyethanol, ammonium polyacryloyldimethyl taurate, stearic acid, dicaprylyl carbonate, cetyl alcohol, palmitic acid, capryloyl salicylic acid, caprylyl glycol, xanthan gum, dimethicone/vinyl dimethicone crosspolymer, fragrance, disodium EDTA, tocopherol, sodium hyaluronate, adenosine, linalool, sodium hydroxide, *Jasminum officinale* (jasmine) flower extract, citronellol, geraniol, citral, benzyl alcohol, citric acid Production Example 218. SPF 30 Lotion (Avobenzone, Homosalate, Octisalate and Octocrylene)

Active Ingredient
  Avobenzone 3% (Sunscreen)
  Homosalate 7% (Sunscreen)
  Octisalate 5% (Sunscreen)
  Octocrylene 5% (Sunscreen)
Inactive Ingredient
  Water, propylene glycol, dicaprylyl ether, glycerin, PEG-100 stearate, glyceryl stearate, squalane, hydrogenated polyisobutene, phenoxyethanol, sorbitan oleate, caprylyl glycol, acrylates/c10-30 alkyl acrylate crosspolymer, triethanolamine, beeswax, tocopherol, disodium EDTA, stearic acid, myristyl alcohol, *Prunus amygdalus dulcis* (sweet almond) oil, *Prunus armeniaca* (apricol) kernel oil, *Persea gratissima* (avocado) oil Production Example 219. SPF 50 Cream (Avobenzone, Homosalate, Octisalate, Octocrylene and Oxybenzone)

Active Ingredient
  Avobenzone 3% (Sunscreen)
  Homosalate 10.7% (Sunscreen)
  Octisalate 3.2% (Sunscreen)
  Octocrylene 6% (Sunscreen)
  Oxybenzone 3.9% (Sunscreen)
Inactive Ingredient
  Water, cyclopentasiloxane, alcohol denat, silica, dicaprylyl ether, styrene/acrylates copolymer, PEG-30 dipolyhydroxystearate, di methicone, cyclohexasiloxane, polymethylsilsequioxane, nylon-12, dicaprylyl carbonate, phenoxyethanol, lauryl PEG/PPG-18/18 methicone, cellulose, sodium chloride, caprylyl glycol, PEG-8 laurate, poly C10-30 alkyl acrylate, disteardimonium hectorite, tocopherol, isostearyl alcohol, p-anisic acid, *Scutellaria baicalensis* root extract, disodium EDTA, dodecene, poloxamer 407, propylene carbonate, triethanolamine Production Example 220. SPF 50 Gel (Ethylhexyl Triazone, Diethylamino Hydroxybenzoyl Hexyl Benzoate, Bis-Ethylhexyloxyphenol Methoxyphenyl Triazine and Drometrizole Trisiloxane)

Active Ingredient
  Ethylhexyl triazone 5% (Sunscreen)
  Diethylamino hydroxybenzoyl hexyl benzoate 3% (Sunscreen)
  Bemotrizinol 3% (Sunscreen)
  Drometrizoletrisiloxane 1% (Sunscreen)
  Titanium dioxide 2.5% (Sunscreen)
Inactive Ingredient
  Water, alcohol, diisopropyl sebacate, isopropyl lauroyl sarcosinate, propylene glycol, glycerin, methyl methacrylate/glycol dimethacrylate crosspolymer, tocopherol, stearic acid, phenoxyethanol, cetyl alcohol, palmitic acid, styrene/acrylamide copolymer, ceteth-10, caprylyl glycol, 3-((1-menthyl)oxy)propane-1,2-diol, dextrin palmitate, aluminum hydroxide, ammonium polyacryloyldimethyl taurate, butylene glycol, potassium hydroxide, peg-8 laurate, edetate disodium anhydrous, adenosine, myristic acid, *Gentiana lutea* root, pentylene glycol, *Mentha piperita*, sheanut, *Rosa gallica* flower, sorbitol, *Moringa oleifera* seed, sodium phosphate, dibasic, anhydrous, citric acid monohydrate Production Example 221. SPF 50 Cream (Drometrizole Trisiloxane, Terephthalylidene Dicamphor Sulfonic Acid, Bis-Ethylhexyloxyphenol Methoxyphenyl Triazine, Titanium Dioxide, Ethyihexyl Methoxycinnamate and Diethylamino Hydroxybenzoyl Hexyl Benzoate)

Active Ingredient
  Drometrizole trisiloxane 4% (Sunscreen)
  Ecamsule 12% (Sunscreen)
  Bemotrizinol 5% (Sunscreen)
  Titanium dioxide 4% (Sunscreen)
  Octinoxate 6.75% (Sunscreen)
  Diethylamino hydroxybenzoyl hexyl benzoate 5% (Sunscreen)
Inactive Ingredient
  Aqua/Water, Butylene Glycol, Glycerin, Dimethicone, Isocetyl Stearate, Alcohol Denate., Propylene Glycol, Stearic Acid, Potassium Cetyl Phosphate, Tocopherol, Palmitic Acid, PEG-100 Stearate, Glyceryl Stearate, Phenoxyethanol, Cetyl alcohol, Cellulose, Hydroxyethyl Acrylate/Sodium Acryloyldimethyl Taurate Copolymer, Aluminum Hydroxide, Caprylyl Glycol, Sodium Cocoyl Sarcosinate, Carbomer, *Scutellaria baicalensis* Extract/*Scutellaria baicalensis* Root Extract, Acrylamide/Sodium Acryloyldimethyltaurate Copolymer, Citric Acid, Isohexadecane, Xanthan Gum, Myristic Acid, *Pelargonium graveolens* Flower Oil, *Citrus aurantium dulcis* (Orange) Peel Oil, Disodium EDTA, *Litchi chinensis* Pedcarp Extract, Adenosine, Polysorbate 80, Ethylhexyl Hydroxystearate, Sorbitan Isostearate, Sorbitan Oleate, Polysorbate 60, BHT, Sodium Chloride. May Contain: C177891/Titanium Dioxide, Cl 77491, Cl 77492, Cl 77499/Iron Oxides, Cl 77163/Bismuth Oxychloride Production Example 222. SPF 30 Lotion (Homosalate, Meradimate, Octinoxate, Zinc Oxide, and Octocrylene)

Active Ingredient
  Homosalate 10% (Sunscreen)
  Meradimate 5% (Sunscreen)
  Octinoxate 5% (Sunscreen)
  Octocrylene 2% (Sunscreen)
  Zinc Oxide 6.3% (Sunscreen)
Inactive Ingredient
  Water, niacinamide, cetearyl alcohol, glycerin, dimethicone, behentrimonium methosulfate, ceramide 3, ceramide 6-II, ceramide 1, hyaluronic acid, sodium hydroxide, aluminum starch octenylsuccinate, hydroxyethylcellulose, methylparaben, disodium EDTA, propylparaben, sodium lauroyl lactylate, phytosphingosine, cholesterol, carbomer, xanthan gum Production Example 223. SPF 45 Lotion (Titanium Dioxide and Zinc Oxide)

Active Ingredient
  Titanium dioxide 7.4% (Sunscreen)
  Zinc oxide 11.4% (Sunscreen)
Inactive Ingredient
  Water, butyloctyl salicylate, C12-15 alkyl benzoate, glycerin, caprylyl methicone, isohexadecane, triethylhexanoin, mica, glyceryl stearate, trimethylsiloxy silicate, PEG-100 stearate, alumina, polyhydroxystearic acid, aluminum stearate, caprylic/capric triglycerides, polypropyl silsesquioxane, xanthan gum, hydrogenated dimer dilinoleyl/dimethylcarbonate copolymer, ceramide 3, ceramide 6-II, ceramide 1, aloe barbadensis leaf juice, carthamus tinctorius (safflower) seed oil, niacinamide, hyaluronic acid, sodium hydroxide, phenoxyethanol, cetyl alcohol, isostearic acid, PEG-75 stearate, citric acid, tetrasodium EDTA, propylene glycol stearate, glyceryl isostearate, propylene glycol isostearate, oleth-25, ceteth-25, inulin lauryl carbamate, ceteth-20, steareth-20, stearic acid, ethylhexyl glycerin, glucamine, triethoxycaprylylsilane, sodium lauroyl lactylate, silica, phytosphingosine, cholesterol, carbomer Production Example 224. SPF 30 Lotion (Titanium Dioxide and Zinc Oxide)

Active Ingredient
  Titanium dioxide 6% (Sunscreen)
  Zinc oxide 5% (Sunscreen)
Inactive Ingredient
  water, glycerin, C12-25 alkyl benzoate, dimethicone, glyceryl stearate, isododecane, butyloctyl salicylate, styrene/acrylates copolymer, propanediol, stearic acid, PEG-100 stearate, sorbitan stearate, acrylates/dimethicone copolymer, PEG-8 laurate, ceramide NP, ceramide A P, ceramide EOP, sorbitan isostearate, carbomer, ceteraryl alcohol, ceteareth-20, triethoxycaprylylsilane, dimethiconol, sodium citrate, sodium lauroyl lactylate, sodium dodecylbenzenesulfonate, myristic acid, sodium hyaluronate, cholesterol, aluminum hydroxide, palmitic acid, phenoxyethanol, chlorphenesin, hydroxyethyl acrylate/sodium acryloyldimetyl taurate copolymer, caprylyl glycol, citric acid, xanthan gum, phytosphinfosine, polyhydroxystearic acid, polysorbate 60, ethylhexylglycerin Production Example 225. SPF 30 Lotion (Titanium Dioxide and Zinc Oxide)

Active Ingredient
  Titanium dioxide 6% (Sunscreen)
  Zinc oxide 5% (Sunscreen)
Inactive Ingredient
  Water, glycerin, C12-15 alkyl benzoate, dimethicone, glyceryl stearate, isododecane, butyloctyl salicylate, styrene/acrylates copolymer, propanediol, stearic acid, PEG-100 sterate, sorbitan stearate, niacinamide, acrylates/dimethicone copolymer, PEG-8 laurate, ceramide NP, ceramide AP, ceramide EOP, sorbitan isostearate, carbomer, cetearyl alcohol, ceteareth-20, triethoxycaprylylsilane, dimethiconol, sodium citrate, sodium lauroyl lactylate, sodium dodecylbenzenesulfonate, myristic acid, sodium hyaluronate, cholesterol, aluminum hydroxide, palmitic acid, phenoxyethanol, chlorphenesin, hydroxyethyl acrylate/sodium acryloyldimethyl taurate copolymer, caprylyl glycol, citric acid, panthenol, xanthan gum, phytosphingosine, polyhydroxystearic acid, polysorbate 60, ethylhexylglycerin Production Example 226. SPF 50 Lotion (Titanium Dioxide and Zinc Oxide)

Active Ingredient
  Titanium dioxide 9% (Sunscreen)
  Zinc oxide 7% (Sunscreen)
Inactive Ingredient
  Water, glycerin, C12-15 alkyl benzoate, dimethicone, isododecane, styrene/acrylates copolymer, glyceryl stearate, butyloctyl salicylate, dicaprylyl carbonate, propanediol, stearic acid, aluminum hydroxide, PEG-100 stearate, sorbitan stearate, PEG-8 laurate, ceramide NP, ceramide AP, ceramide EOP, sorbitan isostearate, carbomer, cetearyl alcohol, cetearth-20, triethoxycaprylylsilane, dimethiconol, sodium citrate, sodium lauroyl lactylate, sodium dodecylbenzenesulfonate, myristic acid, sodium hyaluronate, cholesterol, palmitic acid, phenoxyethanol, chlorphenesin, tocopherol, hydroxyethyl acrylate/sodium acryloyldimetyl taurate copolymer, caprylyl glycol, citric acid, xanthan gum, phytosphinfosine, polyhydroxystearic acid, polysorbate 60, ethylhexylglycerin Production Example 227. SPF 50 Lotion (Titanium Dioxide and Zinc Oxide)

Active Ingredient
  Titanium dioxide 9% (Sunscreen)
  Zinc oxide 7% (Sunscreen)
Inactive Ingredient
  Water, glycerin, C12-15 alkyl benzoate, dimethicone, isododecane, styrene/acrylates copolymer, glyceryl stearate, butyloctyl salicylate, dicaprylyl carbonate, propanediol, stearic acid, aluminum hydroxide, PEG-100 stearate, sorbitan stearate, niacinamide, PEG-8 laurate, ceramide N P, ceramide AP, ceramide EOP, sobitan isostearate, carbomer, cetearyl alcohol, ceteareth-20, triethoxycaprylylsilane, dimethiconol, sodium citrate, sodium lauroyl lactylate, sodium dodecylbenzenesulfonate, myristic acid, sodium hyaluronate, cholesterol, palmitic acid, phenoxyethanol, chlorphenesin, tocopherol, hydroxyethyl acrylate/sodium acryloyldimethyl taurate copolymer, caprylyl glycol, citric acid, panthenol, xanthan gum, phytosophingosine, polyhydroxystearic acid, palysorbate 60, ethylhexylglycerin Production Example 228. SPF 30 Cream (Octinoxate and Zinc Oxide)

Active Ingredient
  Octinoxate 7.5% (Sunscreen)
  Zinc oxide 10.5% (Sunscreen)
Inactive Ingredient
  Water, cyclomethicone, pentylene glycol, phenyl trimethicone, cetearyl alcohol, PEG-40 stearate, dimethicone, glycerin, stearyl alcohol, phenoxyethanol, hydroxyethyl acrylate, sodium acryloyldimethyl taurate copolymer, ceramide 3, ceramide 6-II, ceramide 1, potassium cetyl phosphate, squalane, phytosphingosine, cholesterol, lecithin, hydrogenated palm glycerides, behentrimonium methosulfate, polysorbate 60, hyaluronic acid, retinol, disodium EDTA, xanthan gum, iris florentina root extract, ceteareth-20, polysilicone-11, polysorbate 20, chiorphenesin, sodium lauroyl lactylate, tetrahexyldecyl ascorbate, alcohol, butylene glycol, ethylhexylglycerin, dimethicone crosspolymer-3, sodium polyacrylate, sodium hydroxide, carbomer, citric acid Production Example 229. SPF 30 Lotion (Titanium Dioxide, Zinc Oxide)

Active Ingredient
  Titanium dioxide 3.67% (Sunscreen)
  Zinc oxide 3.5% (Sunscreen)

Inactive Ingredient

Water, Dimethicone, Cetyl Dimethicone, Butyloctyl Salicylate, Trimethylsiloxysilicate, Styrene/Acrylates Copolymer, Dimethicone PEG-8 Laurate, Polysorbate 60, Ceramide 3, Ceramide 6 II, Ceramide 1, Cholesterol, Phytosphingosine, Trisiloxane, Isohexadecane, Arachidyl Alcohol, Butylene Glycol, Polyhydroxystearic Acid, Hydrated Silica, PEG-100 Stearate, Glyceryl Stearate, Ascorbic Acid, *Avena sativa* (Oat) Kernel Extract, Arachidyl Glucoside, Beeswax, Behenyl Alcohol, Benzyl Alcohol, Stearic Acid, Bisabolol, Dipotassium Glycyrrhizate, Ethylhexylglycerin, Glycerin, Hydroxyethyl Acrylate/Sodium cryloyldimethyl Taurate Copolymer, Pantothenic Acid/Yeast Polypeptide, PEG-8, Xanthan Gum, Polyaminopropyl Biguanide, Polymethyl Methacrylate, Alumina, Potassium Sorbate, Retinyl Palmitate, Sodium Lauroyl Lactylate, Carbomer, Tocopheryl Acetate, BHT, Disodium EDTA, Methicone, Methylisothiazolinone, Triethoxycaprylylsilane Production Example 230. SPF 50 Lotion (Titanium Dioxide, Zinc Oxide)

Active Ingredient
  Titanium dioxide 4.9% (Sunscreen)
  Zinc oxide 4.7% (Sunscreen)
Inactive Ingredient
  Water, Butyloctyl Salicylate, Cetyl Dimethicone, Dimethicone, Styrene/Acrylates Copolymer, Trimethylsiloxysilicate, Dimethicone PEG-8 Laurate, Isohexadecane, Butylene Glycol, Polysorbate 60, Trisiloxane, Arachidyl Alcohol, Polyhydroxystearic Acid, Hydrated Silica, Ceramide 3, Ceramide 6-II, Ceramide 1, Cholesterol, Phytosphingosine, PEG-100 Stearate, Glyceryl Stearate, Ascorbic Acid, *Avena sativa* (Oat) Kernel Extract, Arachidyl Glucoside, Beeswax, Behenyl Alcohol, Benzyl Alcohol, Stearic Acid, Bisabolol, Dipotassium Glycyrrhizate, Ethylhexyl glycerin, Glycerin, Hydroxyethyl Acrylate/Sodium Acryloyldimethyl Taurate Copolymer, Pantothenic Acid/Yeast Polypeptide, PEG-8, Xanthan Gum, Polyaminopropyl Biguanide, Polymethyl Methacrylate, Alumina, Potassium Sorbate, Retinyl Palmitate, Sodium Lauroyl Lactylate, Carbomer, Tocopheryl Acetate, BHT, Disodium EDTA, Methicone, Methylisothiazolinone, Triethoxycaprylylsilane.

Production Example 231. SPF 30 Lotion (Titanium Dioxide, Zinc Oxide)

Active Ingredient
  Titanium dioxide 3.7% (Sunscreen)
  Zinc oxide 3.5% (Sunscreen)
Inactive Ingredient
  Water, dimethicone, cetyl dimethicone, butyloctyl salicylate, trimethylsiloxysilicate, styrene/acrylates copolymer, dimethicone PEG-8 laurate, polysorbate 60, ceramide 3, ceramide 6 II, ceramide 1, cholesterol, phytosphingosine, niacinamide, trisiloxane, isohexadecane, arachidyl alcohol, butyleneglycol, polyhydroxystearic acid, hydrated silica, PEG-100 stearate, glyceryl stearate, ascorbic acid, *Avena sativa* (oat) kernel extract, arachidyl glucoside, beeswax, behenyl alcohol, benzyl alcohol, stearic acid, bisabolol, dipotassium glycyrrhizate, ethylhexylglycerin, glycerin, hydroxyethyl acrylate/sodium acryloyldimethyl taurateco-polymer, pantothenic acid/yeast polypeptide, PEG-8, xanthan gum, polyaminopropyl biguanide, polymethyl methacrylate, alumina, potassium sorbate, retinyl palmitate, sodium lauroyl lactylate, carbomer, tocopheryl acetate, BHT, disodium EDTA, methicone, methylisothiazolInone, triethoxycaprylylsilane Production Example 232. SPF 50 Lotion (Titanium Dioxide, Zinc Oxide)

Active Ingredient
  Titanium dioxide 4.9% (Sunscreen)
  Zinc oxide 4.7% (Sunscreen)
Inactive Ingredient
  Water, butyloctyl salicylate, cetyl dimethicone, dimethicone, styrene/acrylates copolymer, trimetylsiloxysilicate, dimethicone PEG-8 laurate, isohexadecane, butylene glycol, polysorbate 60, trisiloxane, arachidyl alcohol, polyhydroxystearic acid, hydrated silica, ceramide 3, ceramide 6-II, ceramide 1, niacinamide, cholesterol, phytosphingosine, PEG-100 stearate, glyceryl stearate, ascorbic acid, *Avena sativa* (oat) kernel extract, arachidyl glucoside, beeswax, behenyl alcohol, benzyl alcohol, stearic acid, bisabolol, dipotassium glycyrrhizate, ethylhexylglycerin, glycerin, hydroxyethyl acrylate/sodium acryloyldimethyl taurate copolymer, pantothenic acid/yeast polypeptide, PEG-8, xanthan gum, polyaminopropyl biguanide, polymethyl methacrylate, alumina, potassium sorbate, retinyl palmitate, sodium lauroyl lactylate, carbomer, tocopheryl acetate, BHT, disodium EDTA, methicone, methylisothiazolinone, triethoxycaprylylsilane Production Example 233. SPF 30 Lotion (Avobenzone, Homosalate, Octisalate and Octocrylene)

Active Ingredient
  Avobenzone 3% (Sunscreen)
  Homosalate 10% (Sunscreen)
  Octisalate 5% (Sunscreen)
  Octocrylene 2.7% (Sunscreen)
Inactive Ingredient
  Water, C12-15 alkyl benzoate, glyceryl stearate SE, methyl methacrylate crosspolymer, glycerin, pentylene glycol, ceramide N P (ceramide 3), ceramide A P (ceramide 6-II), ceramide EOP (ceramide 1), phytosphingosine, sodium acryloyldimethyltaurate VP crosspolymer, sodium lauroyl lactylate, cholesterol, xanthan gum, carbomer, hydroxyacetophenone, disodium EDTA, citric acid, sodium hyaluronate Production Example 234. SPF 30 Lotion (Octinoxate and Zinc Oxide)

Active Ingredient
  Octinoxate 7.5% (Sunscreen)
  Zinc oxide 10.5% (Sunscreen)
Inactive Ingredient
  Water, cyclomethicone, pentylene glycol, phenyl trimethicone, cetearyl alcohol, PEG-40 stearate, dimethicone, glycerin, stearyl alcohol, phenoxyethanol, hydroxyethyl acrylate, sodium acryloyldimethyl taurate copolymer, ceramide 3, ceramide 6-II, ceramide 1, potassium cetyl phosphate, squalane, phytosphingosine, cholesterol, lecithin, hydrogenated palm glycerides, behentrimonium methosulfate, polysorbate 60, hyaluronic acid, retinol, disodium EDTA, xanthan gum, iris florentina root extract, ceteareth-20, polysilicone-11, polysorbate 20, chlorphenesin, sodium lauroyl lactylate, tetrahexyldecyl ascorbate, alcohol, butylene glycol, ethylhexylglycerin, dimethicone crosspolymer-3, sodium polyacrylate, sodium hydroxide, carbomer, citric acid

Production Example 235. SPF 30 Lotion (Titanium Dioxide, Zinc Oxide)

Active Ingredient
  Titanium dioxide 3.67% (Sunscreen)
  Zinc oxide 3.5% (Sunscreen)
Inactive Ingredient
  Water, Dimethicone, Cetyl Dimethicone, Butyloctyl Salicylate, Trimethylsiloxysilicate, Styrene/Acrylates Copolymer, Dimethicone PEG-8 Laurate, Polysorbate 60, Ceramide 3, Ceramide 6 II, Ceramide 1, Cholesterol, Phytosphingosine, Trisiloxane, Isohexadecane, Arachidyl Alcohol, Butylene Glycol, Polyhydroxystearic Acid, Hydrated Silica, PEG-100 Stearate, Glyceryl Stearate, Ascorbic Acid, *Avena sativa* (Oat) Kernel Extract Arachidyl Glucoside, Beeswax, Behenyl Alcohol, Benzyl Alcohol, Stearic Acid, Bisabolol, Dipotassium Glycyrrhizate, Ethylhexylglycerin, Glycerin, Hydroxyethyl Acrylate/Sodium Acryloyldimethyl Taurate Copolymer, Pantothenic Acid/Yeast Polypeptide, PEG-8, Xanthan Gum, Polyaminopropyl Biguanide, Polymethyl Methacrylate, A lumina, Potassium Sorbate, Retinyl Palmitate, Sodium Lauroyl Lactylate, Carbomer, Tocopheryl Acetate, BHT, Disodium EDTA, Methicone, Methylisothiazolinone, Triethoxycaprylylsilane

Production Example 236. SPF 30 Lotion (Titanium Dioxide, Zinc Oxide)

Active Ingredient
  Titanium dioxide 3.7% (Sunscreen)
  Zinc oxide 3.5% (Sunscreen)
Inactive Ingredient
  Water, dimethicone, cetyl dimethicone, butyloctyl salicylate, trimethylsiloxysilicate, styrene/acrylates copolymer, dimethicone PEG-8 laurate, polysorbate 60, ceramide 3, ceramide 6 II, ceramide 1, cholesterol, phytosphingosine, niacinamide, trisiloxane, isohexadecane, arachidyl alcohol, butyleneglycol, polyhydroxystearic acid, hydrated silica, PEG-100 stearate, glyceryl stearate, ascorbic acid, *Avena sativa* (oat) kernel extract, arachidyl glucoside, beeswax, behenyl alcohol, benzyl alcohol, stearic acid, bisabolol, dipotassium glycyrrhizate, ethylhexylglycerin, glycerin, hydroxyethyl acrylate/sodium acryloyldimethyl taurateco-polymer, pantothenic acid/yeast polypeptide, PEG-8, xanthan gum, polyarninopropyl biguanide, polymethyl methacrylate, alumina, potassium sorbate, retinyl palmitate, sodium lauroyl lactylate, carbomer, tocopheryl acetate, BHT, disodium EDTA, methicone, methylisothiazolinone, triethoxycaprylylsilane

Production Example 237. SPF 50 Lotion (Titanium Dioxide, Zinc Oxide)

Active Ingredient
  Titanium dioxide 4.9% (Sunscreen)
  Zinc oxide 4.7% (Sunscreen)
Inactive Ingredient
  Water, Butyloctyl Salicylate, Cetyl Dimethicone, Dimethicone, Styrene/Acrylates Copolymer, Trimethylsiloxysilicate, Dimethicone PEG-8 Laurate, Isohexadecane, Butylene Glycol, Polysorbate 60, Trisiloxane, Arachidyl Alcohol, Polyhydroxystearic Acid, Hydrated Silica, Ceramide 3, Ceramide 6-II, Ceramide 1, Cholesterol, Phytosphingosine, PEG-100 Stearate, Glyceryl Stearate, Ascorbic Acid, *Avena sativa* (Oat) Kernel Extract, Arachidyl Glucoside, Beeswax, Behenyl Alcohol, Benzyl Alcohol, Stearic Acid, Bisabolol, Dipotassium Glycyrrhizate, Ethyl Glycerin, Hydroxyethyl Acrylate/Sodium Acryloyldimethyl Taurate Copolymer, Pantothenic Acidly east Polypeptide, PEG-8, Xanthan Gum, Polyaminopropyl Biguanide, Polymethyl Methacrylate, Alumina, Potassium Sorbate, Retinyl Palmitate, Sodium Lauroyl Lactylate, Carbomer, Tocopheryl Acetate, BHT, Disodium EDTA, Methicone, Methylisothiazolinone, Triethoxycaprylylsilane.

Production Example 238. SPF 35 Cream (Octinoxate, Octocrylene, and Zinc Oxide)

Active Ingredient
  Octinoxate 4.9% (Sunscreen)
  Octocrylene 3.0% (Sunscreen)
  Zinc oxide 6.7% (Sunscreen)
Inactive Ingredient
  Water, isododecane, butylene glycol, dimethicone, sd alcohol 40-b, polymethyl methacrylate, cyclomethicone, lauryl peg-9 polydimethylsiloxyethyl dimethicone, glycerin, disteardimonium hectorite, xylitol, methyl gluceth-10, peg/ppg-14/7 dimethyl ether, thiotaurine, *Scutellaria baicalensis* root extract, arginine hcl, *Ononis spinosa* root extract, ectoin, sodium pca, hydrogenated polydecene, benzophenone-3, isostearic acid, triethoxycaprylylsilane, trisodium edta, silica, polybutylene glycol/ppg-9/1 copolymer, bht, *Syzygium jambos* leaf extract, tocopherol, phenoxyethanol, fragrance

Production Example 239. SPF 18 Cream (Avobenzone, Octinoxate, and Octocrylene)

Active Ingredient
  Avobenzone 2.5% (Sunscreen)
  Octinoxate 7.4% (Sunscreen)
  Octocrylene 2.0% (Sunscreen)
Inactive Ingredient
  Water, butylene glycol, glycerin, dipropylene glycol, dimethicone, glyceryl stearate se, behenyl alcohol, peg/ppg-14/7 dimethyl ether, polybutylene glycol/ppg-9/1 copolymer, hydrogenated polydecene, isopropyl myristate, myristyl myristate, microcrystalline wax, peg-40 stearate, silica, carnosine, xanthan gum, erythritol, tocopheryl acetate, potassium ascorbyl tocopheryl phosphate, panthenyl ethyl ether, sodium acetylated hyaluronate, sorbitan tristearate, stearyl alcohol, cellulose gum, sodium metaphosphate, trisodium edta, bht, sodium metabisulfite, tocopherol, phenoxyethanol, fragrance, iron oxides

Production Example 240. SPF 23 Cream (Avobenzone, Homosalate, Octinoxate, Octocrylene, and Oxybenzone)

Active Ingredient
  Avobenzone 2.0% (Sunscreen)
  Homosalate 5.0% (Sunscreen)
  Octinoxate 7.4% (Sunscreen)
  Octocrylene 3.0% (Sunscreen)
  Oxybenzone 1.5% (Sunscreen)
Inactive Ingredient
  Water, glycerin, dipropylene glycol, butylene glycol, behenyl alcohol, sd alcohol 40-b, silica, dimethicone, isododecane, isohexadecane, sorbitol, beheneth-20, myristyl myristate, phytosteryl macadamiate, erythritol, xanthan gum, tocopheryl acetate, peg/ppg-14/7 dimethyl ether, peg/ppg-17/4 dimethyl ether, caffeine, sapindus mukorossi peel extract, *Angelica keiskei* leaf/stem extract, *Camellia sinensis* leaf extract, *Citrus junos* seed extract, *Ziziphus jujuba* fruit extract, eucheuma serra/grateloupia *Sparsa/Saccharina angustata/ulva linza/undaria pinnatifida* extract, *Curcuma longa* (turmeric) rhizome extract, polyquatemium-51, *Saccharina angustata/Undaria pinnatifida* extract, *Chlorella vulgaris* extract, ppg-17, stearyl alcohol, beheneth-30, alcohol, carbomer, cellulose gum, trisodium edta, hdi/trimethylol hexyllactone crosspolymer, sodium citrate, bht, sodium metaphosphate, potassium hydroxide, citric acid, tocopherol, ppg-3 dipivalate•sodium metabisulfite, phenoxyethanol, fragrance, iron oxides Production Example 241. SPF 18 Cream
(Avobenzone, Octinoxate, and Octocrylene)

Active Ingredient
  Avobenzone 2.5% (Sunscreen)
  Octinoxate 7.4% (Sunscreen)
  Octocrylene 2.0% (Sunscreen)
Inactive Ingredient
  Water, glycerin, dipropylene glycol, butylene glycol, phenyl trimethicone, hydrogenated polydecene, sorbitol, myristyl myristate, dimethicone, sd alcohol 40-b, polybutylene glycol/ppg-9/1 copolymer, petrolatum, stearyl alcohol, stearic acid, silica, bentonite, palmitic acid, xanthan gum, peg/ppg-17/4 dimethyl ether, phytosteryl macadamiate, tocopheryl acetate, sapindus mukorossi peel extract, uncaria gambir extract, sodium acetylated hyaluronate, hydroxyproline, thymus serpillum extract, *Chlorella vulgaris* extract, peg-5 glyceryl stearate, glyceryl stearate se, trisodium edta, potassium hydroxide, sodium metaphosphate, ammonium acryloyldimet yltaurate/vp copolymer, alcohol, sodium metabisulfite, bht, tocopherol, phenoxyethanol, fragrance, iron oxide Production Example 242. SPF 18 Emulsion
(Avobenzone, Octinoxate, and Octocrylene)

Active Ingredient
  Avobenzone 2.5% (Sunscreen)
  Octinoxate 7.4% (Sunscreen)
  Octocrylene 2.0% (Sunscreen)
Inactive Ingredient
  Water, glycerin, sd alcohol 40-b, dipropylene glycol, xylitol, butylene glycol, silica, polybutylene glycol/ppg-9/1 copolymer, hydrogenated polydecene, peg-60 glyceryl isostearate, triisostearin, dimethicone, diphenylsiloxy phenyl trimethicone, xanthan gum, peg/ppg-17/4 dimethyl ether, phytosteryl macadamiate, tocopheryl acetate, sapindus mukurossi peel extract, uncaria gambir extract, sodium acetylated hyaluronate, hydroxyproline, thymus serpillum extract, *Chlorella vulgaris* extract, stearic acid, glyceryl stearate se, behenyl alcohol, isostearic acid, behenic acid, beheneth-20, triethanolamine, cellulose gum, disodium edta, sodium metaphosphate, alcohol, bht, tocopherol, phenoxyethanol, fragrance, iron oxides Production Example 243. SPF 15 Cream
(Octinoxate and Octocrylene)

Active Ingredient
  Octinoxate 4.9% (Sunscreen)
  Octocrylene 5.0% (Sunscreen)
Inactive Ingredient
  Water, glycerin, dipropylene glycol, butylene glycol, phenyl trimethicone, hydrogenated polydecene, sorbitol, myristyl myristate, dimethicone, sd alcohol 40-b, petrolatum, stearyl alcohol, stearic acid, silica, palmitic acid, xanthan gum, peg/ppg-17/4 dimethyl ether, phytosteryl macadamiate, tocopheryl acetate, sapindus mukurossi peel extract, uncaria gambir extract, sodium acetylated hyaluronate, hydroxyproline, thymus serpillum extract, *Chlorella vulgaris* extract, peg-5 glyceryl stearate, glyceryl stearate se, butyl methoxydi benzoyl methane, bentonite, trisodium edta, potassium hydroxide, sodium metaphosphate, ammonium acryloyldimethyltaurate/vp copolymer, alcohol, sodium metabisulfite, bht, tocopherol, phenoxyethanol, fragrance, iron oxides Production Example 244. SPF 15 Emulsion
(Octinoxate and Octocrylene)

Active Ingredient
  Octinoxate 4.9% (Sunscreen)
  Octocrylene 5.0% (Sunscreen)
Inactive Ingredient
  Water, glycerin, dipropylene glycol, sd alcohol 40-b, xylitol, butylene glycol, silica, phenyl trimethicone, hydrogenated polydecene, peg-60 glyceryl isostearate, dimethicone, xanthan gum, peg/ppg-17/4 dimethyl ether, phytosteryl macadamiate, tocopheryl acetate, sapindus mukurossi peel extract, uncaria gambir extract, sodium acetylated hyaluronate, hydroxyproline, thymus serpillum extract, *Chlorella vulgaris* extract, butyl methoxydibenzoylmethane, behenyl alcohol, glyceryl stearate se, stearic acid, isostearic acid, behenic acid, beheneth-20, triethanolamine, cellulose gum, sodium metaphosphate, disodium edta, alcohol, bht, tocopherol, phenoxyethanol, fragrance, iron oxides Production Example 245. SPF 15 Cream
(Avobenzone, Octinoxate, Octocrylene, and Oxybenzone)

Active Ingredient
  Avobenzone 2.5% (Sunscreen)
  Octinoxate 4.9% (Sunscreen)
  Octocrylene 5.0% (Sunscreen)
  Oxybenzone 1.5% (Sunscreen)
Inactive Ingredient
  Water, glycerin, dipropylene glycol, caprylic/capric triglyceride, behenyl alcohol, butylene glycol, isohexadecane, sd alcohol 40-b, sorbitol, silica, myristyl myristate, dimethicone, polybutylene glycol/ppg-9/1 copolymer, stearyl alcohol, triisostearin, phytosteryl macadamiate, tocopheryl acetate, 2-o-ethyl ascorbic acid, potassium ascorbyl tocopheryl phosphate, arginine hcl, *Saxifraga sarmentosa* extract, sapindus mukurossi peel extract, *Panax ginseng* root extract, *Angelica acutiloba* root extract, sodium acetylated hyaluronate, hydroxyproline, uncaria gambir extract, *Chlorella vulgaris* extract, thymus serpillum extract, beheneth-20, alcohol, succinoglycan, trisodium edta, sodium citrate, sodium metaphosphate, citric acid, bht, sodium metabisulfite, tocopherol, phenoxyethanol, fragrance, iron oxides Production Example 246. SPF 50 Cream
(Avobenzone, Homosalate, Octinoxate, Octisalate, Octocrylene, and Oxybenzone)

Active Ingredient
  Avobenzone 2.5% (Sunscreen)
  Homosalate 10.0% (Sunscreen)

Octinoxate 4.9% (Sunscreen)
Octocrylene 5.0% (Sunscreen)
Oxybenzone 3% (Sunscreen)
Inactive Ingredient
Diphenylsiloxy phenyl trimethicone, triethylhexanoin, mineral oil, hydroxystearic acid, dibutyl lauroyl glutamide, polyamide-8, peg/ppg-14/7 dimethyl ether, lecithin, *Glycyrrhiza glabra* (licorice) root extract, ppg-17, silica dimethyl silylate, bht, tocopherol, pentaerythrityl tetra-di-t-butyl hydroxyhydrocinnamate, fragrance Production Example 247. SPF 20 Cream
(Avobenzone, Homosalate, Octinoxate, Octocrylene, and Oxybenzone)

Active Ingredient
Avobenzone 2.0% (Sunscreen)
Homosalate 5.0% (Sunscreen)
Octinoxate 7.4% (Sunscreen)
Octocrylene 3.0% (Sunscreen)
Oxybenzone 1.5% (Sunscreen)
Inactive Ingredient
Water, dipropylene glycol, betaine, butylene glycol, glycerin, behenyl alcohol, sd alcohol 40-b, dimethicone, isododecane, isohexadecane, beheneth-20, silica, myristyl myristate, phytosteryl macadamiate, erythritol, xanthan gum, tocopheryl acetate, peg/ppg-14/7 dimethyl ether, peg/ppg-17/4 dimethyl ether, caffeine, *Scutellaria baicalensis* root extract, *Angelica keiskei* leaf/stem extract, sodium acetylated hyaluronate, *Camellia sinensis* leaf extract, *Citrus unshiu* peel extract, *Zingiber aromaticus* extract, hydrolyzed conchiolin protein, polyquaternium-51, *Pyrola incarnata* extract, *Panax ginseng* root extract, ppg-17, stearyl alcohol, beheneth-30, alcohol, disodium edta, carbomer, cellulose gum, bht, sodium metaphosphate, potassium hydroxide, sodium metabisulfite, tocopherol, hdi/trimethylol hexyllactone crosspolymer, *Cinnamomum cassia* bark extract, phenoxyethanol, fragrance, iron oxides Production Example 248. SPF 38 Cream
(Octinoxate, Octocrylene, and Zinc Oxide)

Active Ingredient
Octinoxate 4.9% (Sunscreen)
Octocrylene 3.0% (Sunscreen)
Zinc oxide 12.5% (Sunscreen)
Inactive Ingredient
Water, isododecane, butylene glycol, cyclomethicone, dimethicone, polymethyl methacrylate, lauryl peg-9 polydimethylsiloxyethyl dimethicone, glycerin, sd alcohol 40-b, disteardimonium hectorite, xylitol, methyl gluceth-10, *Scutellaria baicalensis* root extract, *Ononis spinosa* root extract, ectoin, hydrogenated polydecene, hydrogen dimethicone, isostearic acid, trisodium edta, silica, peg-150, polybutylene glycol/ppg-9/1 copolymer, alumina, bht, triethoxycaprylylsilane, *Syzygium jambos* leaf extract, tocopherol, phenoxyethanol, fragrance, titanium dioxide Production Example 249. SPF 38 Lotion
(Octinoxate, Octocrylene, and Zinc Oxide)

Active Ingredient
Octinoxate 4.9% (Sunscreen)
Octocrylene 3.0% (Sunscreen)
Zinc oxide 12.5% (Sunscreen)
Inactive Ingredient
Dimethicone, water, dipropyleneglycol, ethylhexyl palmitate, sd alcohol 40-b, peg-10 dimethicone, talc, polybutylene glycol/ppg-9/1 copolymer, trimethylsiloxysilicate, xylitol, glycerin, peg-9 polydimethylsiloxyethyl dimethicone, methyl gluceth-10, *Scutellaria baicalensis* root extract, ectoin, isostearic acid, hydrogen dimethicone, disteardimonium hectorite, butylene glycol, calcium stearate, trisodium edta, alumina, bht, triethoxycaprylylsilane, *Syzygium jambos* leaf extract, tocopherol, phenoxyethanol, fragrance, titanium dioxide Production Example 250. SPF 15 Cream
(Ensulizole, Octinoxate and Octocrylene)

Active Ingredient
Ensulizole 2% (Sunscreen)
Octinoxate 4.9% (Sunscreen)
Octocrylene 5% (Sunscreen)
Inactive Ingredient
Water, cyclomethicone, glycerin, dipropylene glycol, behenyl alcohol, sd alcohol 40-b, diphenylsiloxy phenyl trimethicone, *Simmondsia chinensis* (jojoba) seed oil, polysorbate 60, dimethicone, glyceryl stearate, triethanolamine, peg-20, erythritol, piperidinepropionic acid, xanthan gum, *saccharomyces* ferment lysate filtrate, glycine, arginine hcl, magnesium ascorbyl phosphate, sodium acetylated hyaluronate, *Ononis spinosa* root extract, *Averrhoa carambola* leaf extract, *Hibiscus esculentus* fruit extract, *Camellia sinensis* leaf extract, sodium methyl stearoyl taurate, butylene glycol, sodium citrate, sodium metaphosphate, citric acid, alcohol, bht, tocopherol, phenoxyethanol, fragrance, iron oxides Production Example 251. SPF 50 Cream
(Octinoxate, Octocrylene, Oxybenzone, and Zinc Oxide)

Active Ingredient
Octinoxate 4.9% (Sunscreen)
Octocrylene 3.0% (Sunscreen)
Oxybenzone 1.0% (Sunscreen)
Zinc oxide 12.5% (Sunscreen)
Inactive Ingredient
Water, isododecane, butylene glycol, sd alcohol 40-b, caprylyl methicone, dimethicone, glycerin, peg-60 hydrogenated castor oil, tocopheryl acetate, piperidinepropionic acid, magnesium aluminum silicate, 2-o-ethyl ascorbic acid, *saccharomyces* ferment lysate filtrate, sodium acetylated hyaluronate, *averrhoa carambola* leaf extract, *Gentiana urnula* flower extract, *Camellia sinensis* leaf extract, peg-100 hydrogenated castor oil, ppg-17, hdi/trimethylol hexyllactone crosspolymer, isostearic acid, di methylacrylamide/sodium acryloyldimethyltauratecrosspolymer, sorbitan sesquiisostearate, hydrogen dimethicone, triethoxycaprylylsilane, succinoglycan, cellulose gum, sodium metaphosphate, citric acid, bht, disodium edta, silica, alumina, sodium metabisulfite, alcohol, sodium citrate, tocopherol, talc, polysilicone-2, barium sulfate, phenoxyethanol, fragrance, titanium dioxide, iron oxides, mica Production Example 252. SPF 18 Cream
(Avobenzone, Octinoxate, and Octocrylene)

Active Ingredient
Avobenzone 2.5% (Sunscreen)
Octinoxate 7.4% (Sunscreen)
Octocrylene 2.0% (Sunscreen)

Inactive Ingredient

Water, dipropylene glycol, dimethicone, glycerin, sd alcohol 40-b, hydrogenated polydecene, behenyl alcohol, diphenylsiloxy phenyl trimethicone, *Simmondsia chinensis* (jojoba) seed oil, polybutylene glycol/ppg-9/1 copolymer, polysorbate 60, glyceryl stearate, peg-20, silica, erythritol, xanthan gum, piperidinepropionic acid, *saccharomyces* ferment lysate filtrate, glycine, magnesium ascorbyl phosphate, arginine hcl, sodium acetylated hyaluronate, *Ononis spinosa* root extract, *averrhoa carambola* leaf extract, *Hibiscus esculentus* fruit extract, *Camellia sinensis* leaf extract, sodium methyl stearoyl taurate, triethanolamine, butylene glycol, distearyldimonium chloride, sodium metaphosphate, alcohol, isopropyl alcohol, bht, tocopherol, phenoxyethanol, fragrance, iron oxides Production Example 253. SPF 18 Cream
(Avobenzone, Octinoxate, and Octocrylene)

Active Ingredient

Avobenzone 2.5% (Sunscreen)

Octinoxate 7.4% (Sunscreen)

Octocrylene 2.0% (Sunscreen)

Inactive Ingredient

Water, dipropylene glycol, dimethicone, glycerin, sd alcohol 40-b, hydrogenated polydecene, behenyl alcohol, diphenylsiloxy phenyl trimethicone, *Simmondsia chinensis* (jojoba) seed oil, polybutylene glycol/ppg-9/1 copolymer, polysorbate 60, glyceryl stearate, peg-20, silica, erythritol, xanthan gum, tocopheryl acetate, piperidinepropionic acid, *saccharomyces* ferment lysate filtrate, sodium acetylated hyaluronate, *Ononis spinosa* root extract, *Averrhoa carambola* leaf extract, *Hibiscus esculentus* fruit extract *Camellia sinensis* leaf extract, *Zanthoxylum piperitum* peel extract, sodium methyl stearoyl taurate, triethanolamine, butylene glycol, distearyldimonium chloride, alcohol, sodium metaphosphate, isopropyl alcohol, bht, tocopherol, phenoxyethanol, fragrance, iron oxides Production Example 254. SPF 18 Emulsion
(Avobenzone, Octinoxate, and Octocrylene)

Active Ingredient

Avobenzone 2.5% (Sunscreen)

Octinoxate 7.4% (Sunscreen)

Octocrylene 2.0% (Sunscreen)

Inactive Ingredient water, dipropylene glycol, sd alcohol 40-b, dimethicone, isododecane, xylitol, silica, triethylhexanoin, glycerin, hydrogenated polydecene, peg-5 glyceryl stearate, isostearic acid, diphenylsiloxy phenyl trimethicone, xanthan gum, erythritol, sodium hyaluronate, tocopheryl acetate, piperidinepropionic acid, *saccharomyces* ferment lysate filtrate, sodium acetylated hyaluronate, *Ononis spinosa* root extract, *averrhoa carambola* leaf extract, *Hibiscus esculentus* fruit extract, *Camellia sinensis* leaf extract, *Zanthoxylum piperitum* peel extract, ppg-17, triethanolamine, glyceryl stearate se, behenic acid, stearic acid, behenyl alcohol, batyl alcohol, peg-30 soy sterol, disodium edta, butylene glycol, alcohol, cellulose gum, sodium metaphosphate, bht, sodium metabisulfite, tocopherol, phenoxyethanol, fragrance, iron oxides Production Example 255. SPF 20 Emulsion
(Avobenzone, Octinoxate, Octocrylene, and Oxybenzone)

Active Ingredient

Avobenzone 2.5% (Sunscreen)

Octinoxate 7.4% (Sunscreen)

Octocrylene 2.0% (Sunscreen)

Oxybenzone 1.0% (Sunscreen)

Inactive Ingredient

Water, dipropylene glycol, sd alcohol 40-b, glycerin, hydrogenated polydecene, xylitol, isododecane, dimethicone, peg-5 glyceryl stearate, isostearic acid, silica, phenyl trimethicone, triethanolamine, xanthan gum, tocopheryl acetate, peg/ppg-17/4 dimethyl ether, piperidinepropionic acid, phytosteryl macadamiate, 2-o-ethyl ascorbic acid, *Prunus speciosa* leaf extract, *Angelica acutiloba* root extract, *Isodonis japonicus* leaf/stalk extract, *Camellia sinensis* leaf extract, *Zanthoxylum piperitum* peel extract, ppg-17, glyceryl stearate se, behenyl alcohol, behenic acid, stearic acid, batyl alcohol, peg-30 phytosterol, butylene glycol, carbomer, disodium edta, alcohol, bht, cellulose gum, sodium metaphosphate, talc, dextrin palmitate, tocopherol, ethylparaben, methylparaben, fragrance, iron oxides Production Example 256. SPF 18 Emulsion
(Avobenzone, Octinoxate, Octocrylene, and Oxybenzone)

Active Ingredient

Avobenzone 2.5% (Sunscreen)

Octinoxate 7.4% (Sunscreen)

Octocrylene 2.0% (Sunscreen)

Oxybenzone 1.0% (Sunscreen)

Inactive Ingredient

Water, sd alcohol 40-b, glycerin, dipropyleneglycol, dimethicone, ethylhexyl palmitate, polybutylene glycol/ppg-9/1 copolymer, silica, trehalose, betaine, glycyl glycine, lauryl betaine, *Paeonia albiflora* root extract, *Hamamelis virginiana* (witch hazel) leaf extract, *Lamium album* flower extract, *Citrus junos* seed extract, *Zingiber aromaticus* extract, peg-20 glyceryl isostearate, triisostearin, triethanolamine, isostearic acid, alcohol, butylene glycol, carbomer, batyl alcohol, behenyl alcohol, acrylates/c10-30 alkyl acrylate crosspolymer, trisodium edta, sodium metabisulfite, bht, phenoxyethanol, sodium benzoate, benzoic acid, fragrance, titanium dioxide, mica Production Example 257. SPF 38 Cream
(Octinoxate and Zinc Oxide)

Active Ingredient

Octinoxate 7.4% (Sunscreen)

Zinc oxide 9.6% (Sunscreen)

Inactive Ingredient

Water, cyclomethicone, butylene glycol, dimethicone, peg-10 dimethicone, methyl gluceth-10, polybutylene glycol/ppg-9/1 copolymer, disteardimonium hectorite, polymethyl methacrylate, talc, trimethylsiloxysilicate, glycerin, xylitol, *Scutellaria baicalensis* root extract, *Ononis spinosa* root extract, ectoin, hydrogenated polydecene, triethoxycaprylylsilane, isostearic acid, aluminum hydroxide, peg-150, calcium stearate, stearic acid, silica, trisodium edta, bht, *Syzygium jambos* leaf extract, tocopherol, phenoxyethanol, fragrance, titanium dioxide

Production Example 258. SPF 28 Lotion
(Octinoxate and Zinc Oxide)

Active Ingredient
  Octinoxate 7.4% (Sunscreen)
  Zinc oxide 9.6% (Sunscreen)
Inactive Ingredient
  Cyclomethicone, water, dipropylene glycol, dimethicone, sd alcohol 40-b, talc, polybutylene glycol/ppg-9/1 copolymer, trimethylsiloxysilicate, glycerin, peg-9 polydimethylsiloxyethyl dimethicone, xylitol, methyl gluceth-10, *Scutellaria baicalensis* root extract, ectoin, isostearic acid, triethoxycaprylylsilane, disteardimonium hectorite, aluminum hydroxide, butylene glycol, calcium stearate, stearic acid, trisodium edta, bht, *Syzygium jambos* leaf extract, phenoxyethanol, fragrance, titanium dioxide

Production Example 259. SPF 60 Lotion
(Ensulizole, Octinoxate, and Zinc Oxide)

Active Ingredient
  Ensulizole 2.0% (Sunscreen)
  Octinoxate 7.4% (Sunscreen)
  Zinc oxide 16.3% (Sunscreen)
Inactive Ingredient
  Cyclomethicone, water, butylene glycol, dimethicone, cetyl ethylhexanoate, polymethylsilsesquioxane, sd alcohol 40-b, polybutylene glycol/ppg-9/1 copolymer, octorylene, trimethylsiloxysilicate, lauryl peg-9 polydimethylsiloxyethyl dimethicone, triethanolamine, glycerin, xylitol, methyl gluceth-10, *Scutellaria baicalensis* root extract, ectoin, cyclopentasiloxane, triethoxycaprylylsilane, isostearic acid, acrylates/dimethicone copolymer, trisodium edta, bht, *Syzygium jambos* leaf extract, tocopherol, phenoxyethanol, fragrance

Production Example 260. SPF 55 Cream
(Octinoxate, Titanium Dioxide, and Zinc Oxide)

Active Ingredient
  Octinoxate 7.4% (Sunscreen)
  Titanium dioxide 2.2% (Sunscreen)
  Zinc oxide 16.3% (Sunscreen)
Inactive Ingredient
  cyclomethicone, water, butylene glycol, dimethicone, polymethylsilsesquioxane, peg-10 dimethicone, polybutylene glycol/ppg-9/1 copolymer, trimethylsiloxysilicate, disteardimonium hectorite, glycerin, xylitol, methyl gluceth-10, *Scutellaria baicalensis* root extract, *Ononis spinosa* root extract, ectoin, hydrogenated polydecene, cyclopentasiloxane, triethoxycaprylylsilane, aluminum hydroxide, stearic acid, acrylates/dimethicone copolymer, isostearic acid, trisodium edta, bht, *Syzygium jambos* leaf extract, tocopherol, phenoxyethanol, fragrance

Production Example 261. SPF 18 Emulsion
(Avobenzone, Octinoxate, and Octocrylene)

Active Ingredient
  Avobenzone 2.5% (Sunscreen)
  Octinoxate 7.4% (Sunscreen)
  Octocrylene 2.0% (Sunscreen)
Inactive Ingredient
  water, glycerin, dipropylene glycol, diphenylsiloxy phenyl trimethicone, sd alcohol 40-b, xylitol, butylene glycol, dimethicone, polybutylene glycol/ppg-9/1 copolymer, peg-60 glyceryl isostearate, xanthan gum, erythritol, trehalose, peg/ppg-14/7 dimethyl ether, *scutellaria baicalensis* root extract, hydroxypropyl cyclodextrin, *Mentha piperita* (peppermint) leaf extract, sodium hyaluronate, *Citrus junos* seed extract, phytosteryl macadamiate, stearic acid, glyceryl stearate se, behenyl alcohol, isostearic acid, behenic acid, beheneth-20, triethanolamine, carbomer, alcohol, trisodium edta, bht, tocopherol, phenoxyethanol, fragrance

Production Example 262. SPF 18 Cream
(Avobenzone, Octinoxate, and Octocrylene)

Active Ingredient
  Avobenzone 2.5% (Sunscreen)
  Octinoxate 7.4% (Sunscreen)
  Octocrylene 2.0% (Sunscreen)
Inactive Ingredient
  Water, butylene glycol, glycerin, diphenylsiloxy phenyl trimethicone, dipropylene glycol, xylitol, sd alcohol 40-b, peg-60 glyceryl isostearate, isostearic acid, silica, bentonite, polybutylene glycol/ppg-9/1 copolymer, glyceryl stearate se, erythritol, xanthan gum, trehalose, peg/ppg-14/7 dimethyl ether, *Scutellaria baicalensis* root extract, hydroxypropyl cyclodextrin, *Mentha piperita* (peppermint) leaf extract, sodium hyaluronate, *Citrus junos* seed extract, phytosteryl macadamiate, hydrogenated polydecene, stearyl alcohol, behenyl alcohol, peg-5 glyceryl stearate, stearic acid, trisodium edta, sodium hydroxide, behenic acid, alcohol, sodium metaphosphate, bht, tocopherol, phenoxyethanol, fragrance, iron oxides

Production Example 263. SPF 50 Cream
(Avobenzone, Octinoxate, Octocrylene, and Oxybenzone)

Active Ingredient
  Avobenzone 2.5% (Sunscreen)
  Octinoxate 4.9% (Sunscreen)
  Octocrylene 5.0% (Sunscreen)
  Oxybenzone 3.0% (Sunscreen)
Inactive Ingredient
  Water, dimethicone, sd alcohol 40-b, talc, methyl methacrylate crosspolymer, isododecane, cetyl ethylhexanoate, diisopropyl sebacate, triethylhexanoin, lauryl peg-9 polydimethylsiloxyethyl dimethicone, glycerin, dextrin palmitate, sucrose tetrastearate triacetate, polybutylene glycol/ppg-9/1 copolymer-, trimethylsiloxysilicate, xylitol, silica, sodium chloride, peg/ppg-14/7 dimethyl ether, *Saxifraga sarmentosa* extract, *Sophora angustifolia* root extract, disteardimonium hectorite, isostearic acid, calcium stearate, trisodium edta, vinyl dimethicone/methicone silsesquioxane crosspolymer, alcohol, bht, butylene glycol, stearic acid, sodium metabisulfite, *Syzygium jambos* leaf extract, tocopherol, polysilicone-2, methylparaben, fragrance, iron oxides

Production Example 264. SPF 50 Cream
(Octinoxate, Octocrylene, Titanium Dioxide, and Zinc Oxide)

Active Ingredient
  Octinoxate 7.4% (Sunscreen)
  Octocrylene 3.0% (Sunscreen)
  Titanium dioxide 1.4% (Sunscreen)
  Zinc oxide 16.4% (Sunscreen)
Inactive Ingredient
  Water, dimethicone, sd alcohol 40-b, isohexadecane, butylene glycol, isopropyl myristate, methyl methacrylate crosspolymer, lauryl peg-9 polydimethylsiloxyethyl dimethicone, xylitol, glycerin, polybutylene glycol/ppg-9/1 copolymer, isododecane, trimethylsiloxysilicate, disteardimonium hectorite, peg-6, dextrin palmitate, peg-32, peg/ppg-14/7 dimethyl ether, *Saxifraga sarmentosa* extract, *Scutellaria baicalensis* root extract, *Ononis spinosa* root extract, ectoin, *Sophora angustifolia* root extract, silica, hydrogen dimethicone, carboxydecyl trisiloxane, aluminum hydroxide, stearic acid, trisodium edta, polymethylsilsesquioxane, talc, alcohol, bht, *Syzygium jambos* leaf extract, tocopherol, phenoxyethanol, fragrance Production Example 265. SPF 50 Lotion
(Octinoxate, Octocrylene, Titanium Dioxide, and Zinc Oxide)

Active Ingredient
  Octinoxate 7.4% (Sunscreen)
  Octocrylene 3.0% (Sunscreen)
  Titanium dioxide 1.4% (Sunscreen)
  Zinc oxide 16.4% (Sunscreen)
Inactive Ingredient
  Water, dimethicone, butylene glycol, isopropyl myristate, isohexadecane, sd alcohol 40-b, isododecane, methyl methacrylate crosspolymer, peg-9 polydimethylsiloxyethyl dimethicone, trimethylsiloxysilicate, polybutylene glycol/ppg-9/1 copolymer, xylitol, glycerin, methyl gluceth-10, peg/ppg-14/7 dimethyl ether, *Saxifraga sarmentosa* extract, *Scutellaria baicalensis* root extract, ectoin, *Sophora angustifolia* root extract hydrogenated polydecene, hydrogen dimethicone, isostearic acid, dextrin palmitate, aluminum hydroxide, stearic acid, disteardimoniurn hectorite, silica, polymethylsilsesquioxane, talc, alcohol, trisodium edta, bht. *Syzygium jambos* leaf extract, tocopherol, fragrance Production Example 266. SPF 50 Cream
(Octinoxate, Octocrylene, Titanium Dioxide, and Zinc Oxide)

Active Ingredient
  Octinoxate 7.4% (Sunscreen)
  Octocrylene 3.0% (Sunscreen)
  Titanium dioxide 1.7% (Sunscreen)
  Zinc oxide 19.3% (Sunscreen)
Inactive Ingredient
  water, sd alcohol 40-b, isohexadecane, butylene glycol, dimethicone, isopropyl myristate, polymethyl methacrylate, lauryl peg-9 polydimethylsiloxyethyl dimethicone, xylitol, glycerin, disteardimonium hectorite, polybutylene glycol/ppg-9/1 copolymer, isododecane, trimethylsiloxysilicate, peg-6, peg-32, *Saxifraga sarmentosa* extract, *Scutellaria baicalensis* root extract, *Ononis spinosa* root extract, ectoin, *Sophora angustifolia* root extract, hydrogen dimethicone, silica, carboxydecyl trisiloxane, trisodium edta, sodium acryloyldimethyltaurate/methacrylamidolauric acid copolymer, alumina, polymethylsilsesquioxane, talc, alcohol, triethoxycaprylylsilane, bht, *Syzygium jambos* leaf extract, tocopherol, phenoxyethanol, fragrance Production Example 267. SPF 50 Cream
(Octinoxate, Octocrylene, Titanium Dioxide, and Zinc Oxide)

Active Ingredient
  Octinoxate 7.4% (Sunscreen)
  Octocrylene 3.0% (Sunscreen)
  Titanium dioxide 1.7% (Sunscreen)
  Zinc oxide 19.3% (Sunscreen)
Inactive Ingredient
  water, dimethicone, butylene glycol, isopropyl myristate, sd alcohol 40-b, isododecane, polymethyl methacrylate, peg-9 polydimethylsiloxyethyl dimethicone, trimethylsiloxysilicate, polybutylene glycol/ppg-9/1 copolymer, xylitol, glycerin, methyl gluceth-10, *Saxifraga sarmentosa* extract, *Scutellaria baicalensis* root extract, ectoin, *Sophora angustifolia* root extract, hydrogenated polydecene, hydrogen dimethicone, isostearic acid, disteardimonium hectorite, sodium acryloyldimethyltaurate/methacrylamidolauric acid copolymer, silica, alumina, polymethylsilsesquioxane, talc, alcohol, trisodium edta, triethoxycaprylylsilane, bht, *Syzygium jambos* leaf extract, tocopherol, phenoxyethanol, fragrance Production Example 268. SPF 50 Lotion (Titanium Dioxide and Zinc Oxide)

Active Ingredient
  Titanium dioxide 9.1% (Sunscreen)
  Zinc oxide 19.3% (Sunscreen)
Inactive Ingredient
  Dimethicone, water, butylene glycol, glycerin, diisopropyl sebacate, polymethyl methacrylate, hydrogenated polydecene, peg-10 dimethicone, cyclomethicone, peg-9 polydimethylsiloxyethyl dimethicone, bis-butyldimethicone polyglyceryl-3, peg-6, trimethylsiloxysilicate, peg-32, peg/ppg-14/7 dimethyl ether, *Scutellaria baicalensis* root extract, *Rubus idaeus* (raspberry) fruit extract, aloe barbadensis leaf extract, thymus serpillum extract, aluminum distearate, aluminum hydroxide, hydrogen dimethicone, isostearic acid, disteardimonium hectorite, hydrated silica, sodium metaphosphate, triethoxycaprylylsilane, stearic acid, dextrin palmitate, distearyldimonium chloride, tocopherol, *Syzygium jambos* leaf extract Production Example 269. SPF 42 Emulsion
(Octinoxate, Octocrylene, and Zinc Oxide)

Active Ingredient
  Octinoxate 7.4% (Sunscreen)
  Octocrylene 3.0% (Sunscreen)
  Zinc oxide 8.6% (Sunscreen)
Inactive Ingredient
  water, dimethicone, isododecane, sd alcohol 40-b, dipropylene glycol, ethylhexyl palmitate, glycerin, polymethylsilsesquioxane, vinyl di methicone/methicone silsesquioxane crosspolymer, polybutylene glycol/ppg-9/1 copolymer, dimethicone/vinyl dimethicone crosspolymer, xylitol, methyl methacrylate crosspolymer, thiotaurine, *Scutellaria baicalensis* root extract, *Paeonia albiflora* root extract, *Ononis spinosa* root extract, ectoin, lauryl peg-9 polydimethylsiloxyethyl dimethicone, triethoxycaprylylsilane, butylene glycol, disodium edta, disteardimonium hectorite, bht, *Syzygium jambos* leaf extract, tocopherol, phenoxyethanol, benzoic acid, fragrance, mica, titanium dioxide Production Example 270. SPF 42 Lotion
(Octinoxate, Octocrylene, and Zinc Oxide)

Active Ingredient
  Octinoxate 4.9% (Sunscreen)
  Octocrylene 3.0% (Sunscreen)
  Zinc oxide 12.5% (Sunscreen)
Inactive Ingredient
  water, dimethicone, isododecane, sd alcohol 40-b, dipropylene glycol, ethylhexyl palmitate, peg-10 dimethicone, glycerin, polymethylsilsesquioxane, vinyl di methicone/methicone silsesquioxane crosspolymer, polybutylene glycol/ppg-9/1 copolymer, dimethicone/vinyl dimethicone crosspolymer, xylitol, methyl methacrylate crosspolymer, thiotaurine, *Scutellaria baicalensis* root extract, *Paeonia albiflora* root extract, *Ononis spinosa* root extract, ectoin, lauryl peg-9 polydimethylsiloxyethyl dimethicone, hydrogen dimethicone, butylene glycol, disodium edta, disteardimonium hectorite, alumina, bht, triethoxycaprylylsilane, *Syzygium jambos* leaf extract, tocopherol, phenoxyethanol, benzoic acid, fragrance, titanium dioxide, mica

Production Example 271. SPF 43 Cream
(Ensulizole, Octinoxate, and Titanium Dioxide)

Active Ingredient
  Ensulizole 2.0% (Sunscreen)
  Octinoxate 7.4% (Sunscreen)
  Titanium dioxide 7.2% (Sunscreen)
Inactive Ingredient
  Water, dimethicone, sd alcohol 40-b, pentaerythrityl tetraethylhexanoate, peg-9 polydimethylsiloxyethyl dimethicone, polymethyl methacrylate, glycerin, di propylene glycol, disteardimonium hectorite, hydrogenated polydecene, trimethylsiloxysilicate, silica, xylitol, peg-6, peg-32, peg/ppg-14/7 dimethyl ether, thiotaurine, *Saxifraga sarmentosa* extract, arginine hcl, *Ononis spinosa* root extract, sodium pca, *Sophora angustifolia* root extract, ppg-17, aluminum hydroxide, aminomethyl propanol, aluminum distearate, isostearic acid, stearic acid, trisodium edta, polymethylsilsesquioxane, talc, butylene glycol, alcohol, alumina, polysilicone-2, triethoxycaprylylsilane, polybutylene glycol/ppg-9/1 copolymer, bht, *Syzygium jambos* leaf extract, tocopherol, phenoxyethanol, fragrance, iron oxides, titanium dioxide

Production Example 272. SPF 35 Cream
(Octinoxate, Octocrylene, and Zinc Oxide)

Active Ingredient
  Octinoxate 4.9% (Sunscreen)
  Octocrylene 3.0% (Sunscreen)
  Zinc oxide 6.7% (Sunscreen)
Inactive Ingredient
  water, isododecane, butylene glycol, dimethicone, sd alcohol 40-b, polymethyl methacrylate, cyclomethicone, lauryl peg-9 polydimethylsiloxyethyl dimethicone, glycerin, disteardimonium hectorite, xylitol, methyl gluceth-10, peg/ppg-14/7 dimethyl ether, thiotaurine, *Scutellaria baicalensis* root extract, arginine hcl, *Ononis spinosa* root extract, ectoin, sodium pca, hydrogenated polydecene, benzophenone-3, isostearic acid, triethoxycaprylylsilane, trisodium edta, silica, polybutylene glycol/ppg-9/1 copolymer, bht, *Syzygium jambos* leaf extract, tocopherol, phenoxyethanol, fragrance

Production Example 273. SPF 40 Cream
(Octinoxate, Octocrylene, and Zinc Oxide)

Active Ingredient
  Octinoxate 2.9% (Sunscreen)
  Octocrylene 3.0% (Sunscreen)
  Zinc oxide 10.6% (Sunscreen)
Inactive Ingredient
  water, isododecane, cyclomethicone, dimethicone, butylene glycol, sd alcohol 40-b, polymethyl methacrylate, lauryl peg-9 polydimethylsiloxyethyl dimethicone, glycerin, disteardimonium hectorite, xylitol, methyl gluceth-10, peg/ppg-14/7 dimethyl ether, thiotaurine, *Scutellaria baicalensis* root extract, arginine hcl, *Ononis spinosa* root extract, ectoin, sodium pca, hydrogenated polydecene, hydrogen dimethicone, isostearic acid, benzophenone-3, trisodium edta, silica, polybutylene glycol/ppg-9/1 copolymer, alumina, triethoxycaprylylsilane, bht, *Syzygium jambos* leaf extract, tocopherol, phenoxyethanol, fragrance, titanium dioxide

Production Example 274. SPF 30 Cream
(Octinoxate and Titanium Dioxide)

Active Ingredient
  Octinoxate 7.4% (Sunscreen)
  Titanium dioxide 4.2% (Sunscreen)
Inactive Ingredient
  Water, dimethicone, glycerin, sd alcohol 40-b, pentaerythrityl tetraethylhexanoate, peg-9 polydimethylsiloxyethyl dimethicone, triisostearin, methyl methacrylate crosspolymer, hydrogenated polydecene, di propylene glycol, disteardimonium hectorite, erythritol, silica, trehalose, peg-6, peg-32, caffeine, betaine, peg/ppg-17/4 dimethyl ether, dipeptide-15, phytosteryl/octyldodecyl lauroyl glutamate, *Paeonia albiflora* root extract, *Lamium album* flower/leaf/stem extract, *Daucus carota sativa* (carrot) root protoplasts, *Citrus junos* seed extract, ppg-17, aluminum hydroxide, stearic acid, isostearic acid, trisodium edta, butylene glycol, polyester-1, alcohol, silica dimethyl silylate, bht, alumina, triethoxycaprylylsilane•sodium metabisulfite, tocopherol, phenoxyethanol, benzoic acid, fragrance, titanium dioxide, iron oxides, mica

Production Example 275. SPF 30 Cream
(Octinoxate and Titanium Dioxide)

Active Ingredient
  Octinoxate 7.4% (Sunscreen)
  Titanium dioxide 4.9% (Sunscreen)
Inactive Ingredient
  Water, cyclopentasiloxane, sd alcohol 40-b, glycerin, methyl methacrylate crosspolymer, dimethicone, peg-10 dimethicone, polymethylsilsesquioxane, polybutylene glycol/ppg-9/1 copolymer, talc, erythritol, aluminum hydroxide, silica, trehalose, peg/ppg-17/4 dimethyl ether, trimethylsiloxysilicate, caffeine, betaine, phytosteryl/octyldodecyl lauroyl glutamate, dipeptide-15, *Eriobotrya japonica* leaf protoplasts, *Paeonia albiflora* root extract, *Lamium album* flower/leaf/stem extract, *citrus junos* seed extract, *Eriobotrya japonica* leaf extract-stearic acid, disteardimonium hectorite, butylene glycol, trisodium edta, isostearic acid, polyester-1, alcohol, silica dimethyl silylate, alumina, triethoxycaprylylsilane, hydrogen dimethicone, bht, tocopherol, phenoxyethanol, benzoic acid, fragrance, titanium dioxide, iron oxides, mica

Production Example 276. SPF 30 Emulsion
(Octinoxate and Titanium Dioxide)

Active Ingredient
  Octinoxate 7.4% (Sunscreen)
  Titanium dioxide 5.3% (Sunscreen)
Inactive Ingredient
  Water, cyclopentasiloxane, sd alcohol 40-b glycerin, methyl methacrylate crosspolymer, dimethicone, peg-10 dimethicone, polybutylene glycol/ppg-9/1 copolymer, lauryl peg-9 polydimethylsiloxyethyl dimethicone, polymethylsilsesguioxane, talc, erythritol, silica, trehalose, disteardimonium hectorite, trimethylsiloxysilicate, caffeine, betaine, peg/ppg-17/4 dimethyl ether, phytosteryl/octyldodecyl lauroyl glutamate, dipeptide-15, *Eriobotrya japonica* leaf protoplasts, *Paeonia albiflora* root extract, *Lamium album* flower/leaf/stem extract, *Citrus junos* seed extract, *Eriobotrya japonica* leaf extract, aluminum hydroxide, stearic acid isostearic acid, butylene glycol, trisodium edta, polyester-1 alcohol, silica dimethyl silylate, alumina, triethoxycaprylylsilane hydrogen dimethicone, bht, tocopherol, phenoxyethanol, benzoic acid, fragrance, titanium dioxide, iron oxides, mica

Production Example 277. SPF 15 Cream
(Ensulizole, Octinoxate, and Titanium Dioxide)

Active Ingredient
　Ensulizole 2.5% (Sunscreen)
　Octinoxate 7.4% (Sunscreen)
　Titanium dioxide 1.9% (Sunscreen)
Inactive Ingredient
　water, butylene glycol, glycerin, dipropylene glycol, hydrogenated polydecene, pentaerythrityl tetraethylhexanoate, dimethicone, sd alcohol 40-b, behenyl alcohol, polybutylene glycol/ppg-9/1 copolymer, tranexamic acid, beheneth-20, triethanolamine, silica, xanthan gum, peg/ppg-14/7 dimethyl ether, erythritol, peg/ppg-17/4 dimethyl ether, 2-o-ethyl ascorbic acid, glucosyl hesperidin, phytosteryl/octyldodecyl lauroyl glutamate, sodium hyaluronate, stearyl alcohol, hydrogenated palm oil, *Elaeis guineensis* (palm) kernel oil, *Elaeis guineensis* (palm) oil, sodium metaphosphate, trisodium edta, cellulose gum, aluminum hydroxide, bht, sodium metabisulfite, tocopherol, citric acid, phenoxyethanol, fragrance, iron oxides

Production Example 278. SPF 15 Emulsion
(Octinoxate and Octocrylene)

Active Ingredient
　Octinoxate 4.9% (Sunscreen)
　Octocrylene 5.0% (Sunscreen)
Inactive Ingredient
　water, glycerin, dipropylene glycol, sd alcohol 40-b, dimethicone, silica, diisopropyl sebacate, tranexamic acid, hydrogenated polyisobutene, *Euphorbia cerifera* (candelilla) wax, peg/ppg-14/7 dimethyl ether, erythritol, peg/ppg-17/4 dimethyl ether, 2-o-ethyl ascorbic acid, xanthan gum glucosyl hesperidin, phytosteryl/octyldodecyl lauroyl glutamate, sodium hyaluronate, butyl methoxydibenzoylmethane peg/ppg-19/19 dimethicone, behenyl alcohol, ppg-8-ceteth-20, beheneth-20, trisodium edta, acrylates/c10-30 alkyl acrylate crosspolymer, carbomer, stearyl alcohol, potassium hydroxide, hydroxypropylcellulose, bht, polysilicone-2, sodium metabisulfite, tocopherol, phenoxyethanol, fragrance, titanium dioxide, iron oxides

Production Example 279. SPF 22 Cream
(Avobenzone, Octinoxate, and Octocrylene)

Active Ingredient
　Avobenzone 2.5% (Sunscreen)
　Octinoxate 7.4% (Sunscreen)
　Octocrylene 3.0% (Sunscreen)
Inactive Ingredient
　Water, sd alcohol 40-b, dimethicone, dipropylene glycol, diisopropyl sebacate, glycerin, peg-60 hydrogenated castor oil, potassium methoxysalicylate, xanthan gum, peg/ppg-14/7 dimethyl ether, peg/ppg-17/4 dimethyl ether, dipotassium glycyrrhizate, 2-o-ethyl ascorbic acid, glycyl glycine, ascorbyl tetraisopalmitate, tocopheryl acetate, phytosteryl macadamiate, sodium hyaluronate, *Paeonia suffruticosa* root extract, *Rehmannia chinensis* root extract, glucosyl hesperidin, *Houttuynia cordata* extract, ppg-17, peg-240/hdi copolymer bis-decyltetradeceth-20 ether, triethanolamine, silica, isostearic acid, butylene glycol, acrylates/c10-30 alkyl acrylate crosspolymer, carbomer, alcohol, sodium metaphosphate, disodium edta, zinc oxide, bht, sodium metabisulfite, alumina, tocopherol, phenoxyethanol, fragrance, titanium dioxide, mica

Production Example 280. SPF 23 Cream
(Avobenzone, Octinoxate, Octocrylene, and Oxybenzone)

Active Ingredient
　Avobenzone 2.5% (Sunscreen)
　Octinoxate 7.4% (Sunscreen)
　Octocrylene 3.0% (Sunscreen)
　Oxybenzone 1.0% (Sunscreen)
Inactive Ingredient
　Water, sd alcohol 40-b, dimethicone, dipropylene glycol, diisopropyl sebacate, glycerin, peg-60 hydrogenated castor oil, potassium methoxysalicylate, xanthan gum, peg/ppg-14/7 dimethyl ether, tocopheryl acetate, 2-o-ethyl ascorbic acid, ascorbyl tetraisopalmitate, sodium hyaluronate, *Paeonia suffruticosa* root extract, *Crataegus monogyna* flower extract, polyquaternium-51, *Rehmannia chinensis* root extract, uncaria gambir extract, *Houttuynia cordata* extract, ppg-17, peg-240/hdi copolymer bis-decyltetradeceth-20 ether, triethanolamine, silica, isostearic acid, butylene glycol, carbomer, acrylates/c10-30 alkyl acrylate crosspolymer, alcohol, bht, sodium metaphosphate, disodium edta, tocopherol, zinc oxide, sodium metabisulfite, alumina, *Prunus yedoensis* leaf extract, methylparaben, ethylparaben, phenoxyethanol, fragrance, titanium dioxide, mica, iron oxides

Production Example 281. SPF 18 Cream
(Avobenzone, Octinoxate, and Octocrylene)

Active Ingredient
　Avobenzone 2.5% (Sunscreen)
　Octinoxate 7.4% (Sunscreen)
　Octocrylene 2.0% (Sunscreen)
Inactive Ingredient
　water, butylene glycol, dipropylene glycol, glycerin, pentaerythrityl tetraethylhexanoate, dimethicone, sd alcohol 40-b, behenyl alcohol, tranexamic acid, polybutylene glycol/ppg-9/1 copolymer, hydrogenated polydecene, beheneth-20, silica, xanthan gum, peg/ppg-14/7 dimethyl ether, erythritol, peg/ppg-17/4 dimethyl ether, 2-o-ethyl ascorbic acid, glucosyl hesperidin, phytosteryl/octyldodecyl lauroyl glutamate, sodium hyaluronate, stearyl alcohol, hydrogenated palm oil, *Elaeis guineensis* (palm) kernel oil, *Elaeis guineensis* (palm) oil, cellulose gum, sodium metaphosphate, trisodium edta, bht, aluminum hydroxide, sodium metabisulfite, tocopherol, citric acid, phenoxyethanol, fragrance, titanium dioxide, iron oxides

Production Example 282. SPF 18 Emulsion
(Avobenzone, Octinoxate, and Octocrylene)

Active Ingredient
　Avobenzone 2.5% (Sunscreen)
　Octinoxate 7.4% (Sunscreen)
　Octocrylene 2.0% (Sunscreen)

Inactive Ingredient water, dipropylene glycol, glycerin, sd alcohol 40-b, dimethicone, silica, tranexamic acid, polybutylene glycol/ppg-9/1 copolymer, hydrogenated polyisobutene, *Euphorbia cerifera* (candelilla) wax, peg/ppg-14/7 dimethyl ether, erythritol, peg/ppg-17/4 dimethyl ether, xanthan gum, 2-o-ethyl ascorbic acid, glucosyl hesperidin, phytosteryl/octyldodecyl lauroyl glutamate, sodium hyaluronate, peg/ppg-19/19 dimethicone, behenyl alcohol, ppg-8-ceteth-20, beheneth-20, trisodium edta, acrylates/c10-30 alkyl acrylate crosspolymer, carbomer, stearyl alcohol, potassium hydroxide, hydroxypropylcellulose, bht, sodium metabisulfite, aluminum hydroxide, polysilicone-2, tocopherol, phenoxyethanol, fragrance, titanium dioxide, iron oxides Production Example 283. SPF 50 Lotion
(Avobenzone, Homosalate, Octisalate, Octocrylene, and Oxybenzone)

Active Ingredient
  Avobenzone 3.00% (Sunscreen)
  Homosalate 5.00% (Sunscreen)
  Octisalate 5.00% (Sunscreen)
  Octocrylene 2.70% (Sunscreen)
  Oxybenzone 3.00% (Sunscreen)
Inactive Ingredient Water, butyloctyl salicylate, methyl trimethicone, neopentyl glycol diheptanoate, *Aleurites moluccana* (kukui) seed oil, lauryl peg-9 polydimethylsiloxyethyl dimethicone, peg-100 stearate, butylene glycol, glyceryl stearate, dipentaerythrityl tri-polyhydroxystearate, *Laminaria ochroleuca* extract, *Laminaria digitata* extract, algae extract, *Lavandula angustifolia* (lavender), *Pelargonium graveolens* (geranium) flower oil, sodium hyaluronate, caffeine, ergothioneine, sorbitol, ethyl hexyl glycerin, potassium cetyl phosphate, cetyl alcohol, vp/eicosene copolymer, Saccharide isomerate, caprylic/capric triglyceride, caprylyl glycol, ammonium acryloyldimethyltaurate/vp copolymer, stearic acid, dehydroxanthan gum, sodium dehydroacetate, disodium edta, phenoxyethanol, citric acid, citronellol, geraniol, linalool, mica Production Example 284. External Sunscreen Agents Production Example 284 illustrates active ingredients (external sunscreen agents) suitable for topical sunscreens. Any one or more of the external sunscreen agents can be formulated with the appropriate substances (e.g., excipients) of a carrier system, to provide a topical sunscreen composition having the requisite SPF.

Active ingredients: 2-Ethylhexyl-4-phenylbenzophenone-2-carboxylic acid; allantoin (with aminobenzoic acid); amiloxate (isoamyl p-methoxycinnamate); para aminobenzoic acid (PABA); avobenzone; bemotrizinol; bisoctrizole; bornelone (5-(3,3-dimethyl-2-norbornyliden)3-pentene-2-one); camphor; cinoxate; diethylhexyl butamido triazone; digalloyl trioleate; diolamine methoxycinnamate (diethanolamine methoxycinnamate); dioxybenzone; dipropylene glycol salicylate; drometrizole trisiloxane; ecamsule; ensulizole (phenylbenzimidazole sulfonic acid); enzacamene (4-methylbenzylidene camphor); ethyl 4-[bis(hydroxypropyl)] aminobenzoate (roxadimate); glyceryl aminobenzoate (lisadimate, glyceryl PABA); homosalate; lawsone (w/dihydroxyacetone); meradimate (menthyl anthranilate); octinoxate (octyl methoxycinnamate; ethylhexyl methoxycinnamate); octisalate (octyl salicylate; ethylhexyl salicylate); octocrylene; octyl triazone (ethylhexyl triazone); oxybenzone (benzophenone-3); padimate a; padimate o; red petrolatum; sodium 3,4-dimethylphenyl-glyoxylate; sulisobenzone; titanium dioxide; trolamine salicylate; zinc oxide; or zinc phenol sulfonate.

Production Example 285

Active Ingredients (External Sunscreen Agents)

Active ingredients (external sunscreen agents) suitable for formulation with: (1) suitable inactive ingredients (excipients), and (2) a cannabinoid, terpene, flavonoid, or combination thereof, to provide various topical dosage forms (e.g., creams, gels, lotions, etc.).

TABLE 1

| ACTIVE | AMOUNT |
| --- | --- |
| Octinoxate | 7.50 wt. % |
| Octinoxate/Avobenzone | 7.5 wt. %/3.0 wt. % |
| Octinoxate/Octisalate | 7.0 wt. %/3.0 wt. % |
| Octinoxate/Oxybenzone | 7.5 wt. %/5.0 wt. % |
| Octinoxate/Octocrylene | 4.9 wt. %/5.0 wt. % |
| Octinoxate/Zinc oxide | 6.0 wt. %/3.0 wt. % |
| Octinoxate/Zinc oxide | 7.5 wt. %/10.5 wt. % |
| Octinoxate/Zinc oxide | 7.4 wt. %/9.6 wt. % |
| Octinoxate/Titanium dioxide | 7.4 wt. %/4.2 wt. % |
| Octinoxate/Titanium dioxide | 7.4 wt. %/4.9 wt. % |
| Octinoxate/Titanium dioxide | 7.4 wt. %/5.3 wt. % |
| Octinoxate/Titanium dioxide | 7.5 wt. %/3.0 wt. % |
| Octinoxate/Titanium dioxide | 3.0 wt. %/15.0 wt. % |
| Octinoxate/Octocrylene/Zinc oxide | 2.9 wt. %/3.0 wt. %/10.6 wt. % |
| Octinoxate/Octocrylene/Zinc oxide | 4.9 wt. %/3.0 wt. %/6.7 wt. % |
| Octinoxate/Octocrylene/Zinc oxide | 4.9 wt. %/3.0 wt. %/8.6 wt. % |
| Octinoxate/Octocrylene/Zinc oxide | 4.9 wt. %/3.0 wt. %/12.5 wt. % |
| Octinoxate/Zinc oxide/Oxybenzone | 7.5 wt. %/4.0 wt. %/2.5 wt. % |
| Octinoxate/Zinc oxide/Titanium dioxide | 7.4 wt. %/16.3 wt. %/2.2 wt. % |
| Octinoxate/Octocrylene/Zinc oxide/Titanium dioxide | 7.4 wt. %/3.0 wt. %/16.4 wt. %/1.4 wt. % |
| Octinoxate/Octocrylene/Zinc oxide/Titanium dioxide | 7.4 wt. %/3.0 wt. %/19.3 wt. %/1.7 wt. % |
| Octinoxate/Octisalate/Oxybenzone/Titanium dioxide | 7.5 wt. %/4.0 wt. %/2.5 wt. %/1.1 wt. % |

TABLE 1-continued

| ACTIVE | AMOUNT |
| --- | --- |
| Octinoxate/Octisalate/Oxybenzone/Zinc oxide | 7.5 wt. %/2.5 wt. %/2.5 wt. %/7.0 wt. % |
| Octinoxate/Octocrylene/Oxybenzone/Zinc oxide | 4.9 wt. %/3.0 wt. %/1.0 wt. %/12.5 wt. % |
| Octisalate/Homosalate/Oxybenzone/Avobenzone/Octocrylene | 3.21 wt. %/10.72 wt. %/3.86 wt. %/3.0 wt. %/6.0 wt. % |
| Octisalate/Homosalate/Oxybenzone/Avobenzone/Octocrylene | 3.2 wt. %/10.7 wt. %/3.9 wt. %/3.0 wt. %/6.0 wt. % |
| Octisalate/Homosalate/Oxybenzone/Avobenzone/Octocrylene | 5.0 wt. %/5.0 wt. %/4.0 wt. %/3.0 wt. %/2.7 wt. % |
| Octisalate/Homosalate/Oxybenzone/Avobenzone/Octocrylene | 5.0 wt. %/5.0 wt. %/5.0 wt. %/3.0 wt. %/2.7 wt. % |
| Octisalate/Homosalate/Oxybenzone/Avobenzone/Octocrylene | 5.0 wt. %/5.0 wt. %/3.0 wt. %/3.0 wt. %/2.7 wt. % |
| Octisalate/Homosalate/Oxybenzone/Avobenzone/Octocrylene | 5.0 wt. %/5.0 wt. %/6.0 wt. %/3.0 wt. %/7.0 wt. % |
| Octisalate/Homosalate/Oxybenzone/Avobenzone/Octocrylene | 4.0 wt. %/2.0 wt. %/3.0 wt. %/3.0 wt. %/1.8 wt. % |
| Octisalate/Homosalate/Oxybenzone/Avobenzone/Octocrylene | 4.0 wt. %/7.0 wt. %/2.0 wt. %/2.0 wt. %/1.5 wt. % |
| Octisalate/Homosalate/Oxybenzone/Avobenzone/Octocrylene | 5.0 wt. %/4.0 wt. %/5.0 wt. %/3.0 wt. %/5.0 wt. % |
| Octisalate/Homosalate/Oxybenzone/Avobenzone/Octocrylene | 5.0 wt. %/4.0 wt. %/5.0 wt. %/3.0 wt. %/4.0 wt. % |
| Octisalate/Homosalate/Oxybenzone/Avobenzone/Octocrylene | 4.0 wt. %/7.0 wt. %/2.0 wt. %/1.8 wt. %/1.5 wt. % |
| Octisalate/Homosalate/Oxybenzone/Avobenzone/Octocrylene | 4.0 wt. %/8.0 wt. %/4.0 wt. %/2.7 wt. %/3.5 wt. % |
| Octisalate/Homosalate/Oxybenzone/Avobenzone/Octocrylene | 5.0 wt. %/8.0 wt. %/4.0 wt. %/2.7 wt. %/3.5 wt. % |
| Octisalate/Homosalate/Oxybenzone/Avobenzone/Octocrylene | 5.0 wt. %/8.0 wt. %/4.0 wt. %/3.0 wt. %/4.0 wt. % |
| Octisalate/Homosalate/Oxybenzone/Avobenzone/Octocrylene | 4.0 wt. %/8.0 wt. %/5.0 wt. %/3.0 wt. %/4.0 wt. % |
| Octisalate/Homosalate/Oxybenzone/Avobenzone/Octocrylene | 5.0 wt. %/10 wt. %/3.0 wt. %/3.0 wt. %/5.0 wt. % |
| Octisalate/Homosalate/Oxybenzone/Avobenzone/Octocrylene | 5.0 wt. %/10 wt. %/6.0 wt. %/3.0 wt. %/5.0 wt. % |
| Octisalate/Homosalate/Oxybenzone/Avobenzone/Octocrylene | 5.0 wt. %/10 wt. %/4.0 wt. %/3.0 wt. %/4.5 wt. % |
| Octisalate/Homosalate/Oxybenzone/Avobenzone/Octocrylene | 5.0 wt. %/10 wt. %/6.0 wt. %/3.0 wt. %/2.8 wt. % |
| Octisalate/Homosalate/Oxybenzone/Avobenzone/Octocrylene | 5.0 wt. %/10 wt. %/5.0 wt. %/3.0 wt. %/7.5 wt. % |
| Octisalate/Homosalate/Oxybenzone/Avobenzone/Octocrylene | 5.0 wt. %/10 wt. %/6.0 wt. %/3.0 wt. %/7.5 wt. % |
| Octisalate/Homosalate/Oxybenzone/Avobenzone/Octocrylene | 5.0 wt. %/10 wt. %/5.0 wt. %/3.0 wt. %/6.0 wt. % |
| Octisalate/Homosalate/Oxybenzone/Avobenzone/Octocrylene | 4.0 wt. %/5.0 wt. %/4.0 wt. %/2.5 wt. %/3.0 wt. % |
| Octisalate/Homosalate/Oxybenzone/Avobenzone/Octocrylene | 4.5 wt. %/4.0 wt. %/4.5 wt. %/2.7 wt. %/6.0 wt. % |
| Octisalate/Homosalate/Oxybenzone/Avobenzone/Octocrylene | 5.0 wt. %/9.0 wt. %/4.5 wt. %/2.7 wt. %/9.0 wt. % |
| Octisalate/Homosalate/Oxybenzone/Avobenzone/Octocrylene | 5.0 wt. %/15.0 wt. %/6.0 wt. %/3.0 wt. %/10 wt. % |
| Octisalate/Homosalate/Oxybenzone/Avobenzone/Octocrylene | 5.0 wt. %/15.0 wt. %/6.0 wt. %/3.0 wt. %/7.0 wt. % |
| Octisalate/Homosalate/Oxybenzone/Avobenzone/Octocrylene | 5.0 wt. %/15.0 wt. %/6.0 wt. %/3.0 wt. %/6.0 wt. % |
| Octisalate/Homosalate/Oxybenzone/Avobenzone/Octocrylene | 5.0 wt. %/15.0 wt. %/6.0 wt. %/3.0 wt. %/2.8 wt. % |
| Octisalate/Homosalate/Oxybenzone/Avobenzone/Octocrylene | 5.0 wt. %/15.0 wt. %/6.0 wt. %/3.0 wt. %/2.7 wt. % |
| Octisalate/Homosalate/Oxybenzone/Avobenzone/Octocrylene | 5.0 wt. %/15.0 wt. %/6.0 wt. %/3.0 wt. %/2.6 wt. % |
| Octisalate/Homosalate/Oxybenzone/Avobenzone/Octocrylene | 5.0 wt. %/15.0 wt. %/6.0 wt. %/3.0 wt. %/4.0 wt. % |
| Octisalate/Homosalate/Oxybenzone/Avobenzone/Octocrylene | 5.0 wt. %/15.0 wt. %/5.0 wt. %/3.0 wt. %/4.0 wt. % |
| Octisalate/Homosalate/Oxybenzone/Avobenzone/Octocrylene | 5.0 wt. %/15.0 wt. %/6.0 wt. %/3.0 wt. %/4.5 wt. % |
| Octisalate/Homosalate/Oxybenzone/Avobenzone/Octocrylene | 5.0 wt. %/15.0 wt. %/5.0 wt. %/3.0 wt. %/5.0 wt. % |
| Octisalate/Homosalate/Oxybenzone/Avobenzone/Octocrylene | 5.0 wt. %/15.0 wt. %/6.0 wt. %/3.0 wt. %/5.0 wt. % |
| Octisalate/Homosalate/Oxybenzone/Avobenzone/Octocrylene | 4.5 wt. %/9.0 wt. %/4.5 wt. %/2.7 wt. %/8.0 wt. % |

TABLE 1-continued

| ACTIVE | AMOUNT |
| --- | --- |
| Octisalate/Homosalate/Oxybenzone/Avobenzone/Octocrylene | 5.0 wt. %/12.0 wt. %/3.0 wt. %/3.0 wt. %/5.0 wt. % |
| Octisalate/Homosalate/Oxybenzone/Avobenzone/Octocrylene | 5.0 wt. %/12.0 wt. %/6.0 wt. %/3.0 wt. %/2.35 wt. % |
| Octisalate/Homosalate/Oxybenzone/Avobenzone/Octocrylene | 5.0 wt. %/12.0 wt. %/3.0 wt. %/3.0 wt. %/1.7 wt. % |
| Octisalate/Homosalate/Oxybenzone/Avobenzone/Octocrylene | 4.0 wt. %/4.0 wt. %/6.0 wt. %/2.0 wt. %/2.0 wt. % |
| Octinoxate/Homosalate/Oxybenzone/Avobenzone/Octocrylene | 7.4 wt %/5.0 wt. %/1.5 wt. %/2.0 wt. %/3.0 wt. % |
| Octinoxate/Homosalate/Oxybenzone/Avobenzone/Octocrylene | 4.9 wt. %/10.0 wt. %/3.0 wt. %/2.5 wt. %/5.0 wt. % |
| Titanium dioxide/Zinc oxide | 9.1 wt. %/19.3 wt. % |
| Titanium dioxide/Zinc oxide | 3.2 wt. %/2.0 wt. % |
| Titanium dioxide/Zinc oxide | 3.67 wt. %/3.5 wt. % |
| Titanium dioxide/Zinc oxide | 3.7 wt. %/3.5 wt. % |
| Titanium dioxide/Zinc oxide | 9.0 wt. %/7.0 wt. % |
| Titanium dioxide/Zinc oxide | 6.2 wt. %/4.0 wt. % |
| Titanium dioxide/Zinc oxide | 6.0 wt. %/5.0 wt. % |
| Titanium dioxide/Zinc oxide | 6.4 wt. %/2.0 wt. % |
| Titanium dioxide/Zinc oxide | 6.3 wt. %/4.0 wt. % |
| Titanium dioxide/Zinc oxide | 5.0 wt. %/3.0 wt. % |
| Titanium dioxide/Zinc oxide | 4.1 wt. %/3.0 wt. % |
| Titanium dioxide/Zinc oxide | 5.1 wt. %/2.9 wt. % |
| Titanium dioxide/Zinc oxide | 4.9 wt. %/2.9 wt. % |
| Titanium dioxide/Zinc oxide | 4.9 wt. %/4.7 wt. % |
| Titanium dioxide/Zinc oxide | 4.3 wt. %/3.0 wt. % |
| Titanium dioxide/Zinc oxide | 6.0 wt. %/3.0 wt. % |
| Titanium dioxide/Zinc oxide | 7.4 wt. %/11.4 wt. % |
| Octinoxate/Octisalate/Titanium dioxide/Zinc oxide | 7.5 wt. %/4.5 wt. %/4.6 wt. %/5.0 wt. % |
| Octinoxate/Octisalate/Titanium dioxide/Zinc oxide | 7.5 wt. %/5 wt. %/1.7 wt. %/4.6 wt. % |
| Homosalate/Octinoxate/Octisalate/Oxybenzone/Titanium dioxide | 5.0 wt. %/7.5 wt. %/5.0 wt. %/4.0 wt. %/2.9 wt. % |
| Homosalate/Octinoxate/Octisalate/Titanium dioxide | 5.0 wt. %/7.5 wt. %/5.0 wt. %/2.3 wt. % |
| Octinoxate/Octisalate/Oxybenzone/Titanium dioxide/Zinc oxide | 7.5 wt. %/4 wt. %/2.5 wt. %/1.1 wt. %/3.3 wt. % |
| Avobenzone/Homosalate/Octisalate | 3.0 wt. %/10 wt. %/4.5 wt. % |
| Octisalate/Avobenzone/Octocrylene | 5.0 wt. %/3.0 wt. %/2.7 wt. % |
| Octisalate/Avobenzone/Octocrylene | 5.0 wt. %/3.0 wt. %/5.0 wt. % |
| Octisalate/Avobenzone/Octocrylene | 7.5 wt. %/3.0 wt. %/2.0 wt. % |
| Octinoxate/Avobenzone/Octocrylene | 7.4 wt. %/2.5 wt. %/2.0 wt. % |
| Octinoxate/Avobenzone/Octocrylene | 7.4 wt. %/2.5 wt. %/3.0 wt. % |
| Octinoxate/Avobenzone/Octisalate/Oxybenzone | 7.4 wt. %/3.0 wt. %/5.0 wt. %/2.0 wt. % |
| Octisalate/Avobenzone/Homosalate/Oxybenzone | 5.0 wt. %/3.0 wt. %/5.0 wt. %/5.0 wt. % |
| Octisalate/Avobenzone/Octocrylene/Oxybenzone | 4.9 wt. %/2.5 wt. %/5.0 wt. %/1.5 wt. % |
| Octisalate/Avobenzone/Octocrylene/Oxybenzone | 5.0 wt. %/1.5 wt. %/3.0 wt. %/4.0 wt. % |
| Octisalate/Avobenzone/Octocrylene/Oxybenzone | 5.0 wt. %/3.0 wt. %/1.3 wt. %/5.0 wt. % |
| Octisalate/Avobenzone/Octocrylene/Oxybenzone | 5.0 wt. %/1.5 wt. %/3.0 wt. %/4.0 wt. % |
| Octisalate/Avobenzone | 5.0 wt. %/3.0 wt. % |
| Octisalate/Octinoxate/Avobenzone | 5.0 wt. %/7.5 wt. %/2.0 wt. % |
| Octisalate/Octinoxate/Avobenzone | 2.0 wt. %/7.5 wt. %/3.0 wt. % |
| Octinoxate/Octisalate/Titanium dioxide | 7.5 wt. %/3.5 wt. %/1.7 wt. % |
| Octinoxate/Octisalate/Titanium dioxide | 7.0 wt. %/3.0 w4. %o/5.1 wt. % |
| Octisalate/Homosalate/Avobenzone/Octocrylene | 4.86 wt. %/8.78 wt. %/2.96 wt. %/5.92 wt. % |
| Octisalate/Homosalate/Avobenzone/Octocrylene | 4.88 wt. %/8.78 wt. %/2.96 wt. %/5.92 wt % |
| Octisalate/Homosalate/Avobenzone/Octocrylene | 4.9 wt. %/8.8 wt. %/3.0 wt. %/5.9 wt. % |
| Octisalate/Homosalate/Avobenzone/Octocrylene | 2.4 wt. %/8.0 wt. %/2.24 wt. %/4.48 wt. % |
| Octisalate/Homosalate/Avobenzone/Octocrylene | 3.21 wt. %/10.72 wt. %/3.0 wt. %/6.0 wt. % |
| Octisalate/Homosalate/Avobenzone/Octocrylene | 5.0 wt. %/10 wt. %/3.0 wt. %/2.7 wt. % |
| Octisalate/Homosalate/Avobenzone/Octocrylene | 5.0 wt. %/10 wt. %/3.0 wt. %/7.0 wt. % |
| Octisalate/Homosalate/Avobenzone/Octocrylene | 4.5 wt. %/9 wt. %/3.0 wt. %/6.0 wt. % |

TABLE 1-continued

| ACTIVE | AMOUNT |
| --- | --- |
| Octisalate/Homosalate/Avobenzone/Octocrylene | 4.0 wt. %/5.0 wt. %/1.5 wt. %/6.0 wt. % |
| Octisalate/Homosalate/Avobenzone/Octocrylene | 1.7 wt. %/5.0 wt. %/3.0 wt. %/3.0 wt. % |
| Octisalate/Homosalate/Avobenzone/Octocrylene | 4.0 wt. %/4.0 wt. %/2.0 wt. %/2.0 wt. % |
| Octisalate/Homosalate/Avobenzone/Octocrylene | 5.0 wt. %/5.0 wt. %/3.0 wt. %/2.7 wt. % |
| Octisalate/Homosalate/Avobenzone/Octocrylene | 5.0 wt. %/4.7 wt. %/3.0 wt. %/7.0 wt. % |
| Octisalate/Homosalate/Avobenzone/Octocrylene | 5.0 wt. %/2.0 wt. %/3.0 wt. %/7.0 wt. % |
| Octisalate/Homosalate/Avobenzone/Octocrylene | 5.0 wt. %/2.0 wt. %/3.0 wt. %/5.5 wt. % |
| Octisalate/Homosalate/Avobenzone/Octocrylene | 5.0 wt. %/2.7 wt. %/3.0 wt. %/7.0 wt. % |
| Octisalate/Homosalate/Avobenzone/Octocrylene | 5.0 wt. %/5.0 wt. %/3.0 wt. %/5.0 wt. % |
| Octisalate/Homosalate/Avobenzone/Octocrylene | 5.0 wt. %/7.0 wt. %/3.0 wt. %/5.0 wt. % |
| Octisalate/Homosalate/Avobenzone/Octocrylene | 5.0 wt. %/5.0 wt. %/3.0 wt. %/7.0 wt. % |
| Octisalate/Homosalate/Avobenzone/Octocrylene | 4.5 wt. %/4.0 wt. %/3.0 wt. %/2.6 wt. % |
| Octisalate/Homosalate/Avobenzone/Octocrylene | 4.0 wt. %/8 wt. %/3.0 wt. %/5.0 wt. % |
| Octisalate/Homosalate/Avobenzone/Oxygenzone | 5.0 wt. %/5 wt. %/3.0 wt. %/3.0 wt. % |
| Octinoxate/Oxybenzone/Homosalate/Avobenzone | 7.5 wt. %/5.0 wt. %/10 wt. %/2.0 wt. % |
| Octinoxate/Oxybenzone/Octocrylene/Avobenzone | 4.9 wt. %/1.5 wt. %/5.0 wt. %/2.5 wt. % |
| Octinoxate/Oxybenzone/Octocrylene/Avobenzone | 7.4 wt. %/1.0 wt. %/2.0 wt. %/2.5 wt. % |
| Octinoxate/Oxybenzone/Octocrylene/Avobenzone | 7.4 wt. %/1.0 wt. %/3.0 wt. %/2.5 wt. % |
| Octinoxate/Oxybenzone/Octocrylene/Avobenzone | 4.9 wt. %/3.0 wt. %/5.0 wt. %/2.5 wt. % |
| Octinoxate/Oxybenzone/Homosalate/Avobenzone | 7.5 wt. %/5.0 wt. %/5 wt. %/2.0 wt. % |
| Octinoxate/Ensulizole | 6.0 wt. %/1.0 wt. % |
| Octinoxate/Ensulizole | 7.5 wt. %/1.7 wt. % |
| Octinoxate/Ensulizole | 7.0 wt. %/2.0 wt. % |
| Octinoxate/Ensulizole | 7.5 wt. %/2.0 wt. % |
| Octinoxate/Octocrylene/Ensulizole | 4.9 wt. %/5.0 wt. %/2.0 wt. % |
| Octinoxate/Zinc oxide/Ensulizole | 7.4 wt. %/16.3 wt. %/2.0 wt. % |
| Octinoxate/Titanium dioxide/Ensulizole | 7.4 wt. %/7.2 wt. %/2.0 wt. % |
| Octinoxate/Titanium dioxide/Ensulizole | 7.4 wt. %/1.9 wt. %/2.5 wt. % |
| Titanium dioxide | 11 wt. % |
| Titanium dioxide | 15 wt. % |
| Zinc oxide | 21.60 wt. % |
| Zinc oxide | 18.24 wt. % |
| Avobenzone/Octocrylene/Terephthalylidene dicamphor sulfonic acid/Titanium dioxide | 3.0 wt. %/10 wt. %/1 wt. %/2.2 wt. % |
| Ethylhexyl Triazone/Drometrizole Trisiloxane/Homosalate/Ecamsule/Octisalate/Bemotrizinol/Diethylamino hydroxybenzoyl hexyl benzoate | 3.0 wt. %/5.0 wt. %/10 wt. %/3.0 wt. %/5.0 wt. %/4.0 wt. %/3.0 wt. % |
| Drometrizole Trisiloxane/Titanium dioxide/Ecamsule/Bemotrizinol/Di ethylamino hydroxybenzoyl hexyl benzoate/Octinoxate | 5.0 wt. %/4.0 wt. %/12 wt. %/5.0 wt. %/5.0 wt. %/6.75 wt. % |
| Ethylhexyl Triazone/Diethylamino hydroxybenzoyl hexyl benzoate/Bemotrizinol/Drometrizole Trisiloxane/Titanium dioxide | 5.0 wt. %/3.0 wt. %/3.0 wt. %/1.0 wt. %/2.5 wt. % |
| Homosalate/Meradimate/Octinoxate/Octocrylene/Zinc oxide | 10 wt. %/5.0 wt. %/5.0 wt. %/2.0 wt. %/6.3 wt. % |

TABLE 2

| ACTIVE | AMOUNT |
| --- | --- |
| allantoin (with aminobenzoic acid) | 0.5 wt. % to 2 wt. % |
| aminobenzoic acid (PABA) | up to 15 wt. % |
| avobenzone | up to 3 wt. % |
| cinoxate | up to 3 wt. % |
| dioxybenzone | up to 3 wt. % |
| ensulizole (phenylbenzimidazole sulfonic acid) | up to 4 wt. % |
| homosalate | up to 15 wt. % |
| meradimate (menthyl anthranilate) | up to 5 wt. % |
| octinoxate (octyl methoxycinnamate; ethylhexyl methoxycinnamate) | up to 7.5 wt. % |
| octisalate (octyl salicylate; ethylhexyl salicylate) | up to 5 wt. % |
| octocrylene | up to 10 wt. % |
| oxybenzone (benzophenone-3) | up to 6 wt. % |
| sulisobenzone | up to 10 wt. % |
| titanium dioxide | up to 25 wt. % |
| trolamine salicylate | up to 12 wt. % |
| zinc oxide | up to 25 wt. % |

Enumerated Embodiments

Specific enumerated embodiments <1> to <104> provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

<1> A topical sunscreen including the formulation of any one of Production Examples 1-285, further including a cannabinoid, terpene, flavonoid, or combination thereof.

<2> A topical sunscreen including the formulation of any one of Production Examples 1-285, further including a cannabinoid.

<3> A topical sunscreen including the formulation of any one of Production Examples 1-285, further including a cannabinoid obtained as a distillate from cannabis.

<4> A topical sunscreen including the formulation of any one of Production Examples 1-285, further including a cannabinoid obtained as an extract from cannabis.

<5> A topical sunscreen including the formulation of any one of Production Examples 1-285, further including a cannabinoid obtained as a resin from cannabis.

<6> A topical sunscreen including the formulation of any one of Production Examples 1-285, further including a cannabinoid isolate obtained from cannabis.

<7> A topical sunscreen including the formulation of any one of Production Examples 1-285, further including a cannabinoid obtained from Cannabis indica, Cannabis ruderalis, or Cannabis sativa.

<8> A topical sunscreen including the formulation of any one of Production Examples 1-285, further including a cannabinoid present as an oil from cannabis.

<9> A topical sunscreen including the formulation of any one of Production Examples 1-285, further including a cannabinoid present as hempseed oil.

<10> A topical sunscreen including the formulation of any one of Production Examples 1-285, further including a cannabinoid that is synthetically prepared.

<11> A topical sunscreen including the formulation of any one of Production Examples 1-285, further including a cannabinoid that is at least one of THC (tetrahydrocannabinol), TH CA (tetrahydrocannabinolic acid), CBD (cannabidiol), CBDA (cannabidiolic acid), CBN (cannabinol), CBG (cannabigerol), CBC (cannabichromene), CBL (cannabicyclol) CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), and CBT (cannabicitran).

<12> A topical sunscreen including the formulation of any one of Production Examples 1-285, further including a cannabinoid that is at least one of CB D and TH C.

<13> A topical sunscreen including the formulation of any one of Production Examples 1-285, further including a terpene.

<14> A topical sunscreen including the formulation of any one of Production Examples 1-285, further including a terpene that is a sesquiterpene.

<15> A topical sunscreen including the formulation of any one of Production Examples 1-285, further including a terpene obtained as a distillate from plant matter.

<16> A topical sunscreen including the formulation of any one of Production Examples 1-285, further including a terpene obtained as an extract from plant matter.

<17> A topical sunscreen including the formulation of any one of Production Examples 1-285, further including a terpene obtained as a resin from plant matter.

<18> A topical sunscreen including the formulation of any one of Production Examples 1-285, further including a terpene obtained from Cannabis sativa, Syzygium aromaticum (cloves), rosemary, or hops.

<19> A topical sunscreen including the formulation of any one of Production Examples 1-285, further including a terpene that is synthetically prepared.

<20> A topical sunscreen including the formulation of any one of Production Examples 1-285, further including a terpene that is Beta-Caryophyllene.

<21> The topical sunscreen of any one of the above embodiments, wherein the amount of external sunscreen agent expressed in terms of concentration (weight percent), present in the formulation of the any one of Production Examples 1-285, remains unchanged with the addition of the cannabinoid, terpene, flavonoid, or combination thereof. For Example, if the amount of external sunscreen agent present in the formulation of the any one of Production Examples 1-285 is 1 wt. % PABA. With the addition of the cannabinoid, terpene, flavonoid, or combination thereof, the resulting amount of the PABA will remain at 1 wt. %.

<22> The topical sunscreen of any one of the above embodiments, wherein the amount of inactive ingredient expressed in terms of concentration (weight percent), present in the formulation of the any one of Production Examples 1-285, decreases with the amount added of the cannabinoid, terpene, flavonoid, or combination thereof. For Example, if the amount of external sunscreen agent present in the formulation of the any one of Production Examples 1-285 is 1 wt % PABA, with the addition of the cannabinoid, terpene, flavonoid, or combination thereof, the resulting amount of the PABA will be less than 1 wt %.

<23> The topical sunscreen of any one of the above embodiments, wherein the aggregate amount of inactive ingredients, present in the formulation of the any one of Production Examples 1-285, decreases in proportion to the amount added of the cannabinoid, terpene, flavonoid, or combination thereof. For Example, if the aggregate amount of inactive ingredients present in the formulation of the any one of Production Examples 1-285 is 90 wt % (and the aggregate amount of active ingredient(s) is 10%). In such an embodiment, with the addition of 1 wt % of cannabinoid, terpene, flavonoid, or combination thereof, the resulting aggregate amount of those inactive ingredients will be 89 wt %.

<24> The topical sunscreen of any one of the above embodiments, wherein the aggregate amount of active ingredient (external sunscreen agent) and inactive ingredient in terms of concentration (weight percent), present in the formulation of the any one of Production Examples 1-285, decreases in proportion to the amount added of the cannabinoid, terpene, flavonoid, or combination thereof. For Example, the aggregate amount of active and inactive ingredients present in the formulation of the any one of Production Examples 1-285 is 100 wt %. With the addition of 1 wt % of cannabinoid, terpene, flavonoid, or combination thereof, the resulting aggregate amount of those active and inactive ingredients will be 99 wt %.

<25> The topical sunscreen of any one of the above embodiments, wherein the cannabinoid, terpene, flavonoid, or combination thereof, is present in an aggregate amount of up to 20 wt %.

<26> The topical sunscreen of any one of the above embodiments, wherein the cannabinoid, terpene, flavonoid, or combination thereof, is present in an aggregate amount of up to 10 wt %.

<27> The topical sunscreen of any one of the above embodiments, wherein the cannabinoid, terpene, flavonoid, or combination thereof, is present in an aggregate amount of up to 5 wt %.

<28> The topical sunscreen of any one of the above embodiments, wherein the cannabinoid, terpene, flavonoid, or combination thereof, is present in an aggregate amount of up to 1 wt %.

<29> The topical sunscreen of any one of the above embodiments, wherein the cannabinoid, terpene, flavonoid, or combination thereof, is present in an aggregate amount of up to 0.5 wt. %.

<30> The topical sunscreen of any one of the above embodiments, wherein the cannabinoid, terpene, flavonoid, or combination thereof, is present in an aggregate amount of 0.330±0.1 wt %.

<31> The topical sunscreen of any one of the above embodiments, wherein the cannabinoid, terpene, flavonoid, or combination thereof, is present in an aggregate amount of 0.1 to 20 wt. %.

<32> The topical sunscreen of any one of the above embodiments, wherein the cannabinoid, terpene, flavonoid, or combination thereof, is present in an aggregate amount of 0.1 to 10 wt. %.

<33> The topical sunscreen of any one of the above embodiments, wherein the cannabinoid, terpene, flavonoid, or combination thereof, is present in an aggregate amount of 0.1 to 5 wt. %.

<34> The topical sunscreen of any one of the above embodiments, wherein the cannabinoid, terpene, flavonoid, or combination thereof, is present in an aggregate amount of 0.01 to 2.5 wt. %.

<35> The topical sunscreen of any one of the above embodiments, wherein the cannabinoid, terpene, flavonoid, or combination thereof, is present in an aggregate amount of 0.01 to 1 wt %.

<36> The topical sunscreen of any one of the above embodiments, wherein the cannabinoid, terpene, flavonoid, or combination thereof, is present in an aggregate amount of 0.01 to 0.5 wt. %.

<37> The topical sunscreen of any one of the above embodiments, wherein the cannabinoid, terpene, flavonoid, or combination thereof, is present in an aggregate amount of 1 to 20 wt %.

<38> The topical sunscreen of any one of the above embodiments, wherein the cannabinoid, terpene, flavonoid, or combination thereof, is present in an aggregate amount of 1 to 10 wt %.

<39> The topical sunscreen of any one of the above embodiments, wherein the cannabinoid, terpene, flavonoid, or combination thereof, is present in an aggregate amount of 1 to 5 wt. %.

<40> The topical sunscreen of any one of the above embodiments, wherein the cannabinoid, terpene, flavonoid, or combination thereof, is present in an aggregate amount of 0.05 to 2.5 wt %.

<41> The topical sunscreen of any one of the above embodiments, wherein the cannabinoid, terpene, flavonoid, or combination thereof, is present in an aggregate amount of 0.05 to 1 wt. %.

<42> The topical sunscreen of any one of the above embodiments, wherein the cannabinoid, terpene, flavonoid, or combination thereof, is present in an aggregate amount of 0.05 to 0.5 wt %.

<43> The topical sunscreen of any one of the above embodiments, which is in the form of a gel, pump gel, gel packet, cream, lotion, emulsion, roll-on liquid, roll-on gel, spray, pump spray, aerosol spray, stick, patch, ointment, liniment, or balm.

<44> A topical sunscreen including the formulation of any one of Production Examples 1-285, further including a cannabinoid, terpene, flavonoid, or combination thereof; wherein the cannabinoid, terpene, flavonoid, or combination thereof, while present in the aggregate amounts, are characterized as inactive ingredients.

<45> A topical sunscreen including the formulation of any one of Production Examples 1-285, further including a cannabinoid, terpene, flavonoid, or combination thereof; wherein the cannabinoid, terpene, flavonoid, or combination thereof, while present in the aggregate amounts, are characterized as an excipient <46> A topical sunscreen including the formulation of any one of Production Examples 1-285, further including a cannabinoid, terpene, flavonoid, or combination thereof; wherein the cannabinoid, terpene, flavonoid, or combination thereof, while present in the aggregate amounts, are characterized as active ingredients.

<47> A topical sunscreen including the formulation of any one of Production Examples 1-285, further including a cannabinoid, terpene, flavonoid, or combination thereof; wherein the cannabinoid, terpene, flavonoid, or combination thereof, while present in the aggregate amounts, are characterized as an external sunscreen agent <48> A topical sunscreen including one or more external sunscreen agents of Production Example 74, further including a cannabinoid, terpene, flavonoid, or combination thereof, and a carrier system.

<49> A topical sunscreen including one or more external sunscreen agents of Production Example 74, further including a cannabinoid, and a carrier system.

<50> A topical sunscreen including one or more external sunscreen agents of Production Example 74, further including a cannabinoid obtained as a distillate from *cannabis*, and a carrier system.

<51> A topical sunscreen including one or more external sunscreen agents of Production Example 74, further including a cannabinoid obtained as an extract from *cannabis*, and a carrier system.

<52> A topical sunscreen including one or more external sunscreen agents of Production Example 74, further including a cannabinoid obtained as a resin from *cannabis*, and a carrier system.

<53> A topical sunscreen including one or more external sunscreen agents of Production Example 74, further including a cannabinoid isolate obtained from *cannabis*, and a carrier system.

<54> A topical sunscreen including one or more external sunscreen agents of Production Example 74, further including a cannabinoid obtained from *Cannabis indica, Cannabis ruderalis*, or *Cannabis sativa*, and a carrier system.

<55> A topical sunscreen including one or more external sunscreen agents of Production Example 74, further including a cannabinoid present as an oil from *cannabis*, and a carrier system.

<56> A topical sunscreen including one or more external sunscreen agents of Production Example 74, further including a cannabinoid present as hempseed oil, and a carrier system.

<57> A topical sunscreen including one or more external sunscreen agents of Production Example 74, further including a cannabinoid that is synthetically prepared, and a carrier system.

<58> A topical sunscreen including one or more external sunscreen agents of Production Example 74, further including a cannabinoid that is at least one of TH C (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol) CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), and CBT (cannabicitran), and a carrier system.

<59> A topical sunscreen including one or more external sunscreen agents of Production Example 74, further including a cannabinoid that is at least one of CB D and TH C, and a carrier system.

<60> A topical sunscreen including one or more external sunscreen agents of Production Example 74, further including a terpene, and a carrier system.

<61> A topical sunscreen including one or more external sunscreen agents of Production Example 74, further including a terpene that is a sesquiterpene, and a carrier system.

<62> A topical sunscreen including one or more external sunscreen agents of Production Example 74, further including a terpene obtained as a distillate from plant matter, and a carrier system.

<63> A topical sunscreen including one or more external sunscreen agents of Production Example 74, further including a terpene obtained as an extract from plant matter, and a carrier system.

<64> A topical sunscreen including one or more external sunscreen agents of Production Example 74, further including a terpene obtained as a resin from plant matter, and a carrier system.

<65> A topical sunscreen including one or more external sunscreen agents of Production Example 74, further including a terpene obtained from *Cannabis sativa, Syzygium aromaticum* (cloves), rosemary, or hops, and a carrier system.

<66> A topical sunscreen including one or more external sunscreen agents of Production Example 74, further including a terpene that is synthetically prepared, and a carrier system.

<67> A topical sunscreen including one or more external sunscreen agents of Production Example 74, further including a terpene that is Beta-Caryophyllene, and a carrier system.

<68> The topical sunscreen of any one of the above embodiments, wherein the cannabinoid, terpene, flavonoid, or combination thereof, is present in an aggregate amount of up to 20 wt. %.

<69> The topical sunscreen of any one of the above embodiments, wherein the cannabinoid, terpene, flavonoid, or combination thereof, is present in an aggregate amount of up to 10 wt. %.

<70> The topical sunscreen of any one of the above embodiments, wherein the cannabinoid, terpene, flavonoid, or combination thereof, is present in an aggregate amount of up to 5 wt %.

<71> The topical sunscreen of any one of the above embodiments, wherein the cannabinoid, terpene, flavonoid, or combination thereof, is present in an aggregate amount of up to 1 wt. %.

<72> The topical sunscreen of any one of the above embodiments, wherein the cannabinoid, terpene, flavonoid, or combination thereof, is present in an aggregate amount of up to 0.5 wt. %.

<73> The topical sunscreen of any one of the above embodiments, wherein the cannabinoid, terpene, flavonoid, or combination thereof, is present in an aggregate amount of 0.330±0.1 wt. %.

<74> The topical sunscreen of any one of the above embodiments, wherein the cannabinoid, terpene, flavonoid, or combination thereof, is present in an aggregate amount of 0.1 to 20 wt. %.

<75> The topical sunscreen of any one of the above embodiments, wherein the cannabinoid, terpene, flavonoid, or combination thereof, is present in an aggregate amount of 0.1 to 10 wt. %.

<76> The topical sunscreen of any one of the above embodiments, wherein the cannabinoid, terpene, flavonoid, or combination thereof, is present in an aggregate amount of 0.1 to 5 wt. %.

<77> The topical sunscreen of any one of the above embodiments, wherein the cannabinoid, terpene, flavonoid, or combination thereof, is present in an aggregate amount of 0.01 to 2.5 wt. %.

<78> The topical sunscreen of any one of the above embodiments, wherein the cannabinoid, terpene, flavonoid, or combination thereof, is present in an aggregate amount of 0.01 to 1 wt. %.

<79> The topical sunscreen of any one of the above embodiments, wherein the cannabinoid, terpene, flavonoid, or combination thereof, is present in an aggregate amount of 0.01 to 0.5 wt %.

<80> The topical sunscreen of any one of the above embodiments, wherein the cannabinoid, terpene, flavonoid, or combination thereof, is present in an aggregate amount of 1 to 20 wt %.

<81> The topical sunscreen of any one of the above embodiments, wherein the cannabinoid, terpene, flavonoid, or combination thereof, is present in an aggregate amount of 1 to 10 wt %.

<82> The topical sunscreen of any one of the above embodiments, wherein the cannabinoid, terpene, flavonoid, or combination thereof, is present in an aggregate amount of 1 to 5 wt %.

<83> The topical sunscreen of any one of the above embodiments, wherein the cannabinoid, terpene, flavonoid, or combination thereof, is present in an aggregate amount of 0.05 to 2.5 wt %.
<84> The topical sunscreen of any one of the above embodiments, wherein the cannabinoid, terpene, flavonoid, or combination thereof, is present in an aggregate amount of 0.05 to 1 wt %.
<85> The topical sunscreen of any one of the above embodiments, wherein the cannabinoid, terpene, flavonoid, or combination thereof, is present in an aggregate amount of 0.05 to 0.5 wt %.
<86> The topical sunscreen of any one of the above embodiments, which is in the form of a gel, pump gel, gel packet, cream, lotion, roll-on liquid, roll-on gel, spray, pump spray, aerosol spray, stick, patch, ointment, liniment, or balm.
<87> A topical sunscreen including one or more external sunscreen agents of Production Example 74, further including a cannabinoid, terpene, flavonoid, or combination thereof, and a carrier system; wherein the cannabinoid, terpene, flavonoid, or combination thereof, while present in the aggregate amounts, are characterized as inactive ingredients.
<88> A topical sunscreen including one or more external sunscreen agents of Production Example 74, further including a cannabinoid, terpene, flavonoid, or combination thereof, and a carrier system; wherein the cannabinoid, terpene, flavonoid, or combination thereof, while present in the aggregate amounts, are characterized as an excipient.
<89> A topical sunscreen including one or more external sunscreen agents of Production Example 74, further including a cannabinoid, terpene, flavonoid, or combination thereof, and a carrier system; wherein the cannabinoid, terpene, flavonoid, or combination thereof, while present in the aggregate amounts, are characterized as active ingredients.
<90> A topical sunscreen including one or more external sunscreen agents of Production Example 74, further including a cannabinoid, terpene, flavonoid, or combination thereof, and a carrier system; wherein the cannabinoid, terpene, flavonoid, or combination thereof, while present in the aggregate amounts, are characterized as an external sunscreen agent
<91> The topical sunscreen of any one of the above embodiments, which is in the form of a cream, gel, or lotion.
<92> The topical sunscreen of any one of the above embodiments, having a total THC content of less than 0.05 mg/mL, wherein the total THC content is defined as the amount of TH CA/mL 0.877, plus the amount of THC/mL*1, expressed as: Total THC content=(amount of THCA/mL*0.877)+(amount of T H C/mL*1)<0.05 mg/mL
<93> The topical sunscreen of any one of the above embodiments, having a total TH C content of less than 0.025 mg/mL, wherein the total TH C content is defined as the amount of TH CA/mL*0.877, plus the amount of THC/mL*1, expressed as: Total T H C content=(amount of THCA/mL*0.877)+(amount of T H C/mL*1)<0.025 mg/mL
<94> The topical sunscreen of any one of the above embodiments, substantially free from (a)-(e):
  (a) Tetrahydrocannabinol (THC),
  (b) Tetrahydrocannabinolic Acid (THCA),
  (c) Cannabidiolic Acid (CBDA),
  (d) Cannabinol (CBN),
  (e) Cannabigerol (CBG),
such that any of (a)-(e) present in the topical sunscreen is present such that the topical sunscreen includes each in no more than 0.01 mg/mL.
<95> The topical sunscreen of any one of the above embodiments, substantially free from (a)-(e):
  (a) Tetrahydrocannabinol (THC),
  (b) Tetrahydrocannabinolic Acid (THCA),
  (c) Cannabidiolic Acid (CBDA),
  (d) Cannabinol (CBN),
  (e) Cannabigerol (CBG),
such any one or more of (a)-(e) that is present in the topical sunscreen is present in a total amount of up to 0.02 mg/mL.
<96> A method that includes topically administering to a subject the topical sunscreen of any one of the above embodiments.
<97> The method of embodiment <96>, wherein the topical sunscreen is administered to the skin surface of the subject to help prevent sunburn.
<98> The method of any one of embodiments <96> to <97>, wherein the topical sunscreen is applied to a clean and dry topical skin surface of the subject.
<99> The method of any one of embodiments <96> to <98>, wherein the topical sunscreen is applied to at least one of the face, neck, chest, shoulders, arms, back, legs, hands and feet of the subject.
<100> The method of any one of embodiments <96> to <99>, wherein the topical sunscreen is applied up to four times a day.
<101> The method of any one of embodiments <96> to <100>, wherein the subject is at least 12 years old.
<102> The method of any one of embodiments <96> to <100>, wherein the subject is at least 18 years old.
<103> The method of any one of embodiments <96> to <102>, wherein the subject is a human.
<104> The method of any one of embodiments <96> to <103>, wherein after administering to a topical skin surface, the hands are washed with soap and water.

The invention claimed is:

1. A method comprising topically administering to a skin surface of a human subject a topical sunscreen composition comprising:
  external sunscreen agent comprising avobenzone, homosalate, octisalate, octocrylene, zinc phenol sulfonate, ensulizole, and oxybenzone;
  solvent comprising water and glycerin;
  emulsifier comprising glyceryl stearate and PEG-100 stearate;
  thickening agent comprising acrylates/C10-30 alkyl acrylate crosspolymer and silica;
  emollient comprising C12-15 alkyl benzoate, cetearyl alcohol, dimethicone, isododecane, and caprylyl glycol; and
  a cannabinoid, terpene, and flavonoid;
wherein,
  the topical sunscreen composition is administered to the skin surface of the subject to help prevent sunburn;
  the external sunscreen agent is present in 0.1-7.5 wt. % of the topical sunscreen composition;
  the topical sunscreen composition is formulated as a cream or lotion;
  the external sunscreen agent and the cannabinoid, terpene, and flavonoid are dispersed throughout the topical sunscreen composition;
  the topical sunscreen composition is substantially free from (a)-(c): (a) Cannabidiolic Acid (CBDA), (b) Cannabinol (CBN), and (c) Cannabigerol (CBG); such that any of (a)-(c) present in the topical sunscreen composition is present such that the topical sunscreen composition includes each in no more than 0.01 mg/mL; and the topical sunscreen composition has a total tetrahydrocannabinol (THC) content of less than 0.02 mg/mL, wherein the total tetrahydrocannabinol (THC) content is defined as the amount of tetrahydrocannabinolic acid (THCA)*0.877, plus the amount of THC*1, expressed as:

Total THC content=(amount of THCA/mL*0.877)+ (amount of THC/mL*1)<0.02 mg/mL.

2. The method of claim 1, wherein the solvent is present in 60-80 wt. % of topical sunscreen composition.

3. The method of claim 1, wherein the emulsifier is present in 3-8 wt. % of the topical sunscreen composition.

4. The method of claim 1, wherein the thickening agent is present in 0.3-3 wt. % of the topical sunscreen composition.

5. The method of claim 1, wherein the emollient is present in 10-22 wt. % of the topical sunscreen composition.

6. The method of claim 1, wherein the topical sunscreen composition further comprises a pH adjusting agent, antioxidant, transdermal delivery agent, preservative, fragrance, coloring agent, and exfoliant.

7. The method of claim 1, wherein the topical sunscreen composition further comprises a pH adjusting agent comprising triethanolamine.

8. The method of claim 1, wherein the topical sunscreen composition further comprises a preservative comprising methylparaben.

9. The method of claim 1, wherein the topical sunscreen composition further comprises a transdermal delivery agent comprising ethanol.

10. The method of claim 1, wherein the topical sunscreen composition further comprises an antioxidant comprising tocopherol or vitamin E.

11. The method of claim 1, wherein the topical sunscreen composition further comprises an antioxidant present in 0.05-0.5 wt. %.

12. The method of claim 1, wherein the topical sunscreen composition further comprises a fragrance comprising blood orange.

13. The method of claim 1, wherein the topical sunscreen composition further comprises a coloring agent comprising Red No. 6 D&C Lake liquid.

14. The method of claim 1, wherein the topical sunscreen composition further comprises an exfoliant comprising citric acid.

15. The method of claim 1, wherein the topical sunscreen composition further comprises an exfoliant present in 1-2 wt. %.

* * * * *